(12) United States Patent
Karabed

(10) Patent No.: US 11,804,284 B2
(45) Date of Patent: Oct. 31, 2023

(54) MODULO BASED GENETIC MATERIAL ALIGNMENT

(71) Applicant: Razmik Karabed, Brentwood, CA (US)

(72) Inventor: Razmik Karabed, Brentwood, CA (US)

(73) Assignee: OmniTier, Inc., San Jose, CA (US)

( * ) Notice: Subject to any disclaimer, the term of this patent is extended or adjusted under 35 U.S.C. 154(b) by 0 days.

(21) Appl. No.: 17/871,837

(22) Filed: Jul. 22, 2022

(65) Prior Publication Data

US 2023/0076750 A1    Mar. 9, 2023

Related U.S. Application Data

(60) Provisional application No. 63/224,849, filed on Jul. 22, 2021.

(51) Int. Cl.
*G01N 33/48*    (2006.01)
*G01N 33/50*    (2006.01)
*G16B 30/10*    (2019.01)
*G16B 40/20*    (2019.01)
*G06F 17/16*    (2006.01)

(52) U.S. Cl.
CPC ............ *G16B 30/10* (2019.02); *G16B 40/20* (2019.02); *G06F 17/16* (2013.01)

(58) Field of Classification Search
CPC .......... G16B 30/10; G16B 40/20; G06F 17/16
See application file for complete search history.

(56) References Cited

U.S. PATENT DOCUMENTS 4,870,414 A    9/1989    Karabed et al.
2004/0059721 A1*   3/2004    Patzer ................. G16B 50/00

OTHER PUBLICATIONS

Gotoh, Osamu, "An Improved Algorithm for Matching Biological Sequences", J. Mol. Biol. 162, month unknown 1982, pp. 705-708.
Huson, Daniel, "Algorithms in Bioinformatics I," Uni Tubingen, Wintersemester, month unknown, 2002, pp. 1-163.
Emms, Martin, et al., "On order equivalences between distance and similarity measures on sequences and trees," School of Computer Science and Statistics, Trinity College, Dublin, Ireland, Feb. 2012, pp. 1-10.
Fu, Yao, et al., "Deep Learning with INT8 Optimization on Xilinx Devices," Xilinx, Apr. 2017, pp. 1-11.
(Continued)

*Primary Examiner* — Russell S Negin
(74) *Attorney, Agent, or Firm* — Makoui Law, PC; Ali Makoui

(57) ABSTRACT

A modulo based alignment system for aligning genetic material sequences is provided. The modulo based alignment system reduces the size of data required for the genetic material sequence alignment, reduces the number of the registers required for processing, reduces the power requirements, and reduces the amount of heat generated during processing. The modulo based alignment system provides methods of performing dynamic programs for global, overlapping and local alignments using modular arithmetic. The methods produce smaller parameters requiring fewer processor register bits. In addition, with customized hardware optimized for 8-bit arithmetic, the dynamic programs are sped up.

14 Claims, 34 Drawing Sheets

(56) References Cited

OTHER PUBLICATIONS

Suzuki, Hajime, et al., "Introducing difference recurrence relations for faster semi-global alignment of long sequences," BMC Bioinformatics 19, Article No. 45(2018), Feb. 2018, pp. 33-47.
Welser, Jeffrey, "Dual 8-Bit Breakthroughs Bring AI to the Edge," IBM Research Blog, Dec. 2018, pp. 1-4,.

* cited by examiner

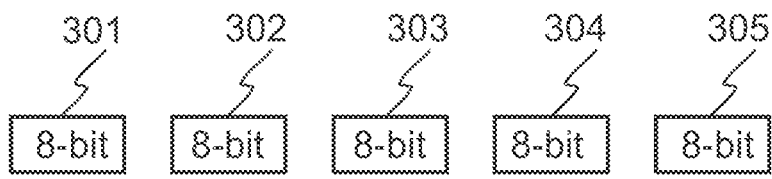
FIG. 4A
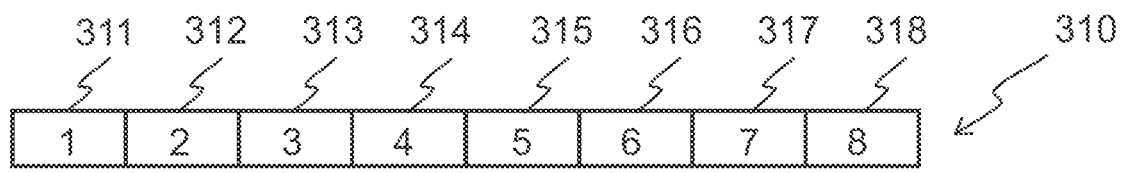
FIG. 4B
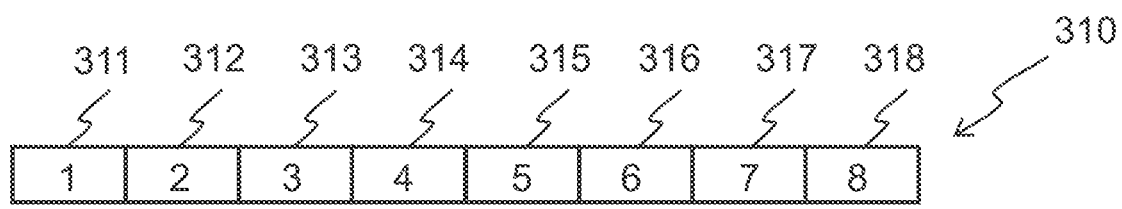
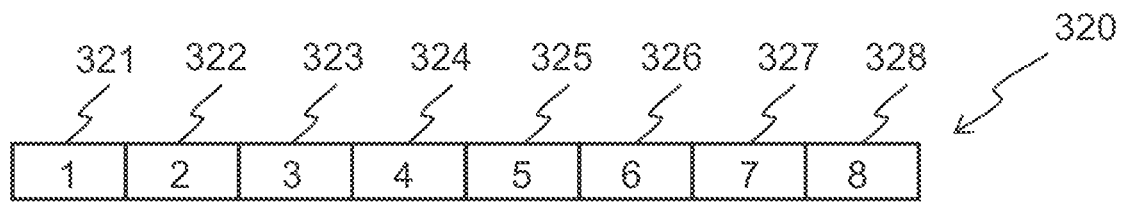
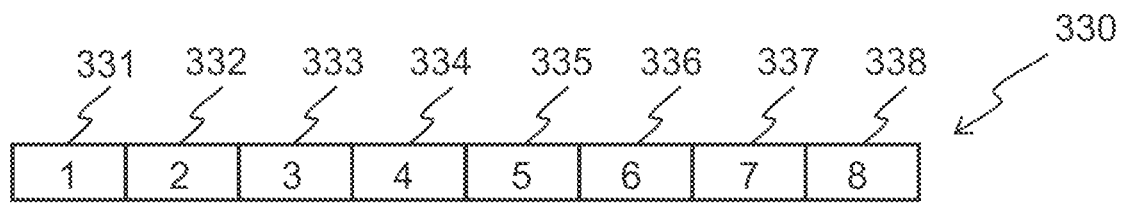
FIG. 4C

| 1 row>1 col=2 | | Modified, with Tail | Modified, w/o Tail | AS, with Tail | AS, w/o Tail |
|---|---|---|---|---|---|
| | Triangle | 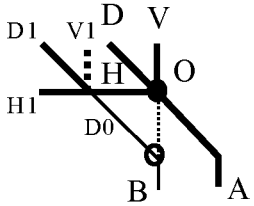 | NOT VALID | 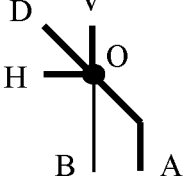 | NOT VALID |
| | Rectangle | NOT VALID 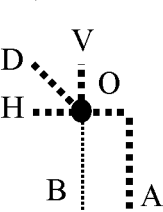 | NOT VALID | 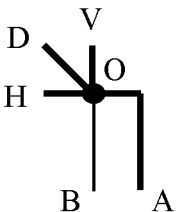 | NOT VALID |
| | Flat | 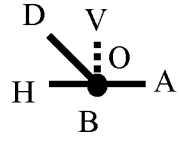 | NOT VALID | 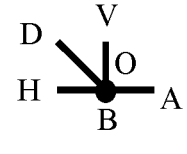 | NOT VALID |
1800
FIG. 18

| 2 row>1 col>2 | | Modified, with Tail | Modified, w/o Tail | AS, with Tail | AS, w/o Tail |
|---|---|---|---|---|---|
| | triangle | | NOT VALID | | NOT VALID |
| | rectangle | NOT VALID | NOT VALID | | NOT VALID |
| | flat | | NOT VALID | | NOT VALID |

FIG. 19  1900

| 3 row=1 col=2 | | Modified, with Tail | Modified, w/o Tail | AS, with Tail | AS, w/o Tail |
|---|---|---|---|---|---|
| | triangle | | NOT VALID | | NOT VALID |
| | rectangle | NOT VALID | NOT VALID | | NOT VALID |
| | flat | | NOT VALID | | NOT VALID |

FIG. 20  2000

| 4 row=1 col>2 | | Modified, with Tail | Modified, w/o Tail | AS, with Tail | AS, w/o Tail |
|---|---|---|---|---|---|
| | triangle | (figure) | NOT VALID | (figure) | NOT VALID |
| | rectangle | NOT VALID (figure) | NOT VALID | (figure) | NOT VALID |
| | flat | (figure) | NOT VALID | (figure) | NOT VALID |

FIG. 21 2100

| 5 row>1 col=1 | | Modified, with Tail | Modified, w/o Tail | AS, with Tail | AS, w/o Tail |
|---|---|---|---|---|---|
| | triangle | (figure) | NOT VALID | (figure) | NOT VALID |
| | rectangle | NOT VALID (figure) | NOT VALID | (figure) | NOT VALID |
| | flat | NOT VALID (figure) | NOT VALID | (figure) | NOT VALID |

FIG. 22 2200

| 6 row=1 col=1 | | Modified, with Tail | Modified, w/o Tail | AS, with Tail | AS, w/o Tail |
|---|---|---|---|---|---|
| | triangle | 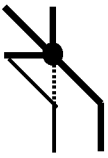 | NOT VALID | 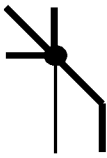 | NOT VALID |
| | rectangle | NOT VALID 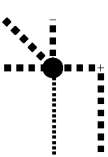 | NOT VALID |  | NOT VALID |
| | flat |  | NOT VALID |  | NOT VALID |
FIG. 23            2300
| 7 row>0 col=0 | | Modified, with Tail | Modified, w/o Tail | AS, with Tail | AS, w/o Tail |
|---|---|---|---|---|---|
| | triangle | 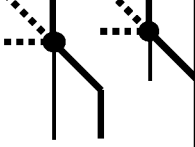 | NOT VALID | 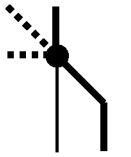 | NOT VALID |
| | rectangle | NOT VALID 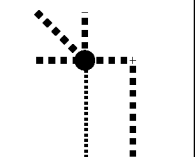 | NOT VALID | 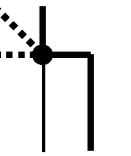 | NOT VALID |
| | flat | NOT VALID  | NOT VALID |  | NOT VALID |
FIG. 24            2400

| 8 row=0 col>1 | | Modified, with Tail | Modified, w/o Tail | AS, with Tail | AS, w/o Tail |
|---|---|---|---|---|---|
| | triangle | [diagram] | NOT VALID | [diagram] | NOT VALID |
| | rectangle | NOT VALID | NOT VALID | [diagram] | NOT VALID |
| | flat | [diagram] | NOT VALID | [diagram] | NOT VALID |

FIG. 25  2500

| 9 row=0 col=1 | | Modified, with Tail | Modified, w/o Tail | AS, with Tail | AS, w/o Tail |
|---|---|---|---|---|---|
| | triangle | [diagram] | NOT VALID | [diagram] | NOT VALID |
| | rectangle | NOT VALID | NOT VALID | [diagram] | NOT VALID |
| | flat | [diagram] | NOT VALID | [diagram] | NOT VALID |

FIG. 26  2600

| 10 row=0 col=0 | | Modified, with Tail | Modified, w/o Tail | AS, with Tail | AS, w/o Tail |
|---|---|---|---|---|---|
| | triangle | NOT VALID  |  | NOT VALID 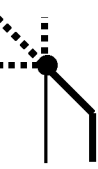 |  |
| | rectangle | NOT VALID 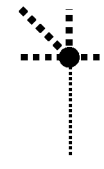 | NOT VALID | NOT VALID 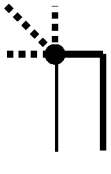 |  |
| | flat |  |  | NOT VALID  |  |
2700
FIG. 27

| 1 row>1 col=2 | | Modified, with Tail | Modified, w/o Tail | AS, with Tail | AS, w/o Tail |
|---|---|---|---|---|---|
| | Triangle | (diagram with D1, V1, H, O, H1, D0, B, A) | NOT VALID | (diagram with D, V, H, O, B, A) | (diagram with B, A) |
| | Rectangle | NOT VALID | (diagram with D, V, H, O, B, A) | NOT VALID | (diagram with D, V, H, O, B, A) | NOT VALID |
| | Flat | (diagram with D, V, H, O, A, B) | NOT VALID | (diagram with D, V, H, O, A, B) | (diagram with B, A) |

| | | Modified | AS |
|---|---|---|---|
| | top circle | NOT VALID | (diagram) |

| 2 row>1 col>2 | | Modified, with Tail | Modified, w/o Tail | AS, with Tail | AS, w/o Tail |
|---|---|---|---|---|---|
| | triangle | 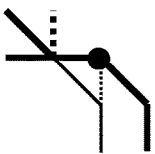 | NOT VALID | 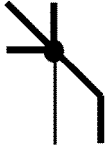 |  |
| | rectangle | NOT VALID 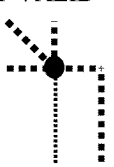 | NOT VALID | 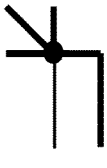 | NOT VALID |
| | flat |  | NOT VALID |  |  2901 |
FIG. 29A
| | | Modified | AS |
|---|---|---|---|
| | top circle | NOT VALID |  2902 |
FIG. 29B

| 3 row=1 col=2 | | Modified, with Tail | Modified, w/o Tail | AS, with Tail | AS, w/o Tail |
|---|---|---|---|---|---|
| | triangle | 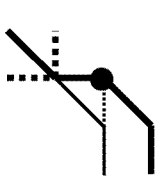 | NOT VALID | 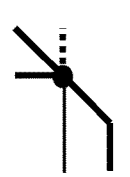 |  |
| | rectangle | NOT VALID 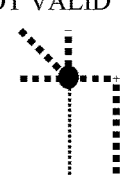 | NOT VALID | 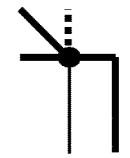 | NOT VALID |
| | flat |  | NOT VALID |  |  3001 |
FIG. 30A
| | | Modified | AS |
|---|---|---|---|
| | top circle | NOT VALID |  3002 |
FIG. 30B

| 4 row=1 col>2 | | Modified, with Tail | Modified, w/o Tail | AS, with Tail | AS, w/o Tail |
|---|---|---|---|---|---|
| | triangle | | NOT VALID | | |
| | rectangle | NOT VALID | NOT VALID | | NOT VALID |
| | flat | | NOT VALID | |  |

3101

| | | Modified | AS |
|---|---|---|---|
| | top circle | NOT VALID | |

3102

| 5 row>1 col=1 | | Modified, with Tail | Modified, w/o Tail | AS, with Tail | AS, w/o Tail |
|---|---|---|---|---|---|
| | triangle |  | NOT VALID |  |  |
| | rectangle | NOT VALID 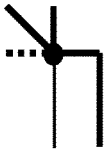 | NOT VALID |  | NOT VALID |
| | flat |  | NOT VALID |  |  3201 |
FIG. 32A
| | | Modified | AS |
|---|---|---|---|
| | top circle | NOT VALID | ● <br> 3202 |
FIG. 32B

| 6 row=1 col=1 | | Modified, with Tail | Modified, w/o Tail | AS, with Tail | AS, w/o Tail |
|---|---|---|---|---|---|
| | triangle |  | NOT VALID |  |  |
| | rectangle | NOT VALID 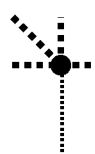 | NOT VALID |  | NOT VALID |
| | flat |  | NOT VALID |  |  3301 |
FIG. 33A
| | | Modified | AS |
|---|---|---|---|
| | top circle | NOT VALID |  |
3302
FIG. 33B

| 7 row>0 col=0 | | Modified, with Tail | Modified, w/o Tail | AS, with Tail | AS, w/o Tail |
|---|---|---|---|---|---|
| | triangle | NA | NOT VALID | NOT VALID 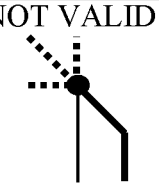 |  |
| | rectangle | NA | NOT VALID | NOT VALID 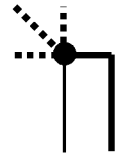 | NOT VALID |
| | flat | NA | NOT VALID | NOT VALID 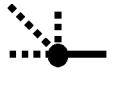 |  |
3401
FIG. 34A
| | | Modified | AS |
|---|---|---|---|
| | top circle | NA | NOT VALID |
3402
FIG. 34B

| 8 row=0 col>1 | | Modified, with Tail | Modified, w/o Tail | AS, with Tail | AS, w/o Tail |
|---|---|---|---|---|---|
| | triangle | NA | NOT VALID | NOT VALID 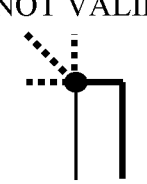 |  |
| | rectangle | NA | NOT VALID | NOT VALID 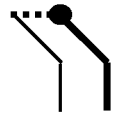 | NOT VALID |
| | flat | NA | NOT VALID | NOT VALID 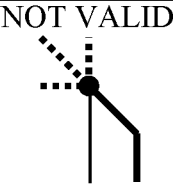 |  3501 |
FIG. 35A
| | | Modified | AS |
|---|---|---|---|
| | top circle | NOT VALID |  |
3502
FIG. 35B

| 9 row=0 col=1 | | Modified, with Tail | Modified, w/o Tail | AS, with Tail | AS, w/o Tail |
|---|---|---|---|---|---|
| | triangle | NA | NOT VALID | NOT VALID 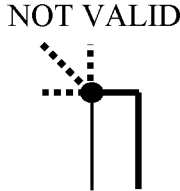 | 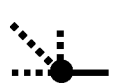 |
| | rectangle | NA | NOT VALID | NOT VALID  | NOT VALID |
| | flat | NA | NOT VALID | NOT VALID 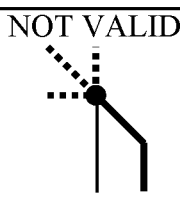 |  3601 |
FIG. 36A
| | | Modified | AS |
|---|---|---|---|
| | top circle | NOT VALID |  3602 |
FIG. 36B

| 10 row=0 col=0 | | Modified, with Tail | Modified, w/o Tail | AS, with Tail | AS, w/o Tail |
|---|---|---|---|---|---|
| | triangle | NA | NOT VALID | NOT VALID 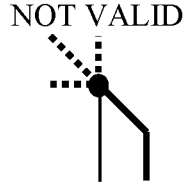 |  |
| | rectangle | NA | NOT VALID | NOT VALID 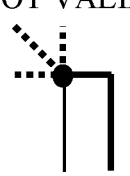 | NOT VALID |
| | flat | NA | NOT VALID | NOT VALID  |  |
FIG. 37A 3701
| | | Modified | AS |
|---|---|---|---|
| | top circle | NOT VALID | NOT VALID |
FIG. 37B 3702

MODULO BASED GENETIC MATERIAL ALIGNMENT

CLAIM OF BENEFIT TO PRIOR APPLICATIONS

This application claims the benefit of U.S. Provisional Patent Application Ser. No. 63/224,849, filed on Jul. 22, 2021. The contents of U.S. Provisional Patent Application 63/224,849 are hereby incorporated by reference.

BACKGROUND

Genetic material includes deoxyribonucleic acid (DNA), messenger ribonucleic acid (mRNA), proteins, genes, chromosomes, various types of data including nucleotide and amino acid sequences, etc. Sequencing of the genetic material involves revealing the order of bases present in the genetic material. During sequencing, often set of two or more sequences of genetic material are aligned. Sequence alignment is a way of arranging DNA, mRNA, or protein to identify regions of similarity that indicate functional, structural, or evolutionary relationship between the sequences.

Methods used for alignment are often computationally intensive due to the large-scale nature of genetic materials. Alignment methods are implemented using either a software running on a computer, or a software/firmware running on a specialized computer or a customized hardware. Often computational and memory (such as, register, cache, and page) requirements of these methods are high. Further, these high requirements demand high power and burden the speed of alignment.

BRIEF DESCRIPTION OF THE DRAWINGS

The various embodiments of the present modulo based genetic material alignment now will be discussed in detail with an emphasis on highlighting the advantageous features. These embodiments depict the novel and non-obvious modulo based genetic material alignment shown in the accompanying drawings, which are for illustrative purposes only. These drawings include the following figures, in which like numerals indicate like parts:

FIG. 4A illustrates five 8-bit registers, according to various aspects of the present disclosure;

FIG. 4B illustrates a 64-bit registers with two 8-bit accessible 8-bit segments, according to various aspects of the present disclosure;

FIG. 4C illustrates storing data in the accessible portion of registers, according to various aspects of the present disclosure;

FIG. 18 shows a table that for each affine gap function, characterized all pairs of walks that diverge from a vertex in a row>1 and column=2, such that one ends in A and the other ends in B, according to various aspects of the present disclosure;

FIG. 19 shows a table that for each affine gap function, characterized all pairs of walks that diverge from a vertex in a row>1 and column>2, such that one ends in A and the other ends in B, according to various aspects of the present disclosure;

FIG. 20 shows a table that for each affine gap function, characterized all pairs of walks that diverge from a vertex in a row=1 and column=2, such that one ends in A and the other ends in B, according to various aspects of the present disclosure;

FIG. 21 shows a table that for each affine gap function, characterized all pairs of walks that diverge from a vertex in a row=1 and column>2, such that one ends in A and the other ends in B, according to various aspects of the present disclosure;

FIG. 22 shows a table that for each affine gap function, characterized all pairs of walks that diverge from a vertex in a row>1 and column=1, such that one ends in A and the other ends in B, according to various aspects of the present disclosure;

FIG. 23 shows a table that for each affine gap function, characterized all pairs of walks that diverge from a vertex in a row=1 and column=1, such that one ends in A and the other ends in B, according to various aspects of the present disclosure;

FIG. 24 shows a table that for each affine gap function, characterized all pairs of walks that diverge from a vertex in a row=0 and column=0, such that one ends in A and the other ends in B, according to various aspects of the present disclosure;

FIG. 25 shows a table that for each affine gap function, characterized all pairs of walks that diverge from a vertex in a row=1 and column>1, such that one ends in A and the other ends in B, according to various aspects of the present disclosure;

FIG. 26 shows a table that for each affine gap function, characterized all pairs of walks that diverge from a vertex in a row=0 and column=1, such that one ends in A and the other ends in B, according to various aspects of the present disclosure;

FIG. 27 shows a table that for each affine gap function, characterized all pairs of walks that diverge from a vertex in a row=0 and column=0, such that one ends in A and the other ends in B, according to various aspects of the present disclosure;

FIG. 28A shows a table that for each affine gap function, characterized all pairs of walks that diverge from a vertex in a row>1 and column=2, such that one ends in A and the other ends in B, according to various aspects of the present disclosure;

FIG. 28B shows a table that for each affine gap function, characterized whether the walk from the top circle (row>1 and column=2) to A could be a valid walk for $\rho(A)$ with respect to local alignment with the specific affine gap function, according to various aspects of the present disclosure;

FIG. 29A shows a table that for each affine gap function, characterized all pairs of walks that diverge from a vertex in a row>1 and column>2, such that one ends in A and the other ends in B, according to various aspects of the present disclosure;

FIG. 29B shows a table that for each affine gap function, characterized whether the walk from the top circle (row>1 and column>2) to A could be a valid walk for $\rho(A)$ with respect to local alignment with the specific affine gap function, according to various aspects of the present disclosure;

FIG. 30A shows a table that for each affine gap function, characterized all pairs of walks that diverge from a vertex in a row=1 and column=2, such that one ends in A and the other ends in B according to various aspects of the present disclosure;

FIG. 30B shows a table that for each affine gap function, characterized whether the walk from the top circle (row=1 and column=2) to A could be a valid walk for $\rho(A)$ with respect to local alignment with the specific affine gap function according to various aspects of the present disclosure;

FIG. 32A shows a table that for each affine gap function, characterized all pairs of walks that diverge from a vertex in a row>1 and column=1, such that one ends in A and the other ends in B, according to various aspects of the present disclosure;

FIG. 32B shows a table that for each affine gap function, characterized whether the walk from the top circle (row>1 and column=1) to A could be a valid walk for $\rho(A)$ with respect to local alignment with the specific affine gap function, according to various aspects of the present disclosure;

FIG. 33A shows a table that for each affine gap function, characterized all pairs of walks that diverge from a vertex in a row=1 and column=1, such that one ends in A and the other ends in B, according to various aspects of the present disclosure;

FIG. 33B shows a table that for each affine gap function, characterized whether the walk from the top circle (row=1 and column=1) to A could be a valid walk for $\rho(A)$ with respect to local alignment with the specific affine gap function, according to various aspects of the present disclosure;

FIG. 34A shows a table that for each affine gap function, characterized all pairs of walks that diverge from a vertex in a row=0 and column=0, such that one ends in A and the other ends in B, according to various aspects of the present disclosure;

FIG. 34B shows a table that for each affine gap function, characterized whether the walk from the top circle (row=0 and column=0) to A could be a valid walk for $\rho(A)$ with respect to local alignment with the specific affine gap function, according to various aspects of the present disclosure;

FIG. 35A shows a table that for each affine gap function, characterized all pairs of walks that diverge from a vertex in a row=1 and column>1, such that one ends in A and the other ends in B, according to various aspects of the present disclosure;

FIG. 35B shows a table that for each affine gap function, characterized whether the walk from the top circle (row=1 and column>1) to A could be a valid walk for $\rho(A)$ with respect to local alignment with the specific affine gap function, according to various aspects of the present disclosure;

FIG. 36A gives a table that for each affine gap function, characterized all pairs of walks that diverge from a vertex in a row=0 and column=1, such that one ends in A and the other ends in B, according to various aspects of the present disclosure;

FIG. 36B gives a table that for each affine gap function, characterized whether the walk from the top circle (row=0 and column=1) to A could be a valid walk for $\rho(A)$ with respect to local alignment with the specific affine gap function, according to various aspects of the present disclosure;

FIG. 37A shows a table that for each affine gap function, characterized all pairs of walks that diverge from a vertex in a row=0 and column=0, such that one ends in A and the other ends in B, according to various aspects of the present disclosure; and FIG. 37B shows a table that for each affine gap function, characterized whether the walk from the top circle (row=0 and column=0) to A could be a valid walk for $\rho(A)$ with respect to local alignment with the specific affine gap function, according to various aspects of the present disclosure.

DETAILED DESCRIPTION

Figure 1:
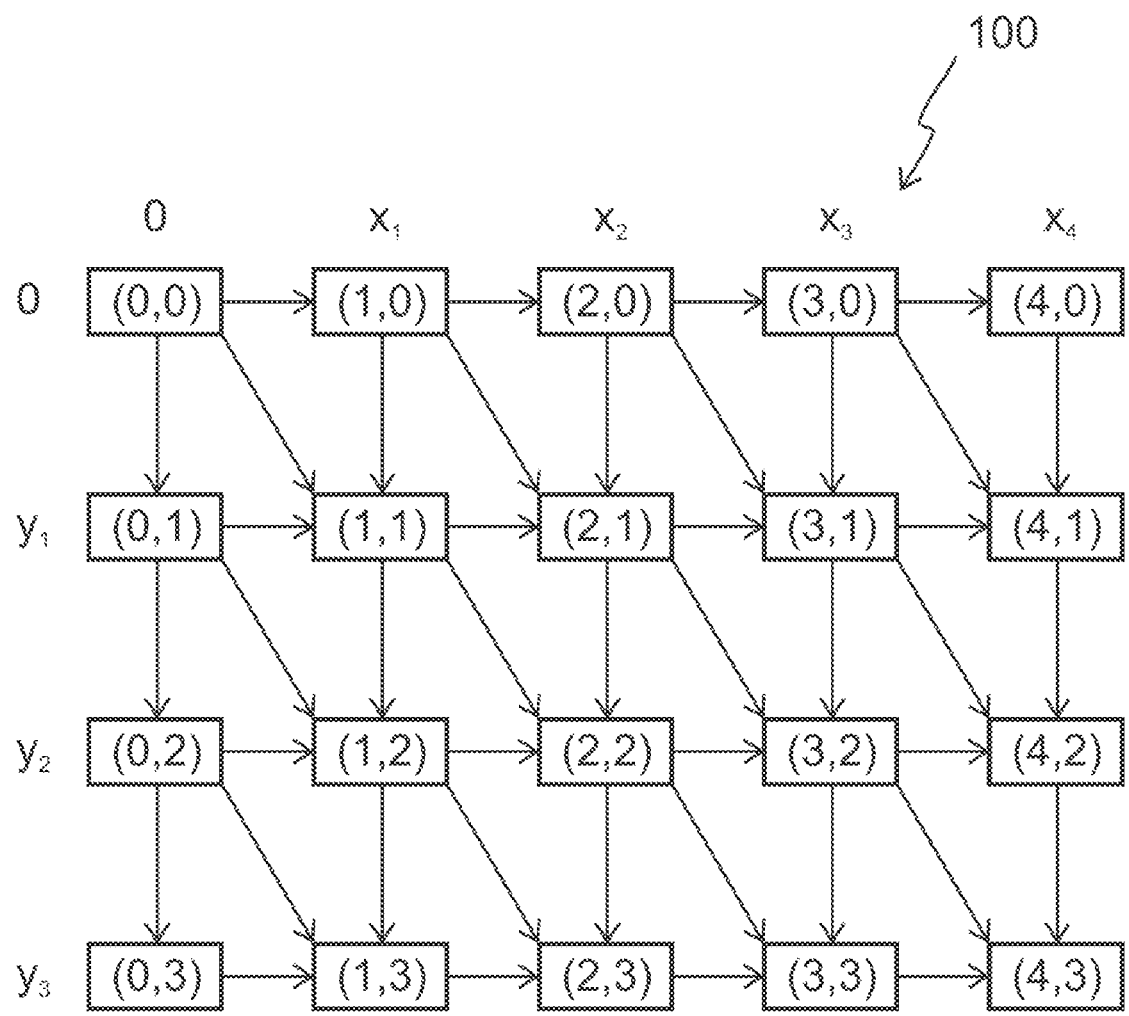
FIG. 1 illustrates an alignment digraph, according to various aspects of the present disclosure.

One aspect of the present embodiments includes the realization that the existing methods of sequencing genetic material are often computationally intensive and memory intensive. Further, these high requirements demand high power and burden the speed of alignment. For example, DNA may include billions of bases and the alignment of two DNA sequences may require maintaining and processing large matrixes.

The present embodiments, as described in detail below, solve the above-mentioned problems by providing a modulo based genetic alignment system that reduces the size of data required for the alignment, reduces the number of the registers required for processing, reduces the power requirements, and reduces the amount of heat generated during processing.

The present embodiments provide methods of performing dynamic programs for global, overlapping and local alignments using modular arithmetic. The methods produce smaller parameters requiring fewer processor register bits. In addition, with customized hardware optimized for 8-bit arithmetic, the dynamic programs are sped up.

The remaining detailed description describes the present embodiments with reference to the drawings. In the drawings, reference numbers label elements of the present embodiments. These reference numbers are reproduced below in connection with the discussion of the corresponding drawing features.

I. Genetic Material Alignment

A. Definitions

A sequence, $\underline{x}=x_1\ x_2\ x_3\ \ldots\ x_n$, of a genetic material over a genetic base alphabet $\mathbb{Q}$ is a finite string of letters, each chosen from the alphabet $\mathbb{Q}$. A gap character, "-", "-"$\notin \mathbb{Q}$ is used to signify an absent letter. An expanded sequence $\underline{x}'$ of the sequence $\underline{x}$ is $\underline{x}$ with an arbitrary number of gap characters inserted at its beginning, end, or between any two of its characters.

An alignment of two sequences $\underline{x}$ and $\underline{y}$ of genetic materials is any pair of expanded sequences $\underline{x}'$ and $\underline{y}'$ such that (1) length ($\underline{x}'$)=length ($\underline{y}'$) and (2) {locations of the gaps in $\underline{x}'$}$\cap$ {locations of the gaps in $\underline{y}'$}=$\phi$, i.e., the intersection of the set of the locations of the gaps of $\underline{x}'$ and the set of the locations of the gaps of $\underline{y}'$ is empty.

The 2×k matrix, $$M = \begin{bmatrix} \underline{x}' \\ \underline{y}' \end{bmatrix},$$

is referred to as the alignment matrix of the sequences $\underline{x}$ and $\underline{y}$. Given sequences $\underline{x}=x_1\ x_2\ x_3\ \ldots\ x_n$ and $\underline{y}=y_1\ y_2\ y_3\ \ldots\ y_m$, a 2×1 vector is referred to as a substitution if it is of the form $$\begin{pmatrix} x \\ y \end{pmatrix},$$

for x and y in $\mathbb{Q}$, an x-gap if it is of the form $$\begin{pmatrix} x \\ "\text{-}" \end{pmatrix},$$

for x in $\mathbb{Q}$, or a y-gap if it is of the form $$\begin{pmatrix} "\text{-}" \\ y \end{pmatrix},$$

for y in $\mathbb{Q}$. A substitution, $$\begin{pmatrix} x \\ y \end{pmatrix},$$

is referred to as a match if x=y, and it is called a mismatch if x≠y.

Given sequences $\underline{x}=x_1\ x_2\ x_3\ \ldots\ x_n$ and $\underline{y}=y_1\ y_2\ y_3\ \ldots\ y_m$ over the alphabet $\mathbb{Q}$, four sets: $\mathbb{Z}_y^x$, $\mathbb{Z}_-^x$, $\mathbb{Z}_y^-$, and $\mathbb{Z}$ are defined as follows:

$$\mathbb{Z}_y^x = \left\{ \begin{pmatrix} x \\ y \end{pmatrix} : x \text{ and } y \in \mathbb{Q} \right\},$$

and is called the substitution set, $$\mathbb{Z}_-^x = \left\{ \begin{pmatrix} x \\ "\text{-}" \end{pmatrix} : x \in \mathbb{Q}, \text{ and } "\text{-}" \text{ is the gap charactor} \right\},$$

and is called the x-gap set, $$\mathbb{Z}_y^- \left\{ \begin{pmatrix} "\text{-}" \\ y \end{pmatrix} : y \in \mathbb{Q}, \text{ and } "\text{-}" \text{ is the gap charactor} \right\},$$

and is called the y-gap set, and $\mathbb{Z} = \mathbb{Z}_y^x \cup \mathbb{Z}_-^x \cup \mathbb{Z}_y^-$, and it is called the column space of alignment matrices.

B. Alignment Digraph

For every pair of sequences $\underline{x}=x_1\ x_2\ x_3\ \ldots\ x_n$ and $\underline{y}=y_1\ y_2\ y_3\ \ldots\ y_m$, there is a digraph $D(\underline{x},\underline{y})$ that characterizes their alignments. Vertex set of $D(\underline{x},\underline{y})$ is $\mathbb{V}=\{(i,j)$, for $0 \le i \le n$ and $0 \le j \le m\}$. An arc from $(i_1,j_1) \in \mathbb{V}$ to $(i_2,j_2) \in \mathbb{V}$ is denoted by either $(i_1,j_1) \to (i_2,j_2)$ or a shorter notation $(i_1,j_1)(i_2,j_2)$. A digraph (or directed graph) is a graph that is made of a set of vertices that are connected by directed edges (or arcs), where each edge is an ordered pair of two vertices.

The horizontal arc set of $D(\underline{x},\underline{y})$ is $A^h=\{(i,j)(i+1,j)$ for, $0 \le i \le n-1$, and $0 \le j \le m\}$. The set $A^h$ includes all horizontal arcs of $D(\underline{x},\underline{y})$. The vertical arc set of $D(\underline{x},\underline{y})$ is $A^v=\{(i,j)(i,j+1)$ for, $0 \le i \le n$, and $0 \le j \le m-1\}$. The set $A^v$ includes all vertical arcs of $D(\underline{x},\underline{y})$. And the diagonal arc set of $D(\underline{x},\underline{y})$ is $A^d=\{(i,j)(i+1,j+1)$ for, $0 \le i \le n-1$, and $0 \le j \le m-1\}$. The set $A^d$ includes all diagonal arcs of $D(\underline{x},\underline{y})$.

Clearly, the sets $A^h$, $A^v$, and $A^d$ are pairwise disjoint. $A^h \cap A^v = A^h \cap A^d = A^v \cap A^d = \phi$. The arc set of $D(\underline{x},\underline{y})$ is $\mathbb{A}=A^h \cup A^v \cup A^d$.

FIG. 1 illustrates an alignment digraph 100, according to various aspects of the present disclosure. The digraph 100 corresponds to a pair of sequences $\underline{x}=x_1\ x_2\ x_3\ x_4$ and $\underline{y}=y_1\ y_2\ y_3$, n=4, m=3. In order to identify the columns of the digraph 100 with the sequence $\underline{x}=x_1\ x_2\ x_3\ x_4$ an auxiliary base is augmented to $\underline{x}$, in the beginning. The auxiliary base is typically set to '0' and is not in the genetic base alphabet, $\mathbb{Q}$, of $\underline{x}$. Similarly, in order to identify the rows of the digraph 100 with the sequence $\underline{y}=y_1\ y_2\ y_3$ the auxiliary base is augmented to $\underline{y}$, in the beginning. The augmented sequence become $\underline{x}=(0\ x_1\ x_2\ x_3\ x_4)$ and $\underline{y}=(0\ y_1\ y_2\ y_3)$.

Lemma 1: There is a 1-to-1 correspondence between, the alignments of sequences $\underline{x}=x_1\ x_2\ x_3\ \ldots\ x_n$ and $\underline{y}=y_1\ y_2\ y_3\ \ldots\ y_m$, and directed walks from (0,0) to (n, m) on $D(\underline{x},$ y). A directed walk is a sequence of edges directed in the same direction which joins a sequence of vertices. The proof for Lemma 1 is as follows:

1) define a map F: $\mathbb{A} \to \mathbb{Z}$. F is referred to as the "$\mathbb{A}$ to $\mathbb{Z}$" map For every arc $(i,j)(p,q) \in \mathbb{A}$, $$F((i,j)(p,q)) \stackrel{\Delta}{=} \begin{cases} \begin{pmatrix} x_p \\ y_q \end{pmatrix} & \text{if } (i,j)(p,q) \in A^d \\ \begin{pmatrix} x_p \\ "-" \end{pmatrix} & \text{if } (i,j)(p,q) \in A^h \\ \begin{pmatrix} "-" \\ y_q \end{pmatrix} & \text{if } (i,j)(p,q) \in A^v \end{cases}$$

2) based on F, define a map $\mathbb{F}$ from walks to alignment matrices
3) show the map $\mathbb{F}$ is 1-to-1
4) show the map $\mathbb{F}$ is onto (that is to show for every alignment matrix, M, there is a walk, W, such that $\mathbb{F}(W)=M$).

C. Introduction

In a first medical application example, one might have two sequences $\underline{x}=x_1 x_2 x_3 \ldots x_n$ and $\underline{y}=y_1 y_2 y_3 \ldots y_m$ of genetic materials collected from a cancer patient before and after use of a medication, respectively. To understand the effect of the mediation on the patient in the genetic level, the two sequences may be compared. The medication might have caused a letter in sequences $\underline{x}$ to change into another letter, a letter in sequences $\underline{x}$ to be eliminated, and/or a letter to be inserted in sequences $\underline{x}$. A best comparison would reveal all these changes from x to y.

Figure 2A:
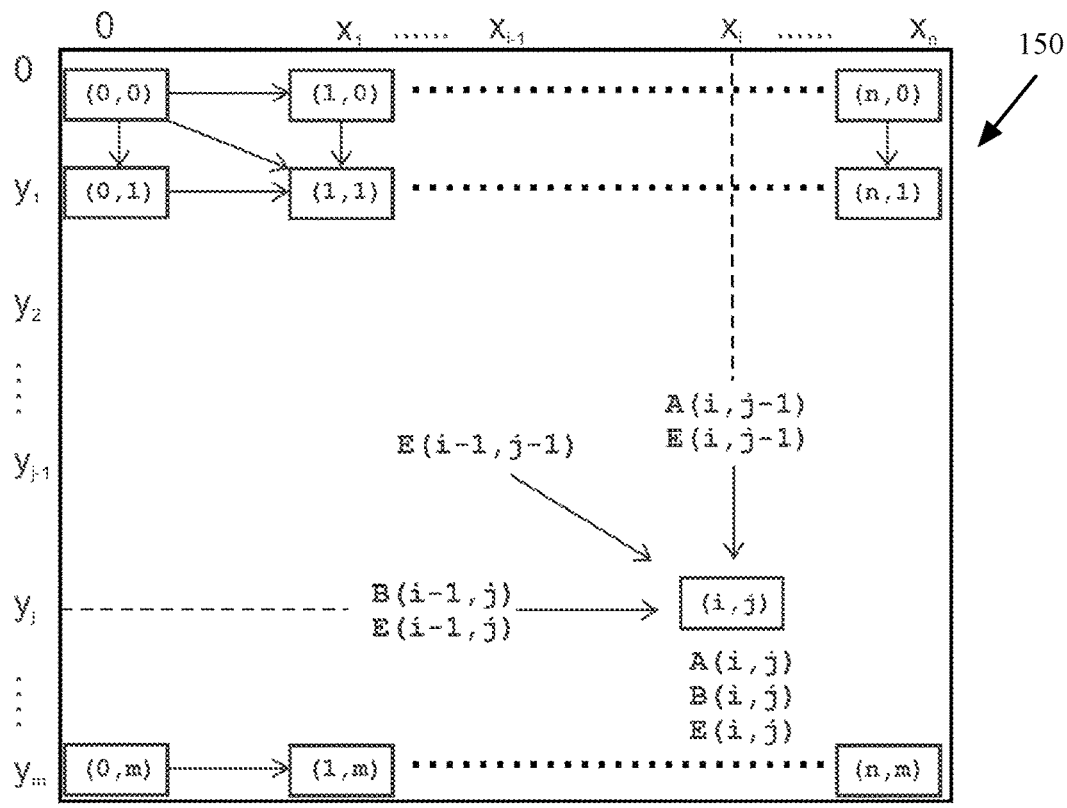
FIGS. 2A-2D illustrate dynamic programing on an alignment digraph, according to various aspects of the present disclosure.

FIG. 2A illustrates dynamic programing on an alignment digraph, according to various aspects of the present disclosure. With reference to FIG. 2A, to make a comparison, first an alignment (comparison) diagraph 150 is generated based on the sequences $\underline{x}$ and $\underline{y}$. The vertices are (i,j) for $0 \leq i \leq n$ and or $0 \leq j \leq m$. As shown in FIG. 2A, from the vertex (i,j), there are 3 arcs to (i+1,j), (i,j+1), and (i+1,j+1), boundary conditions allowing.

Each possible walk from (0,0) to (n, m) corresponds to a comparison of sequences $\underline{x}$ and $\underline{y}$. A score may be calculated for each walk. The score is a measure of how well the walk characterizes (e.g., identifies) the difference in the sequences. The present embodiments provide a system that searches for a walk with the best score, the one that gives the best characterization (e.g., the best identification) of the differences. Some embodiments perform dynamic programing to do the search. Dynamic programming refers to simplifying a complicated problem by breaking it down into simpler sub-problems in a recursive manner.

In the example of FIG. 2A, for every (i,j) in the diagraph 150, E(i,j) is the best score over all walks from (0,0) to (i,j). A(i,j) is the best score over all walks from (0,0) to (i,j) that ends with a vertical arc. B(i,j) is the best score over all walks from (0,0) to (i,j) that ends with a horizontal arc.

Using a dynamical program, E(i,j) may be generated based on E(i−1,j−1), E(i−1,j), E(i,j−1), A(i,j−1), and B(i−1,j). A(i,j) may be generated based on E(i,j−1) and A(i,j−1), and B(i,j) may be generated based on E(i,j−1) and B(i−1,j).

Parameters A, B, and C may be stored as binary numbers of lengths 32, 64, 128, or more. In practice, the length of sequences $\underline{x}$ and $\underline{y}$ could be in thousands. This puts a heavy burden on storage. When a processor (also referred herein as a central processing unit, or CPU) is used to implement the dynamical program, the CPU registers are used to store the parameters. Furthermore, in order to have a fast process, it is desirable to use the fast registers of the CPU to store the parameters. This puts a burden on the availability of the fast registers of the CPU.

In other problems with such demands, the parameters may be quantized to have length 8 bits or 16 bits to reduce the storage requirement. For example, in artificial intelligence and deep learning, the parameters may be quantized to 8 bits to reduce the storage and to speed up the process. However, quantization is not desirable for processes of alignments of genetic materials because quantization introduces loss of accuracy, which is important to medical, criminal and other application.

Figure 2B:
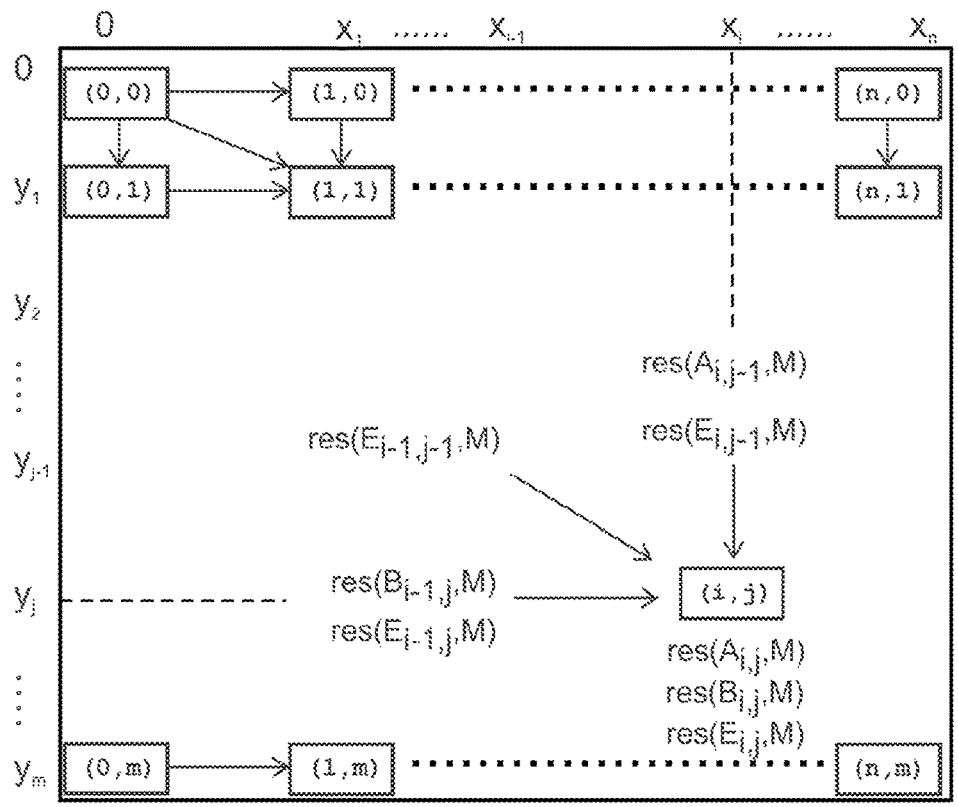

In some of the systems of the present embodiments the dynamic program runs on residues of the parameters modulus M, instead of the parameters themselves. FIG. 2B illustrates dynamic programing on an alignment digraph using parameters modulus instead of the parameters themselves, according to various aspects of the present disclosure. In many practical applications the residues are small, requiring only 8 bits while the parameters are 16 bits, 32 bits, or more. A typical CPU register size is 64 bits. Using the single-instruction multiple-data (SIMID) operations, in many CPUs in modular methods of the present invention, 1) the calculation of the dynamic program may be accelerated, and 2) the demand for a large number of registers may be reduced. The methods of the present embodiments are lossless and solve the storage problems without sacrificing accuracy.

In a second medical application example, two sequences $\underline{x}=x_1 x_2 x_3 \ldots x_n$ and $\underline{y}=y_1 y_2 y_3 \ldots y_m$ of genetic materials are collected. The goal in this example is not to find an alignment of the whole sequences $\underline{x}$ and $\underline{y}$, as was in the first medical application described above. Instead, the goal is to find a stretch of $\underline{x}$ and a stretch of $\underline{y}$ that are most similar over all possible stretches.

Figure 2C:
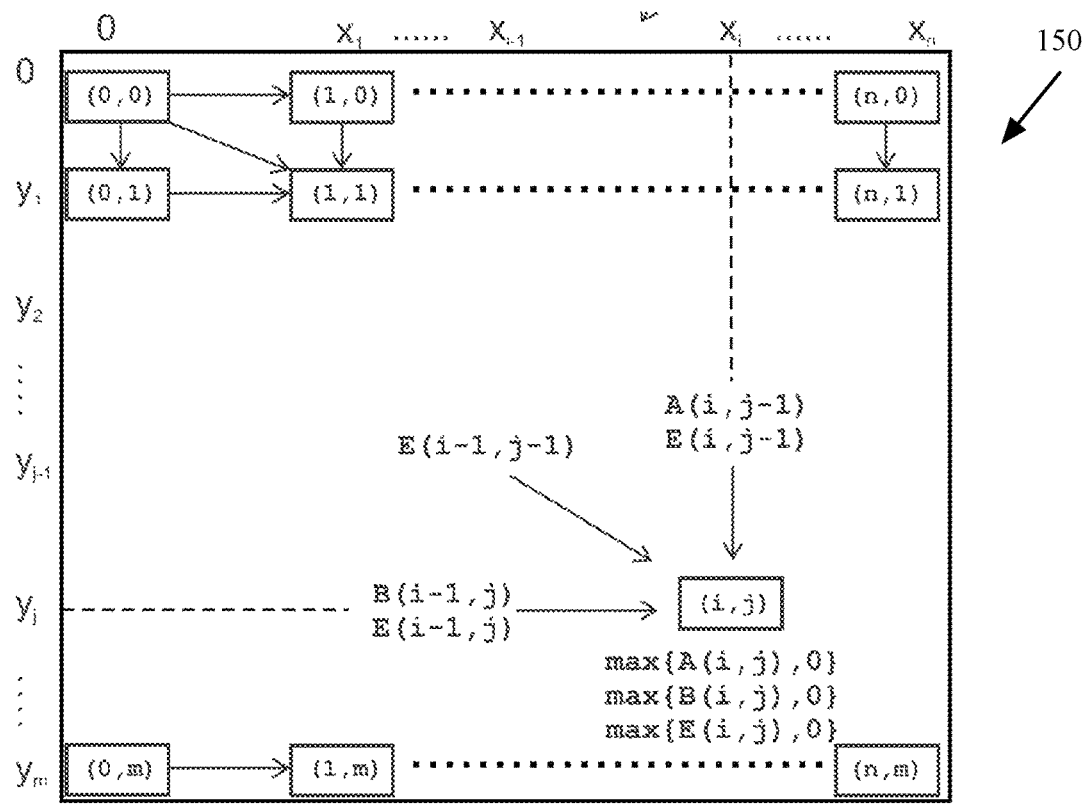

FIG. 2C illustrates further details of a dynamical program used to solve the problem shown in FIG. 2B, according to various aspects of the present disclosure. First, the parameters A(i,j), B(i,j), and E(i,j) are computed as before, then any parameter that is less that zero is replaced by zero before it is used for another vertex. This method has the same problem as before, large demand on storage.

Figure 2D:
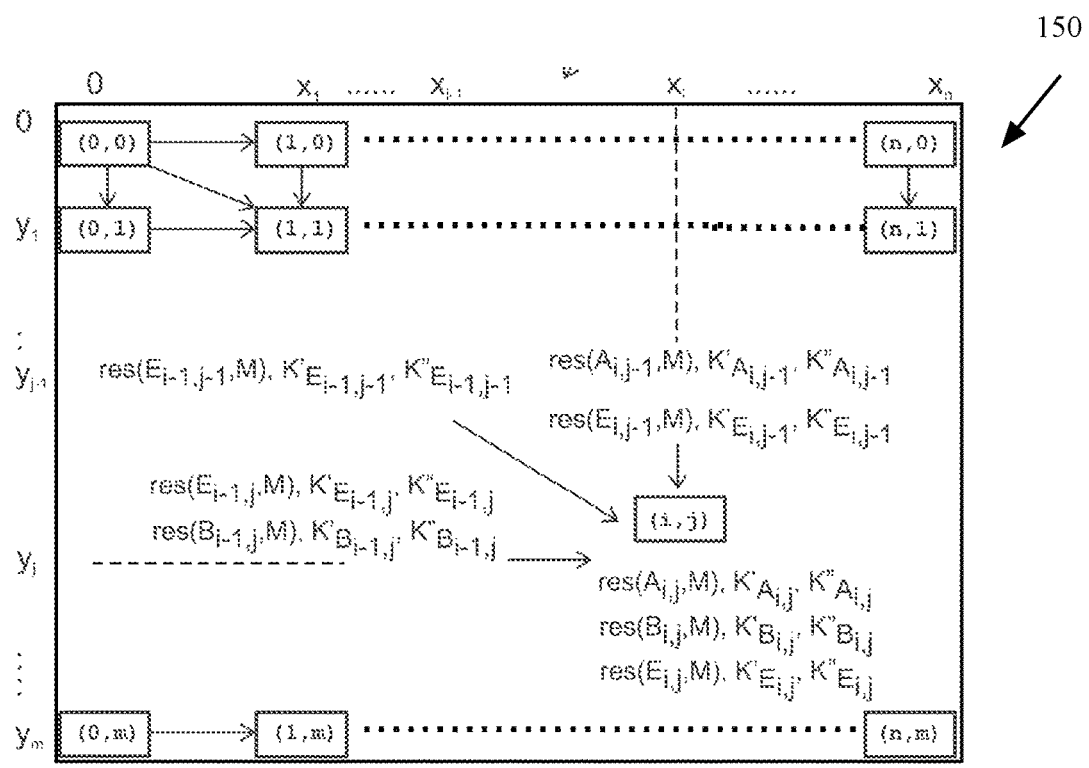

FIG. 2D illustrates further details of a dynamical program that runs on modulus and quotients of the parameters, according to various aspects of the present disclosure. With respect to FIG. 2D, the dynamic program may run on the residues of the parameters modulus M, and the quotients of the parameters modulus M, where for $X \in \{A, B, E\}$, quotient of X, KX=K"X+K'X, where K"X is a small number, and K"X is the major portion of KX.

Similar saving in storage from storing the residues of the parameters is achieved as before but store K"X and K'X values have to be stored. The method of FIG. 2D provides the following technical advantages: The K'X values do not need fast registers to be stored since they are slow changing values, and the K"X values are small. Therefore, the demand on fast registers is reduced.

In most applications like criminal investigation application and DNA sequencing, there are many (e.g., hundred, thousands, millions) pieces of sequences involves that need to be aligned and the dynamical program is repeated many times. Therefore, any improvement of the dynamical program benefits most applications significantly.

Further details of the systems and methods of the present embodiment are described below with reference to six exemplary embodiments. The first embodiment demonstrates the modular based dynamical program using a CPU and software for global alignment. The second embodiment demonstrates the modular based dynamical program using a software and/or firmware running on a specialized computer for global alignment. The third embodiment demonstrates the modular based dynamical program using a customized hardware for global alignment.

The fourth embodiment demonstrates the modular based dynamical program using a customized hardware in a parallel processing setting for global alignment. The fifth embodiment demonstrates the modular based dynamical program using a customized hardware for an overlapping alignment with affine gap score. The sixth embodiment demonstrates the modular based dynamical program using a customized hardware for a local alignment with affine gap score.

D. Scoring a Walk on Digraph D($\underline{x},\underline{y}$)

Given sequences $\underline{x}=x_1 x_2 x_3 \ldots x_n$ and $\underline{y}=y_1 y_2 y_3 \ldots y_m$ over alphabet $\mathbb{Q}$, the $\underline{x}$ and $\underline{y}$ alignment digraph, D($\underline{x},\underline{y}$), with vertex set $\mathbb{V}$, and a walk $W=((i_0,j_0), (i_1,j_1), \ldots, (i_l,j_l))$ starting on a vertex $(i_0,j_0) \in \mathbb{V}$ and ending on a vertex $(i_l,j_l) \in \mathbb{V}$, the score of the walk W is:

$\bar{S}_W = (\hat{\varphi}_0(\omega_1) + \Sigma_{t=2}^{l} \hat{\varphi}_1(\omega_{t-1}, \omega_t)$, where $\omega_t = (i_{t-1},j_{t-1})(i_t,j_t)$, for integer t, $1 \leq t \leq l$, and maps $\hat{\varphi}_0$ and $\hat{\varphi}_1$ are described in Table 1 below using a map, $\kappa$, and parameters: h, v, $h_d$, $v_d$, $h_h$, $v_h$, $h_v$, and $v_v$. Rows numbered 1-3 in Table 1 show the map $\hat{\varphi}_0(\omega_1)$ and rows numbered 4-10 show the map $\hat{\varphi}_1(\omega_{t-1}, \omega_t)$.

TABLE 1

| | $\omega_1$ | $\hat{\varphi}_0(\omega_1)$ |
|---|---|---|
| 1 | $\omega_1 \in A^d$ | $\kappa(x_{i_1}, y_{j_1})$ |
| 2 | $\omega_1 \in A^h$ | h |
| 3 | $\omega_1 \in A^v$ | v |
| | $(\omega_{t-1}, \omega_t)$ | $\hat{\varphi}_1(\omega_{t-1}, \omega_t)$ |
| 4 | $\omega_2 \in A^d$ | $\kappa(x_{i_t}, y_{j_t})$ |
| 5 | $\omega_1 \in A^d$, $\omega_2 \in A^h$ | $h_d$ |
| 6 | $\omega_1 \in A^h$, $\omega_2 \in A^h$ | $h_h$ |
| 7 | $\omega_1 \in A^v$, $\omega_2 \in A^h$ | $h_v$ |
| 8 | $\omega_1 \in A^d$, $\omega_2 \in A^v$ | $v_d$ |
| 9 | $\omega_1 \in A^h$, $\omega_2 \in A^v$ | $v_h$ |
| 10 | $\omega_1 \in A^v$, $\omega_2 \in A^v$ | $v_v$ |

$\kappa$ is a map, $\kappa: \mathbb{Q} \times \mathbb{Q} \to \mathbb{R}$ such that $\kappa(c, d)$, is the value (or score) of the substitution $\binom{c}{d}$, for $c \in \mathbb{Q}$ and $d \in \mathbb{Q}$. The map $\kappa$ is called the substitution value map. (match if a=b, mismatch if a≠b). Table 2 shows the parameters h, v, $h_d$, $v_d$, $h_h$, $v_h$, $h_v$, and $v_v$.

TABLE 2

| | |
|---|---|
| h | value of an x-gap |
| v | value of an y-gap |

TABLE 2-continued

| | |
|---|---|
| $h_d$ | value of an x-gap that follows a substitution |
| $v_d$ | value of an y-gap that follows a substitution |
| $h_h$ | value of an x-gap that follows a x-gap |
| $v_h$ | value of an y-gap that follows a x-gap |
| $h_v$ | value of an x-gap that follows a y-gap |
| $v_v$ | value of an y-gap that follows a y-gap |

The maps $\hat{\varphi}_0$ and $\hat{\varphi}_1$ closely fit experimental statistics without being computationally prohibitive. The maps $\hat{\varphi}_0$ and $\hat{\varphi}_1$ include the following features. The substitution value matrix, $\kappa$, and constants: h, v, $h_d$, $v_d$, $h_h$, $v_h$, $h_v$, and $v_v$ may be split into two parts: 1) the matrix, $\kappa$, that scores the substitutions and 2) the constants (referred to herein as gap score constants) h, v, $h_d$, $v_d$, $h_h$, $v_h$, $h_v$, and $v_v$ that score the gaps.

In alignment literature, several settings may be used for the constants. An uncomplicated setting is assigning a fixed score, g, to all constants. Such a setting is referred to as a linear gap setting. Linear gap setting woks well when the experimental results show a linear relationship between score of a run of gaps and the length of the run. But it does not work well when a lower score is desirable for the first gap of the run than for the rest of the gaps in the run.

E. Three Main Alignment in Bioinformatics

There are three main alignments of two sequences $\underline{x}=x_1 x_2 x_3 \ldots x_n$ and $\underline{y}=y_1 y_2 y_3 \ldots y_m$ in bioinformatics, the global alignment, the local alignment, and the overlap alignment. In the global alignment, the emphasis is on walks on D($\underline{x},\underline{y}$) that start from vertex (0,0) and end on vertex (n, m). In the local alignment, the emphasis is on walks on D($\underline{x},\underline{y}$) that start from vertex (0,0) and end on vertex (n, m) that contain an "optimum" sub-walk. In the overlap alignment, the emphasis is on walks on D($\underline{x},\underline{y}$) that start from a vertex on the top row or leftmost column and end on a vertex on the bottom row or the rightmost column.

F. Global Alignment

1. The Goal of the Global Alignment

Given two sequences $\underline{x}=x_1 x_2 x_3 \ldots x_n$ and $\underline{y}=y_1 y_2 y_3 \ldots y_m$, the $\underline{x}$ and $\underline{y}$ alignment digraph D($\underline{x},\underline{y}$) with vertex set $\mathbb{V}$, and the score maps $\hat{\varphi}_0$ and $\hat{\varphi}_1$, the goal of the global alignment is as follows.

Find a walk, $W^{max}$, starting from vertex (0,0) and ending on vertex (n, m) on the alignment digraph D($\underline{x},\underline{y}$), such that $W^{max}=((i_0,j_0)=(0,0), (i_1,j_1), \ldots, (i_k,j_k)=(n, m))$, has a maximal score.

More specifically, the goal of the global alignment is to find $$W^{max} = \underset{W: W \in \mathbb{W}_{(0,0)}^{(n,m)}}{\arg\max} \bar{S}_W,$$

where $\mathbb{W}_{(0,0)}^{(n,m)}\{W: W$ is a walk on D($\underline{x},\underline{y}$) from (0,0) to (n, m)} and $\bar{S}_W = \hat{\varphi}_0((i_0,j_0)(i_1,j_1)) + \Sigma_{t=2}^{k} \hat{\varphi}_1((i_{t-2},j_{t-2})(i_{t-1},j_{t-1}), (i_{t-1},j_{t-1})(i_t,j_t))$.

The score functions $\hat{\varphi}_0$ and $\hat{\varphi}_1$ are as defined earlier. It is further assumed that an affine gap score is used. The affine gap score is defined in Table 3, where $\alpha$ and $\beta$ are nonnegative real numbers.

TABLE 3

| | |
|---|---|
| v | $-\beta - \alpha$ |
| h | $-\beta - \alpha$ |
| $h_v$ | $-\beta - \alpha$ |
| $h_d$ | $-\beta - \alpha$ |
| $h_h$ | $-\beta$ |
| $v_v$ | $-\beta$ |
| $v_d$ | $-\beta - \alpha$ |
| $v_h$ | $-\beta - \alpha$ |

Now, $W^{max}$ may be generated using a dynamical program, defined in "An Improved Algorithm for Matching Biological Sequences", Osamu Gotoh, J. Mol. Biol. (1982) 162, 705-708, the contents of which are incorporate, herein, by reference.

It should be noted that an alignment digraph $D(\underline{x},\underline{y})$ is not a trellis. A trellis is digraph D=(V, E), V is the vertex set of D, and E is the edge set of D with the property that, given any two vertices v and v' in V, if there is a path of length n from v to v' in D, then every path from v to v' in D has length n. For example, in FIG. 1, there are three paths in the digraph $D(\underline{x},\underline{y})$ 100 from vertex (0,0) to (1,1), one is of length one, $P_1=((0,0)(1,1))$, and two are of length two, $P_2=((0,0)(0,1)(1,1))$ and $P_2=((0,0)(1,0)(1,1))$.

For every (i,j) in the diagraph 150 of FIG. 2A, E(i,j) is the best score over all walks from (0,0) to (i,j). A(i,j) is the best score over all walks from (0,0) to (i,j) that ends with a vertical arc. If no such walk exists, then A(i,j)=−Inf, where Inf denotes a large number. B(i,j) is the best score over all walks from (0,0) to (i,j) that end with a horizontal arc. If no such walk exists, then B(i,j)=−Inf.

Now, using a dynamical program, E(i,j) may be generated based on E(i−1,j−1), E(i−1,j), E(i,j−1), A(i,j−1), and B(i−1, j). A(i,j) may be generated based on E(i,j−1) and A(i,j−1), and B(i,j) may be generated based on E(i−1,j) and B(i,j−1).

The following initialization may be performed:

$E(0,0)=0$ $E(k_1,k_2)=-Inf$ if $k_1<0$ or $k_2<0$ $A(0,0)=-Inf$ $A(k_1,k_2)=-Inf$ if $k_1<0$ or $k_2<0$ $B(0,0)=-Inf$ $B(k_1,k_2)=-Inf$ if $k_1<0$ or $k_2<0$

The key recursion equations are as follows:

$(i, j) \neq (0, 0)$ $$E(i, j) = \max \begin{cases} E(i-1, j-1) + \kappa(x_i, y_j) \\ A(i, j) \\ B(i, j) \end{cases}$$

$$A(i, j) = \max \begin{cases} E(i, j-1) + v \\ A(i, j-1) + v_v \end{cases}$$

$$B(i, j) = \max \begin{cases} E(i-1, j) + h \\ B(i-1, j) + h_h \end{cases}$$

The key recursion equations are computed for the vertices on the top row of the digraph $D(\underline{x},\underline{y})$ 150, from (1,0) to (n, 0), next it is repeated for the vertices on the second row from (0,1) to (n, 1), then repeated for the vertices on the third row, etc.

Now, E(n, m) is the score, $\overline{S}_{W^{max}}$, of $W^{max}$, a walk of maximal score. To find $W^{max}$ a path of choices may be found that the key recursion equations made to generate the score. This process is called a traceback. Trackback is based on variables $I_{A(i,j)}$, $I_{B(i,j)}$, and $I_{E(i,j)}$, which are the indices to the maximal elements in in A(i,j) in B(i,j) in E(i,j) equations, respectively.

Often, the global alignment with affine gap score is implemented using (1) a software running on a central processing unit (CPU) or (2) a software/firmware running on a specialized computer or a customized hardware. Further, often, the values: E, A, and B are held in the CPU registers, caches, etc. during the computation of the key recursion equation.

Figure 3:
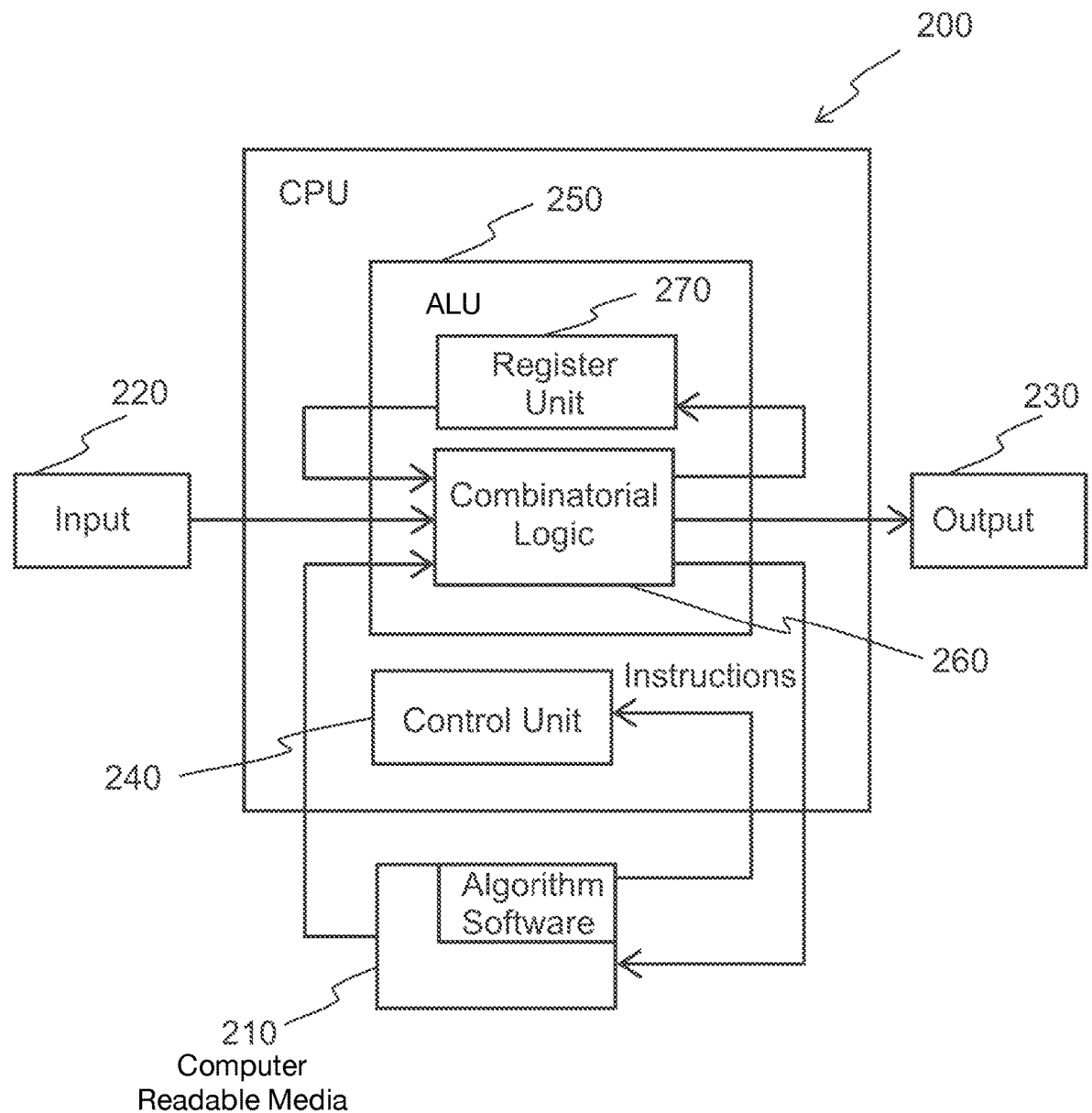
FIG. 3 illustrates a CPU architecture, according to various aspects of the present disclosure.

2. The First Embodiment—The Modular Based Dynamical Program Using a CPU and Software for Global Alignment In the first embodiment of modulo based, genetic material alignment methods, the global alignment is implemented using a software running on a CPU. FIG. 3 illustrates a CPU architecture, according to various aspects of the present disclosure. With reference to FIG. 3, the CPU 200 may be connected to one or more computer readable media 210 (e.g., volatile memory and non-volatile memory) 210, input devices 220, and output devices 230. The CPU 200 may include a control unit 240 and an arithmetic-logic unit (ALU) 250. The ALU 250 may include a combinational logic 260 and several processor registers 270. The processor registers 270 may comprise a plurality of digital registers that are quickly accessible to the CPU 190. The computer readable media 210 may hold data and executable instructions. The control unit 240 may receive instructions from the computer readable media 210. Some of the instructions may pertain to one or more of the followings: receiving an input from an input device 220, sending an output to an output device 230, retrieving data from the computer readable media 210, performing arithmetic and logic operations on the received data using the combinatorial logic 260 and the registers unit 270 of the ALU 250.

The computer readable media 210 may be non-transitory computer readable media. The computer readable media 210 may include different types of memory units, such as, read-only-memory, volatile read-and-write memory, and/or non-volatile read-and-write memory. The read-only-memory may store static data and instructions that are needed by the processor 195. The non-volatile read-and-write memory may store instructions and data even when the power to the non-volatile memory is off. Some embodiments may use a mass-storage device (such as a magnetic or optical disk and its corresponding disk drive) as the non-volatile read-and-write memory.

The volatile read-and-write memory device may be random access memory and may be used as system memory. The system memory may store some of the instructions and data that the processor needs at runtime. In some embodiments, the processes of the present embodiments may be stored in the system memory, the non-volatile memory, and/or the read-only memory. From these various memory units, the ALU 250 may retrieve instructions to execute and data to process in order to execute the processes of some embodiments.

The registers 270 may include an assortment of digital registers of varying lengths, for example 16-bit, 32-bit, 64-bit, etc. Data may be loaded from computer readable media 210 into registers 270 where the data may be used by the CPU 195 for arithmetic and/or logic operations and may manipulated by machine instructions (e.g., the low level programming instructions).

In general, a CPU or a microprocessor has a native or a default register length, which is used much of the time, unless instructed otherwise. Usually, the default register length is specified with the name of the CPU or the microprocessor, for example 32-bit CPU, or 64-bit microprocessor.

During the computation of the key equations of the global alignment with affine gap score, the CPU 200 uses its registers in the registers unit 270 to hold the values: E, A, and B, described above.

In order to explain an important part of the present embodiments, the modulo operation is defined as follows. For any integer n, and a positive integer $\mathcal{M}$, there is a unique integer r in $\{0, 1, \ldots, \mathcal{M}-1\}$ such that $n \equiv r \bmod \mathcal{M}$. ($\equiv$ denotes congruency). Then r is called the residue of n modulo m, and equivalently n mod $\mathcal{M}$. One may find the residue of a number n by taking the remainder when dividing by $\mathcal{M}$. The notation $r = \text{res}(n, \mathcal{M})$ may also be used.

Lemma 7.1: For integers p and q, $1 \leq p \leq q \leq 5$, $|Q_p - Q_q| \leq Q$, where $$Q_1(i,j) \triangleq D(i-1,j-1) + \kappa(x_i, y_j)$$

$$Q_2(i,j) \triangleq D(i,j-1) + v$$

$$Q_3(i,j) \triangleq A(i,j-1) + v_v$$

$$Q_4(i,j) \triangleq D(i-1,j) + h$$

$$Q_5(i,j) \triangleq B(i-1,j) + h_h$$

and $$LB = \min\{-2\kappa_{max} - 5(\alpha+\beta), -\kappa_{max} - 2(\alpha+\beta) + \kappa_{min} + \beta\}$$

$$UB = \max\{2\kappa_{max} + 5(\alpha+\beta), \kappa_{max} - \kappa_{min}\}, \text{ and}$$

$$Q = \max\{\text{abs}(LB), UB\}$$

Proof of Lemma 7.1 is described below.

Lemmas 7.1, 7.2 and 7.3 play major roles in the present embodiments. They state that differences between pairs of terms for integers p and q, $1 \leq p \leq q \leq 5$, the absolute difference $|Q_p - Q_q|$ is bounded by Q, and the bound is independent of the length of the sequences $\underline{x} = x_1 x_2 x_3 \ldots x_n$ and $\underline{y} = y_1 y_2 y_3 \ldots y_m$, for global, overlapping and local alignments, respectively. Together with Lemma 10, they enable comparing $Q_p(i,j)$ and $Q_q(i,j)$ based on their residues modulus $\mathcal{M}$.

The next lemma shows that if $\mathcal{M} \geq 2Q+1$, then for every p and q, $1 \leq p < q \leq 10$, $Q_p$ and $Q_q$ may be compared using $r_p$ and $r_q$.

Lemma 10: There are two integers U and V such that $-W \leq U - V \leq +W$ for some positive integer W. Let $r_U$ and $r_V$ be the residues of U and V mod $\mathcal{M} = 2W+1+Z$, where Z is a non-negative integer.

$$U = k_U \cdot \mathcal{M} + r_U, 0 \leq r_U < \mathcal{M}, \text{ and}$$

$$V = k_V \cdot \mathcal{M} + r_V, 0 \leq r_V < \mathcal{M}.$$

Then, $$\begin{cases} U > V \text{ and } k_U - k_V = 0 & \text{if } r_V < r_U \leq r_V + W \\ U < V \text{ and } k_U - k_V = -1 & \text{if } r_V + W < r_U \\ U < V \text{ and } k_U - k_V = 0 & \text{if } r_U < r_V \leq r_U + W \\ U > V \text{ and } k_U - k_V = 1 & \text{if } r_U + W < r_V \\ U = V \text{ and } k_U - k_V = 0 & \text{if } r_U = r_V \end{cases} \quad \text{Equation (1)}$$

Proof:

$$U - V = (k_U - k_V) \cdot (2W+1+Z) + r_U - r_V$$

Proof of Line 1 of Equation (1)
if $r_U \leq r_V + W$, then:

$$-W \leq U - V = (k_U - k_V) \cdot (2W+1+Z) + r_U - r_V \leq (k_U - k_V) \cdot (2W+1+Z) + r_V + W - r_V = (k_U - k_V) \cdot (2W+1+Z) + W$$

Thus $(k_U - k_V) \geq 0$
But if $r_V < r_U$, then $$+W \geq U - V = (k_U - k_V) \cdot (2W+1+Z) + r_U - r_V > (k_U - k_V) \cdot (2W+1+Z)$$

leading to $(k_U - k_V) \leq 0$
Thus, $k_U - k_V = 0$.
Therefore, if $r_V < r_U \leq r_V + W$ then $U > V$ and $k_U - k_V = 0$.
Proof of Line 2 of Equation (1)
if $r_V + W < r_U$, then $$+W \geq U - V = (k_U - k_V) \cdot (2W+1+Z) + r_U - r_V > (k_U - k_V) \cdot (2W+1+Z) + r_V + W - r_V = (k_U - k_V) \cdot (2W+1+Z) + W$$

Thus $(k_U - k_V) \leq -1$.
But if $(k_U - k_V) \leq -2$ then:

$$-W \leq U - V = (k_U - k_V) \cdot (2W+1+Z) + r_U - r_V \leq -2 \cdot (2W+1+Z) + r_U - r_V \leq -2 \cdot (2W+1+Z) + W = -3W - 2 - Z$$

Thus $(k_X - k_Y) = -1$
Therefore, if $r_V + W < r_U$ then $U < V$ and $k_U - k_V = 1$
Proof of Line 3 of Equation (1) is similar to the proof of Line 1, described above.
Proof of Line 4 of Equation (1) is similar to the proof of Line 2, described above.
Proof of Line 5 of Equation (1)
If $r_U = r_V$, then $U - V = (k_U - k_V) \cdot \mathcal{M} = (k_U - k_V) \cdot (2W+1+Z)$. But $-W \leq U - V \leq +W$, hence $k_U = k_V$, and $U = V$.

Corollary 1, to Lemma 10: The index variables of traceback: $I_{A(i,j)}$, $I_{B(i,j)}$, and $I_{E(i,j)}$ may be computed based on residues of $Q_1$-$Q_5$. As discussed in the examples below, frequently it requires smaller registers to hold the residues than $Q_1$-$Q_5$.

Corollary 2, to Lemma 10: $\mathcal{M}$ and W may be picked such that $\mathcal{M} = 2^\omega$ and $W = 2^{\omega-1} - 1$, for some $\omega$. These selections ease the hardware implementation of the alignment system of the present embodiment. In addition, they allow a faster software implementation.

In general, if $-LB \neq UB$, then the values $Q_1$-$Q_5$ may be shifted by $\delta Q = \lceil (UB+LB)/2 \rceil$, for $1 \leq p \leq 5$, $Q'_p = Q_p - \delta Q$. Where $\lceil x \rceil$ denotes the smallest integer greater than or equal to x. Such shifts often reduce the number of bits needed to represent $Q'_1$-$Q'_5$.

This would result a smaller Q and a smaller $\mathcal{M}$, and fewer bits to represent and store $\overline{Q}_1$-$\overline{Q}_5$.

$$LB = \min\{-2\kappa_{max} - 5(\alpha+\beta), -\kappa_{max} - 2(\alpha+\beta) + \kappa_{min} + \beta\}$$

$$UB = \max\{2\kappa_{max} + 5(\alpha+\beta), \kappa_{max} - \kappa_{min}\},$$

There are 3 main equations in the key recursion equations in global alignment. Each equation requires finding a maximal element of a set.

1) A(i,j) equals a maximal element of a set $\text{Set}_{A(i,j)} = \{E(i,j-1) + v, A(i,j-1) + v_v\}$ 2) B(i,j) equals a maximal element of $\text{Set}_{B(i,j)} = \{E(i-1,j) + h, B(i-1,j) + h_h\}$ 3) E(i,j) equals a maximal element of $\text{Set}_{E(i,j)} = \{E(i-1,j-1) + K(x_i, y_j), A(i,j), B(i,j)\}$ Let $\text{res}(A(i,j-1), \mathcal{M})$, $\text{res}(B(i-1,j), \mathcal{M})$, $\text{res}(E(i,j-1), \mathcal{M})$, res($E(i-1,j), \mathcal{M}$), res($E(i-1,j-1), \mathcal{M}$), res($A(i,j-1)+v_v, \mathcal{M}$), res($B(i-1,j)+h_h, \mathcal{M}$), res($E(i,j-1)+v, \mathcal{M}$), res($E(i-1,j)+h, \mathcal{M}$), and res($E(i-1,j-1)+\kappa(x_i,y_j), \mathcal{M}$), to denote the residues of A(i,j−1), B(i−1,j), E(i,j−1), E(i−1,j), E(i−1,j−1), A(i,j−1)+$v_v$, B(i−1,j)+$h_h$, E(i,j−1)+v, E(i−1,j)+h, and E(i−1,j−1)+κ($x_i,y_j$), respectively, with respect to a modulus $\mathcal{M}$.

To simplify notation, let's define $R_1$-$R_5$ and $r_1$-$r_5$ as follows:

$R_1 = A(i,j-1)+v_v$ $R_2 = E(i,j-1)+v$ $R_3 = B(i-1,j)+h_h$ $R_4 = E(i-1,j)+h$ $R_5 = E(i-1,j-1)+\kappa(x_i,y_j)$ $r_1 = res(A(i,j-1)+v_v, \mathcal{M})$, $r_2 = res(E(i,j-1)+v, \mathcal{M})$, $r_3 = res(B(i-1,j)+h_h, \mathcal{M})$, $r_4 = res(E(i-1,j)+h, \mathcal{M})$, $r_5 = res(E(i-1,j-1)+\kappa(x_i,y_j), \mathcal{M})$.

For global alignment, the present disclosure gives the following 3 functions, $F_A$, $F_B$, and $F_E$ for generating

[res($A(i,j), \mathcal{M}$), $I_{A(i,j)}$] = $F_A$(res($A(i,j-1), \mathcal{M}$), res($E(i,j-1), \mathcal{M}$)))

[res($B(i,j), \mathcal{M}$), $I_{B(i,j)}$] = $F_B$(res($B(i-1,j), \mathcal{M}$), res($E(i-1,j), \mathcal{M}$)))

[res($E(i,j),M), I_{E(i,j)}$] = $F_E$(res($E(i-1,j-1), \mathcal{M}$), res($A(i,j), \mathcal{M}$), res($B(i,j), \mathcal{M}$)))

Where, $A(i,j) = k_{A(i,j)} \times \mathcal{M} + res(A(i,j), \mathcal{M}), 0 \leq res(A(i,j), \mathcal{M}) < \mathcal{M}$ $B(i,j) = k_{B(i,j)} \times \mathcal{M} + res(B(i,j), \mathcal{M}), 0 \leq res(B(i,j), \mathcal{M}) < \mathcal{M}$ $E(i,j) = k_{E(i,j)} \times \mathcal{M} + res(E(i,j), \mathcal{M}), 0 \leq res(E(i,j), \mathcal{M}) < \mathcal{M}$ $I_{A(i,j)}$ is the index to the maximal element in $Set_{A(i,j)}$, that is $I_{A(i,j)}=1$ if the first element in $Set_{A(i,j)}$ is the maximal element, $I_{A(i,j)}=2$ if the second element in $Set_{A(i,j)}$ is the maximal element, etc.

$I_{B(i,j)}$ is the index to the maximal element in $Set_{B(i,j)}$.
$I_{E(i,j)}$ is the index to the maximal element in $Set_{E(i,j)}$.
$I_{A(i,j)}$, $I_{B(i,j)}$, and $I_{E(i,j)}$ are stored for traceback.

Now $F_A$ decides on max $\{R_1, R_2\}$, based on $\{r_1, r_2\}$ using the conditions of Lemma 10.

Conditions of the Lemma 10:

$$\begin{cases} R_1 > R_2 & \text{if } r_2 < r_1 \leq r_2 + Q \\ R_1 < R_2 & \text{if } r_2 + Q < r_1 \\ R_1 < R_2 & \text{if } r_1 < r_2 \leq r_1 + Q \\ R_1 > R_2 & \text{if } r_1 + Q < r_2 \\ R_1 = R_2 & \text{if } r_1 = r_2 \end{cases}$$

And $F_B$ decides on max $\{R_3, R_4\}$, based on $\{r_3, r_4\}$ using the conditions of Lemma 10.

Conditions of the Lemma 10:

$$\begin{cases} R_3 > R_4 & \text{if } r_4 < r_3 \leq r_4 + Q \\ R_3 < R_4 & \text{if } r_4 + Q < r_3 \\ R_3 < R_4 & \text{if } r_3 < r_4 \leq r_3 + Q \\ R_3 > R_4 & \text{if } r_3 + Q < r_4 \\ R_3 = R_4 & \text{if } r_3 = r_4 \end{cases}$$

And $F_E$ decides on max$\{A(i,j), B(i,j), R_5\}$, based on $\{res(A(i,j), \mathcal{M}), res(B(i,j), \mathcal{M}), r_5\}$ and the conditions of Lemma 10.

The followings describe a first example. For the substitution score map κ, some embodiments may use Blosum50, one of the Blocks Substitution Matrices. In bioinformatics, the Blocks Substitution Matrices, (Blosum), may be used in sequence alignment of proteins. Blosum matrices are used to score alignments between evolutionarily divergent protein sequences.

Using Blosum50, the values of $\kappa_{max}=15$, and $\kappa_{min}=-5$ may be found. Further details may be found at "Selecting the Right Similarity-Scoring Matrix", by William R. Pearson, first published: 16 Feb. 2018.

Further, let's use α=10, and β=1.
Then, from Lemma 7.1:

$LB = \min\{-2\kappa_{max}-5(\alpha+\beta),-\kappa_{max}-2(\alpha+\beta)+\kappa_{min}+\beta\} = \min\{-85,-41\} = -85$ $UB = \max\{2\kappa_{max}+5(\alpha+\beta),\kappa_{max}-\kappa_{min}\} = \max\{85,10\} = 85$ Therefore, Q=max{abs(LB), UB}}=85.

Thus, the modulus $\mathcal{M}$ may be picked to be $\mathcal{M}$ =2Q+1=171. Therefore, each $r_1$-$r_5$ may be represented and stored with 8 bits while each Q1-Q5 would require a longer register to be stored. Therefore, the memory requirement of the global alignment with affine gap score is reduced using the present invention.

FIG. 4A illustrates five 8-bit registers, according to various aspects of the present disclosure. FIG. 4B illustrates a 64-bit registers with two 8-bit accessible 8-bit segments, according to various aspects of the present disclosure. FIG. 4C illustrates storing data in the accessible portion of registers, according to various aspects of the present disclosure.

With reference to FIG. 4A, five registers 301-305 are shown. Each of the register 301-305 has 8 bits memory. The residue values $r_1$-$r_5$ are stored in the registers 301-305, respectively. With reference to FIGS. 4B and 4C, a second efficient method to storing the residues are explained.

FIG. 4B shows a register 310 that has 64 bits memory in eight bytes segments 311-318. Only the segments 317 and 318 are directly accessible to the software, and the rest are not directly accessible as bytes. FIG. 4C shows the register 310 and two other register 320 and 330 that have the same architecture as the register 310. Next, the residues may be stored in the accessible segments of the registers 310, 320, and 330.

The followings are examples of the values that may be stored in the registers 310, 320, and 330. The residue $r_1$ in the segment 317 of the register 310. The residue $r_2$ in the segment 318 of the register 310. The residue $r_3$ in the segment 327 of the register 320. The residue $r_4$ in the segment 328 of the register 320. The residue $r_5$ in the segment 328 of the register 330.

Another method to lessen the register memory requirement is to use segments of registers that are not directly accessible, and recover the residues by masking and/or bit shifting. However, frequently it is faster (requires less clock cycles) to executed directly accessible memory than memory through masking and/or bit shifting.

Figure 5A:
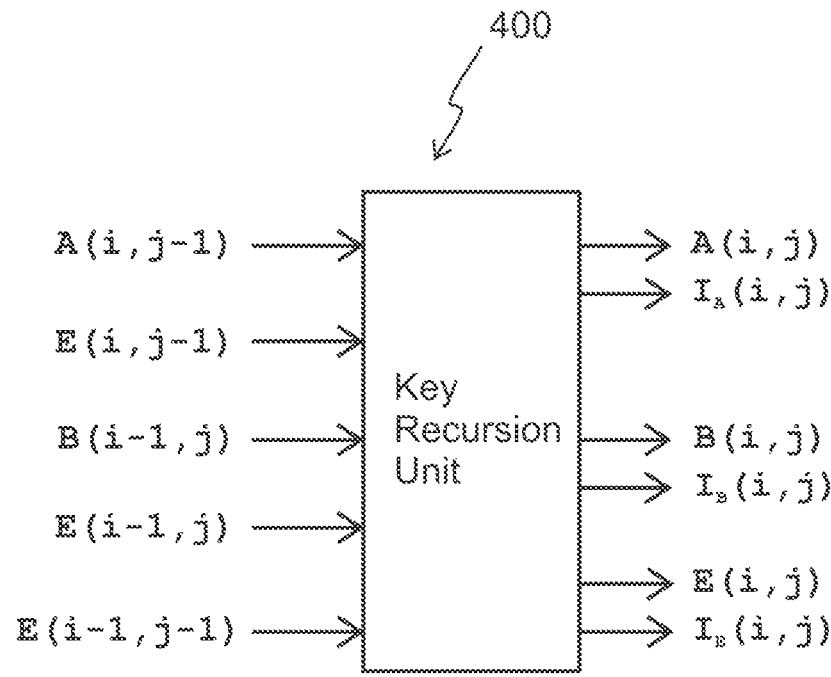
FIG. 5A illustrates a key recursion unit for the global alignment, according to the traditional approaches.

The followings describe how the key recursion equations are processed according to the various aspects of the present disclosure. FIG. 5A illustrates the key recursion unit for the global alignment, according to the traditional approaches. With reference to FIG. 5A, a key recursion unit 400 is shown according to the traditional approaches. The key recursion unit 400 receives the following input: A(i,j−1), E(i,j−1), B(i−1,j), E(i−1,j), and E(i−1,j−1). And it generates the following output: A(i,j), B(i,j), E(i,j), $I_{A(i,j)}$, $I_{B(i,j)}$, and $I_{E(i,j)}$.

The key recursion unit 400 performs the following calculations of the key recursion equations:

$$A(i, j) = \max \begin{cases} E(i, j-1) + v \\ A(i, j-1) + v_v \end{cases}$$

$$B(i, j) = \max \begin{cases} E(i-1, j) + h \\ B(i-1, j) + h_h \end{cases}$$

$$E(i, j) = \max \begin{cases} E(i-1, j-1) + \kappa(x_i, y_j) \\ A(i, j) \\ B(i, j) \end{cases}$$

Figure 5B:
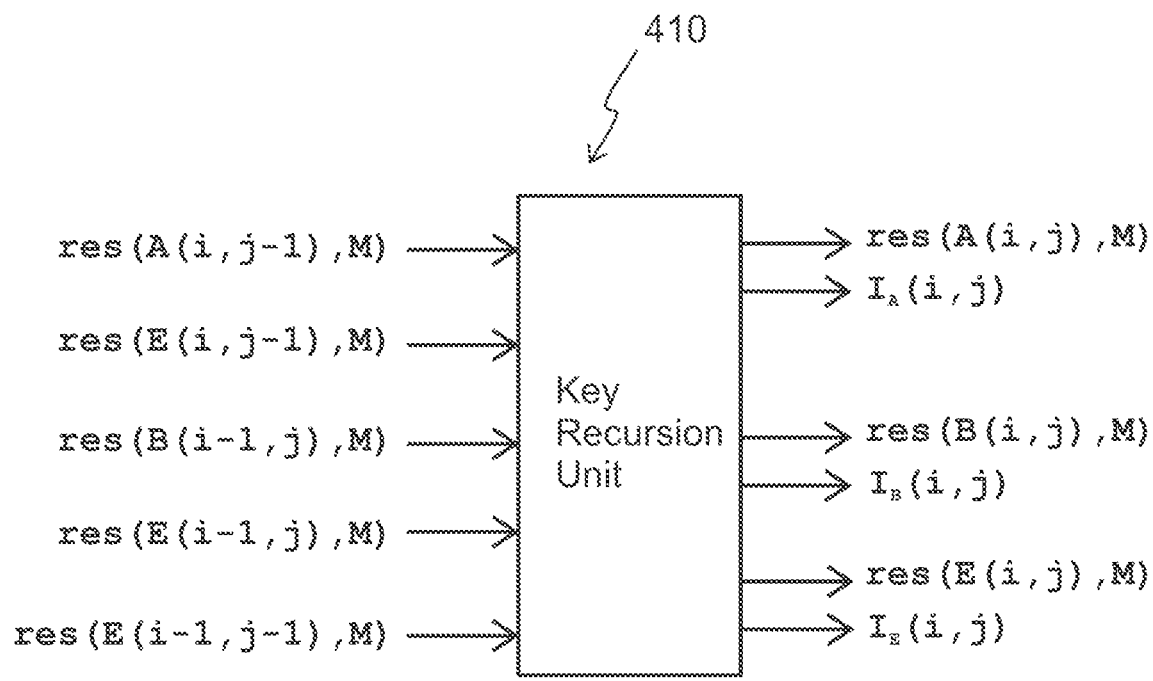
FIG. 5B illustrates a key recursion unit for the global alignment, based on residues, according to various aspects of the present disclosure.

FIG. 5B illustrates the key recursion unit 410 for the global alignment, based on residues, according to various aspects of the present disclosure. The key recursion unit 410 receives the following input: res(A(i,j−1),$\mathcal{M}$), res(B(i−1,j),$\mathcal{M}$), res(E(i,j−1),$\mathcal{M}$), res(E(i−1,j),$\mathcal{M}$), and res(E(i−1,j−1),$\mathcal{M}$). The key recursion unit 410 of the present embodiments generates the following results: res(A(i,j),$\mathcal{M}$), res(B(i,j),$\mathcal{M}$), res(E(i,j),$\mathcal{M}$), $I_{A(i,j)}$, $I_{B(i,j)}$, and $I_{E(i,j)}$. Thus, the first embodiment computes the traceback variables based on the residues instead of the dividends.

Figure 6:
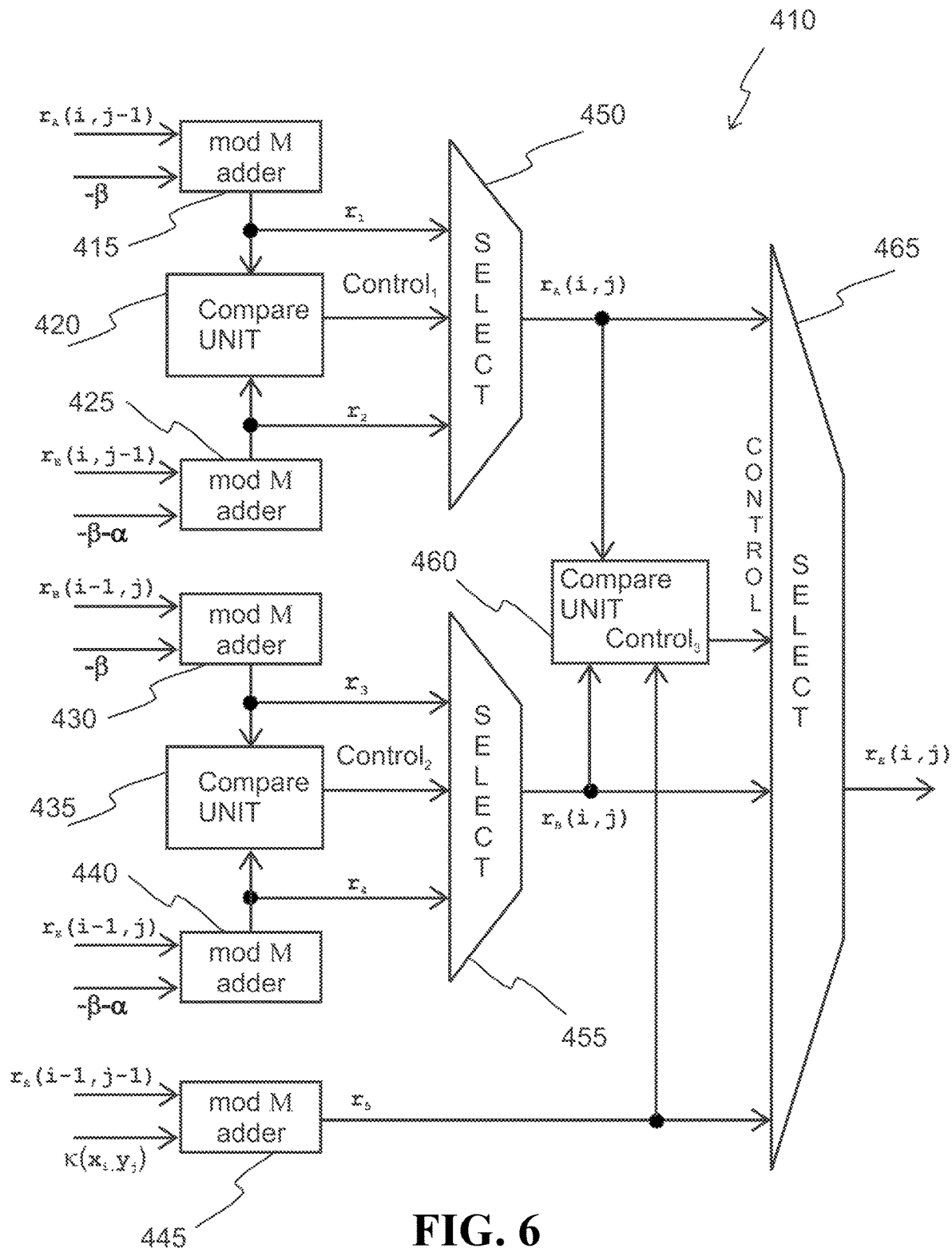
FIG. 6 illustrates a hardware and software block diagram of the first embodiment, according to various aspects of the present disclosure.

FIG. 6 illustrates a hardware and software block diagram of the first embodiment, according to various aspects of the present disclosure. With reference to FIG. 6, different blocks performing the key recursion unit 410 are shown. The operations may be explained in the following three parts.

In Part 1, res(A(i,j),$\mathcal{M}$) and $I_{A(i,j)}$ may be found. In order to compute res(A(i,j),$\mathcal{M}$), the key recursion unit 410 performs an add/compare/select using two mod $\mathcal{M}$ adders 415 and 425, a compare unit (e.g., a combinational logic comparator) 420, and a select unit (e.g., a multiplexer) 450. The mod $\mathcal{M}$ adder 415 receives two inputs: res(A(i,j−1),$\mathcal{M}$) and $v_v$ (note $v_v=-\beta$), and computes their sum modulo $\mathcal{M}$. The mod $\mathcal{M}$ adder 415 outputs $r_1$, which is res(A(i,j−1)+$v_v$,$\mathcal{M}$). The mod $\mathcal{M}$ adder 425 receives two inputs: res(E(i,j−1),$\mathcal{M}$) and v (note $v=-\beta-\alpha$), and computes their sum modulo $\mathcal{M}$. The mod $\mathcal{M}$ adder 425 outputs $r_2$, which is res(E(i,j−1)+v,$\mathcal{M}$).

The task of the compare unit 420 is to decide whether $R_2$=E(i,j−1)+v is less than, equal or greater than $R_1$=A(i,j−1)+$v_v$. The compare unit 420 performs its task based on $r_1$, $r_2$ and Lemma 10, where $r_1=R_1$ mod $\mathcal{M}$ and $r_2=R_2$ mod $\mathcal{M}$. Specifically, $$\begin{cases} R_1 > R_2 & \text{if } r_2 < r_1 \leq r_2 + Q \\ R_1 < R_2 & \text{if } r_2 + Q < r_1 \\ R_1 < R_2 & \text{if } r_1 < r_2 \leq r_1 + Q \\ R_1 > R_2 & \text{if } r_1 + Q < r_2 \\ R_1 = R_2 & \text{if } r_1 = r_2 \end{cases}$$

The compare unit 420 outputs a signal $Control_1$. $Control_1$ is '2' if $R_1 \geq R_2$, and is '1' otherwise. Thus, the compare unit 420 breaks ties toward $R_1$'s favor. The select unit 450 receives the values: $r_1$, $r_2$, and $Control_1$. The select unit 450 outputs res(A(i,j),$\mathcal{M}$)=$r_1$ if the $Control_1$ value is '2', and outputs res(A(i,j),$\mathcal{M}$)=$r_2$ if the $Control_1$ value is '1'. Therefore, the select unit 450 outputs not A(i,j) but res(A(i,j),$\mathcal{M}$). Further, $I_{A(i,j)}$=$Control_1$.

In Part 2, res(B(i,j),$\mathcal{M}$) and $I_{B(i,j)}$ may be found. In order compute res(B(i,j),$\mathcal{M}$), the key recursion unit 410 performs an add/compare/select using two mod $\mathcal{M}$ adders 430 and 440, a compare unit 435, and a select unit 455. The mod $\mathcal{M}$ adder 430 receives two inputs: res(B(i−1,j),$\mathcal{M}$) and $v_v$ (note $v_v=-\beta$), and computes their sum modulo $\mathcal{M}$. The mod $\mathcal{M}$ adder 430 outputs $r_3$, which is res(B(i−1,j)+$v_v$,$\mathcal{M}$). The mod $\mathcal{M}$ adder 440 receives two inputs: res(E(i−1,j),$\mathcal{M}$) and v (note $v=-\beta-\alpha$), and computes their sum modulo $\mathcal{M}$. The mod $\mathcal{M}$ adder 440 outputs $r_4$, which is res(E(i−1,j)+v,$\mathcal{M}$). The task of the compare unit 435 is to decide whether $R_3$=E(i−1,j)+v is less than, equal or greater than $R_4$=B(i−1,j)+$v_v$. The compare unit 435 performs its task based on $r_3$, $r_4$ and Lemma 10, where $r_3=R_3$ mod $\mathcal{M}$ and $r_4=R_4$ mod $\mathcal{M}$. Specifically, $$\begin{cases} R_3 > R_4 & \text{if } r_4 < r_3 \leq r_4 + Q \\ R_3 < R_4 & \text{if } r_4 + Q < r_3 \\ R_3 < R_4 & \text{if } r_3 < r_4 \leq r_3 + Q \\ R_3 > R_4 & \text{if } r_3 + Q < r_4 \\ R_3 = R_4 & \text{if } r_3 = r_4 \end{cases}$$

The compare unit 435 outputs a signal $Control_2$. $Control_2$ is '2' if $R_3 \geq R_4$, and is '1' otherwise. Thus, the compare unit 435 breaks ties toward $R_3$'s favor. The select unit 455 receives the values: $r_3$, $r_4$, and $Control_2$. The select unit 455 outputs res(B(i,j),$\mathcal{M}$)=$r_3$ if the $Control_2$ value is '2', and outputs res(A(i,j),$\mathcal{M}$)=$r_4$ if the $Control_2$ value is '1'. Therefore, the select unit 455 outputs not B(i,j) but res(B(i,j),$\mathcal{M}$). Further, $I_{B(i,j)}$=$Control_2$.

In Part 3, res(E(i,j),$\mathcal{M}$) and $I_{E(i,j)}$ may be found. In order compute res(E(i,j),$\mathcal{M}$), the key recursion unit 410 performs an add/compare/select using a mod $\mathcal{M}$ adders 445, a 3 way compare unit 460, and a select unit 465. The mod $\mathcal{M}$ adder 445 receives two inputs: res(E(i−1,j−1),$\mathcal{M}$) and $\kappa(x_i,y_j)$, and computes their sum modulo $\mathcal{M}$. The mod $\mathcal{M}$ adder 445 outputs $r_5$, which is res(E(i−1,j−1)+$\kappa(x_i,y_j)$,$\mathcal{M}$).

The task of the compare unit 460 is to decide a maximal value among: A(i,j), B(i,j), and $R_5$=E(i−1,j−1)+$\kappa(x_i,y_j)$. The compare unit 460 performs its task based on res(A(i,j),$\mathcal{M}$), res(B(i,j),$\mathcal{M}$), and $r_5$, using Lemma 10. One way to compute a maximal value of a set of values is to compare two values at a time using Lemma 10, and keeping the/a larger one.

The compare unit 460 outputs a signal $Control_3$ shown below.

$$Control_3 = \begin{cases} '2' & \text{if } A(i, j) \geq B(i, j) \text{ and } A(i, j) \geq R_5 \\ '3' & \text{if } B(i, j) > A(i, j) \text{ and } B(i, j) \geq R_5 \\ '1' & \text{if } R_5 > A(i, j) \text{ and } R_5 > B(i, j) \end{cases}$$

The select unit 465 outputs res(E(i,j),$\mathcal{M}$ =) res(A(i,j),$\mathcal{M}$) if the Control$_3$ value is '2', outputs res(E(i,j),$\mathcal{M}$)=res(B(i,j),$\mathcal{M}$) if the Control$_3$ value is '3', and outputs res(E(i,j),$\mathcal{M}$)=$r_5$ if the Control$_3$ value is '1'. Therefore, the select unit 465 outputs not E(i,j) but $r_E$(i,j), where $r_E$(i,j)=E(i,j)mod $\mathcal{M}$. Further, $I_{E(i,j)}$=Control$_3$.

Thus, used recursively, the key recursion equations processed according to the present invention produce the same decisions based on residues as when processed according to the traditional methods. Using the residues lessens the requirement on memory.

Using less registers or using shorter registers leads to using less electric power (watts). Less electric power used leads to less heat generated in hardware, which enables faster speed.

The followings describe a second example. In this example, scores for DNA segments alignment are picked. Let match score=$\kappa_{max}$=1, mis-match score=$\kappa_{min}$=−5, and opening gap score=$\alpha$+$\beta$=5.

Then, from Lemma 7.1:

$$LB=\min\{-2\kappa_{max}-5(\alpha+\beta), -\kappa_{max}-2\alpha-\beta+\kappa_{min}\}=\min\{-27,-16\}=-27$$

$$UB=\max\{2\kappa_{max}+5(\alpha+\beta),\kappa_{max}-\kappa_{min}\}=\max\{27,6\}=27,$$
and Q=max{abs(LB), UB}}=27. Thus, the modulus $\mathcal{M}$ may be picked to be $\mathcal{M}$=2*Q+1=55.

Therefore, each $r_1$-$r_5$ may be represented and stored with 6 bits. Therefore, the present disclosure according to the first embodiment reduces the storage requirement by performing the key recursion equations based on residues of values modulo a suitable modulus $\mathcal{M}$.

Traceback may be done the traditional way by using the variables: $I_A$'s, $I_B$'s, and $I_E$'s.

One way to compute the score of final alignment, E(n,m), is to generate a best alignment based on the backtrack variables, then use the score functions to evaluate the alignment score. It should be noted that the backtrack or traceback variables may be arranges in a matrix with (i,j) coordinates.

Another way is to evaluate it during the backtrack stage. Since the memory of the score map is limited to two for gaps, it is needed to traceback two steps to resolve the score when a gap is reached during the backtrack, except when the vertex (0,0) is reached.

3. The Second Embodiment—The Modular Based Dynamical Program Using a Software and/or Firmware Running on a Specialized Computer, for Global Alignment In the second embodiment of modulo based, genetic material alignment methods, the global alignment is implemented using a software running on a CPU, with accelerating features in software or hardware. Examples of a software language include python, C, Assembly, etc.

Figure 7:
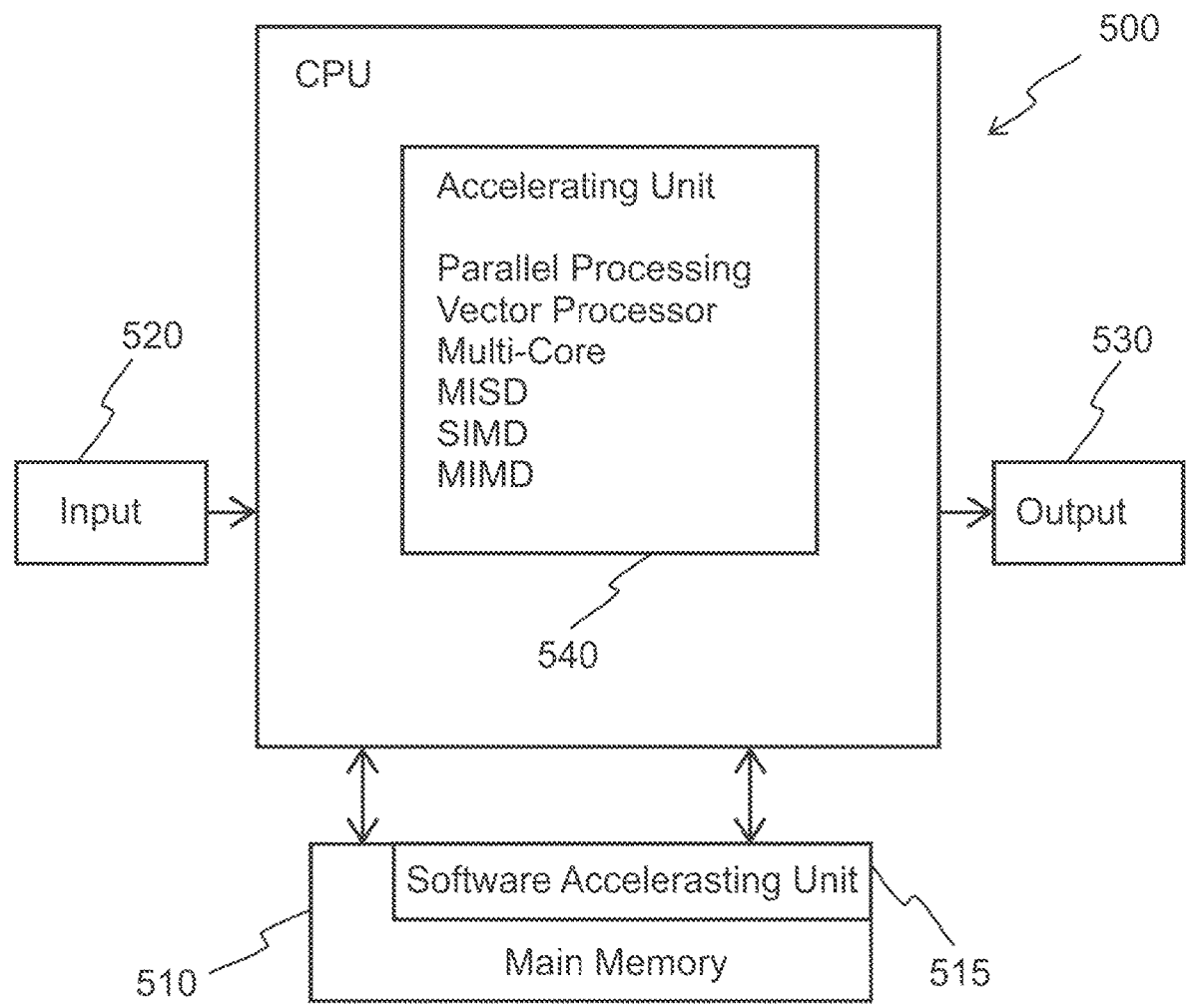
FIG. 7 illustrates a CPU architecture with an accelerating unit, according to various aspects of the present disclosure.

Accelerating hardware features are described with reference to FIG. 7. FIG. 7 illustrates a CPU architecture with an accelerating unit, according to various aspects of the present disclosure. With reference to FIG., the CPU 500 may be connected to a main memory 510, an input 520 and an input 530. The CPU 500 has an accelerating unit 540.

The accelerating unit 540 may have at least one of the following technologies:
1) Multithreading
2) Multi-Arithmetic Logic Unit (ALU)
3) Vector processor
4) Multi-core
5) Parallel processing
6) Multiple Instruction, Single Data (MISD)
7) Single Instruction, Multiple Data (SIMD)
8) Multiple Instruction, Multiple Data (MIMD)

These accelerating features may allow the CPU 500 to speed up the alignment. For example, the CPU 500 may be enabled by the accelerating unit 540 to operate the mod $\mathcal{M}$ adders 415, 425, 430, 440, and 445 simultaneously (FIG. 6). The CPU 500 may be enabled by the accelerating unit 540 to operate the computation of the res(A(i,j),$\mathcal{M}$) and the computation of the res(B(i,j),$\mathcal{M}$) simultaneously, (FIG. 6). The CPU 500 may be enabled by the accelerating unit 540 to operate the computation of res(E(i,j),$\mathcal{M}$) and the computation of the $r_E$(i',j') simultaneously, (FIG. 5B), as long as res(A(i,j−1),$\mathcal{M}$), res(B(i−1,j),$\mathcal{M}$), res(E(i,j−1),$\mathcal{M}$), res(E(i−1,j),$\mathcal{M}$), res(E(i−1,j−1),$\mathcal{M}$), res(A(i',j'−1),$\mathcal{M}$), res(B(i'−1,j'),$\mathcal{M}$), res(E(i'j'−1),$\mathcal{M}$), res(E(i'−1,j'),$\mathcal{M}$), and res(E(i'−1,j'−1),$\mathcal{M}$) are available.

Figure 8:
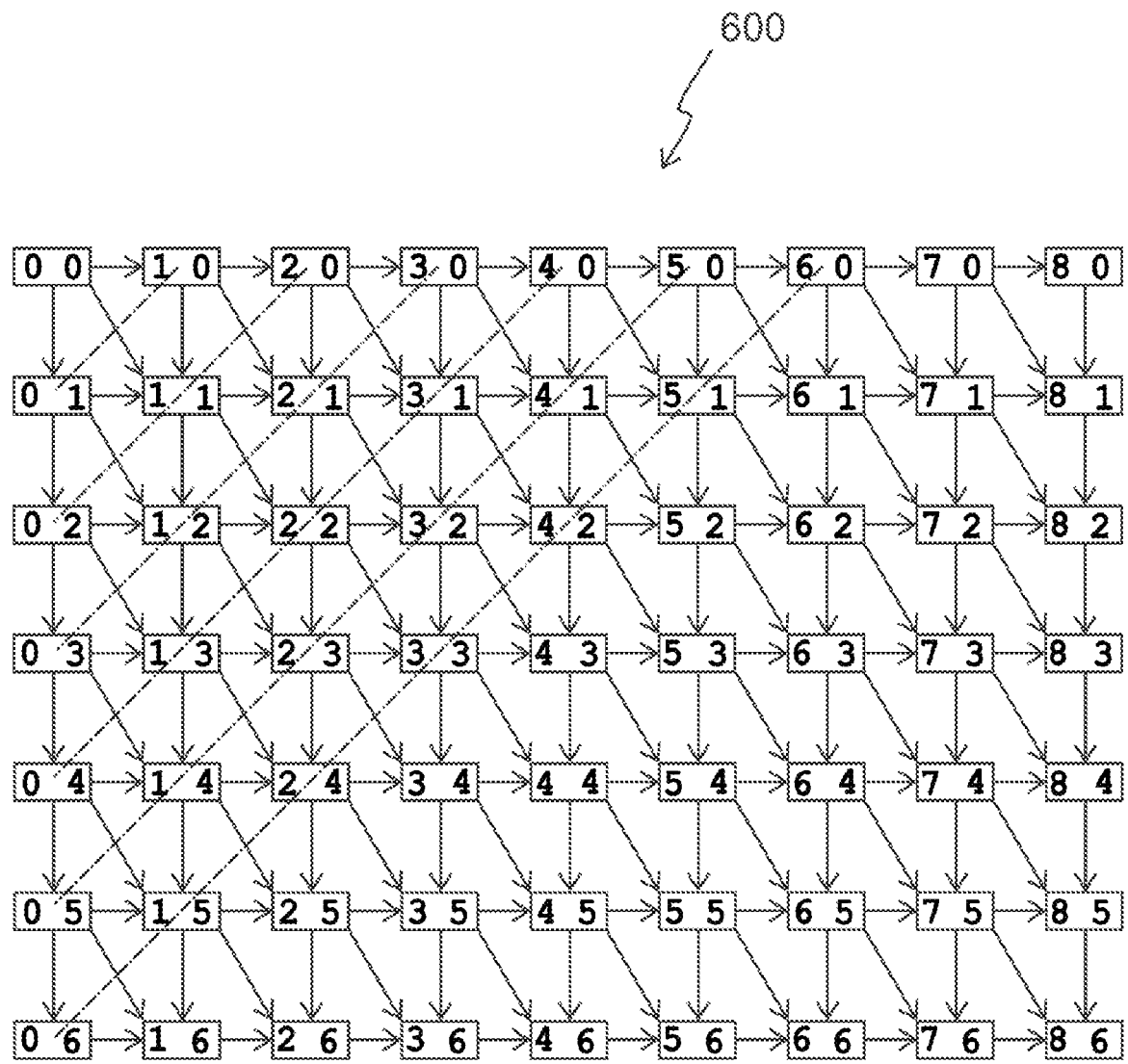
FIG. 8 illustrates the diagonal vertices used in parallel processing, according to various aspects of the present disclosure.

The followings are the features of the accelerating software. The main memory 510 may have a software accelerating unit 515. One feature in the software accelerating unit 515 is parallelized architecture. A parallelized architecture in the software accelerating unit 515 is processing of the global alignment for vertices that are on a same diagonal (from upper right to lower left). FIG. 8 illustrates the diagonal vertices used in parallel processing, according to various aspects of the present disclosure. With reference to FIG. 8, an alignment digraph 600 is shown. Vertices of the alignment digraph 600 that are on a same diagonal are connected with a dash-dotted line.

No two vertex of the alignment digraph 600 that are on a same diagonal are connected. Therefore, the key recursion equations of the vertices that are on a same diagonal are computed in parallel based on values for the left two diagonals. The CPU 500 may take advantage of the parallelized architecture by the accelerating unit 540 to speed up the alignment. More specifically, the CPU 500 processes the key recursion equations of vertices on a diagonal in parallel.

4. The Third Embodiment—The Modular Based Dynamical Program Using a Customized Hardware, for Global Alignment The third embodiment of modulo based, genetic material alignment methods is a hardware implementation for computing the key recursion equations with residues. There are 3 main equations in the key recursion equations in global alignment. Each equation requires finding a maximal element of a set.

1) A(i,j) equals a maximal element of a set $Set_{A(i,j)}$={E(i,j−1)+v, A(i,j−1)+$v_v$}
2) B(i,j) equals a maximal element of $Set_{B(i,j)}$={E(i−1,j)+h, B(i−1,j)+$h_h$}
3) E(i,j) equals a maximal element of $Set_{E(i,j)}$={E(i−1,j−1)+$\kappa(x_i,y_j)$, A(i,j), B(i,j)}

For global alignment, the third embodiment of the present disclosure gives a hardware implementation of the following 3 functions, $F_A$, $F_B$, and $F_E$ for generating $$[\text{res}(A(i,j),\mathcal{M}),J_{A(i,j)}]=F_A(\text{res}(A(i,j-1),\mathcal{M}),\text{res}(E(i,j-1),\mathcal{M})))$$

$$[\text{res}(B(i,j),\mathcal{M}),J_{B(i,j)}]=F_A(\text{res}(B(i-1,j),\mathcal{M}),\text{res}(E(i-1,j),\mathcal{M})))$$

$$[\text{res}(E(i,j),\mathcal{M}),J_{E(i,j)}]=F_E(\text{res}(E(i-1,j-1),\mathcal{M}),\text{res}(A(i,j),\mathcal{M}),\text{res}(B(i,j),\mathcal{M})).$$

Now $F_A$ decides on max {$R_1$, $R_2$}, based on {$r_1$, $r_2$} using the conditions of Lemma 10.

Conditions of the Lemma 10:

$$\begin{cases} R_1 > R_2 & \text{if } r_2 < r_1 \le r_2 + Q \\ R_1 < R_2 & \text{if } r_2 + Q < r_1 \\ R_1 < R_2 & \text{if } r_1 < r_2 \le r_1 + Q \\ R_1 > R_2 & \text{if } r_1 + Q < r_2 \\ R_1 = R_2 & \text{if } r_1 = r_2 \end{cases}$$

And $F_B$ decides on max $\{R_3, R_4\}$, based on $\{r_3, r_4\}$ using the conditions of Lemma 10.

Conditions of the Lemma 10:

$$\begin{cases} R_3 > R_4 & \text{if } r_4 < r_3 \le r_4 + Q \\ R_3 < R_4 & \text{if } r_4 + Q < r_3 \\ R_3 < R_4 & \text{if } r_3 < r_4 \le r_3 + Q \\ R_3 > R_4 & \text{if } r_3 + Q < r_4 \\ R_3 = R_4 & \text{if } r_3 = r_4 \end{cases}$$

And $F_E$ decides on max$\{A(i,j), B(i,j), R_5\}$, based on $\{res(A(i,j), \mathcal{M}), res(B(i,j), \mathcal{M}), r_5\}$ and the conditions of Lemma 10.

In some of the present embodiments, the conditions of the Lemma 10 are first applied to residues: res(A(i,j), $\mathcal{M}$), res(B(i,j), $\mathcal{M}$) to find the larger of the $\{A(i,j), B(i,j)\}$. If $A(i,j) \ge B(i,j)$ (A is biased arbitrarily), then the conditions of the Lemma 10 are applied to: res(A(i,j), $\mathcal{M}$) and $r_5$ to find an overall largest among $\{A(i,j), B(i,j), R_5\}$. But if $A(i,j) < B(i,j)$, then the conditions of the Lemma 10 are applied to: res(B(i,j), $\mathcal{M}$) and $r_5$ to find an overall largest.

The third embodiment gives a hardware implementation of the above process. The residues may be represented in 2's complement, and the example 2 parameters for DNA segment alignment may be used. Thus, match score=$\kappa_{max}$=1, mis-match score=$\kappa_{min}$=−5, opening gap score=$\alpha+\beta$=5.

Then, from Lemma 7.1: Q=27 (see above). Thus, the modulus $\mathcal{M}$ may be picked to be $\mathcal{M} \ge 2*Q+1=55$. $\mathcal{M}$ may be chosen to be $\mathcal{M} = 64 = 2^6$, to ease the hardware architecture. Therefore, there may be 7 bits 2's complement representation to handle mod $2^6$. In 7 bits 2's complement, a binary vector $(x_6, x_5, x_4, x_3, x_2, x_1, x_0)$ represent the integer x as follows: $x = x_6(-2^6) + x_5 2^5 + x_4 2^4 + x_3 2^3 + x_2 2^2 + x_1 2^1 + x_0 2^0$.

The 2's complement representation of x may be denoted by $t_x$. Let's use $t_{res(A(i,j-1), \mathcal{M})}$, $t_{res(B(i-1,j), \mathcal{M})}$, $t_{res(E(i,j-1), \mathcal{M})}$, $t_{res(E(i-1,j), \mathcal{M})}$, and $t_{res(E(i-1,j-1), \mathcal{M})}$ to denote the 7 bits 2's complement representations of res(A(i,j−1), $\mathcal{M}$), res(B(i−1,j), $\mathcal{M}$), res(E(i,j−1), $\mathcal{M}$), res(E(i−1,j), $\mathcal{M}$), and res(E(i−1,j−1), $\mathcal{M}$), respectively.

Figure 9:
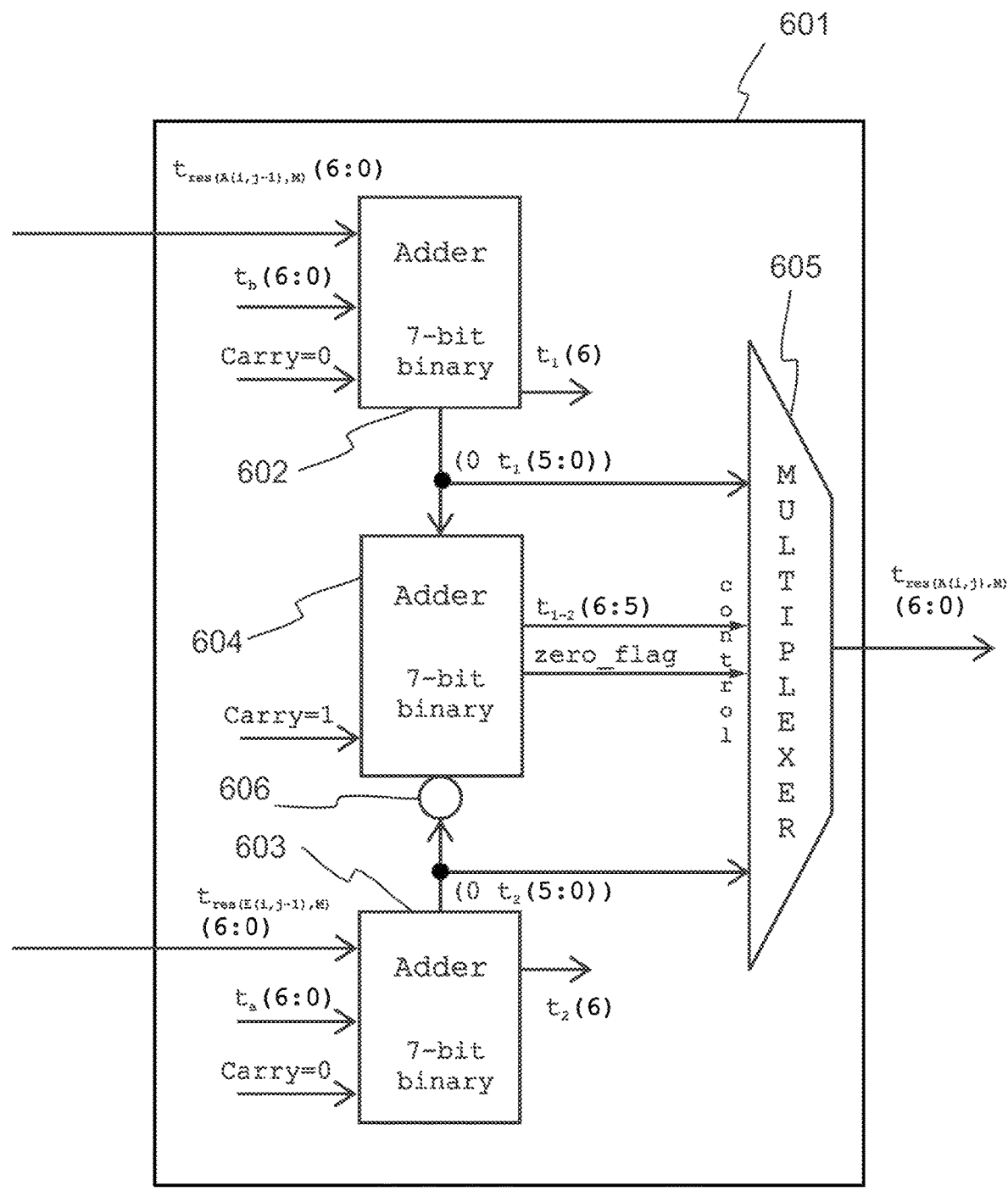
FIG. 9 illustrates the hardware that implements the function $F_A$ of the third embodiment, according to various aspects of the present disclosure.

Also let $t_b$, $t_a$, and $t_c$ to denote the 7 bits 2's complement representation of $-\beta \mod \mathcal{M}$, $-\alpha-\beta \mod \mathcal{M}$, and $\kappa(x_i, y_j) \mod \mathcal{M}$, respectively. FIG. 9 illustrates the $F_A$ hardware of the third embodiment, according to various aspects of the present disclosure. With reference to FIG. 9, an $F_A$ hardware 601 may be described. The $F_A$ hardware 601 may comprise three 7-bit adders 602, 603, and 604, and a multiplexer 605. The inputs to the adder 602 may be $t_{res(A(i,j-1), \mathcal{M})}$(6:0) and $t_b$(6:0).

A carry signal to the adder 602 may be '0'. The output of the adder 602 may be $t_1$(6:0), where $t_{r_1}$=(0 $t_1$(5:0)). The inputs to the adder 603 may be: $t_{res(E(i,j-1), \mathcal{M})}$(6:0) and $t_a$(6:0).

A carry signal to the adder 603 may be '0'. The output of the adder 603 may be $t_2$(6:0), where $t_{r_2}$=(0 $t_2$(5:0)). The inputs to the adder 604 may be: $\overline{t_{r_2}(6:0)}$ and $t_{r_1}$(6:0), ($\overline{x}$ denoted the complement of x). The output of the adder 603, (0 $t_2$(5:0)), may be complemented by a not gate 606 before entering the adder 604.

A carry signal to the adder 604 may be '1'. In this shape, the adder 604 may function as a 2's complement subtractor. It generates, $t_{1-2}$(6:0), which is $t_{r_1} - t_{r_2}$ in 2's complement. The adder 604 outputs $t_{1-2}$(6:5), which is bits at locations 5 and 6 in $t_{1-2}$(6:0) and a zero flag, which is '0' unless $t_{1-2}$(6:0)= (0,0,0,0,0,0,0).

The main function of the adder 604 is to generate $I_A$.
Recall:

$I_A$=2, if $R_1 > R_2$ $I_A$=1, if $R_1 < R_2$ $I_A$=2, if $R_1 = R_2$

The adder 604 generates $I_A$, based on $r_1$ and $r_2$, using the conditions of the Lemma 10.

$$\begin{cases} R_1 > R_2 & \text{if } r_2 < r_1 \le r_2 + Q \\ R_1 < R_2 & \text{if } r_2 + Q < r_1 \\ R_1 < R_2 & \text{if } r_1 < r_2 \le r_1 + Q \\ R_1 > R_2 & \text{if } r_1 + Q < r_2 \\ R_1 = R_2 & \text{if } r_1 = r_2 \end{cases}$$

In terms of $t_{1-2}$:

$R_1 > R_2$ if $t_{1-2}$(6)=0 and $t_{1-2}$(5)=0 and zero flag='0'

$R_1 < R_2$ if $t_{1-2}$(6)=0 and $t_{1-2}$(5)=1

$R_1 < R_2$ if $t_{1-2}$(6)=1 and $t_{1-2}$(5)=1

$R_1 > R_2$ if $t_{1-2}$(6)=1 and $t_{1-2}$(5)=0

$R_1 = R_2$ zero flag='1'

Therefore, $I_A$=2 if($t_{1-2}$(6:5)=(0,0) and zero flag='0') OR $t_{1-2}$(6: 5)=(1,0)

$I_A$=1 if $t_{1-2}$(6:5)=(0,1) OR $t_{1-2}$(6:5)=(1,1)

$I_A$=2 if zero flag='1'

The multiplexer 605 receives values, $t_{r_1}$=(0 $t_1$(5:0)) and $t_{r_2}$=(0 $t_2$(5:0)), and it outputs $t_{r_1}$ unless $t_{1-2}$(5)=1, in which case it outputs $t_{r_2}$. This makes the output of the multiplexer 605 to be $t_{res(A(i,j), \mathcal{M})}$(6:0). Therefore, only $t_{1-2}$(5) is sufficient to control the multiplexer. The multiplexer 605 and the $F_A$ hardware 601 may be made arbitrarily biased toward $t_{r_1}$, that is when $t_{r_1}$=$t_{r_2}$, it breaks the tie in favor of $t_{r_1}$.

Figure 10:
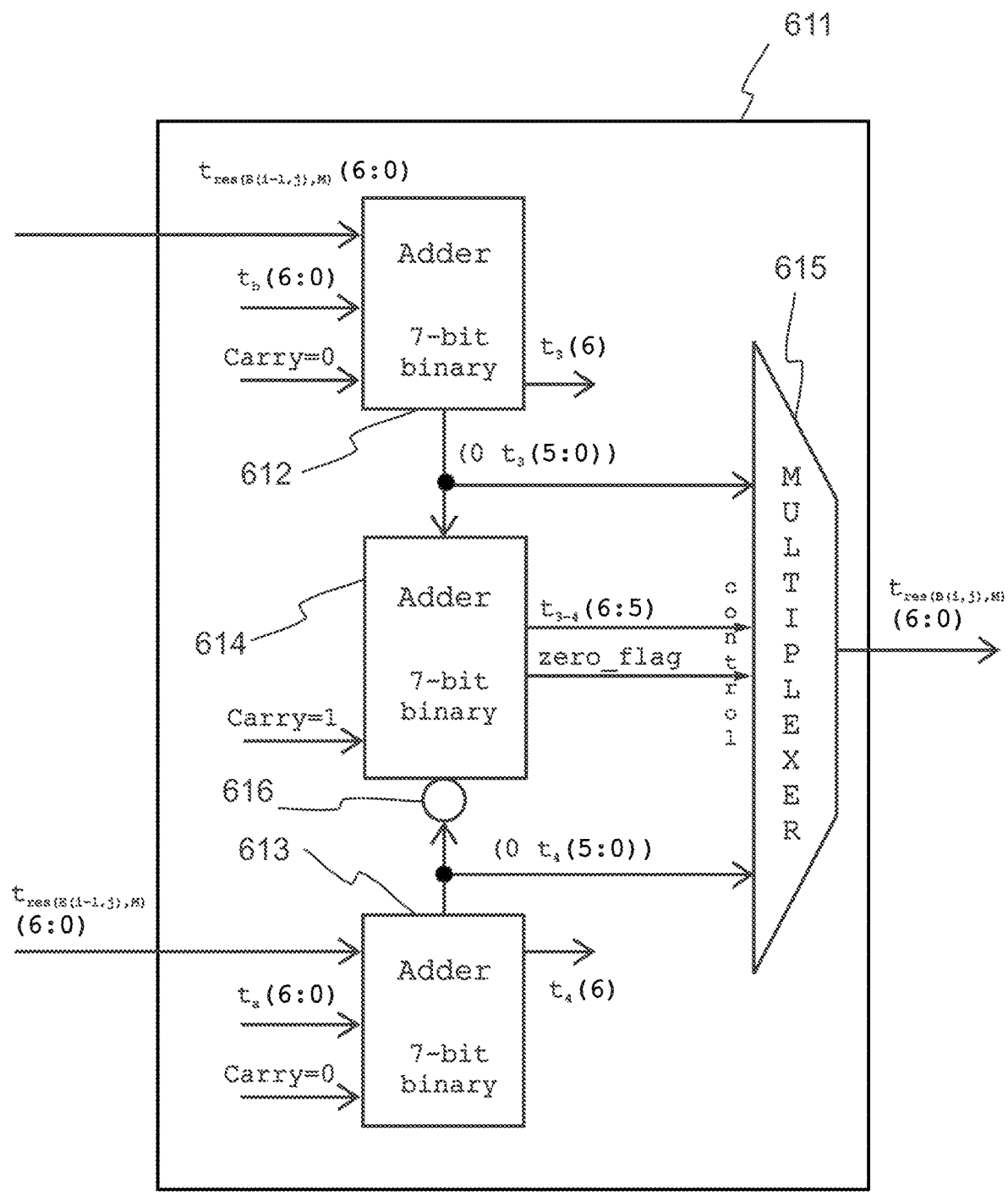
FIG. 10 illustrates the hardware that implements the function $F_B$ of the third embodiment, according to various aspects of the present disclosure.

FIG. 10 illustrates the FB hardware of the third embodiment, according to various aspects of the present disclosure. With reference to FIG. 10, an $F_B$ hardware 611 may be described. The $F_B$ hardware 611 may comprise three 7-bit adders 612, 613, and 614, and a multiplexer 615. The inputs to the adder 612 may be $t_{res(B(i-1,j), \mathcal{M})}$(6:0) and $t_b$(6:0). A carry signal to the adder 612 may be '0'.

The output of the adder 612 may be $t_3$(6:0), where $t_{r_3}$=(0 $t_3$(5:0)). The inputs to the adder 613 may be $t_{res(E(i-1,j), \mathcal{M})}$ 6:0) and $t_a$(6:0). A carry signal to the adder 613 may be '0'. The output of the adder 613 may be $t_4$(6:0), where $t_{r_4}$=(0 $t_4$(5:0)).

The inputs to the adder 614 may be $\overline{t_{r_4}(6:0)}$ and $t_{r_3}$(6:0). The output of the adder 613, (0 $t_4$(5:0)), may be complemented by a not gate 616 before entering the adder 614. A carry signal to the adder 614 may be '1'. In this shape, the adder 614 may functions as a 2's complement subtractor. It generates, $t_{3-4}$(6:0), which is $t_{r_3} - t_{r_4}$ in 2's complement. The adder 614 outputs $t_{3-4}(6:5)$, which is bits at locations 5 and 6 in $t_{3-4}(6:0)$ and a zero flag, which is '0' unless $t_{3-4}(6:0)=$ (0,0,0,0,0,0,0). The main function of the adder 614 may be to generate $I_B$.

Recall:

$I_B=2$, if $R_3 > R_4$ $I_B=1$, if $R_3 < R_4$ $I_B=2$, if $R_3 = R_4$

The adder 614 generates $I_A$, based on $r_1$ and $r_2$, using the conditions of the Lemma 10.

$$\begin{cases} R_3 > R_4 & \text{if } r_4 < r_3 \leq r_4 + Q \\ R_3 < R_4 & \text{if } r_4 + Q < r_3 \\ R_3 < R_4 & \text{if } r_3 < r_4 \leq r_3 + Q \\ R_3 > R_4 & \text{if } r_3 + Q < r_4 \\ R_3 = R_4 & \text{if } r_3 = r_4 \end{cases}$$

In terms of $t_{3-4}$:

$R_3 > R_4$ if $t_{3-4}(6)=0$ and $t_{3-4}(5)=0$ and zero flag='0'

$R_3 < R_4$ if $t_{3-4}(6)=0$ and $t_{3-4}(5)=1$ $R_3 < R_4$ if $t_{3-4}(6)=1$ and $t_{3-4}(5)=1$ $R_3 > R_4$ if $t_{3-4}(6)=1$ and $t_{3-4}(5)=0$ $R_3 = R_4$ zero flag='1'

Therefore, $I_B=2$ if $t_{3-4}(6:5)=(0,0)$ and zero flag='0') OR $t_{3-4}(6:5)=(1,0)$ $I_B=1$ if $t_{3-4}(6:5)=(0,1)$ OR $t_{3-4}(6:5)=(1,1)$ $I_B=2$ if zero flag='1'

The multiplexer 615 receives values, $t_{r_3}=(0 \; t_3(5:0))$ and $t_{r_4}=(0 \; t_4(5:0))$, and it outputs $t_{r_3}$ unless $t_{3-4}(5)=1$, in which case it outputs $t_{r_4}$. This makes the output of the multiplexer 615 to be $t_{res(B(i,j),\mathcal{M})}(6:0)$. Therefore, only $t_{3-4}(5)$ is sufficient to control the multiplexer. The multiplexer 615 and the $F_B$ hardware 611 may be made arbitrarily biased toward $t_{r_3}$, that is when $t_{r_3}=t_{r_4}$, it breaks the tie in favor of $t_{r_3}$.

Figure 11A:
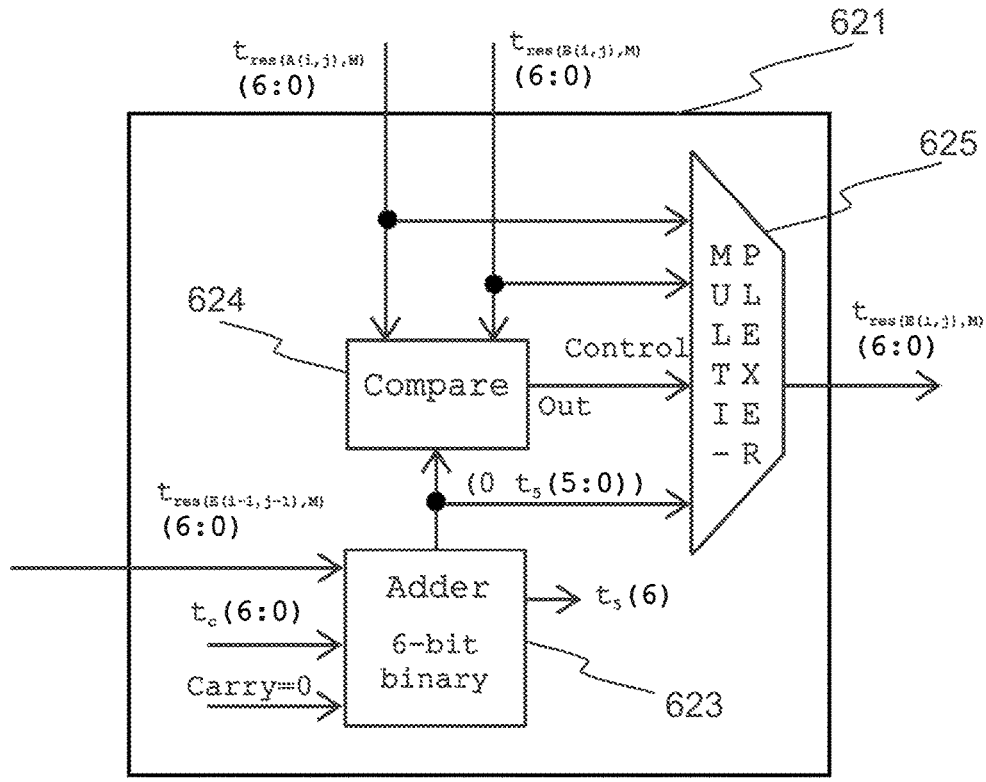
FIGS. 11A and 11B illustrate the hardware that implements the function $F_E$ of the third embodiment, according to various aspects of the present disclosure.
Figure 11B:
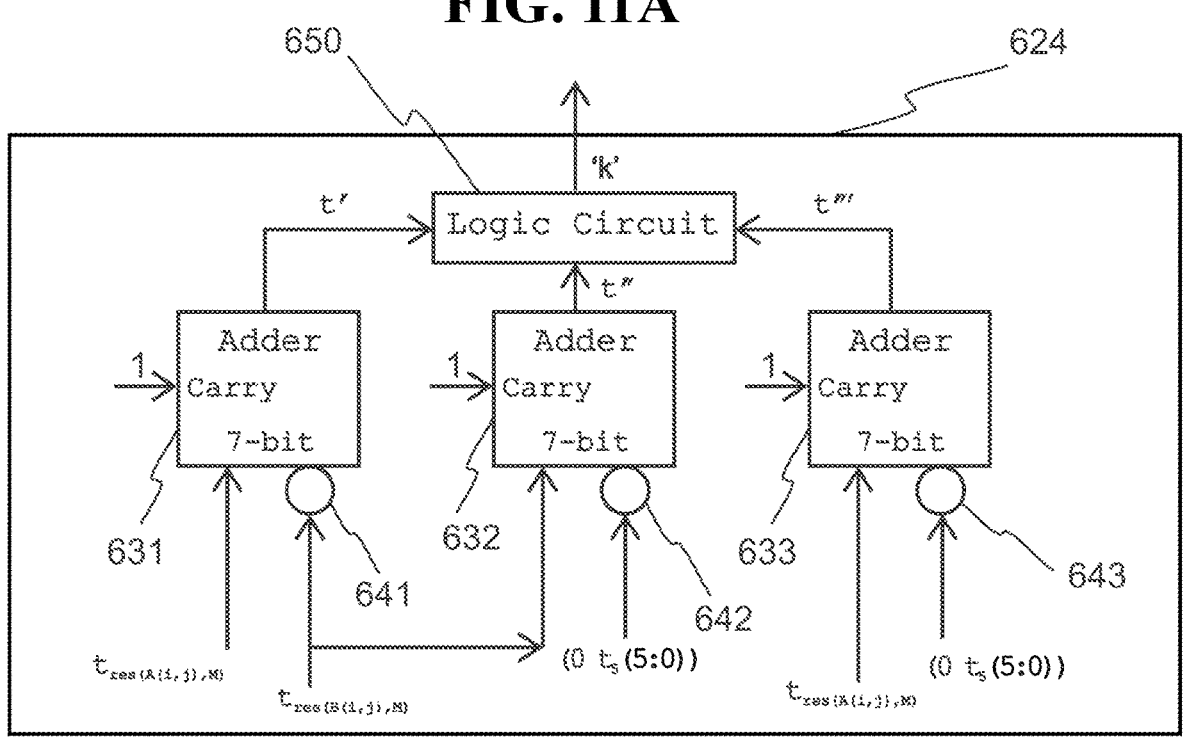

FIGS. 11A and 11B illustrate the FE hardware of the third embodiment, according to various aspects of the present disclosure. An $F_E$ hardware 621 is described with reference to FIG. 11A. The $F_E$ hardware 621 may comprise a 7-bit adder 623, a 3 way compare 624, and a multiplexer 625.

The inputs to the adder 623 may be $t_{res(E(i-1,j-1),\mathcal{M})}(6:0)$ and $t_c(6:0)$. A carry signal to the adder 623 may be '0'. The output of the adder 623 may be $t_5(6:0)$, where $t_{r_5}=(0 \; t_5(5:0))$. The compare 624 may have 3 inputs: $t_{res(A(i,j),\mathcal{M})}$, $t_{res(B(i,j),\mathcal{M})}$, and $t_{r_5}=(0 \; t_5(5:0))$. The compare 624 may find $I_E$. It is arbitrarily biased first toward A, next toward B, as follows:

$I_E=2$ if $A(i,j) \geq B(i,j)$ and $A(i,j) \geq R_5$ $I_E=3$ if $A(i,j) < B(i,j)$ and $B(i,j) \geq R_5$ $I_E=1$ if $A(i,j) < R_5$ and $B(i,j) < R_5$ The compare 624 may output out=$I_E$.

One way the compare 624 finds $I_E$ is by first comparing $A(i,j)$ and $B(i,j)$ using Lemma 10, second comparing $R_5$ with the winner of $A(i,j)$ and $B(i,j)$ using Lemma 10. Here there may be two compares of the type performed by the adder 604 and adder 614, in series.

Another way is by first making 3 compares in parallel:
1) $A(i,j)$ and $B(i,j)$
2) $A(i,j)$ and $R_5$
3) $B(i,j)$ and $R_5$ Second, find $I_E$ based on the 3 parallel compares.

FIG. 11B shows an implementation of the compare 624 based on the parallel compare method. The compare 624 has 3 adders 632 and 633. The inputs to the adder 631 are: $t_{res(B(i,j),\mathcal{M})}\overline{(6:0)}$ and $t_{res(A(i,j),\mathcal{M})}(6:0)$. A not gate 641 may complement $t_{res(B(i,j),\mathcal{M})}(6:0)$ to generate $t_{res(B(i,j),\mathcal{M})}\overline{(6:0)}$. A carry signal to the adder 631 may be '1'.

The adder 631 may produce $t'=t_{res(A(i,j),\mathcal{M})-res(B(i,j),\mathcal{M})}(6:0)$. Based on Lemma 10, $(i,j) \geq B(i,j)$ if $t'(5)=0$, and $A(i,j) < B(i,j)$ if $t'(5)=1$, as was described above.

The inputs to the adder 632 may be $\overline{t_{r_5}(6:0)}$ and $t_{res(B(i,j),\mathcal{M})}(6:0)$. A not gate 642 may complement $t_{r_5}(6:0)$ to generate $\overline{t_{r_5}(6:0)}$. A carry signal to the adder 632 may be '1'. The adder 632 may produces $t''=t_{res(B(i,j),\mathcal{M})}-r_5(i,j)$ (6:0).

Based on Lemma 10, $B(i,j) \geq R_5$ if $t''(5)=0$, and $B(i,j) < R_5$ if $t''(5)=1$. The inputs to the adder 633 may be $t_{r_5}(6:0)$ and $t_{res(A(i,j),\mathcal{M})}(6:0)$. A not gate 642 may complement $t_{r_5}(6:0)$ to generate $\overline{t_{r_5}(6:0)}$. A carry signal to the adder 633 may be '1'. The adder 633 may produce $t'''=t_{res(A(i,j),\mathcal{M})}-r_5(i,j)$ (6:0).

Based on Lemma 10, $A(i,j) \geq R_5$ if $t'''(5)=0$, and $A(i,j) < R_5$ if $t'''(5)=1$. With further reference to FIG. 11B, the compare 624 may further have a logic circuit 650. The logic circuit 650 may function according to Table 4.

TABLE 4

| t'(5) | t''(5) | t'''(5) | largest | 'k' = (t'(5) t''(5) AND t'''(5)) |
|---|---|---|---|---|
| 0 | 0 | 0 | A | (0, 0) => k = 2 |
| A >= B | B >= C | A >= C | | |
| 0 | 0 | 1 | NA | |
| A >= B | B >= C | A < C | | |
| 0 | 1 | 0 | A | (0, 0) => k = 2 |
| A >= B | B < C | A >= C | | |
| 0 | 1 | 1 | C | (0, 1) => k = 1 |
| A >= B | B < C | A < C | | |
| 1 | 0 | 0 | B | (1 0) => k = 3 |
| A < B | B >= C | A >= C | | |
| 1 | 0 | 1 | B | (1 0) => k = 3 |
| A < B | B >= C | A < C | | |
| 1 | 1 | 0 | NA | |
| A < B | B < C | A >= C | | |
| 1 | 1 | 1 | C | (1, 1) => k = 1 |
| A < B | B < C | A < C | | |

The output of the compare 624 is out (2 bits)='k'=(t'(2) (t''(2) AND t'''(2))). The multiplexer 625 may receive values, $t_{res(A(i,j),\mathcal{M})}(6:0)$, $t_{res(B(i,j),\mathcal{M})}(6:0)$, and $t_{r_5}$ (6:0), and it outputs may be $t_{res(A(i,j),\mathcal{M})}(6:0)$ if out '2', $t_{res(B(i,j),\mathcal{M})}(6:0)$ if out='3', and $t_{r_5}(6:0)$, if out='1'. This makes the output of the multiplexer 625 to be $t_{res(E(i,j),\mathcal{M})}$.

By optimizing the 7-bit operations of the customized hardware of FIGS. 9, 10, 11A and 11B for speed, the dynamic program of the alignment may be sped up.

5. The Fourth Embodiment—The Modular Based Dynamical Program Using a Customized Hardware in a Parallel Processing Setting for Global Alignment The fourth embodiment of modulo based, genetic material alignment methods is a hardware implementation of the key recursion equations with residues, in a parallel processing setting. Referring to the alignment digraph 600 in FIG. 8, the vertices are labeled (i,j), where i points to a column and j points to a row. The labels, (i,j), of vertices on a same diagonal have the same sum, i+j. In the fourth embodiment, vertices of a same diagonal are processes in parallel. Let's label a diagonal by the sum of the coordinates of the vertices on the diagonal. For example, diagonal 0 has only one vertex, (0,0), the diagonal 1 has two vertices: (0,1) and (1,0), so on.

Figure 12:
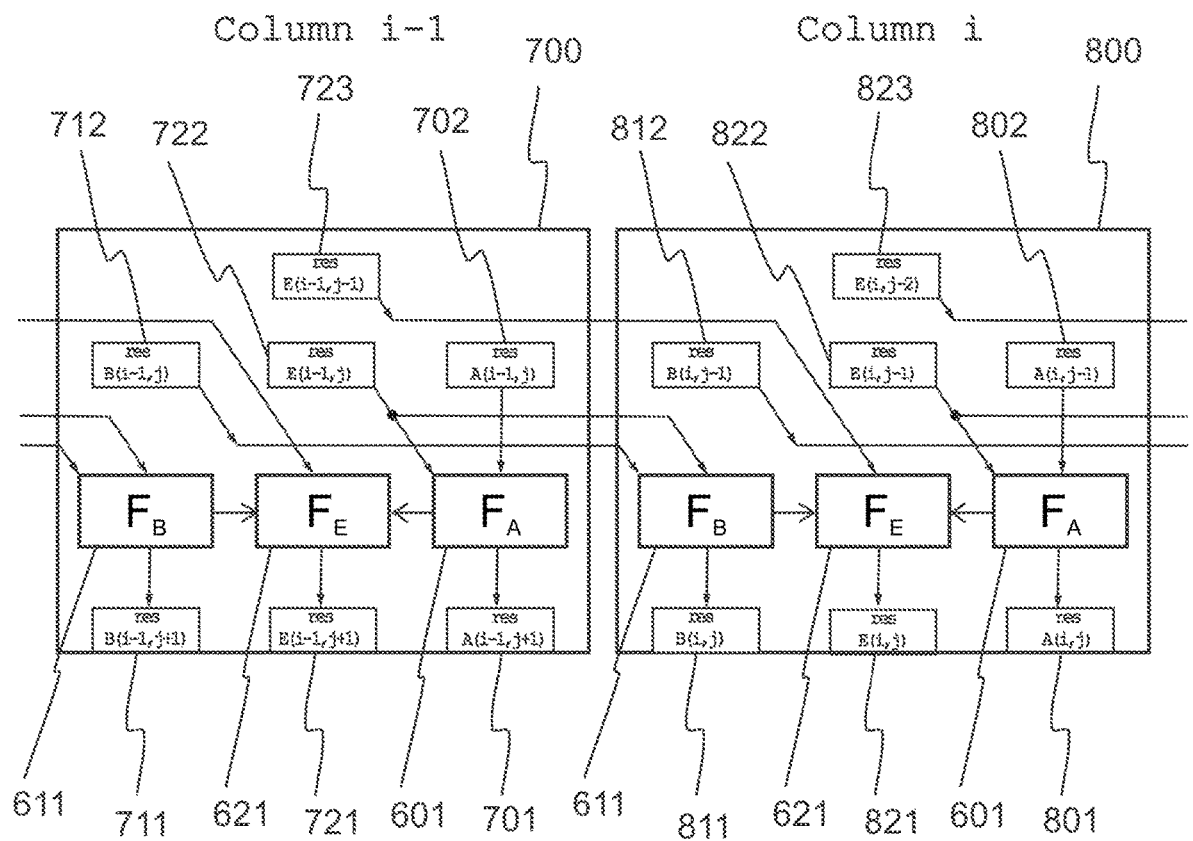
FIG. 12 illustrates parallel processing in the fourth embodiment, according to various aspects of the present disclosure.

The processing starts with diagonal 2; diagonals 0 and 1 are initialized. Each column, i, may have a specialized hardware of its own, $H_i$. FIG. 12 illustrates parallel processing in the fourth embodiment, according to various aspects of the present disclosure. With reference to FIG. 12, a specialized hardware $H_{i-1}$ 700 for column i−1 and a specialized hardware $H_i$ 800 for column i are shown. The hardware $H_{i-1}$ 700 may have the $F_A$ hardware 601, the $F_B$ hardware 611, and the $F_E$ hardware 621. In addition, the hardware $H_{i-1}$ 700 may have 7 registers $Reg0_A$ 701, $Reg1_A$ 702, $Reg0_B$ 711, $Reg1_B$ 712, $Reg0_E$ 721, $Reg1_E$ 722, and $Reg2_E$ 723.

The hardware $H_i$ 800 may have the $F_A$ hardware 601, the $F_B$ hardware 611, and the $F_E$ hardware 621. The hardware $H_i$ 800 may have 7 registers: $Reg0_A$ 801, $Reg1_A$ 802, $Reg0_B$ 811, $Reg1_B$ 812, $Reg0_E$ 821, $Reg1_E$ 822, and $Reg2_E$ 823. Connectivity in $H_i$ 800 and between $H_i$ 800 and $H_{i-1}$ 700 are explained below.

At the start of processing vertices on diagonal k, the register values are:

$Reg0_A$ 701 value all 0's
$Reg1_A$ 702 value is $t_{res(A(i-1,j),M)}$
$Reg0_B$ 711 value all 0's
$Reg1_B$ 712 value is $t_{res(B(i-1,j),M)}$
$Reg0_E$ 721 value all 0's
$Reg1_E$ 722 value is $t_{res(E(i-1,j),M)}$
$Reg2_E$ 723 value is $t_{res(E(i-1,j-1),M)}$
$Reg0_A$ 801 value all 0's
$Reg1_A$ 802 value is $t_{res(A(i,j-1),M)}$
$Reg0_B$ 811 value all 0's
$Reg1_B$ 812 value is $t_{res(B(i,j-1),M)}$
$Reg0_E$ 821 value all 0's
$Reg1_E$ 822 value is $t_{res(E(i,j-1),M)}$
$Reg2_E$ 823 value is $t_{res(E(i,j-2),M)}$ Now, the hardware $H_{i-1}$ 700 will process the vertex (i−1,k−i+1), and the hardware $H_i$ 800 will process the vertex (i,k−i).

The process is explained in the following 3 steps. In Step 1, the $F_A$ hardware 601 of the hardware $H_i$ 800 receives the values $t_{res(A(i,j-1),M)}$ and $t_{res(E(i,j-1),M)}$ from the registers $Reg1_A$ 802 and $Reg1_E$ 822, respectively. It will output $t_{res(A(i,j),M)}$, which will be sent to both the $F_E$ hardware 621 of the hardware $H_i$ 800 and the register $Reg0_A$ 801. For every column, t, t≠i, the $F_A$ hardware $H_t$ is processed in a similar manner, during step 1. Index variables, $I_A$, are stored.

The $F_B$ hardware 601 of the hardware $H_i$ 800 receives the values $t_{res(B(i-1,j),M)}$ and $t_{res(E(i-1,j),M)}$ from the registers $Reg1_B$ 712 and $Reg1_E$ 722, respectively. It will output $t_{res(B(i,j),M)}$, which will be sent to both the $F_E$ hardware 621 of the hardware $H_i$ 800 and the register $Reg0_B$ 811. For every column, t, t≠i, the $F_B$ hardware $H_t$ is processed in a similar manner, during step 1. Index variables, $I_B$, are stored.

In Step 2, the $F_E$ hardware 621 of the hardware $H_i$ 800 receives the value $t_{res(E(i-1,j-1),M)}$ from the register $Reg2_E$ 723 of the hardware $H_{i-1}$ 700. And it generates value $t_{res(E(i,j),M)}$ based on $t_{res(A(i,j),M)}$, $t_{res(B(i,j),M)}$, and $t_{res(E(i-1,j-1),M)}$. Now, the $F_E$ hardware 621 of the hardware $H_i$ 800 sends $t_{res(E(i,j),M)}$ to the register $Reg0_E$ 821. For every column, t, t≠i, the $F_E$ hardware $H_t$ is processed in a similar manner, during step 2. Index variables, $I_E$, are stored.

In Step 3, the register $Reg0_A$ 801 may be shifted into the register $Reg1_A$ 802, the register $Reg0_B$ 811 may be shifted into the register $Reg1_B$ 812, the register $Reg1_E$ 822 may be shifted into the register $Reg2_E$ 823, and the register $Reg0_E$ 821 may be shifted into the register $Reg1_E$ 822. For every column, t, t≠i, the registers of hardware $H_t$ is processed in a similar manner, during step 3. A rendering of the fourth embodiment is as follows. Instead of assigning columns distinct H hardware, the columns may be partitioned into intervals. Then the first interval may be processed as in the fourth embodiment, at the same time the values for the boundary condition may be collected. Next, the second interval may be processed as in the fourth embodiment using the collect boundary values. This rendering needs fewer hardware H's, but it requires extra register to store the boundary conditions of B's and E's.

G. Overlapping Alignment

The fifth embodiment of modulo based, genetic material alignment methods is a hardware implementation for computing the key recursion equations with residues for an overlapping alignment with affine gap score.

1. The Goal of the Overlapping Alignment

Given two sequences $\underline{x}=x_1 x_2 x_3 \ldots x_n$ and $\underline{y}=y_1 y_2 y_3 \ldots y_m$, the $\underline{x}$ and $\underline{y}$ alignment digraph $D(\underline{x},\underline{y})$ with vertex set $\mathbb{V}$, and the score maps $\hat{\varphi}_0$ and $\hat{\varphi}_1$, the goal of the overlapping alignment is to find a walk, $W^{max}$, starting from a vertex on the top row or leftmost column and end on a vertex on the bottom row or the rightmost column on the alignment digraph $D(\underline{x},\underline{y})$, such that $W^{max}=((i_0,j_0), (i_1,j_1), \ldots, (i_k,j_k))$, where $i_0=0$ or $j_0=0$, and where $i_k=0$ or $j_k=0$, having a maximal score. The score functions $\hat{\varphi}_0$ and $\hat{\varphi}_1$ are as defined above. Further, an affine gap score with values in Table 3 may be assumed.

The global alignment may be modified with affine score to perform the overlapping alignment with affine gap score. The main modification is simple, and it requires a change in the update rules for i=0, and j=0 cases. These cases are often considered as part of the initialization since they address i=0, and j=0.

For the overlapping alignment with affine gap score:

D(i,j) is the best score over all walks from (0,0) to (i,j). If no such walk exists, then D(i,j)=−Inf.

A(i,j) is the best score over all walks from (0,0) to (i,j) that end with a vertical arc. If no such walk exists, then A(i,j)=−Inf.

B(i,j) is the best score over all walks from (0,0) to (i,j) that end with a horizontal arc. If no such walk exists, then B(i,j)=−Inf.

Initialization:

$E(0,0)=0$ $E(k_1,k_2)=-Inf$ if $k_1<0$ or $k_2<0$ $A(0,0)=-Inf$ $A(k_1,k_2)=-Inf$ if $k_1<0$ or $k_2<0$ $B(0,0)=-Inf$ $B(k_1,k_2)=-Inf$ if $k_1<0$ or $k_2<0$

Update Rules:

$(i, j) \neq (0, 0)$ $$E(i, j) = \max \begin{cases} E(i-1, j-1) + \kappa(x_i, y_j) \\ A(i, j) \\ B(i, j) \end{cases}$$

$$A(i, j) = \max \begin{cases} D(i, j-1) + V \\ A(i, j-1) + V_V \end{cases} \text{ if } i = 0$$

$$A(i, j) = \max \begin{cases} D(i, j-1) + v \\ A(i, j-1) + v_v \end{cases} \text{ if } i \neq 0$$

$$B(i, j) = \max \begin{cases} D(i-1, j) + H \\ B(i-1, j) + H_H \end{cases} \text{ if } j = 0$$

$$B(i, j) = \max \begin{cases} D(i-1, j) + h \\ B(i-1, j) + h_h \end{cases} \text{ if } j \neq 0$$

$H_H = H = 0$ $V_V = V = 0$

2. The Fifth Embodiment—The Modular Based Dynamical Program Using a Customized Hardware for an Overlapping Alignment with Affine Gap Score The fifth embodiment of modulo based, genetic material alignment methods is a hardware implementation for computing the key recursion equations with residues for an overlapping alignment with affine gap score. Because of its similarity to the global alignment with affine gap score, the Lemma 7.1 holds for the overlapping alignment as well, Lemma 7.2 for overlapping alignment gives the same result as Lemma 7.1 for global alignment. Proofs of Lemma 7.1 and 7.2 are provided below.

Figure 13:
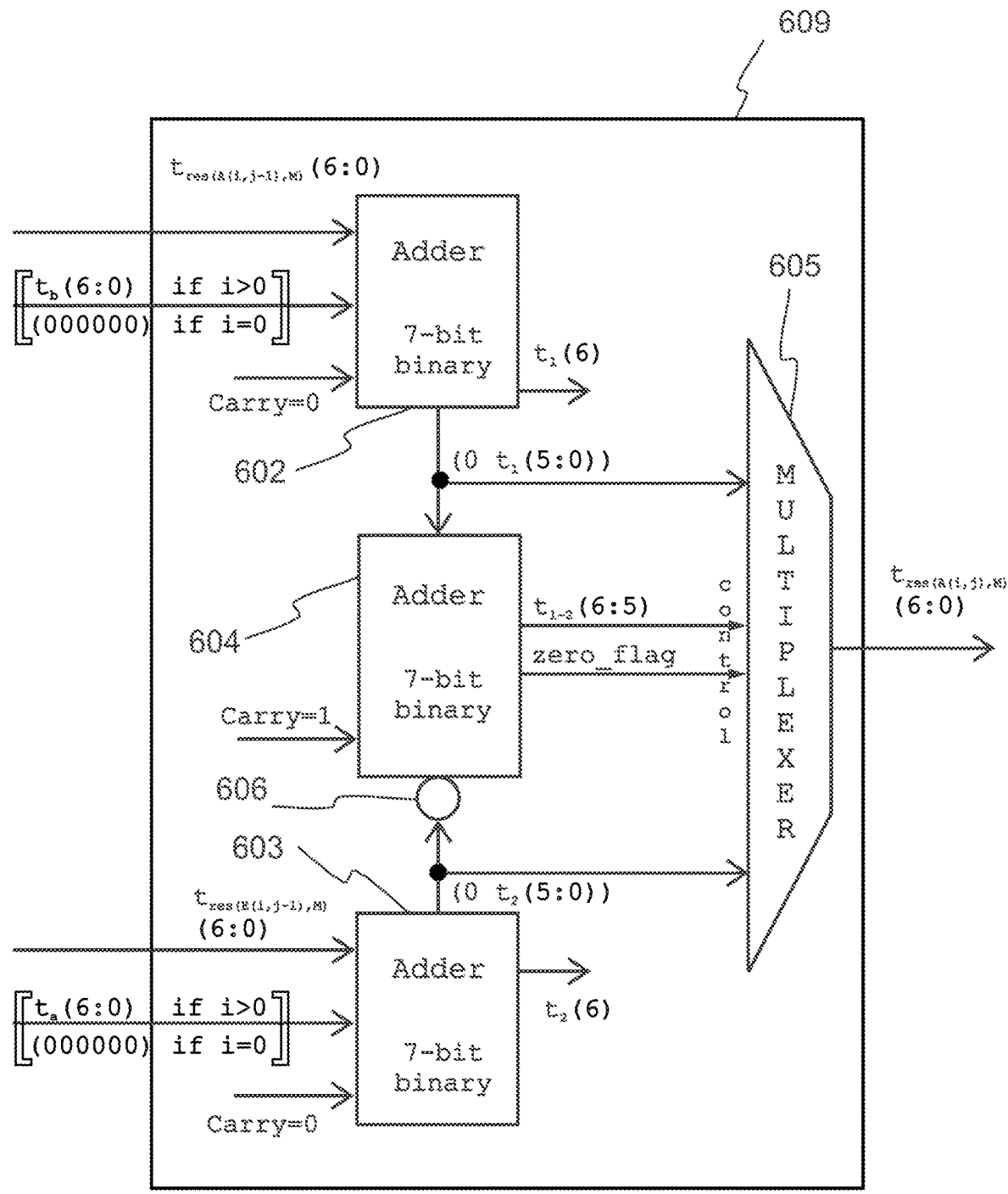
FIG. 13 illustrates the hardware that implements the function $F_A$ of the fifth embodiment, according to various aspects of the present disclosure.

FIG. 13 illustrates the FA hardware of the fifth embodiment, according to various aspects of the present disclosure. With reference to FIG. 13, an $F_A$ hardware 609 is explained. The $F_A$ hardware 609 in FIG. 13, differs from the $F_A$ hardware 601 in FIG. 9 in the following two aspects. The first difference is that the adder 602 input in FIG. 13 is:

$$\begin{cases} (0000000) & \text{if } i = 0 \\ t_b(6:0) & \text{if } i > 0 \end{cases}$$

But the adder 602 input in FIG. 9 is: $t_b(6:0)$. Thus, the two inputs differ when i=0. The adder 602 input in FIG. 13 is all zeros for i=0. Therefore, when i=0, $v_V$=0 is added to A(i,j−1), according to the update rules.

The second difference is that the adder 603 input in FIG. 13 is:

$$\begin{cases} (0000000) & \text{if } i = 0 \\ t_a(6:0) & \text{if } i > 0 \end{cases}$$

But the adder 603 input in FIG. 9 is: $t_a(6:0)$. Thus, the two inputs differ when i=0. The adder 603 input in FIG. 13 is all zeros for i=0. Therefore, when i=0, V=0 is added to E(i,j−1), according to the update rules.

Figure 14:
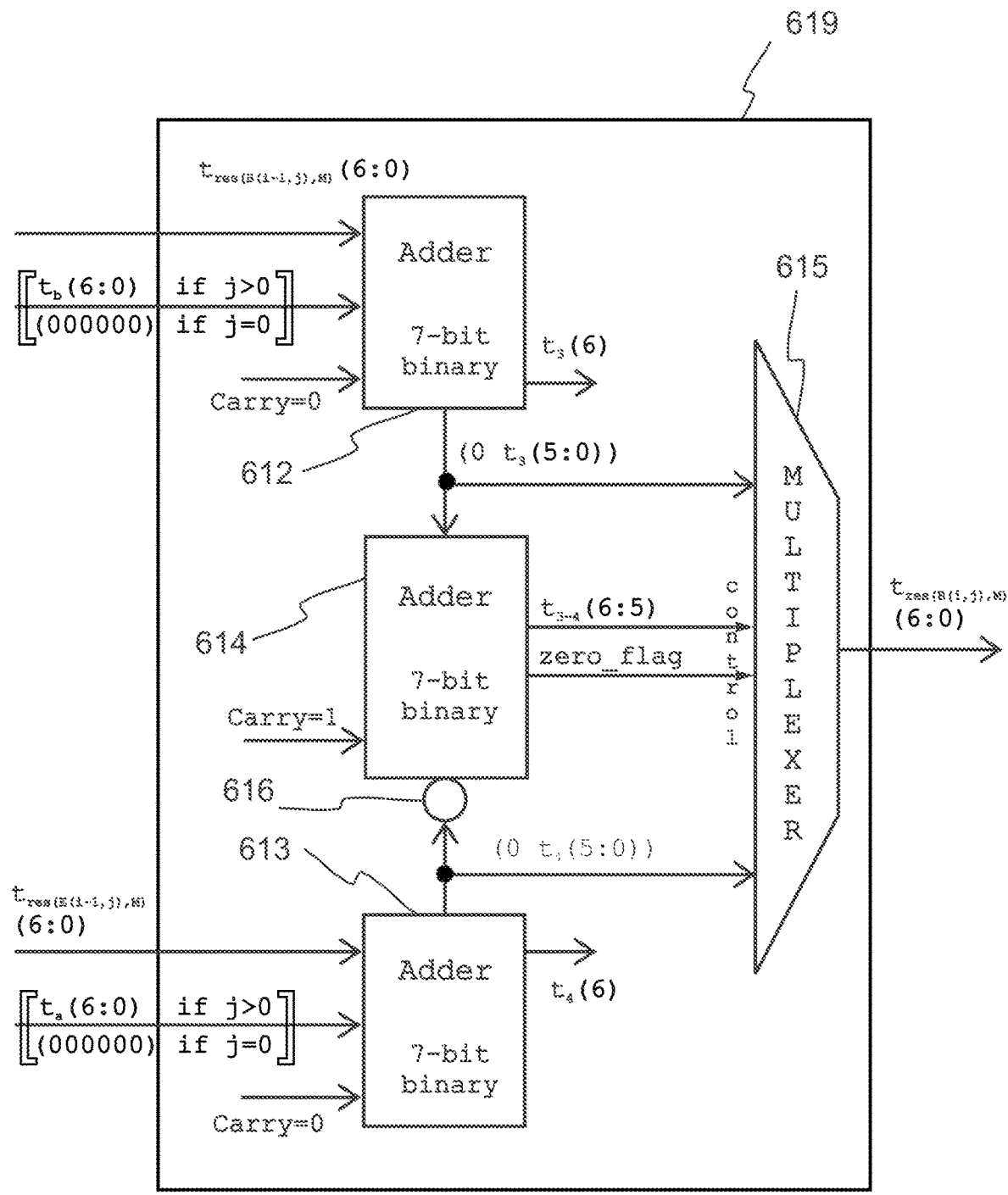
FIG. 14 illustrates the hardware that implements the function $F_B$ of the fifth embodiment, according to various aspects of the present disclosure.

FIG. 14 illustrates the FB hardware of the fifth embodiment, according to various aspects of the present disclosure. With reference to FIG. 14, an $F_B$ hardware 619 is explained. The $F_B$ hardware 619 in FIG. 14, differs from the $F_B$ hardware 611 in FIG. 10 in the following two aspects. The first difference is that the adder 612 input in FIG. 14 is:

$$\begin{cases} (0000000) & \text{if } j = 0 \\ t_b(6:0) & \text{if } j > 0 \end{cases}$$

But the adder 612 input in FIG. 10 is $t_b(6:0)$. Thus, the two inputs differ when j=0. The adder 612 input in FIG. 14 is all zeros for j=0. Thus, when j=0, $H_H$=0 is added to B(i−1,j), according to the update rules.

The second difference is that the adder 613 input in FIG. 14 is:

$$\begin{cases} (0000000) & \text{if } j = 0 \\ t_b(6:0) & \text{if } j > 0 \end{cases}$$

But the adder 613 input in FIG. 10 is: $t_a(6:0)$. Thus, the two inputs differ when j=0. The adder 613 input in FIG. 14 is all zeros for j=0. Thus, when j=0, H=0 is added to E(i−1,j), according to the update rules. The $F_E$ hardware of the overlapping alignment is identical with the $F_E$ hardware of the global alignment shown in FIGS. 11A and 11B.

H. Local Alignment

Some embodiments of the present modulo based, genetic material alignment methods provide a hardware implementation for computing the key recursion equations with residues for a local alignment with affine gap score.

2. The Goal of the Local Alignment

Given two sequences $\underline{x}=x_1\ x_2\ x_3\ \ldots\ x_n$ and $\underline{y}=y_1\ y_2\ y_3\ \ldots\ y_m$, the $\underline{x}$ and $\underline{y}$ alignment digraph $D(\underline{x},\underline{y})$ with vertex set $W$, and the score maps $\hat{\varphi}_0$ and $\hat{\varphi}_1$, the goal of the local alignment is to find a walk, $W^{max}$, starting from a vertex $(i_0,j_0)$ ending on a vertex $(i_k,j_k)$ on the alignment digraph $D(\underline{x},\underline{y})$, such that $W^{max}=((i_0,j_0), (i_1,j_1), \ldots, (i_k,j_k))$, has a maximal score.

The score functions $\hat{\varphi}_0$ and $\hat{\varphi}_1$ are as defined earlier. An affine gap score with values in Table 3 may be used. For the local alignment with affine gap score, D(i,j) is the best score over all walks to (i,j). If no such walk exists, then D(i,j)=−Inf, A(i,j) is the best score over all walks to (i,j) that end with a vertical arc. If no such walk exists, then A(i,j)=−Inf, and B(i,j) is the best score over all walks to (i,j) that end with a horizontal arc. If no such walk exists, then B(i,j)=−Inf.

The following initialization may be performed:

$E(0,0)=0$ $E(k_1,k_2)=-Inf$ if $k_1 < 0$ or $k_2 < 0$ $A(0,0)=-Inf$ $A(k_1,k_2)=-Inf$ if $k_1 < 0$ or $k_2 < 0$ $B(0,0)=-Inf$ $B(k_1,k_2)=-Inf$ if $k_1 < 0$ or $k_2 < 0$

Update Rules:

$(i, j) \neq (0, 0)$ $$E(i, j) = \max \begin{cases} E(i-1, j-1) + \kappa(x_i, y_j) \\ A(i, j) \\ B(i, j) \\ 0 \end{cases}$$

-continued $$A(i, j) = \max \begin{cases} E(i, j-1) + v \\ A(i, j-1) + v_v \\ 0 \end{cases}$$

$$B(i, j) = \max \begin{cases} E(i-1, j) + h \\ B(i-1, j) + h_h \\ 0 \end{cases}$$

$(k_1, k_2) = -Inf$ if $k_1 < 0$ or $k_2 < 0$

Figure 15:
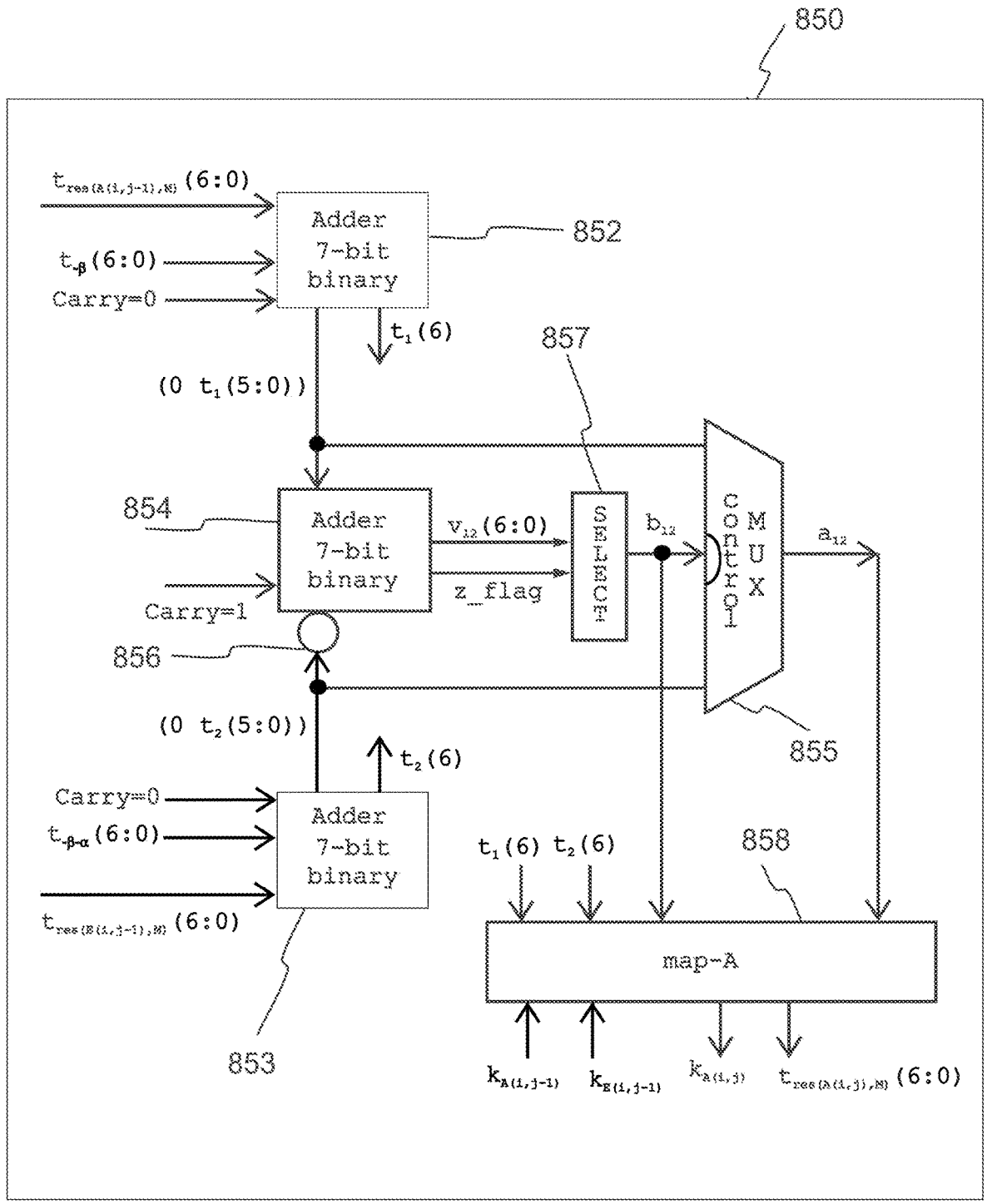
FIG. 15 illustrates the hardware that implements the function $F_A$ of the sixth embodiment, according to various aspects of the present disclosure.
Figure 16:
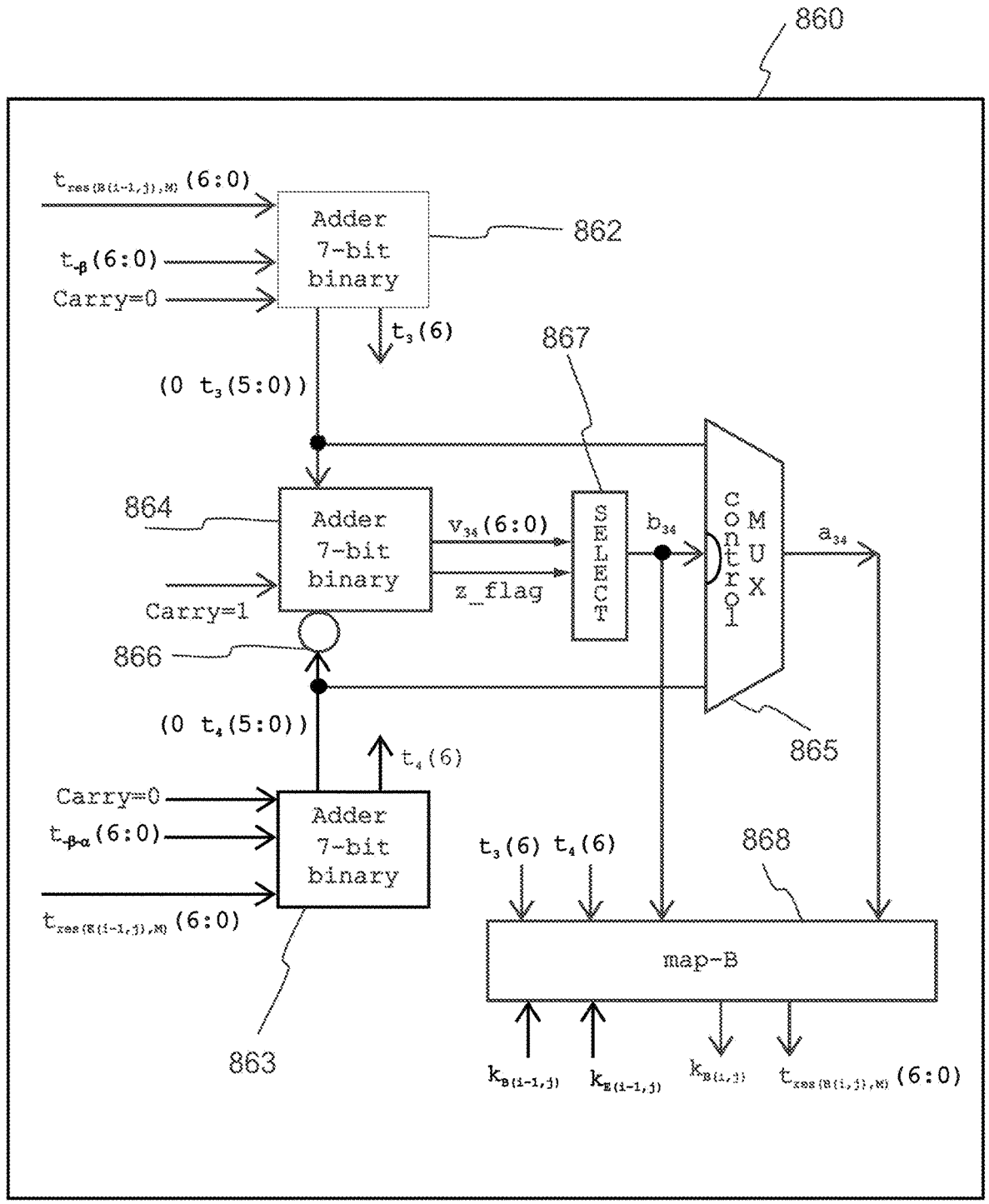
FIG. 16 illustrates the hardware that implements the function $F_B$ of the sixth embodiment, according to various aspects of the present disclosure.
Figure 17:
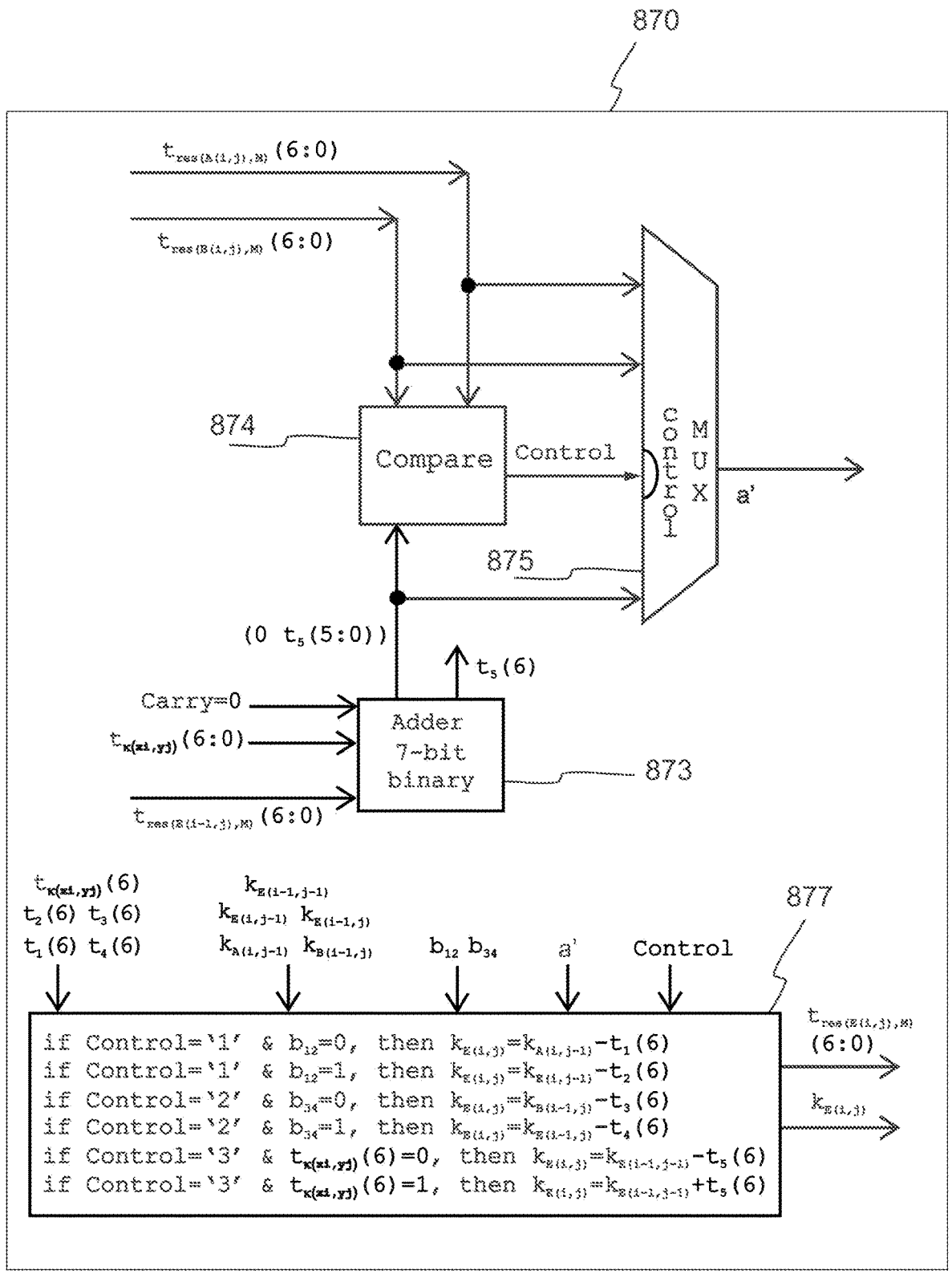
FIG. 17 illustrates the hardware that implements the function $F_E$ of the sixth embodiment, according to various aspects of the present disclosure.

3. The Sixth Embodiment—The Modular Based Dynamical Program Using a Customized Hardware for a Local Alignment with Affine Gap Score The sixth embodiment of modulo based, genetic material alignment methods is a hardware implementation for computing the key recursion equations with residues for a local alignment with affine gap score. FIG. 15 illustrates the FA hardware of the sixth embodiment, according to various aspects of the present disclosure. FIG. 16 illustrates the FB hardware of the sixth embodiment, according to various aspects of the present disclosure. FIG. 17 illustrates the FE hardware of the sixth embodiment, according to various aspects of the present disclosure.

With reference to FIGS. 15-17, the sixth embodiment is explained. In the local alignment with affine gap score, there are 3 main equations in the key recursion equations. Each equation requires finding a maximal element of a set.

1) $A(i,j)$ equals a maximal element of a set $Set_{A(i,j)} = \{A(i,j-1)+v_v, E(i,j-1)+v, 0\}$ 2) $B(i,j)$ equals a maximal element of $Set_{B(i,j)} = \{B(i-1,j)+h_h, E(i-1,j)+h, 0\}$ 3) $E(i,j)$ equals a maximal element of $Set_{E(i,j)} = \{A(i,j), B(i,j), E(i-1,j-1)+\kappa(x_i, y_j), 0\}$ Again, let $res(A(i,j-1), \mathcal{M})$, $res(B(i-1,j), \mathcal{M})$, $res(E(i,j-1), \mathcal{M})$, $res(E(i-1,j), \mathcal{M})$, $res(E(i-1,j-1), \mathcal{M})$, $res(A(i,j-1)+v_v, \mathcal{M})$, $res(B(i-1,j)+h_h, \mathcal{M})$, $res(E(i,j-1)+v, \mathcal{M})$, $res(E(i-1,j)+h, \mathcal{M})$, and $res(E(i-1,j-1)+\kappa(x_i, y_j), \mathcal{M})$, to denote the residues of $A(i,j-1)$, $B(i-1,j)$, $E(i,j-1)$, $E(i-1,j)$, $E(i-1,j-1)$, $A(i,j-1)+v_v$, $B(i-1,j)+h_h t$, $E(i,j-1)+v$, $E(i-1,j)+h$, and $E(i-1,j-1)+\kappa(x_i, y_j)$, respectively, with respect to a modulus $\mathcal{M}$.

Let's define $R_1$-$R_5$ and $r_1$-$r_5$ as follows:

$R_1 = A(i,j-1)+v_v$ $R_2 = E(i,j-1)+v$ $R_3 = B(i-1,j)+h_h$ $R_4 = E(i-1,j)+h$ $R_5 = E(i-1,j-1)+\kappa(x_i, y_j)$ $r_1 = res(A(i,j-1)+v_v, \mathcal{M})$, $r_2 = res(E(i,j-1)+v, \mathcal{M})$, $r_3 = res(B(i-1,j)+h_h, \mathcal{M})$, $r_4 = res(E(i-1,j)+h, \mathcal{M})$, $r_5 = res(E(i-1,j-1)+\kappa(x_i, y_j), \mathcal{M})$.

The present disclosure gives the following 3 functions, $F_A$, $F_B$, and $F_E$ for generating the followings:

$[res(A(i,j), \mathcal{M}), k_{A(i,j)}, I_{A(i,j)}] = F_A(res(A(i,j-1), \mathcal{M}),$
$k_{A(i,j-1)}, res(E(i,j-1), \mathcal{M})), k_{E(i,j-1)})$ $[res(B(i,j), \mathcal{M}), k_{B(i,j)}, I_{B(i,j)}] = F_A(res(B(i-1,j), \mathcal{M}),$
$k_{B(i-1,j)}, res(E(i-1,j), \mathcal{M})), k_{E(i-1,j)})$ $[res(E(i,j), \mathcal{M}), k_{E(i,j)}, I_{E(i,j)}] =$ $F_E(res(E(i-1,j-1), \mathcal{M}), k_{E(i-1,j-1)}, res(A(i,j), \mathcal{M})$
$k_{A(i,j-1)}, k_{E(i,j-1)}, res(B(i,j), \mathcal{M}), k_{B(i-1,j)}, k_{E(i-1,j)})$ Where, $A(i,j) = k_{A(i,j)} \times \mathcal{M} + res(A(i,j), \mathcal{M}), 0 \leq res(A(i,j), \mathcal{M}) < \mathcal{M}$ $B(i,j) = k_{B(i,j)} \times \mathcal{M} + res(B(i,j), \mathcal{M}), 0 \leq res(B(i,j), \mathcal{M}) < \mathcal{M}$ $E(i,j) k_{E(i,j)} \times \mathcal{M} + res(E(i,j), \mathcal{M}), 0 \leq res(E(i,j), \mathcal{M}) < \mathcal{M}$ $I_{A(i,j)}$ is the index to the maximal element in $Set_{A(i,j)}$, that is $I_{A(i,j)}=1$ if the first element in $Set_{A(i,j)}$ is the maximal element, $I_{A(i,j)}=2$ if the second element in $Set_{A(i,j)}$ is the maximal element, and $I_{A(i,j)}=3$ if the third element in $Set_{A(i,j)}$ is the maximal element.

$I_{B(i,j)}$ is the index to the maximal element in $Set_{B(i,j)}$.

$I_{E(i,j)}$ is the index to the maximal element in $Set_{E(i,j)}$.

$I_{A(i,j)}$, $I_{A(i,j)}$, and $I_{A(i,j)}$ are stored for trackback.

Also let $I'_{A(i,j)}$, $I'_{B(i,j)}$, and $I'_{E(i,j)}$ to denote a maximal element in $Set_{A(i,j)} - \{0\}$, $Set_{B(i,j)} - \{0\}$, and $Set_{E(i,j)} - \{0\}$, respectively.

Again, let's denote the 2's complement representation of $x$ by $t_x$.

$[res(A(i,j), \mathcal{M}), k_{A(i,j)}, I_{A(i,j)}] = F_A(res(A(i,j-1), \mathcal{M}),$
$k_{A(i,j-1)}, res(E(i,j-1), \mathcal{M})), k_{E(i,j-1)})$ Now $F_A$ decides on max $\{R_1, R_2, 0\}$, based on $\{r_1, r_2\}$ using the conditions of Lemma 10 and quotients $k_{A(i,j-1)}$ and $k_{E(i,j-1)}$.

Conditions of the Lemma 10:

$$\begin{cases} R_1 > R_2 & \text{if } r_2 < r_1 \leq r_2 + Q \\ R_1 < R_2 & \text{if } r_2 + Q < r_1 \\ R_1 < R_2 & \text{if } r_1 < r_2 \leq r_1 + Q \\ R_1 > R_2 & \text{if } r_1 + Q < r_2 \\ R_1 = R_2 & \text{if } r_1 = r_2 \end{cases}$$

And $F_B$ decides on max $\{R_3, R_4, 0\}$, based on $\{r_3, r_4\}$ using the conditions of Lemma 10 and quotients $k_{B(i-1,j)}$ and $k_{E(i-1,j)}$.

Conditions of the Lemma 10:

$$\begin{cases} R_3 > R_4 & \text{if } r_4 < r_3 \le r_4 + Q \\ R_3 < R_4 & \text{if } r_4 + Q < r_3 \\ R_3 < R_4 & \text{if } r_3 < r_4 \le r_3 + Q \\ R_3 > R_4 & \text{if } r_3 + Q < r_4 \\ R_3 = R_4 & \text{if } r_3 = r_4 \end{cases}$$

And $F_E$ decides on max{A(i,j),B(i,j),$R_5$,0}, based on {res(A(i,j),$\mathcal{M}$),res(B(i,j),$\mathcal{M}$),$r_5$} and the conditions of Lemma 10 and quotients $k_{A(i,j-1)}$, $k_{B(i-1,j)}$, $k_{E(i,j-1)}$, $k_{E(i-1,j)}$ and $k_{E(i-1,j-1)}$.

The gist approach is
1) to use the residues to find the partial indexing variables $I'_{A(i,j)}$, $I'_{B(i,j)}$, and $I'_{E(i,j)}$, and
2) to use the quotients to complete the variables, $I_{A(i,j)}$, $I_{B(i,j)}$, and $I_{E(i,j)}$.

Part 1) is done with short registers holding the residues, and most of Part 2) is done with slower logic. Therefore, the requirement on fast registers or fast memory units is lowered. In addition, the slower part not only use less power and therefore generates less heat, but also by reducing the overall power consumption and heat produced, it allows faster operation The sixth embodiment provides a hardware implementation of the above process. The residues may be represented in 2's complement, and the example 2 parameters for DNA segment alignment may be used. Thus, the match score=$\kappa_{max}$=1, the mis-match score=$\kappa_{min}$=−5, and the opening gap score=$\alpha$+$\beta$=5.

Lemma 7.1 holds for the sixth embodiment. Lemma 7.3 for local alignment and Lemma 7.1 for global alignment produce the same results. Thus, from Lemma 7.1: Q=27 (see above). Thus, the modulus $\mathcal{M}$ may be picked to be $\mathcal{M} \ge 2*Q+1=55$. $\mathcal{M}$ may be selected to be $\mathcal{M}=64=2^6$, to ease the hardware architecture.

Therefore, there may be 7 bits 2's complement representation to handle mod $2^6$. The 2's complement representation of x may be denoted by $t_x$. It should be noted that $\beta$, $\alpha$+$\beta$, and $\kappa(x_i,y_j)$ are in the range $[-2^6+1, 2^6-1]$.

Referring to FIG. 15, a $F_A$ hardware 850 is explained. The $F_A$ hardware 850 may comprise three 7-bit adders 852, 853, and 854, a multiplexer 855, a select unit 857 and a map-A 858. The inputs to the adder 852 may be $t_{res(A(i,j),\mathcal{M})}$(6:0) and $t_{-\beta}$(6:0). A carry signal to the adder 851 may be '0'.

The output of the adder 852 may be $t_1$ (6:0), where (0 $t_1$(5:0)) is $t_{res(A(i,j-1)-\beta,\mathcal{M})}$ (6:0), which is the 2's complement of residue of A(i,j−1)−$\beta$ modulo $\mathcal{M}$, where $t_1$(6)=1 if $t_1$(6:0) represent a negative number 7-bit, 2's complement.

The inputs to the adder 853 may be $t_{res(E(i,j-1),\mathcal{M})}$ (6:0) and $t_{-\beta-\alpha}$(6:0). A carry signal to the adder 853 may be '0'. The output of the adder 853 may be $t_2$(6:0), where (0 $t_2$(5:0)) is $t_{res(E(i,j-1)-\beta-\alpha,\mathcal{M})}$ (6:0), which is the 2's complement of residue of E(i,j−1)−$\beta$−$\alpha$ modulo $\mathcal{M}$, where $t_2$(6)=1 if $t_2$(6:0) represent a negative number 7-bit, 2's complement.

The inputs to the adder 854 may be $\overline{(0 t_2(5:0))}$ and (0 $t_1$(5:0)). The output of the adder 853, (0 $t_2$(5:0)), may be complemented by a not gate 856 before entering the adder 854. A carry signal to the adder 854 may be '1'.

In this shape, the adder 854 may function as a 2's complement subtractor. The adder 854 may generate, $t_{12}$(6:0), which (0 $t_1$(5:0))−(0 $t_2$(5:0)) in 2's complement. The adder 854 may output $t_{12}$(6:0) and a zero flag, which is '0' unless $t_{12}$(6:0)=(0,0,0,0,0,0,0). The main function of the adder 854 may be to generate $I'_A$.

Recall:
if $R_1$>$R_2$ $I'_A$=1
if $R_1$<$R_2$ $I'_A$=2
if $R_1$=$R_2$ $I'_A$=we choose 1, without loss of generality The adder 854 generates $I'_A$, based on $r_1$ and $r_2$, using the conditions of the Lemma 10, where $r_1$=res(A(i,j−1)+$v_v$,$\mathcal{M}$) and $r_2$ res(E(i,j−1)+$v$,$\mathcal{M}$).

$$\begin{cases} R_1 > R_2 & \text{if } r_2 < r_1 \le r_2 + Q \\ R_1 < R_2 & \text{if } r_2 + Q < r_1 \\ R_1 < R_2 & \text{if } r_1 < r_2 \le r_1 + Q \\ R_1 > R_2 & \text{if } r_1 + Q < r_2 \\ R_1 = R_2 & \text{if } r_1 = r_2 \end{cases}$$

In terms of $t_{12}$:
$R_1$>$R_2$ if $t_{12}$(6)=0 and $t_{12}$(5)=0 and zero flag='0'

$R_1$<$R_2$ if $t_{12}$(6)=0 and $t_{12}$(5)=1

$R_1$<$R_2$ if $t_{12}$(6)=1 and $t_{12}$(5)=1

$R_1$>$R_2$ if $t_{12}$(6)=1 and $t_{12}$(5)=0

$R_1$=$R_2$ zero flag='1'

Above, the inequality $|R_1-R_2| \le Q=27$ is used. Thus, $I'_A$=1 if ($t_{12}$(6:5)=(0,0) and zero flag='0') OR $t_{12}$(6:5)=(1,0) OR zero flag='1', and $I_A$=2 if $t_{12}$(6:5)=(0,1) OR $t_{12}$(6:5)=(1,1). Therefore, $I'_A$=1 if $t_{12}$(5)=0, and $I'_A$=2 if $t_{12}$(5)=1.

Hence, the select unit 857 input are: $t_{12}$(6:0) and the zero flag, and its output is $b_{12}$=$t_{12}$(5) (the other input values are not necessary in this case and may be eliminated). The multiplexer 855 may receive:

(0 $t_1$(5:0))=$t_{res(A(i,j-1)-\beta,\mathcal{M})}$ (6:0), (0 $t_2$(5:0))=$t_{res(E(i,j-1)-\beta-\alpha,\mathcal{M})}$ (6:0), and $b_{12}$, and it outputs:

$a_{12}$=$t_{res(A(i,j-1)-\beta,\mathcal{M})}$ (6:0), when $b_{12}$=0 and it outputs $a_{12}$=$t_{res(E(i,j-1)-\beta-\alpha,\mathcal{M})}$ (6:0), when $b_{12}$=1.

The map-A 858 inputs are:
$t_1$(6), $t_2$(6), $b_{12}$, $a_{12}$, $k_{A(i,j-1)}$, and $k_{E(i,j-1)}$.

The map-A 858 performs the following:

$$k'_{A(i,j)} = \begin{cases} k_{A(i,j-1)} - t_1(6) & \text{if } b_{12} = 0 \\ k_{E(i,j-1)} - t_2(6) & \text{if } b_{12} = 1 \end{cases}$$

$$t_{res(A(i,j),\mathcal{M})}(6:0) = a_{12}$$

$$k_{A(i,j)} = \begin{cases} k'_{A(i,j)} & \text{if } k'_{A(i,j)} \ge 0 \\ 0 & \text{if } k'_{A(i,j)} < 0 \end{cases}$$

$$t_{res(A(i,j),\mathcal{M})}(6:0) = \begin{cases} t_{res(A(i,j),\mathcal{M})}(6:0) & \text{if } k'_{A(i,j)} \ge 0 \\ (0000000) & \text{if } k'_{A(i,j)} < 0 \end{cases}$$

$$I_{A(i,j)} = \begin{cases} I'_A & \text{if } k'_{A(i,j)} \ge 0 \\ 3 & \text{if } k'_{A(i,j)} < 0 \end{cases}$$

Although the quotients $k_{A(i,j-1)}$ and $k_{E(i,j-1)}$ are used in the $F_A$ hardware 850, nevertheless, (1) the additions $k_{A(i,j-1)}$−$t_1$(6) and $k_{E(i,j-1)}$−$t_2$(6) require mostly slower operation than other arithmetic, as explained later, and (2) the condition $k'_{A(i,j)} \ge 0$ may be checked quickly, as explained later. Therefore, the modulo based, genetic material alignment limits fast computing to mostly over the residues.

Referring to FIG. 16, a $F_B$ hardware 860 is explained. The $F_A$ hardware 860 may comprise three 7-bit adders 862, 863, and 864, a multiplexer 865, a select unit 867 and a map-B

868. The inputs to the adder 862 may be $t_{res(B(i-1,j),\mathcal{M})}$ (6:0) and $t_{-\beta}$(6:0). A carry signal to the adder 861 may be '0'.

The output the adder 862 may be $t_3$ (6:0), where (0 $t_3$(5:0)) is $t_{res(B(i-1,j)-\beta,\mathcal{M})}$ (6:0), which is the 2's complement of residue of B(i−1,j)−β modulo $\mathcal{M}$, where $t_3$ (6)=1 if $t_3$(6:0) represent a negative number 7-bit, 2's complement. The inputs to the adder 863 may be $t_{res(E(i-1,j),\mathcal{M})}$ (6:0) and $t_{-\beta-\alpha}$(6:0). A carry signal to the adder 863 may be '0'.

The output of the adder 863 may be $t_4$ (6:0), where (0 $t_4$(5:0)) is $t_{res(E(i-1,j)-\beta-\alpha,\mathcal{M})}$ (6:0), which is the 2's complement of residue of E(i−1,j)−β−α modulo $\mathcal{M}$, where $t_4$(6)=1 if $t_4$(6:0) represent a negative number 7-bit, 2's complement.

The inputs to the adder 864 may be $\overline{(0t_4(5:0))}$ and (0 $t_3$(5:0)). The output of the adder 863, (0 $t_4$(5:0)) may be complemented by a not gate 866 before entering the adder 864. A carry signal to the adder 864 may be '1'.

In this shape, the adder 864 may function as a 2's complement subtractor. The adder 864 generates, $t_{34}$(6:0), which (0 $t_3$(5:0))−(0 $t_4$(5:0)) in 2's complement. The adder 864 outputs $t_{34}$(6:0) and a zero flag, which is '0' unless $t_{34}$(6:0)=(0,0,0,0,0,0,0). The main function of the adder 864 may be to generate I'$_B$.

Recall:
if $R_3 > R_4$ I'$_B$=1
if $R_3 < R_4$ I'$_B$=2
if $R_3 = R_4$ I'$_B$=we choose 1, without loss of generality The adder 864 generates I'$_B$, based on $r_3$ and $r_4$, using the conditions of the Lemma 10, where $r_3$=res(B(i−1,j)+$h_h$,$\mathcal{M}$) and $r_4$=res(E(i−1,j)+h,$\mathcal{M}$).

$$\begin{cases} R_3 > R_4 & \text{if } r_4 < r_3 \le r_4 + Q \\ R_3 < R_4 & \text{if } r_4 + Q < r_3 \\ R_3 < R_4 & \text{if } r_3 < r_4 \le r_3 + Q \\ R_3 > R_4 & \text{if } r_3 + Q < r_4 \\ R_3 = R_4 & \text{if } r_3 = r_4 \end{cases}$$

In terms of $t_{34}$:

$R_3 > R_4$ if $t_{34}$(6)=0 and $t_{34}$(5)=0 and zero flag='0'

$R_3 < R_4$ if $t_{34}$(6)=0 and $t_{34}$(5)=1

$R_3 < R_4$ if $t_{34}$(6)=1 and $t_{34}$(5)=1

$R_3 > R_4$ if $t_{34}$(6)=1 and $t_{34}$(5)=0

$R_3 = R_4$ zero flag='1'

Above, the inequality $|R_3-R_4| \le Q=27$ is used. Thus,

I'$_B$=1 if ($t_{34}$(6:5)=(0,0) and zero flag='0') OR $t_{34}$(6:5)=(1,0) OR zero flag I'$_B$=2 if $t_{34}$(6:5)=(0,1) OR $t_{34}$(6:5)=(1,1)

Therefore, I'$_B$=1 if $t_{34}$(5)=0, and I'$_B$=2 if $t_{34}$(5)=1. Hence, the select unit 867 input are: $t_{34}$(6:0) and the zero flag, and its output is $b_{34}$=$t_{34}$(5) (the other input values are not necessary in this case and may be eliminated).

The multiplexer 865 may receive the followings:

(0 $t_3$ (5:0))=$t_{res(B(i-1,j)-\beta,\mathcal{M})}$ (6:0), (0 $t_4$(5:0))=$t_{res(E(i-1,j)-\beta-\alpha,\mathcal{M})}$ (6:0), and $b_{34}$, and it outputs:

$a_{34}$=$t_{res(B(i-1,j)-\beta,\mathcal{M})}$ (6:0), when $b_{34}$=0 and it outputs
$a_{34}$=$t_{res(E(i-1,j)-\beta-\alpha,\mathcal{M})}$ (6:0), when $b_{34}$=1.

The map-B 868 inputs are:
$t_3$(6), $t_4$(6), $b_{34}$, $a_{34}$, $k_{B(i-1,j)}$, and $k_{E(i-1,j)}$.

The map-B 868 performs the following:

$$k'_{B(i,j)} = \begin{cases} k_{B(i-1,j)} - t_3(6) & \text{if } b_{34} = 0 \\ k_{E(i-1,j)} - t_4(6) & \text{if } b_{34} = 1 \end{cases}$$

$t'_{res(B(i,j),\mathcal{M})}(6:0) = a_{34}$ $$k_{B(i,j)} = \begin{cases} k'_{B(i,j)} & \text{if } k'_{B(i,j)} \ge 0 \\ 0 & \text{if } k'_{B(i,j)} < 0 \end{cases}$$

$$t_{res(B(i,j),\mathcal{M})}(6:0) = \begin{cases} t'_{res(B(i,j),\mathcal{M})}(6:0) & \text{if } k'_{B(i,j)} \ge 0 \\ (0000000) & \text{if } k'_{B(i,j)} < 0 \end{cases}$$

$$I_{B(i,j)} = \begin{cases} I'_B & \text{if } k'_{B(i,j)} \ge 0 \\ 3 & \text{if } k'_{B(i,j)} < 0 \end{cases}$$

Now,
1) the additions $k_{B(i-1,j)}-t_3(6)$ and $k_{E(i-1,j)}-t_4(6)$ require mostly slower operation than other arithmetic, as explained later.
2) the condition k'$_{B(i,j)} \ge 0$ may be checked quickly, as explained later.

Referring to FIG. 17, a F$_E$ hardware 870 is explained.

The F$_E$ hardware 870 comprises a 7-bit adder 873, a 3 way compare 874, a multiplexer 875, and a map-E 877.

The inputs to the adder 873 are: $t_{res(E(i-1,j-1),\mathcal{M})}$ (6:0) and $t_{\kappa(x_i,y_j)}$(6:0).
A carry signal to the adder 873 is '0'.

The output of the adder 873 is $t_5$ (6:0), where (0 $t_5$(5:0)) is $t_{res(E(i-1,j-1)+\kappa(x_i,y_j),\mathcal{M})}$ (6:0), which is the 2's complement of residue of E(i−1,j−1)+κ($x_i,y_j$) modulo $\mathcal{M}$, $t_5$(6)=1 if $t_5$(6:0) represent a negative number 7-bit, 2's complement.

The compare 874 has 3 inputs: $t_{res(A(i,j),\mathcal{M})}$, $t_{res(B(i,j),\mathcal{M})}$, and $t_{res(E(i-1,j-1)+\kappa(x_i,y_j),\mathcal{M})}$. The compare 874 finds I'$_E$ based on its inputs using Lemma 10. In this example there is an arbitrarily bias, first toward A, next toward B, as follows:

I'$_E$=1 if A(i,j)≥B(i,j) and A(i,j)≥$R_5$

I'$_E$=2 if A(i,j)<B(i,j) and B(i,j)≥$R_5$

I'$_E$=3 if A(i,j)<$R_5$ and B(i,j)<$R_5$

The compare 874 outputs Control=I'$_E$.
The multiplexer 875 receives: $t_{res(A(i,j),\mathcal{M})}$, $t_{res(B(i,j),\mathcal{M})}$, and.

(0 $t_5$(5:0))=$t_{res(E(i-1,j-1)+\kappa(x_i,y_j),\mathcal{M})}$, and Control, and it outputs a', where
a'=$t_{res(A(i,j),\mathcal{M})}$ (6:0), when Control=1, it outputs
a'=$t_{res(B(i,j),\mathcal{M})}$ (6:0), when Control=2, and it outputs
a'=$t_{res(E(i-1,j-1)+\kappa(x_i,y_j),\mathcal{M})}$ (6:0), when Control=3.

The map-E 877 inputs are:
$t_1$(6), $t_2$(6), $t_3$(6), $t_4$(6), $t_{\kappa(x_i,y_j)}$(6), $b_{12}$, $b_{34}$, Control, a', $k_{A(i,j-1)}$, $k_{E(i,j-1)}$, $k_{B(i-1,j)}$, $k_{E(i-1,j)}$ and $k_{E(i-1,j-1)}$.

The map-E 877 performs the following:

$$k'_{E(i,j)} = \begin{cases} k_{A(i,j-1)} - t_1(6) & \text{if Control} = 1 \text{ and } b_{12} = 0 \\ k_{E(i,j-1)} - t_2(6) & \text{if Control} = 1 \text{ and } b_{12} = 1 \\ k_{B(i-1,j)} - t_3(6) & \text{if Control} = 2 \text{ and } b_{34} = 0 \\ k_{E(i-1,j)} - t_4(6) & \text{if Control} = 2 \text{ and } b_{34} = 1 \\ k_{E(i-1,j-1)} - t_5(6) & \text{if Control} = 3 \text{ and } t_{\kappa(x_i,y_j)}(6) = 0 \\ k_{E(i-1,j-1)} + t_5(6) & \text{if Control} = 3 \text{ and } t_{\kappa(x_i,y_j)}(6) = 1 \end{cases}$$

-continued $$t'_{res(E(i,j),\mathcal{M})}(6:0) = a'$$

$$k_{E(i,j)} = \begin{cases} k'_{E(i,j)} & \text{if } k'_{E(i,j)} \geq 0 \\ 0 & \text{if } k'_{E(i,j)} < 0 \end{cases}$$

$$t_{res(E(i,j),\mathcal{M})}(6:0) = \begin{cases} t'_{res(E(i,j),\mathcal{M})}(6:0) & \text{if } k'_{E(i,j)} \geq 0 \\ (0000000) & \text{if } k'_{E(i,j)} < 0 \end{cases}$$

$$I_{E(i,j)} = \begin{cases} I'_E & \text{if } k'_{E(i,j)} \geq 0 \\ 4 & \text{if } k'_{E(i,j)} < 0 \end{cases}$$

For $X \in \{A(i,j-1), B(i-1,j), E(i,j-1), E(i-1,j), E(i-1,j-1)\}$, A quotient $k_X$ may be stored in two parts: $k_X = k'_X + k''_X$, where $k''_X$ belongs to $\{0, 1, -1\}$. And $s \in \{0, -1, +1\}$ may be added to $k_X$ as follows.

$$\begin{cases} \text{add } s \text{ to } k'_X & \text{if } k''_X + s \text{ exits } \{0, -1, +1\} \\ \text{add } s \text{ to } k''_X & \text{if } k''_X + s \text{ remains in } \{0, -1, +1\} \end{cases}$$

It requires a bigger fluctuation of X to change $k'_X$ than $k''_X$.

In the local alignment application, some of the present embodiments keep $k'_X \geq 0$, where $k'_X$ may be updated with a slower clock than $k''_X$. Also a negative flag may be generated quickly for $k_X$:

$k_X < 0$ if
$k'_X = 0$ and $k''_X = 0$ and $s = -1$,
$k'_X = 1$ and $k''_X = -1$ and $s = -1$, The case $k'_X = 0$ and $k''_X = -1$ and $s = -1$, does not occur in local alignment since $k_X$ is nulled every time it goes below zero. Therefore $k'_X = 0$ and $k''_X = -1$ would have led to $k'_X = 0$ and $k''_X = 0$ before receiving $s = -1$.

Another way to store a quotient $k_X$ in two parts is to have $k''_X$ in 2-bit 2's complement. Here $s \in \{0, -1, +1\}$ may be added to $k_X$ as follows: $s \in \{0, -1, +1\}$ may be added to $k''_X$, and overflows may be passed to $k'_X$. Again, it requires a bigger fluctuation of X to change $k'_X$ than $k''_X$.

Yet another way is to do addition to $k_X$ in three or more stages cascaded to each other, where overflows are carried to the next stage.

These methods split the addition into a faster part and a slower part. Overall making addition fast.

It should be noted that residues may be formed with respect to a modulus that is negative. the above examples used $\{0, 1, 2, \ldots, M-1\}$ for the domain of the residues, one may use a domain with an offset. For example, $d + \{0, 1, 2, \ldots, M-1\}$. Residue methods may be applied to multi-sequence alignment of DNA sequences as well. Instead of breaking ties when sets have more than one maximal element, all maximal elements may be stored. This may allow the construction of more than one optimum alignment.

Further, the residue methods may be used when the key recursions equations are finding minimal elements instead of maximal elements. The lemmas 2 and 3 enable comparing the variables in the recursion equations, thus, they may be used to find the larger elements as well as the smaller elements. In the alignment literature, there is an equivalence between maximizing "similarity" score and minimizing "distance" scores.

The followings sections provide the proofs for the embodiments described above.

II. Abridged Proof of Global Alignments According to the Present Invention

Here Lemma i.1, i=1-7 are used that are given below. Two vertices A and B are given, A is to the immediate right of B.

In Lemma 1.1-lower bound, described above, a lower bound is found for $\rho(A)-\rho(B)$, for each of the affine, simplified and modified versions. In Lemma 1-upper bound, described above, an upper bound is found for $\rho(A)-\rho(B)$, for each of the affine, simplified and modified versions.

Two vertices A and C are given, A is immediately below C. In Lemma 2.1-Lower bound, described above, a lower bound is found for $\rho(C)-\sigma(A)$, for each of the affine, simplified and modified versions. In Lemma 2.1-upper bound, described above, an upper bound is found for $\rho(C)-\sigma(A)$, for each of the affine, simplified and modified versions.

Using Lemmas 1.1 and 2.1 results lemma 3.1-6.1 are obtained, as described above, for affine, simplified and modified cases. Using Lemmas 1.1-6.1, a bound is generated for modulus operation for affine (Gotoh) algorithm in Lemma 7.1, as described below.

Difference of any pair of values from 1)-5) falls in the range:

[LB UB], where, $$LB = \min\{-2\kappa_{max}-5(\alpha+\beta), -\kappa_{max}-2(\alpha+\beta)+\kappa_{min}+\beta\}$$

$$UB = \max\{2\kappa_{max}+5(\alpha+\beta), \kappa_{max}-\kappa_{min}\}, \text{ and } \kappa_{max} \geq 0$$

1) $\rho(A)+\kappa(B)$, 2) $\rho(B)-(\alpha+\beta)$, 3) $\sigma(B)-\beta$, 4) $\rho(C)-(\alpha+\beta)$, 5) $\tau(C)-\beta$ Next, we show that the Lemmas 1.1-7.1 apply for the banded global alignment. Therefore, the results extend to the banded global alignment case, as described in the Banded Global Alignment section, above.

A. Lemma 1.1—Lower Bound

Given vertices $B=(i,j)$ and $A=(i+1,j)$, we have $-\alpha-\beta \leq \rho(A)-\rho(B)$, for affine and affine simplified gap score, and $\min\{-\alpha-\beta, \kappa_{min}+\beta\} \leq \rho(A)-\rho(B)$, for modified gap score.

Proof: Global alignment produces the same bound as the Local alignment, thus the proof is skipped for brevity. See Lemma 1.3, lower bound in Local alignment.

B. Lemma 1.1—Upper Bound

Given vertices $B=(i,j)$ and $A=(i+1,j)$, $\rho(A)-\rho(B) \leq \kappa_{max}+\alpha+\beta$, for affine and affine simplified gap score, and $\rho(A)-\rho(B) \leq \kappa_{max}-\kappa_{min}$, for modified gap score.

Proof: Global alignment produces the same bound as the Local alignment, thus we skip the proof for brevity. See Lemma 1.3, upper bound in Local alignment.

Global Alignment

| | affine | modified | simplified |
|---|---|---|---|
| Lemma 1.1 lower bound | $-\alpha - \beta$ | $\min\{-\alpha - \beta, \kappa_{min} + \beta\}$ | $-\alpha - \beta$ |
| Lemma 1.1 upper bound | $\kappa_{max} + \alpha + \beta$ | $\max\{\kappa_{max} + \alpha + \beta, -\beta, -\beta + \kappa_{max} - \kappa_{min}\}$ | $\kappa_{max} + \alpha + \beta$ |

Global Alignment: $\kappa_{min} \leq 0$ and $\kappa_{max} \geq 0$

| | affine | modified | simplified |
|---|---|---|---|
| Lemma 1.1 lower bound | $-\alpha - \beta$ | $\min\{-\alpha - \beta, \kappa_{min} + \beta\}$ | $-\alpha - \beta$ |
| Lemma 1.1 upper bound | $\kappa_{max} + \alpha + \beta$ | $\max\{\kappa_{max} + \alpha + \beta, -\beta + \kappa_{max} - \kappa_{min}\}$ | $\kappa_{max} + \alpha + \beta$ |

C. Lemma 2.1—Lower Bound

We are given vertices C=(i,j) and A=(i,j+1), where $\rho(C)$ denotes the best score from (0,0) to C, and $\sigma(A)$ denotes the best score from (0,0) to A, over walks ending with a vertical arc. This lemma shows, $0 \leq \rho(C) - \sigma(A)$, for AS and M gap scores.

Proof: Global alignment produces the same bound as the Local alignment, thus we skip the proof for brevity. See Lemma 2.3, lower bound in Local alignment.

D. Lemma 2.1—Upper Bound

We are given vertices C=(i,j) and A=(i,j+1), where $\rho(C)$ denotes the best score from (0,0) to C, and $\sigma(A)$ denotes the best score from (0,0) to A, over walks ending with a vertical arc. This lemma shows, $\rho(C) - \sigma(A) \leq \alpha + \beta$, for AS and $\rho(C) - \sigma(A) \leq \max\{\kappa_{max} - \kappa_{min} + \alpha + \beta, \kappa_{max} - 2\kappa_{min} + \alpha - \beta\}$, for M gap scores. ($\kappa_{min} \leq 0$ and $\kappa_{max} \geq 0$).

Proof: Global alignment produces the same bound as the Local alignment, thus we skip the proof for brevity. See Lemma 2.3, upper bound in Local alignment.

Global Alignment

| | affine | Modified | simplified |
|---|---|---|---|
| Lemma 2.1 lower bound | 0 | 0 | 0 |
| Lemma 2.1 upper bound | $\alpha + \beta$ | $\max\{\alpha + \beta, -\kappa_{min} + \alpha, \kappa_{max} - \kappa_{min} + (\alpha + \beta), \kappa_{max} - 2\kappa_{min} + \alpha - \beta\}$ | $\alpha + \beta$ |

Global Alignment: $\kappa_{min} \leq 0$ and $\kappa_{max} \geq 0$

| | affine | modified | simplified |
|---|---|---|---|
| Lemma 2.1 lower bound | 0 | 0 | 0 |
| Lemma 2.1 upper bound | $\alpha + \beta$ | $\max\{\kappa_{max} - \kappa_{min} + (\alpha + \beta), \kappa_{max} - 2\kappa_{min} + \alpha - \beta\}$ | $\alpha + \beta$ |

E. Lemma 3.1-7.1

Given the upper and lower bounds in Lemmas 1 and 2, we drive four more set of lower and upper bounds.

We have six vertices X, Y, A, B, C, and D. A is immediately above C, and X is immediately above A. D is immediately to the right of C, B is immediately to the right of A, and Y is immediately to the right of X.

Proof:

| | affine | modified | simplified |
|---|---|---|---|
| Lemma 1.1 lower bound $L_1$ | $-\alpha - \beta$ | $\min\{-\alpha - \beta, \kappa_{min} + \beta\}$ | $-\alpha - \beta$ |
| Lemma 1.1 upper bound $U_1$ | $\kappa_{max} + \alpha + \beta$ | $\max\{\kappa_{max} + \alpha + \beta, -\beta + \kappa_{max} - \kappa_{min}\}$ | $\kappa_{max} + \alpha + \beta$ |
| Lemma 2.1 lower bound $L_2$ | 0 | 0 | 0 |
| Lemma 2.1 upper bound $U_2$ | $\alpha + \beta$ | $\kappa_{max} - 2\kappa_{min} + \alpha - \beta$ | $\alpha + \beta$ |

| Lemma 1.1 | $L_1 \leq \rho(B) - \rho(A) \leq U_1$ |
| --- | --- |
| | $L_1 \leq \rho(C) - \rho(A) \leq U_1$ |
| Lemma 2.1 | $L_2 \leq \rho(B) - \sigma(D) \leq U_2$ |
| | $L_2 \leq \rho(C) - \tau(D) \leq U_2$ |
| Lemma 3.1 | $L_3 = L_1 + L_2 \leq \rho(B) - \sigma(B) \leq U_1 + U_2 = U_3$ |
| | $L_3 = L_1 + L_2 \leq \rho(C) - \tau(C) \leq U_1 + U_2 = U_3$ |
| Lemma 4.1 | $-U_1 + L_3 \leq \rho(A) - \sigma(B) \leq -L_1 + U_3$ |
| | $-U_1 + L_3 \leq \rho(A) - \tau(C) \leq -L_1 + U_3$ |
| Lemma 5.1 | $-U_1 + L_1 \leq \rho(B) - \rho(C) \leq -L_1 + U_1$ |
| | $-U_1 + L_1 \leq \rho(B) - \rho(C) \leq -L_1 + U_1$ |
| Lemma 6.1 | $L_1 - U_1 + L_3 \leq \rho(B) - \tau(C) \leq U_1 - L_1 + U_3$ |
| | $L_1 - U_1 + L_3 \leq \rho(C) - \sigma(B) \leq U_1 - L_1 + U_3$ |

1. Lemma 3.1:

$\rho(B) - \sigma(B) = \rho(B) - \rho(Y) + \rho(Y) - \sigma(B)$ $L_1 + L_2 \leq \rho(B) - \sigma(B) \leq U_1 + U_2$ 2. Lemma 4.1:

$\rho(A) - \sigma(B) = \rho(A) - \rho(B) + \rho(B) - \sigma(B)$ $-U_1 + L_3 \leq \rho(A) - \sigma(B) \leq -L_1 + U_3$ 3. Lemma 5.1:

$\rho(B) - \sigma(C) = \rho(B) - \rho(A) + \rho(A) - \sigma(C)$ $-U_1 + L_1 \leq \rho(B) - \rho(C) \leq -L_1 + U_1$ 4. Lemma 6.1 and Lemma 7.1:

$\rho(B) - \tau(C) = \rho(B) - \rho(A) + \rho(A) - \rho(C) + \rho(C) - \sigma(C)$ $L_1 - U_1 + L_3 \leq \rho(B) - \tau(C) \leq U_1 - L_1 + U_3$ For Affine (Gotoh) gap score, we generate the table below based on above results.

Gotoh $L_1 = -(\alpha + \beta)$  $U_1 = \kappa_{max} + \alpha + \beta$, $\kappa_{max} \geq 0$ $L_2 = 0$  $U_2 = (\alpha + \beta)$

| Lemma 1.1 | $-(\alpha + \beta) \leq \rho(B) - \rho(A) \leq \kappa_{max} + (\alpha + \beta)$ |
| --- | --- |
| | $-(\alpha + \beta) \leq \rho(C) - \rho(A) \leq \kappa_{max} + (\alpha + \beta)$ |
| Lemma 2.1 | $0 \leq \rho(B) - \sigma(D) \leq (\alpha + \beta)$ |
| | $0 \leq \rho(C) - \tau(D) \leq (\alpha + \beta)$ |
| Lemma 3.1 | $-(\alpha + \beta) \leq \rho(B) - \sigma(B) \leq \kappa_{max} + 2(\alpha + \beta)$ |
| | $-(\alpha + \beta) \leq \rho(C) - \tau(C) \leq \kappa_{max} + 2(\alpha + \beta)$ |
| Lemma 4.1 | $-\kappa_{max} - 2(\alpha + \beta) \leq \rho(A) - \sigma(B) \leq \kappa_{max} + 3(\alpha + \beta)$ |
| | $-\kappa_{max} - 2(\alpha + \beta) \leq \rho(A) - \tau(C) \leq \kappa_{max} + 3(\alpha + \beta)$ |
| Lemma 5.1 | $-\kappa_{max} - 2(\alpha + \beta) \leq \rho(B) - \rho(C) \leq \kappa_{max} + 2(\alpha + \beta)$ |
| | $-\kappa_{max} - 2(\alpha + \beta) \leq \rho(C) - \rho(B) \leq \kappa_{max} + 2(\alpha + \beta)$ |
| Lemma 6.1 | $-\kappa_{max} - 3(\alpha + \beta) \leq \rho(B) - \tau(C) \leq 2\kappa_{max} + 4(\alpha + \beta)$ |
| | $-\kappa_{max} - 3(\alpha + \beta) \leq \rho(C) - \sigma(B) \leq 2\kappa_{max} + 4(\alpha + \beta)$ |

Lemma 7.1: The difference of any pair of values 1)-5) below is in the interval:

[LB UB], where, $LB = \min\{-2\kappa_{max} - 5(\alpha + \beta), -\kappa_{max} - 2(\alpha + \beta) + \kappa_{min} + \beta\}$ $UB = \max\{2\kappa_{max} + 5(\alpha + \beta), \kappa_{max} - \kappa_{min}\}$, and $\kappa_{max} \geq 0$ 1) $\rho(A) + \kappa(B)$, 2) $\rho(B) - (\alpha + \beta)$, 3) $\sigma(B) - \beta$, 4) $\rho(C) - (\alpha + \beta)$, 5) $\tau(C) - \beta$.

Proof:

Difference of values 1) and 2): from Lemmas 1.1-6.1

$-(\alpha + \beta) \leq \rho(B) - \rho(A) \leq \kappa_{max} + (\alpha + \beta)$ $-(\alpha + \beta) - (\alpha + \beta) - \kappa(B) \leq (\rho(B) - (\alpha + \beta)) - (\rho(A) + \kappa(B)) \leq \kappa_{max} + (\alpha + \beta) - (\alpha + \beta) - \kappa(B)$ $-2(\alpha+\beta)-\kappa(B) \leq (\rho(B)-(\alpha+\beta))-(\rho(A)+\kappa(B)) \leq \kappa_{max}-\kappa(B)$ $-2(\alpha+\beta)-\kappa_{max} \leq (\rho(B)-(\alpha+\beta))-(\rho(A)+\kappa(B)) \leq \kappa_{max}-\kappa_{min}$ Difference of 1) and 3): from Lemmas 1.1-6.1

$-\kappa_{max}-2(\alpha+\beta) \leq \rho(A)-\sigma(B) \leq \kappa_{max}+3(\alpha+\beta)$ $-\kappa_{max}-2(\alpha+\beta)+\kappa(B)+\beta \leq (\rho(A)+\kappa(B))-(\sigma(B)-\beta) \leq \kappa_{max}+3(\alpha+\beta)+\kappa(B)+\beta$ $-\kappa_{max}-2(\alpha+\beta)+\kappa_{min}+\beta(\rho(A)+\kappa(B))-(\sigma(B)-\beta)2\kappa_{max}+3(\alpha+\beta)+\beta$ Difference of values 1) and 4) is same as difference of 1) and 2)

Difference of values 1) and 5) is same as difference of 1) and 3)

Difference of values 2) and 3): from Lemmas 1.1-6.1

$-(\alpha+\beta) \leq \rho(B)-\sigma(B) \leq \kappa_{max}+2(\alpha+\beta)$ $-(\alpha+\beta)-(\alpha+\beta)+\beta \leq (\rho(B)-(\alpha+\beta))-(\sigma(B)-\beta) \leq \kappa_{max}+2(\alpha+\beta)-(\alpha+\beta)+\beta$ $-2(\alpha+\beta)+\beta \leq (\rho(B)-(\alpha+\beta))-(\sigma(B)-\beta) \leq \kappa_{max}+(\alpha+\beta)+\beta$ Difference of values 2) and 4): from Lemmas 1.1-6.1

$-\kappa_{max}-2(\alpha+\beta) \leq \rho(B)-\rho(C) \leq \kappa_{max}+2(\alpha+\beta)$ $-\kappa_{max}-2(\alpha+\beta) \leq (\rho(B)-(\alpha+\beta))-(\rho(C)-(\alpha+\beta))\kappa_{max}+2(\alpha+\beta)$ $-\kappa_{max}-2(\alpha+\beta) \leq (\rho(B)-(\alpha+\beta))-(\rho(C)-(\alpha+\beta))\kappa_{max}+2(\alpha+\beta)$ Difference of values 2) and 5): from Lemmas 1.1-6.1

$-\kappa_{max}-3(\alpha+\beta) \leq \rho(B)-\tau(C) \leq 2\kappa_{max}+4(\alpha+\beta)$ $-\kappa_{max}-3(\alpha+\beta)-(\alpha+\beta)+\beta \leq (\rho(B)-(\alpha+\beta))-(\tau(C)-\beta) \leq 2\kappa_{max}+4(\alpha+\beta)-(\alpha+\beta)+\beta$ $-\kappa_{max}-4(\alpha+\beta)+\beta \leq (\rho(B)-(\alpha+\beta))-(\tau(C)-\beta) \leq 2\kappa_{max}+3(\alpha+\beta)+\beta$ Difference of values 23) and 4): Same as 2) and 5)

Difference of values 23) and 5): from Lemmas 1.1-6.1

$-2\kappa_{max}-5(\alpha+\beta) \leq \sigma(B)-\beta-(\tau(C)-\beta)=\sigma(B)-\tau(C) \leq 2\kappa_{max}+5(\alpha+\beta)$ Difference of values 24) and 5): Same as 2) and 3)

Bound that satisfy all of the above is: [LB UB], where, $LB=\min\{-2\kappa_{max}-5(\alpha+\beta),-\kappa_{max}-2(\alpha+\beta)+\kappa_{min}+\beta\}$ $UB=\max\{2\kappa_{max}+5(\alpha+\beta),\kappa_{max}-\kappa_{min}\}$, and $\kappa_{max} \geq 0$ The above is repeated to obtain Lemma 3.1-7.1 for the simplified and modified versions.

We use the bound for values 1)-5) that include the score of the arcs.

Alternatively, it is possible to use a similar bound for values 1')-5') that do not include the score of the arcs. The overall expressions in of the recursion must be reduced to a modulus based on the bound used.

1') $\rho(A)$, 2') $\rho(B)$, 3') $\sigma(B)$, 4') $\rho(C)$, 5') $\tau(C)$

III. Banded Global Alignment Proof

The two sequences X and Y, and their alignment digraph $D(\underline{x},\underline{y})$ are given. Let $V=\{(i,j): 0 \leq i \leq n \text{ and } 0 \leq j \leq m\}$, denote the vertex set of the digraph $D(\underline{x},\underline{y})$ as described above. In banded alignment, only vertices BAND=$\{(i,j): (i,j) \in V$, and lower_bound$\leq i+j \leq$upper_bound$\}$, are allowed for integers lower_bound and upper_bound. As described below, Lemma 1.1 lower bound, Lemma 1.1 upper bound, lemma 2.1 lower bound, and Lemma 2.1 upper bound hold for banded global alignments. Therefore, the results hold for banded global alignment.

For lemmas 2 lower bound (banded), the comments are included the proof. For lemmas 2 upper bound (banded) affine and simplified cases, the comments are included the proof. For the modified case: Let $\hat{\sigma}(A)$ denote a best path in the band, reaching A with last arc vertical, and let denote a best path in the band, reaching C. Case 1) Subcase 1.a):

If C, A and $W_{\hat{\rho}(C)}$, belong to a band, then from the definition of a band, we have $W \triangleq W_{\hat{\rho}(C)}*((i_s,j_s+1))$ belongs to the band. Therefore, the difference $\hat{\rho}(C)-\hat{\rho}(A)$ holds over the band.

Case 1) Subcase 1.b) Sub-subcase 1.b.b) Part 1):

If C, A and $W_{\hat{\rho}(C)}$, belong to a band, then $W=W_{\hat{\rho}(C)} \star ((i_p+s,j_p+2)) \ ((i_0,j_0), \ldots, (i_p,j_p), (i_p+1,j_p+1-1), (i_p+2,j_p+1-1), \ldots, (i_p+s-1,j_p+1-1), (i_p+s,j_p+1)) \star ((i_p+s,j_p+2))$ belongs to the band since all diagonals of the BAND that pass through that cover C, A and all the vertices of $W_{\hat{\rho}(C)}$, also cover all the vertices W. Therefore, the upper bound for $\hat{\rho}(C)-\hat{\rho}(A)$ holds over the band.

Case 1) Subcase 1.b) Sub-subcase 1.b.b) Part 2):

If C, A and $W_{\hat{\rho}(C)}$, belong to a band, then $W=((i_0,j_0), \ldots, (i_p,j_p), (i_p+1,j_p+1-1), (i_p+2,j_p+1-1), \ldots, (i_p+s-1,j_p+1-1), (i_p+s,j_p+1)) \star ((i_p+s,j_p+2))= \hat{W}_{\hat{\rho}(C)}((i_p,j_p)) \star ((i_p+1,j_p+1-1), (i_p+2,j_p+1-1), \ldots, (i_p+s-1,j_p+1-1), (i_p+s,j_p+1)) \star ((i_p+s,j_p+2))$ belongs to the band since all diagonals of the BAND that pass through that cover C, A and all the vertices of $W_{\hat{\rho}(C)}$, also cover all the vertices W. Therefore, the upper bound for $\hat{\rho}(C)-\hat{\rho}(A)$ holds over the band.

Case 1) Subcase 1.b) Sub-subcase 1.b.b) Part 3):

If C, A and $W_{\hat{\rho}(C)}$, belong to a band, then $$W = \begin{cases} ((0, 0), (1, 1), (2, 2) \star ((2, 3)) & \text{if } s = 2 \\ ((0, 0), (1, 1), (2, 1), (3, 2)) \star ((3, 3)) & \text{if } s = 3 \\ ((0, 0), (1, 1), (1 + 1, 1), (1 + 2, 1), \ldots, (1 + s - 2, 1), (s, 2)) \star ((s, 3)) & \text{if } 2 > 3 \end{cases}$$

belongs to the band since all diagonals of the BAND that pass through that cover C, A and all the vertices of $W_{\hat{\rho}(C)}$, also cover all the vertices W. Therefore, the upper bound for $\hat{\rho}(C)-\hat{\rho}(A)$ holds over the band.

Case 1) Subcase 1.b) Sub-subcase 1.b.b) Part 4):

If C, A and $W_{\hat{\rho}(C)}$, belong to a band, then $W=((i_0,j_0), \ldots, (i_{p-1},j_{p-1}), (i_p+1,j_p), (i_p+2,j_p), (i_p+3, j_p), \ldots, (i_p+s-1,j_p), (i_p+s,j_p+1))\star((i_p+s,j_p+2))=\hat{W}_{\hat{\rho}(C)}((i_{p-1},j_{p-1}))\star((i_p+1,j_p), (i_p+2,j_p), \ldots, (i_p+s-1,j_p), (i_p+s,j_p+1))\star((i_p+s,j_p+2))$ belongs to the band since all diagonals of the BAND that pass through that cover C, A and all the vertices of $W_{\hat{\rho}(C)}$, also cover all the vertices W. Therefore, the upper bound for $\hat{\rho}(C)-\hat{\rho}(A)$ holds over the band.

Case 2) If C and A belong to a band, then the upper bound for $\hat{\rho}(C)-\hat{\rho}(A)$ holds over the band.

Lemmas 1 lower bound (banded):

In each case, replacing $\rho(B)$ and $W_{\rho(B)}$ with $\hat{\rho}(B)$ and $W_{\hat{\rho}(B)}$, respectively. Then the walk W belongs to the BAND and thus generates the same upper bound for $\hat{\rho}(A)-\hat{\rho}(B)$. W belongs to the BAND since diagonals that pass A, B and $W_{\hat{\rho}(B)}$ pass all vertices of W.

Lemmas 1 upper bound (banded):

In each case, replacing $\rho(A)$ and $W_{\rho(A)}$ with $\hat{\rho}(A)$ and $W_{\hat{\rho}(B)}$, respectively. Now, in each case, by construction, the walk that reaches B is in the BAND, thus the same upper bound is obtained for $\hat{\rho}(A)-\hat{\rho}(B)$.

1) Assume A, B and $\hat{\rho}(A)$ belong to the BAND.

2) Now, given that the sequence denoted by (a) is in the BAND, then the sequence (n) is in the BAND because all its vertices belong to the diagonals that pass through {the vertices of (a)}∪{B}. With the same argument, given sequences denoted by (b), (c), (d), (e), (f), (g), (h), (i), (j), (k), and (l) are in the BAND, then the sequences (o), (p), (q), (n), (o), (p), (q), (r), (s), (t), and (u) are in the BAND, respectively.

IV. Abridged Proof of Overlapping Alignments According to the Present Invention Here Lemma i.2, i=1-7 are used that are given below. Note Lemmas 1.2-7.2 of the overlapping alignment are different than Lemmas 1.1-7.1 of the global alignment. Hoverer the bounds for affine (Gotoh) and affine simplified are the same as in Global alignment.

There are given two vertices A and B, A is to the immediate right of B.

In Lemma 1.2-lower bound for overlapping alignment, described above, a lower bound is found for $\rho(A)-\rho(B)$, for each of the affine, simplified and modified versions.

In Lemma 1.2-upper bound for overlapping alignment, described above, an upper bound is found for $\rho(A)-\rho(B)$, for each of the affine, simplified and modified versions.

There are given two vertices A and C, A is immediately below C.

In Lemma 2.2-lower bound for overlapping alignment, described above, a lower bound is found for $\rho(C)-\sigma(A)$, for each of the affine, simplified and modified versions.

In Lemma 2.2-upper bound for overlapping alignment, described above, an upper bound is found for $\rho(C)-\sigma(A)$, for each of the affine, simplified and modified versions.

Using Lemma 1.2 and 2.2 results Lemma 3.2-6.2 is obtained for affine, simplified and modified cases, as described above with reference to Lemmas 3.2-7.2 for overlapping alignment.

Using Lemmas 1.2-6.2 a bound is generate for modulus operation for affine (Gotoh) algorithm in Lemma 7.2, as described below.

Difference of any pair of values from 1)-5) falls in the range:

[LB UB], where, $LB=\min\{-2\kappa_{max}-5(\alpha+\beta),-\kappa_{max}-2(\alpha+\beta)+\kappa_{min}+\beta\}$ $UB=\max\{2\kappa_{max}+5(\alpha+\beta),\kappa_{max}-\kappa_{min}\}$, and $\kappa_{max}\geq 0$ $\kappa_{max}\geq 0$ 1)$\rho(A)+\kappa(B),2)\rho(B)-(\alpha+\beta)$, 3) $\sigma(B)-\beta$, 4)$\rho(C)-(\alpha+\beta)$, 5)$\tau(C)-\beta$ Next, it is shown that the Lemmas 1.2-7.2 apply for the banded overlapping alignment. Therefore, the results extend to the banded overlapping alignment case, as described above in the Banded Overlapping Alignment Section.

A. Lemma 1.2—Lower Bound

Given vertices B=(i,j) and A=(i+1,j), we have $-\alpha-\beta\leq\rho(A)-\rho(B)$, for affine and affine simplified gap score, and $\min\{-\alpha-\beta, \kappa_{min}+\beta\}\leq\rho(A)-\rho(B)$, for modified gap score. Proof: Let row(B)=i and col(B)=j. Also, M denotes modified gap score and AS denotes Affine and simplified gap scores.

1. Case: Row(B)=0 and Col(B)≥0

Vertex set of D(x,y) is $\mathbb{W}=\{(i,j)$, for $0\leq i\leq n$ and $0\leq j\leq m\}$.

B=(t,0), for an integer t, $0\leq t\leq n-1$.

For AMS:

For B, we have $\rho(B)=0$, for all $0\leq t\leq n-1$.

We have A=(t+1,0).

And $\rho(A)=0$, for all $0\leq t\leq n-1$.

Thus, $\rho(A)-\rho(B)=0$, for all $0\leq t\leq n-1$.

2. Case: Row(B)>0 and Col(B)=0

Vertex set of D(x,y) is $\mathbb{W}\{(i,j)$, for $0\leq i\leq n$ and $0\leq j\leq m\}$.

C=(0,t), for an integer t, $0\leq t\leq m$.

$\rho(C)=0$ for all t, as initialized.

We have B=(0,t), for $1<t\leq m$, hence A=(1, t).

For AMS:

$W_{\rho(B)}=((0,0),(0,1), \ldots ,(0,t)=B), t>0.$

For B, we have $\rho(B)=0$.

$B=(i_B,j_B)$ $W=W_{\rho(B)}\star((1,t))$ $\rho(A)\geq \overline{S}_W=\overline{S}_{W_{\rho(B)}}+\hat{\varphi}_1(0t-1)(0,t),(0,t)(1t)=\overline{S}_{W_{\rho(B)}}+h_V=\rho(B)+h_V$ $h_V\leq\rho(A)-\rho(B)$ For A, $h_V=h_v$. For M, $h_V=h$. For S, $h_V=h$.

3. Case: Row(B)>1 and Col(B)>1

Vertex set of D(x,y) is $\mathbb{W}=\{(i,j)$, for $0\leq i\leq n$ and $0\leq j\leq m\}$.

$B = (i_B, j_B)$ $W_{\rho(B)} = ((i_0, j_0), (i_1, j_1), \ldots, (i_s, j_s) = B), s > 1.$ $W = W_{\rho(B)}((i_A, j_A))$ $\rho(A) \geq \overline{S}_W = \overline{S}_{W_{\rho(B)}} + \hat{\varphi}_1((i_{s-1}, j_{s-1})(i_B, j_B), (i_B, j_B)(i_A, j_A))$ $= \overline{S}_{W_{\rho(B)}} + h_u$ $= \rho(B) + h_u$ For affine and simplified gap scores:

$h_u\leq\rho(A)-\rho(B)$

For x∈{d, h, v}, if $(i_{s-1},j_{s-1})(i_B,j_B)\in A^x$, then u=x.

For modified gap score:

For u=d, both $W_{\rho(B)}$ and W may be valid walks in M.

For u=h, both $W_{\rho(B)}$ and W may be valid walks in M.

For u=v, $W_{\rho(B)}$ may be a valid walk in M. But W is not a valid walk in M.

Thus, we need to find a new W.

Below is with modified gap score:

$$\hat{W}_{\rho(B)}((i_l, j_l)) \triangleq ((i_0, j_0), (i_1, j_1), \ldots, (i_l, j_l)), \text{ for } 0 \le l \le s.$$

$$W_{\rho(B)} = \hat{W}_{\rho(B)}((i_{s-1}, j_{s-1}))((i_s, j_s))$$

$$W = \hat{W}_{\rho(B)}((i_{s-1}, j_{s-1}))((i_A, j_A))$$

$$\rho(A) \ge \overline{S}_W = \overline{S}_{\hat{W}_{\rho(B)}((i_{s-1}, j_{s-1}))} + \hat{\varphi}_1((i_{s-2}, j_{s-2})(i_{s-1}, j_{s-1}), (i_{s-1}, j_{s-1})(i_A, j_A))$$

$$= \overline{S}_{\hat{W}_{\rho(B)}((i_{s-1}, j_{s-1}))} + \kappa(x_{i_A}, y_{j_A})$$

$$\rho(B) = \overline{S}_{W_{\rho(B)}}$$

$$= \overline{S}_{\hat{W}_{\rho(B)}((i_{s-1}, j_{s-1}))} + \hat{\varphi}_1((i_{s-2}, j_{s-2})(i_{s-1}, j_{s-1}), (i_{s-1}, j_{s-1})(i_s, j_s))$$

$$\rho(A) - \rho(B) \ge \kappa(x_{i_A}, y_{j_A}) - \hat{\varphi}_1((i_{s-2}, j_{s-2})(i_{s-1}, j_{s-1}), (i_{s-1}, j_{s-1})(i_s, j_s))$$

$$= \kappa(x_{i_A}, y_{j_A}) - v_z$$

$$\kappa(x_{i_A}, y_{j_A}) - v_z \le \rho(A) - \rho(B)$$

if u=v and z=d, then $\kappa(x_{i_A}, y_{j_A}) - v_d \le \rho(A) - \rho(B)$ in M.
if u=v and z=h, then $W_{\rho(B)}$ is not a valid walk in M.
if u=v and z=v and $j_B=2$, then $W_{\rho(B)}$ IS a valid walk in M. And $\kappa(x_{i_A}, y_{j_A}) - v_v \le \rho(A) - \rho(B)$
if u=v and z=v and $j_B>2$, then $\kappa(x_{i_A}, y_{j_A}) - v_v \le \rho(A) - \rho(B)$ in M 4. Case: Row(B)=1 and Col(B)>1

Vertex set of $D(\underline{x}, \underline{y})$ is $\mathbb{V} = \{(i, j), \text{ for } 0 \le i \le n \text{ and } 0 \le j \le m\}$.

$$B = (i_B, j_B)$$

$$W_{\rho(B)} = ((i_0, j_0), (i_1, j_1), \ldots, (i_s, j_s) = B), s > 0.$$

$$W = W_{\rho(B)}((i_A, j_A))$$

$$\rho(A) \ge \overline{S}_W =$$

$$\overline{S}_{W_{\rho(B)}} + \hat{\varphi}_1((i_{s-1}, j_{s-1})(i_B, j_B), (i_B, j_B)(i_A, j_A)) = \overline{S}_{W_{\rho(B)}} + h_u = \rho(B) + h_u$$

$$h_u \le \rho(A) - \rho(B)$$

For $x \in \{d, h, v\}$, if $(i_{s-1}, j_{s-1})(i_B, j_B) \in A^x$, then u=x.

OK for AS

For M:

For u=d, both $W_{\rho(B)}$ and W are valid walks in M.

For u=h, $W_{\rho(B)}$ may be a valid walk in M. And W is a valid walk in M.

For u=v, $W_{\rho(B)}$ IS a valid walk in M.

$$\rho(B) = v$$

$$\rho(A) \ge \kappa(x_{i_A}, y_{j_A})$$

$$\kappa(x_{i_A}, y_{j_A}) - v \le \rho(A) - \rho(B)$$

Thus, we are done with M.

5. Case: Row(B)>1 and Col(B)=1

Vertex set of $D(\underline{x}, \underline{y})$ is $\mathbb{V} = \{(i, j), \text{ for } 0 \le i \le n \text{ and } 0 \le j \le m\}$.

$$B = (i_B, j_B)$$

$$W_{\rho(B)} = ((i_0, j_0), (i_1, j_1), \ldots, (i_s, j_s) = B), s > 0.$$

$$W = W_{\rho(B)}((i_A, j_A))$$

$$\rho(A) \ge \overline{S}_W =$$

$$\overline{S}_{W_{\rho(B)}} + \hat{\varphi}_1((i_{s-1}, j_{s-1})(i_B, j_B), (i_B, j_B)(i_A, j_A)) = \overline{S}_{W_{\rho(B)}} + h_u = \rho(B) + h_u$$

$$h_u \le \rho(A) - \rho(B)$$

For $x \in \{d, h, v\}$, if $(i_{s-1}, j_{s-1})(i_B, j_B) \in A^x$, then u=x.

OK for AS

For M:

For u=d, both $W_{\rho(B)}$ and W are valid walks in M.

For u=h, $W_{\rho(B)}$ IS a valid walk in M. So is and W.

For u=v, $W_{\rho(B)}$ may be a valid walk in M, but W is not a valid walk in M.

Thus, we need to find a valid W.

OK for M except u=v=>$h_v$=>W not a valid walk for $\rho(A)$ in M

Below is in M space:

$$\hat{W}_{\rho(B)}((i_l, j_l)) \triangleq ((0, 0) = (i_0, j_0), (i_1, j_1), \ldots, (i_l, j_l)),$$

for $0 \le l \le s$.

$$W_{\rho(B)} = \hat{W}_{\rho(B)}((i_{s-1}, j_{s-1}))((i_s, j_s))$$

$$W = \hat{W}_{\rho(B)}((i_{s-1}, j_{s-1}))((i_A, j_A))$$

$$\rho(A) \ge \overline{S}_W = \overline{S}_{\hat{W}_{\rho(B)}((i_{s-1}, j_{s-1}))} + \hat{\varphi}_1((i_{s-2}, j_{s-2})(i_{s-1}, j_{s-1})(i_A, j_A)) =$$

$$\overline{S}_{\hat{W}_{\rho(B)}((i_{s-1}, j_{s-1}))} + \kappa(x_{i_A}, y_{j_A})$$

$$\rho(B) = \overline{S}_{W_{\rho(B)}} = \overline{S}_{\hat{W}_{\rho(B)}((i_{s-1}, j_{s-1}))} +$$

$$\hat{\varphi}_1((i_{s-2}, j_{s-2})(i_{s-1}, j_{s-1}), (i_{s-1}, j_{s-1})(i_s, j_s))$$

$$\rho(A) - \rho(B) \ge \kappa(x_{i_A}, y_{j_A}) - \hat{\varphi}_1((i_{s-2}, j_{s-2})(i_{s-1}, j_{s-1}), (i_{s-1}, j_{s-1})(i_s, j_s)) =$$

$$\kappa(x_{i_A}, y_{j_A}) - v_z$$

$$\kappa(x_{i_A}, y_{j_A}) - v_z \le \rho(A) - \rho(B)$$

if $u = v$ and $z = d$, then $\kappa(x_{i_A}, y_{j_A}) - v_d \le \rho(A) - \rho(B)$ in M if u=v and z=h, then $W_{\rho(B)}$ is not a valid walk in M.

if u=v and z=v and $j_B=2$, then $W_{\rho(B)}$ IS a valid walk in M. So is and W.

And $\kappa(x_{i_A}, y_{j_A}) - v_v \le \rho(A) - \rho(B)$.

if u=v and z=v and $j_B>2$, then $\kappa(x_{i_A}, y_{j_A}) - v_v \le \rho(A) - \rho(B)$ in M 6. Case: Row(B)=1 and Col(B)=1

Vertex set of $D(\underline{x}, \underline{y})$ is $\mathbb{V} = \{(i, j), \text{ for } 0 \le i \le n \text{ and } 0 \le j \le m\}$.

$$B = (i_B, j_B)$$

$$W_{\rho(B)} = ((i_0, j_0), (i_1, j_1), \ldots, (i_s, j_s) = B), s > 0.$$

$$W = W_{\rho(B)}((i_A, j_A))$$

$$\rho(A) \ge \overline{S}_W =$$

$$\overline{S}_{W_{\rho(B)}} + \hat{\varphi}_1((i_{s-1}, j_{s-1})(i_B, j_B), (i_B, j_B)(i_A, j_A)) = \overline{S}_{W_{\rho(B)}} + h_u = \rho(B) + h_u$$

$$h_u \le \rho(A) - \rho(B)$$

For $x \in \{d, h, v\}$, if $(i_{s-1}, j_{s-1})(i_B, j_B) \in A^x$, then u=x.

OK for AS

For M:

u=h=>$W_{\rho(B)}$ IS a valid walk in M. So is W.

For u=d, both $W_{\rho(B)}$ and W are valid walks in M. Thus, we are done for M.

For u=v=>$W_{\rho(B)}$ IS a valid walk in M. But W is not and we need a new W. We pick the one reaching A diagonally. Thus, $\kappa(x_{i_A}, y_{j_A})-v_v \leq \rho(A)-\rho(B)$.

Therefore, overall, for AS, min $\{0, h, h_d, h_h, h_v\} \leq \rho(A)-\rho(B)$ $-\alpha-\beta \leq \rho(A)-\rho(B)$ Overall, for M, min$\{-\alpha-\beta, \kappa_{min}+\beta\} \leq \rho(A)-\rho(B)$.

A. Lemma 1.2—Upper Bound

Given vertices B=(i,j) and A=(i+1,j), we have $\rho(A)-\rho(B) \leq \kappa_{max}+\alpha+\beta$, for affine and affine simplified gap score, and $\rho(A)-\rho(B) \leq \kappa_{max}-\kappa_{min}$, for modified gap score.

Proof: Briefly, for every possible walk for $\rho(A)$, we find a walk W(B) of B such that $\rho(A)$–Score of (W(B))≤upper bound.

Step 1) All possible walks for $\rho(A)$:

This section characterized all possible walks for $\rho(A)$, and their corresponding W(B)

In order to find an upper bound to $\rho(A)-\rho(B)$, following cases are considered.

Notations:

row=row of the dark circle in digraph D(x,y).

col=column of the dark circle on digraph D.

ticker lines are possible walks of $\rho(A)$.

thinner lines are possible arcs leading to B.

D, H and V mark a diagonal, horizontal and vertical arc, respectively.

dashed thick lines are invalid for $\rho(A)$ for modified gap score.

dashed thin lines are invalid for certain walks to B for modified gap score.

1. Case 1: Row>1 and Col=2

FIG. 18 shows a table 1800 that for each affine gap function, characterized all pairs of walks that diverge from a vertex in a row>1 and column=2, such that one ends in A and the other ends in B, according to various aspects of the present disclosure. Table 1800 has 4 rows and 6 columns. Note the rows and columns of Table 1800 are different from the row and columns on Digraph D. With reference to FIG. 18, both walks are valid with respect to overlapping alignment with the specific affine gap function.

The second row and fifth column of Table 1800 show portions of three possible walks for $\rho(A)$ for AS. The first portion has the arc H ending on vertex O, followed by a diagonal edge, followed by r (r>=0) vertical arc(s) ending on A. Let's use, P, to denote the walk from the dark circle to A. Let's denote this walk by HP. The second portion has the arc D ending on vertex O, followed by P. Let's denote this walk by DP. The third portion has the arc V ending on vertex O, followed by P. Let's denote this walk by VP. The second row and fifth column of Table 1800 also shows portions of three possible walks ending on B for AS. The first portion has the arc H ending on vertex O, followed by one or more vertical arcs ending on B.

Let's use, Q, to denote the vertical walk from the dark circle to B. Let's denote the first walk by HQ. The second portion has the arc D ending on vertex O, followed by Q. Let's denote this walk by HQ. The third portion has the arc V ending on vertex O, followed by Q. Let's denote this walk by VP. If $\rho(A)$ contains HP, then we will use HQ to obtain an upper bound for $\rho(A)-\rho(B)$. If $\rho(A)$ contains DP, then we will use DQ to obtain an upper bound for $\rho(A)-\rho(B)$. If $\rho(A)$ contains VP, then we will use VQ to obtain an upper bound for $\rho(A)-\rho(B)$.

It should be noted that the fourth and sixth columns of the table are for cases when the dark circle is on vertex (0,0). These cases are not valid for row>1 and col=2.

The third row and fifth column of Table 1800 shows additional portions of three possible walks for $\rho(A)$ for AS.

The first portion has the arc H ending on vertex O, followed by a horizontal edge, followed by r (r>=1) vertical arc(s) ending on A. Let's use, U, to denote the walk from the dark circle to A. Let's denote this walk by HU. The second portion has the arc D ending on vertex O, followed by U. Let's denote this walk by DU. The third portion has the arc V ending on vertex O, followed by U. Let's denote this walk by VU. The third row and fifth column of Table 1800 also shows portions of three possible walks ending on B for AS. The first portion has the arc H ending on vertex O, followed by one or more vertical arcs ending on B.

Let's use, W, to denote the vertical walk from the dark circle to B. Let's denote the first walk by HW. The second portion has the arc D ending on vertex O, followed by W. Let's denote this walk by HW. The third portion has the arc V ending on vertex O, followed by W. Let's denote this walk by VW.

If $\rho(A)$ contains HU, then we will use HW to obtain an upper bound for $\rho(A)-\rho(B)$. If $\rho(A)$ contains DU, then we will use DW to obtain an upper bound for $\rho(A)-\rho(B)$. If $\rho(A)$ contains VU, then we will use VW to obtain an upper bound for $\rho(A)-\rho(B)$.

The fourth row and fifth column of Table 1800 shows yet more portions of three possible walks for $\rho(A)$ for AS. The first portion has the arc H ending on vertex O, followed by a horizontal arc to A. Let's use, X, to denote the arc from the dark circle to A. Let's denote this walk by HX. The second portion has the arc D ending on vertex O, followed by X. Let's denote this walk by DX. The third portion has the arc V ending on vertex O, followed by X. Let's denote this walk by VX. The fourth row and fifth column of Table 1800 also shows portions of three possible walks for $\rho(A)$ for AS.

The first portion has the arc H ending on vertex O, but vertex O and vertex B are the same here. Let's call this walk H. The second portion has the arc D ending on vertex B (O). Let's denote this walk by D. The third portion has the arc V ending on vertex B. Let's denote this walk by V.

If $\rho(A)$ contains HX, then we will use H to obtain an upper bound for $\rho(A)-\rho(B)$. If $\rho(A)$ contains DX, then we will use D to obtain an upper bound for $\rho(A)-\rho(B)$. If $\rho(A)$ contains VX, then we will use V to obtain an upper bound for $\rho(A)-\rho(B)$. The second row and third column of Table 1800 shows the walks HP, DP and VP of $\rho(A)$ for M.

Here, HQ is not a valid walk to reach B since no right angles are allowed. Therefore, for H, we need to find another walk for B, which is valid in M. To this end, the arc H is extended backwards by arcs H1, D1, and V1. Now, H1 is not valid for $\rho(A)$ since col=2 and it would generate a 90 degree turn from the col=0. Also, V1 is not valid for $\rho(A)$ since it is perpendicular to H. But D1 is a valid extension. We demote a walk for $\rho(A)$ that uses H by D1HP, and a walk for B corresponding to D1HP by D1D0Q', where Q' is the walk from the empty circle square to B. If $\rho(A)$ contains D1HP in M, then we will use D1D0Q' to obtain an upper bound for $\rho(A)-\rho(B)$.

The third row and third column of Table 1800 shows the walks HU, DU and VU of $\rho(A)$ for M. Here, U is not a valid walk for $\rho(A)$ for M since it has a right angle turn. Therefore, there are no walks of the type described in this the third row and third column of Table 1800 for ρ(A) for M. The fourth row and third column of Table 1800 also shows portions of three possible walks for ρ(A) for M: HX, DX, and HX. VX is not valid for M because of its right angle. Therefore, If ρ(A) contains HX, then we will use H to obtain an upper bound for ρ(A)−ρ(B). If ρ(A) contains DX, then we will use D to obtain an upper bound for ρ(A)−ρ(B).

The following cases 2-10, are derived as case 1.

2. Case 2: Row>1 and Col>2

FIG. 19 shows a table 1900 that for each affine gap function, characterized all pairs of walks that diverge from a vertex in a row>1 and column>2, such that one ends in A and the other ends in B, according to various aspects of the present disclosure. Both walks are valid with respect to overlapping alignment with the specific affine gap function.

3. Case 3: Row=1 and Col=2

FIG. 20 shows a table 2000 that for each affine gap function, characterized all pairs of walks that diverge from a vertex in a row=1 and column=2, such that one ends in A and the other ends in B, according to various aspects of the present disclosure. Both walks are valid with respect to overlapping alignment with the specific affine gap function.

4. Case 4: Row=1 and Col>2

FIG. 21 shows a table 2100 that for each affine gap function, characterized all pairs of walks that diverge from a vertex in a row=1 and column>2, such that one ends in A and the other ends in B, according to various aspects of the present disclosure. Both walks are valid with respect to overlapping alignment with the specific affine gap function.

5. Case 5: Row>1 and Col=1

FIG. 22 shows a table 2200 that for each affine gap function, characterized all pairs of walks that diverge from a vertex in a row>1 and column=1, such that one ends in A and the other ends in B, according to various aspects of the present disclosure. Both walks are valid with respect to overlapping alignment with the specific affine gap function.

6. Case 6: Row=1 and Col=1

FIG. 23 shows a table 2300 that for each affine gap function, characterized all pairs of walks that diverge from a vertex in a row=1 and column=1, such that one ends in A and the other ends in B, according to various aspects of the present disclosure. Both walks are valid with respect to overlapping alignment with the specific affine gap function.

7. Case 7: Row>0 and Col=0

FIG. 24 shows a table 2400 that for each affine gap function, characterized all pairs of walks that diverge from a vertex in a row=0 and column=0, such that one ends in A and the other ends in B, according to various aspects of the present disclosure. Both walks are valid with respect to overlapping alignment with the specific affine gap function.

8. Case 8: Row=1 and Col>1

FIG. 25 shows a table 2500 that for each affine gap function, characterized all pairs of walks that diverge from a vertex in a row=1 and column>1, such that one ends in A and the other ends in B, according to various aspects of the present disclosure. Both walks are valid with respect to overlapping alignment with the specific affine gap function.

9. Case 9: Row=0 and Col=1

FIG. 26 shows a table 2600 that for each affine gap function, characterized all pairs of walks that diverge from a vertex in a row=0 and column=1, such that one ends in A and the other ends in B, according to various aspects of the present disclosure. Both walks are valid with respect to overlapping alignment with the specific affine gap function.

10. Case 10: Row=0 and Col=0

FIG. 27 shows a table 2700 that for each affine gap function, characterized all pairs of walks that diverge from a vertex in a row=0 and column=0, such that one ends in A and the other ends in B, according to various aspects of the present disclosure. Both walks are valid with respect to overlapping alignment with the specific affine gap function. With reference to FIG. 27, since the dark circle is on vertex (0,0), column 3 and column 5 cases are not valid since all their H, D, and V arcs are invalid. However, column 6 cases are valid, and two of the three cases of the fourth column are valid. For the second row, third and sixth column of Table 2700: FP denotes the ρ(A) walk. And FQ denotes the walk to B. F denotes no tail. For the third row, sixth column: FU denotes the ρ(A) walk. And FW denotes the walk to B. For the fourth row, third and sixth column: FX denotes the ρ(A) walk. And F denotes the walk to B.

Step 2) Tabulation of all possible walks for ρ(A), and their corresponding W(B).

Tables below describes all possible walks for ρ(A), and their corresponding W(B) for AS and M.

AS:

D=diagonal tail, H=horizontal tail, V=vertical tail, and F=no tail.

Based on the tables on pairs of walks on digraph D(x, y), table below gives pairs of walks that are valid for AS. The pairs in bold are not valid.

| 01 | | DP | HP | VP | FP | DU | HU | VU | FU | DX | HX | VX | FX | FY |
|---|---|---|---|---|---|---|---|---|---|---|---|---|---|---|
| R > 1 | | DQ | HQ | VQ | XX | DW | HW | VW | XX | D | H | V | F | |
| C = 2 | | | | | | | | | | | | | | |
| 02 | | DP | HP | VP | FP | DU | HU | VU | FU | DX | HX | VX | FX | FY |
| R > 1 | | DQ | HQ | VQ | XX | DW | HW | VW | XX | D | H | V | F | |
| C > 2 | | | | | | | | | | | | | | |
| 03 | | DP | HP | VP | FP | DU | HU | VU | FU | DX | HX | VX | FX | FY |
| R = 1 | | DQ | HQ | VQ | XX | DW | HW | VW | XX | D | H | V | F | |
| C = 2 | | | | | | | | | | | | | | |
| 04 | | DP | HP | VP | FP | DU | HU | VU | FU | DX | HX | VX | FX | FY |
| R = 1 | | DQ | HQ | VQ | XX | DW | HW | VW | XX | D | H | V | F | |
| C > 2 | | | | | | | | | | | | | | |
| 05 | | DP | HP | VP | FP | DU | HU | VU | FU | DX | HX | VX | FX | FY |
| R > 1 | | DQ | HQ | VQ | XX | DW | HW | VW | XX | D | H | V | F | |
| C = 1 | | | | | | | | | | | | | | |
| 06 | | DP | HP | VP | FP | DU | HU | VU | FU | DX | HX | VX | FX | FY |
| R = 1 | | DQ | HQ | VQ | XX | DW | HW | VW | XX | D | H | V | F | |
| C = 1 | | | | | | | | | | | | | | |
| 07 | | DP | HP | VP | FP | DU | HU | VU | FU | DX | HX | VX | FX | FY |
| R > 0 | | DQ | HQ | VQ | XX | DW | HW | VW | XX | D | H | V | F | |
| C = 0 | | | | | | | | | | | | | | |

-continued

| | | | | | | | | | | | | | |
|---|---|---|---|---|---|---|---|---|---|---|---|---|---|
| 08 R = 0 C > 1 | DP DQ | HP HQ | VP VQ | FP XX | DU DW | HU HW | VU VW | FU XX | DX D | HX H | VX V | FX F | FY |
| 09 R = 0 C = 1 | DP DQ | HP HQ | VP VQ | FP XX | DU DW | HU HW | VU VW | FU XX | DX D | HX H | VX V | FX F | FY |
| 10 R = 0 C = 0 | DP DQ | HP HQ | VP VQ | FP FQ | DU DW | HU HW | VU VW | FU FW | DX D | HX H | VX V | FX F | FY |

M:
Based on the tables on pairs of walks on digraph D(x, y), table below gives pairs of walks that are valid for M. The pairs in bold are not valid.

| | | | | | | | | | | | | | |
|---|---|---|---|---|---|---|---|---|---|---|---|---|---|
| 01 R > 1 C = 2 | DP DQ | HP HQ DHP DDQ' HHP HDQ' VHP XXX | VP VQ | FP XX | DU XX | HU XX | VU XX | FU XX | DX D | HX H | VX V | FX F | FY |
| 02 R > 1 C > 2 | DP DQ | HP HQ DHP DDQ' HHP HDQ' VHP XXX | VP VQ | FP XX | DU XX | HU XX | VU XX | FU XX | DX D | HX H | VX V | FX F | FY |
| 03 R = 1 C = 2 | DP DQ | HP HQ DHP DDQ' HHP HDQ' VHP XXX | VP VQ | FP XX | DU XX | HU XX | VU XX | FU XX | DX D | HX H | VX V | FX F | FY |
| 04 R = 1 C > 2 | DP DQ | HP HQ DHP DDQ' HHP HDQ' VHP XXX | VP VQ | FP XX | DU XX | HU XX | VU XX | FU XX | DX D | HX H | VX V | FX F | FY |
| 05 R > 1 C = 1 | DP DQ | HP HQ HP DQ' | VP VQ | FP XX | DU XX | HU XX | VU XX | FU XX | DX D | HX H | VX V | FX F | FY |
| 06 R = 1 C = 1 | DP DQ | HP HQ HP DQ' | VP VQ | FP XX | DU XX | HU XX | VU XX | FU XX | DX D | HX H | VX V | FX F | FY |
| 07 R > 0 C = 0 | DP DQ | HP HQ | VP VQ | FP XX | DU XX | HU XX | VU XX | FU XX | DX D | HX H | VX V | FX F | FY |
| 08 R = 0 C > 1 | DP DQ | HP HQ DHP DDQ' HHP HDQ' VHP XXX | VP VQ | FP XX | DU XX | HU XX | VU XX | FU XX | DX D | HX H | VX V | FX F | FY |
| 09 R = 0 C = 1 | DP DQ | HP HQ DHP DDQ' HHP HDQ' VHP XXX FHP FDQ' | VP VQ | FP XX | DU XX | HU XX | VU XX | FU XX | DX D | HX H | VX V | FX F | FY |

-continued

| 10 R = 0 C = 0 | DP DQ | HP HQ | VP VQ | FP FQ | DU XX | HU XX | VU XX | FU XX | DX D | HX H | VX V | FX F | FY |

Step 3) The scores of all possible walks for ρ(A), and their corresponding W(B).

This step we calculate the score of all the walk in the tables of step 2).

We start with the following definitions.

Definitions: For $A=(i_A,j_A)$ and $W_{\rho(A)}=((i_0,j_0),(i_1,j_1),\ldots,(i_t,j_t)=A)$, t>0.

$\dot{W}_{\rho(A)}((i_l,j_l)) \triangleq ((i_0,j_0)(i_1,j_1),\ldots,(i_l,j_l))$  0≤l≤t $\ddot{W}_{\rho(A)}((i_l,j_l)) \triangleq ((i_l,j_l),(i_{l+1},j_{l+1}),\ldots,(i_t,j_t)=A)$ 0≤l≤t $P^|((i,j);r) \triangleq ((i,j+1),(i,j+2),\ldots(i,j+r))$  i,j, and r≥0

$P^|((i,j);0) \triangleq (\phi)$ $P^{d|}((i,j);r) \triangleq ((i,j),(i+1,j+1))P^|((i+1,j+1);r)$  i,j, and r≥0

$P^{h|}((i,j);r) \triangleq ((i,j),(i+1,j))P^|((i+1,j);r)$  i,j, and r≥0

$P^f((i,j)) \triangleq ((i,j),(i+1,j))$  i,j≥0

$P^{v|}((i,j);r) \triangleq ((i,j))P^|((i,j);r)$  i,j, and r≥0

$\rho((0,0)) \triangleq 0$

We use $W_1W_2$ and $W_1 \star W_2$ to represent the concatenation of the sequences (or walks) $W_1$ and $W_2$.

Lemma T. Given two walks $W_1$ and $W_2$, $W_1=((i_0,j_0),(i_1,j_1),\ldots,(i_{k-1},j_{k-1}),(i_k,j_k)(i_{k+1},j_{k+1}),(i_{k+2},j_{k+2}),\ldots,(i_p,j_p))$ $W_2=((i'_0,j'_0),(i'_1,j'_1),\ldots,(i'_{k-1},j'_{k-1}),(i'_k,j'_k)(i'_{k+1},j'_{k+1}),(i'_{k+2},j'_{k+2}),\ldots,(i'_p,j'_p))$ that agree in vertices: $(i_m,j_m)=(i'_m,j'_m)$, m≤k, we have $\bar{S}_{W_1}-\bar{S}_{W_2}=\Sigma_{q=k}{}^p(\hat\varphi_1((i_{q-1},j_{q-1})(i_q,j_q),(i_q,j_q)(i_{q+1},j_{q+1}))-\hat\varphi_1((i_{q-1},j_{q-1})(i'_q,j'_q),(i'_q,j'_q)(i'_{q+1},j'_{q+1})))$ The following correspondence is used.

| | |
|---|---|
| (a) | DP |
| (b) | HD |
| (c) | VD |
| (d) | FD |
| (e) | DU |
| (f) | HU |
| (g) | VH |
| (h) | FU |
| (i) | DX |
| (j) | HX |
| (k) | VX |
| (l) | FX |
| (m) | FY |
| (n) | DP |
| (o) | HD |
| (p) | VD |
| (q) | FD |
| (n) | DU |
| (o) | HU |
| (p) | VH |
| (q) | FU |
| (r) | DX |
| (s) | HX |
| (t) | VX |
| (u) | FX |
| (v) | DHP |
| (w) | HHD |
| (x) | VHD |

-continued

| | |
|---|---|
| (y) | FHD |
| A | DDQ' |
| B | HDQ' |
| C | VDQ' |
| D | FDQ' |

More notions are defined to identify the walks of interest.

For AS:
For r≥0, $T_dP^{d|}((i,j);r) \triangleq ((i-1,j-1))P^{d|}((i,j);r)$  (α)

$T_hP^{d|}((i,j);r) \triangleq ((i-1,j))P^{d|}((i,j);r)$  (b)

$T_vP^{d|}((i,j);r) \triangleq ((i,j-1))P^{d|}((i,j);r)$  (c)

$T_\phi P^{d|}((i,j);r) \triangleq (\phi)P^{d|}((i,j);r)$  (d)

For s>0, $T_dP^{d|}((i,j);s) \triangleq ((i-1,j-1))P^{h|}((i,j);s)$  (e)

$T_hP^{d|}((i,j);s) \triangleq ((i-1,j))P^{h|}((i,j);s)$  (f)

$T_vP^{d|}((i,j);s) \triangleq ((i,j-1))P^{h|}((i,j);s)$  (g)

$T_\phi P^{d|}((i,j);s) \triangleq (\phi)P^{h|}((i,j);s)$  (h)

$T_dP^f(i,j) \triangleq T_d((i,j)(i+1,j))$  (i)

$T_hP^f(i,j) \triangleq T_h((i,j)(i+1,j))$  (j)

$T_vP^f(i,j) \triangleq T_v((i,j)(i+1,j))$  (k)

$T_\phi P^f(i,j) \triangleq _v((i,j)(i+1,j))$  (l)

For s=1, $T_\phi P^{v|}((i,j);r) \triangleq (\phi)((i,j))P^|((i,j);s)$  (m)

For s>0, $T_dP^{v|}((i,j);s) \triangleq T_d((i,j))P^|((i,j);s)$  (n)

$T_hP^{v|}((i,j);s) \triangleq T_h((i,j))P^|((i,j);s)$  (o)

$T_vP^{v|}((i,j);s) \triangleq T_v((i,j))P^|((i,j);s)$  (p)

$T_\phi P^{v|}((i,j);s) \triangleq T_\phi((i,j))P^|((i,j);s)$  (q)

$T_d((i,j))$  (r)

$T_h((i,j))$  (s)

$T_v((i,j))$  (t)

$T_\phi((i,j))$  (u)

For M:
For r≥0, $T_dT_dP^{v|}((i,j+1);r) \triangleq T_dT_d((i,j+1))P^|((i,j+1);r)$  (A)

$T_hT_dP^{v|}((i,j+1);r) \triangleq T_hT_d((i,j+1))P^|((i,j+1);r)$  (B)

$T_vT_dP^{v|}((i,j+1);r) \triangleq T_vT_d((i,j+1))P^|((i,j+1);r)$  (C)

$T_\phi T_dP^{v|}((i,j+1);r) \triangleq T_\phi T_d((i,j+1))P^|((i,j+1);r)$  (D)

Below we compute the score of the walks characterized above:

11. Case: i>1, j>1; (a)(b)(c)(d); r≥0

$T_d P^d|((i,j);r) = ((i-1,j-1))P^d|((i,j);r) =$ $((i-1,j-1))((i,j),(i+1,j+1))P^|((i+1,j+1);r) =$ $((i-1,j-1))((i,j),(i+1,j+1))\binom{(i+1,j+1+1),(i+1,j+1+2),}{\ldots (i+1,j+1+r)}$ $\overline{S}_{T_d P^d|((i,j);r)} = \hat{\varphi}_0((i-1,j-1)(i,j)) + \hat{\varphi}_1((i-1,j-1)(i,j),$ $(i,j)(i+1,j+1)) + \hat{\varphi}_1((i,j)(i+1,j+1),(i+1,j+1)(i+1,j+1+1)) +$ $\sum_{q=2}^{r} \hat{\varphi}_1((i+1,j+1+q-2)(i+1,j+1+q-1),$ $(i+1,j+1+q-1)(i+1,j+1+q))$ $\overline{S}_{T_d P^d|((i,j);r)} = \kappa(x_i, y_j) + \kappa(x_{i+1}, y_{j+1}) + \begin{cases} 0 & r=0 \\ v_d + (r-1)v_v & r \geq 1 \end{cases}$ $T_h P^d|((i,j);r) =$ $((i-1,j))P^d|((i,j);r) = ((i-1,j))((i,j),(i+1,j+1))P^|((i+1,j+1);r) =$ $((i-1,j))((i,j),(i+1,j+1))\binom{(i+1,j+1+1),(i+1,j+1+2),}{\ldots (i+1,j+1+r)}$ $\overline{S}_{T_h P^d|((i,j);r)} = \hat{\varphi}_0((i-1,j)(i,j)) + \hat{\varphi}_1((i-1,j)(i,j),(i,j)(i+1,j+1)) +$ $\hat{\varphi}_1((i,j)(i+1,j+1),(i+1,j+1)(i+1,j+1+1)) + \sum_{q=2}^{r} \hat{\varphi}_1((i+1,$ $j+1+q-2)(i+1,j+1+q-1),(i+1,j+1+q-1)(i+1,j+1+q))$ $\overline{S}_{T_h P^d|((i,j);r)} = h + \kappa(x_{i+1}, y_{j+1}) + \begin{cases} 0 & r=0 \\ v_d + (r-1)v_v & r \geq 1 \end{cases}$ $T_h P^d|((i,j);r) =$ $((i-1,j))P^d|((i,j);r) = ((i-1,j))((i,j),(i+1,j+1))P^|((i+1,j+1);r) =$ $((i-1,j))((i,j),(i+1,j+1))\binom{(i+1,j+1+1),(i+1,j+1+2),}{\ldots (i+1,j+1+r)}$ $\overline{S}_{T_v P^d|((i,j);r)} = \hat{\varphi}_0((i,j-1)(i,j)) + \hat{\varphi}_1((i,j-1)(i,j),(i,j)(i+1,j+1)) +$ $\hat{\varphi}_1((i,j)(i+1,j+1),(i+1,j+1)(i+1,j+1+1)) + \sum_{q=2}^{r} \hat{\varphi}_1((i+1,$ $j+1+q-2)(i+1,j+1+q-1),(i+1,j+1+q-1)(i+1,j+1+q))$ $\overline{S}_{T_v P^d|((i,j);r)} = v + \kappa(x_{i+1}, y_{j+1}) + \begin{cases} 0 & r=0 \\ v_d + (r-1)v_v & r \geq 1 \end{cases}$ $T_\phi P^d|((i,j);r) = (\phi)P^d|((i,j);r) = ((i,j),(i+1,j+1))P^|((i+1,j+1);r) =$ $((i,j),(i+1,j+1))((i+1,j+1+1),(i+1,j+1+2),\ldots(i+1,j+1+r))$ $\overline{S}_{T_\phi P^d|((i,j);r)} = \hat{\varphi}_0((i,j)(i+1,j+1)) + \hat{\varphi}_1((i,j)(i+1,j+1),$ $(i+1,j+1)(i+1,j+1+1)) + \sum_{q=2}^{r} \hat{\varphi}_1((i+1,j+1+q-2)$ $(i+1,j+1+q-1),(i+1,j+1+q-1)(i+1,j+1+q))$ $\overline{S}_{T_\phi P^d|((i,j);r)} = \kappa(x_{i+1}, y_{j+1}) + \begin{cases} 0 & \text{if } r=0 \\ v_d + (r-1)v_v & \text{if } r \geq 1 \end{cases}$ 12. Case: i>1, j>1; (e)(f)(g)(h); s>0

$T_d P^h|((i,j);s) =$ $((i-1,j-1))P^h|((i,j);s) = ((i-1,j-1))((i,j),(i+1,j))P^|((i+1,j);s) =$ $((i-1,j-1))((i,j),(i+1,j))(i+1,j+1),(i+1,j+2),\ldots(i+1,j+s))$ $\overline{S}_{T_d P^h|((i,j);s)} = \hat{\varphi}_0((i-1,j-1)(i,j)) + \hat{\varphi}_1((i-1,j-1)(i,j),(i,j)(i+1,j)) +$ $\hat{\varphi}_1((i,j)(i+1,j),(i+1,j)(i+1,j+1)) +$ $\sum_{q=2}^{s} \hat{\varphi}_1((i+1,j+q-2)(i+1,j+q-1),(i+1,j+q-1)(i+1,j+q))$ $\overline{S}_{T_d P^h|((i,j);s)} = \kappa(x_i, y_j) + h_d + \begin{cases} 0 & \text{if } s=0 \\ v_h + (s-1)v_v & \text{if } s \geq 1 \end{cases}$ s=0 not valid since we assumed it is greater than 0.

$T_h P^h|((i,j);s) =$ $((i-1,j))P^h|((i,j);s) = ((i-1,j))((i,j),(i+1,j))P^|((i+1,j);s) =$ $((i-1,j))((i,j),(i+1,j))(i+1,j+1),(i+1,j+2),\ldots(i+1,j+s))$ $\overline{S}_{T_h P^h|((i,j);s)} = \hat{\varphi}_0((i-1,j)(i,j)) + \hat{\varphi}_1((i-1,j)(i,j),(i,j)(i+1,j)) +$ $\hat{\varphi}_1((i,j)(i+1,j),(i+1,j)(i+1,j+1)) +$ $\sum_{q=2}^{s} \hat{\varphi}_1((i+1,j+q-2)(i+1,j+q-1),(i+1,j+q-1)(i+1,j+q))$ $\overline{S}_{T_h P^h|((i,j);s)} = h + h_h + \begin{cases} 0 & \text{if } s=0 \\ v_h + (s-1)v_v & \text{if } s \geq 1 \end{cases}$ s=0 not valid since we assumed it is greater than 0.

$T_v P^h|((i,j);s) =$ $((i,j-1))P^h|((i,j);s) = ((i,j-1))((i,j),(i+1,j))P^|((i+1,j);s) =$ $((i,j-1))((i,j),(i+1,j))(i+1,j+1),(i+1,j+2),\ldots(i+1,j+s))$ $\overline{S}_{T_v P^h|((i,j);s)} = \hat{\varphi}_0((i,j-1)(i,j)) + \hat{\varphi}_1((i,j-1)(i,j),(i,j)(i+1,j)) +$ $\hat{\varphi}_1((i,j)(i+1,j),(i+1,j)(i+1,j+1)) +$ $\sum_{q=2}^{s} \hat{\varphi}_1((i+1,j+q-2)(i+1,j+q-1),(i+1,j+q-1)(i+1,j+q))$ $\overline{S}_{T_v P^h|((i,j);s)} = v + h_v + \begin{cases} 0 & \text{if } s=0 \\ v_h + (s-1)v_v & \text{if } s \geq 1 \end{cases}$ s=0 not valid since we assumed it is greater than 0.

$T_\phi P^h|((i,j);s) = (\phi)P^h|((i,j);s) = ((i,j),(i+1,j))P^|((i+1,j);s) =$ $((i,j),(i+1,j))((i+1,j+1),(i+1,j+2),\ldots(i+1,j+2))$ $\overline{S}_{T_\phi P^h|((i,j);s)} = \hat{\varphi}_0((i,j)(i+1,j)) + \hat{\varphi}_1((i,j)(i+1,j),(i+1,j)(i+1,j+1)) +$ $\sum_{q=2}^{s} \hat{\varphi}_1((i+1,j+q-2)(i+1,j+q-1),(i+1,j+q-1)(i+1,j+q))$ $\overline{S}_{T_\phi P^h|((i,j);s)} = h + \begin{cases} 0 & \text{if } s=0 \\ v_h + (s-1)v_v & \text{if } s \geq 1 \end{cases}$ s=0 not valid since we assumed it is greater than 0.

13. Case: i>1, j>1; (i)(j)(k)(l); No r in this Case.

$P^f((i,j)) \triangleq ((i,j),(i+1,j)),$ for integers, $i \geq 0$ and $j \geq 0$ $T_d P^f((i,j)) \triangleq T_d((i,j)(i+1,j))$ $T_d P^f((i,j)) = T_d((i,j)(i+1,j)) = ((i-1,j-1))((i,j)(i+1,j))$ $\overline{S}_{T_d P^f((i,j))} = \hat{\varphi}_0((i-1,j-1)(i,j)) + \hat{\varphi}_1((i-1,j-1)(i,j),(i,j)(i+1,j))$ $\overline{S}_{T_d P^f((i,j))} = \kappa(x_i, y_j) + h_d$ $T_h P^f((i,j)) \triangleq T_h((i,j)(i+1,j))$ $T_h P^f((i,j)) = T_h((i,j)(i+1,j)) = ((i-1,j))((i,j)(i+1,j))$ -continued $$\overline{S}_{T_h P^f ((i,j))} = \hat{\varphi}_0((i-1,j)(i,j)) + \hat{\varphi}_1((i-1,j)(i,j), (i,j)(i+1,j))$$

$$\overline{S}_{T_h P^f ((i,j))} = h + h_h$$

$$T_v P^f((i,j)) \stackrel{\Delta}{=} T_v((i,j)(i+1,j))$$

$$T_v P^f((i,j)) = T_v((i,j)(i+1,j)) = ((i,j-1))((i,j)(i+1,j))$$

$$\overline{S}_{T_v P^f ((i,j))} = \hat{\varphi}_0((i,j-1)(i,j)) + \hat{\varphi}_1((i,j-1)(i,j), (i,j)(i+1,j))$$

$$\overline{S}_{T_v P^f ((i,j))} = v + h_v$$

$$T_\phi P^f((i,j)) \stackrel{\Delta}{=} T_\phi((i,j)(i+1,j))$$

$$T_\phi P^f((i,j)) = T_\phi((i,j)(i+1,j)) = (\phi)((i,j)(i+1,j)) = ((i,j)(i+1,j))$$

$$\overline{S}_{T_\phi P^f ((i,j))} = \hat{\varphi}_0((i,j)(i+1,j))$$

$$\overline{S}_{T_\phi P^f ((i,j))} = h$$

14. Case: i>1, j>1; (m); r≥1

This is not a valid case for global alignment.

15. Case: i>1, j>1; (n)(o)(p)(q); s≥1

$$T_d P^{v|}((i,j);s) \stackrel{\Delta}{=} T_d((i,j)) P^|((i,j);s)$$

$$T_d P^{v|}((i,j);s) = T_d((i,j)) P^|((i,j);s)$$
$$= ((i-1,j-1))((i,j)) P^|((i,j);s)$$
$$= ((i-1,j-1))((i,j))(i,j+1), (i,j+2), \ldots (i,j+s))$$

$$\overline{S}_{T_d P^{v|}((i,j);s)} =$$
$$\hat{\varphi}_0((i-1,j-1)(i,j)) + \hat{\varphi}_1((i-1,j-1)(i,j), (i,j)(i,j+1)) +$$
$$\sum_{q=2}^{s} \hat{\varphi}_1((i,j+q-2)(i,j+q-1), (i,j+q-1)(i,j+q))$$

$$\overline{S}_{T_d P^{v|}((i,j);s)} = \kappa(x_i, y_j) + v_d + (s-1)v_v, \text{ for } s \geq 1.$$

$$T_h P^{v|}((i,j);s) \stackrel{\Delta}{=} T_h((i,j)) P^|((i,j);s)$$

$$T_h P^{v|}((i,j);s) = T_h((i,j)) P^|((i,j);s)$$
$$= ((i-1,j))((i,j)) P^|((i,j);s)$$
$$= ((i-1,j))((i,j))(i,j+1), (i,j+2), \ldots (i,j+s))$$

$$\overline{S}_{T_h P^{v|}((i,j);s)} = \hat{\varphi}_0((i-1,j)(i,j)) + \hat{\varphi}_1((i-1,j)(i,j), (i,j)(i,j+1)) +$$
$$\sum_{q=2}^{s} \hat{\varphi}_1((i,j+q-2)(i,j+q-1), (i,j+q-1)(i,j+q))$$

$$\overline{S}_{T_h P^{v|}((i,j);s)} = h + v_h + (s-1)v_v, \text{ for } s \geq 1.$$

$$T_v P^{v|}((i,j);s) \stackrel{\Delta}{=} T_v((i,j)) P^|((i,j);s)$$

$$T_v P^{v|}((i,j);s) = T_v((i,j)) P^|((i,j);s)$$
$$= ((i,j-1))((i,j)) P^|((i,j);s)$$
$$= ((i,j-1))((i,j))(i,j+1), (i,j+2), \ldots (i,j+s))$$

$$\overline{S}_{T_v P^{v|}((i,j);s)} = \hat{\varphi}_0((i,j-1)(i,j)) + \hat{\varphi}_1((i,j-1)(i,j), (i,j)(i,j+1)) +$$
$$\sum_{q=2}^{s} \hat{\varphi}_1((i,j+q-2)(i,j+q-1), (i,j+q-1)(i,j+q))$$

$$\overline{S}_{T_v P^{v|}((i,j);s)} = v + v_v + (s-1)v_v, \text{ for } s \geq 1.$$

$$T_\phi P^{v|}((i,j);s) \stackrel{\Delta}{=} (\phi)((i,j)) P^|((i,j);s)$$

$$P^{v|}((i,j);s) \stackrel{\Delta}{=} ((i,j)) P^|((i,j);s)$$

$$T_\phi P^{v|}((i,j);s) = T_\phi((i,j)) P^|((i,j);s)$$
$$= (\phi)((i,j)) P^|((i,j);s)$$
$$= ((i,j))(i,j+1), (i,j+2), \ldots (i,j+s))$$

$$\overline{S}_{T_\phi P^{v|}((i,j);s)} = \hat{\varphi}_0((i,j)(i,j+1)) +$$
$$\sum_{q=2}^{s} \hat{\varphi}_1((i,j+q-2)(i,j+q-1), (i,j+q-1)(i,j+q))$$

$$\overline{S}_{T_\phi P^{v|}((i,j);s)} = v + (s-1)v_v, \text{ for } s \geq 1.$$

16. Case: i>1, j>1; (r)(s)(t)(u)

$T_d((i,j))$          (r)

$T_h((i,j))$          (s)

$T_v((i,j))$          (t)

$T_\phi((i,j))$          (u)

$$\overline{S}_{T_d((i,j))} = \kappa(x_i, y_j)$$

$$\overline{S}_{T_h((i,j))} = h$$

$$\overline{S}_{T_v((i,j))} = v$$

$$\overline{S}_{T_\phi((i,j))} \stackrel{\Delta}{=} 0 \text{ (This does not occur in global alignment.)}$$

17. Case: i>1, j>1; (v)(w)(x)(y); r≥0

$$T_d T_h P^{d|}((i,j);r) \stackrel{\Delta}{=} ((i-2,j-1))((i-1,j)) P^{d|}((i,j);r) \quad (v)$$

$$T_h T_h P^{d|}((i,j);r) \stackrel{\Delta}{=} ((i-2,j))((i-1,j)) P^{d|}((i,j);r) \quad (w)$$

$$T_v T_h P^{d|}((i,j);r) \stackrel{\Delta}{=} ((i-1,j-1))((i-1,j)) P^{d|}((i,j);r) \quad (x)$$

$$T_\phi T_h P^{d|}((i,j);r) \stackrel{\Delta}{=} (\phi)((i-1,j)) P^{d|}((i,j);r) \quad (y)$$

$$T_d T_h P^{d|}((i,j);r) \stackrel{\Delta}{=} ((i-2,j-1))((i-1,j)) P^{d|}((i,j);r)$$

$$T_d T_h P^{d|}((i,j);r) = ((i-2,j-1))((i-1,j)) P^{d|}((i,j);r)$$
$$= ((i-2,j-1))((i-1,j))((i,j), (i+1,j+1) P^|((i+1,j+1);r)$$
$$= ((i-2,j-1))((i-1,j))((i,j), (i+1,j+1)) \binom{(i+1,j+1+1)}{, \ldots (i+1,j+1+r)}$$

$$\overline{S}_{T_d T_h P^{d|}((i,j);r)} =$$
$$\hat{\varphi}_0((i-2,j-1)(i-1,j)) + \hat{\varphi}_1((i-2,j-1)(i-1,j), (i-1,j)(i,j)) +$$
$$\hat{\varphi}_1((i-1,j)(i,j), (i,j)(i+1,j+1)) +$$
$$\hat{\varphi}_1((i,j)(i+1,j+1), (i+1,j+1)(i+1,j+1+1)) +$$
$$\sum_{q=2}^{s} \hat{\varphi}_1((i+1,j+1+q-2)(i+1,j+1+q-1),$$
$$(i+1,j+1+q-1)(i+1,j+1+q))$$

$$\overline{S}_{T_d T_h P^{d|}((i,j);r)} = \kappa(x_{i-1}, y_j) + h_d + \kappa(x_{i+1}, y_{j+1}) + \begin{cases} 0 & r=0 \\ v_d + (r-1)v_v & r \geq 1 \end{cases}$$

$$T_h T_h P^{d|}((i,j);r) \stackrel{\Delta}{=} ((i-2,j))((i-1,j)) P^{d|}((i,j);r)$$

$$T_h T_h P^{d|}((i,j);r) = ((i-2,j))((i-1,j)) P^{d|}((i,j);r)$$
$$= ((i-2,j))((i-1,j))((i,j), (i+1,j+1)) P^|((i+1,j+1);r)$$
$$= ((i-2,j))((i-1,j))((i,j), (i+1,j+1)) \binom{((i+1,j+2), (i+1,j+3)}{, \ldots (i+1,j+1+r)}$$

$$\overline{S}_{T_h T_h P^{d|}((i,j);r)} = \hat{\varphi}_0((i-2,j)(i-1,j)) +$$
$$\hat{\varphi}_1((i-2,j)(i-1,j), (i-1,j)(i,j)) + \hat{\varphi}_1((i-1,j)(i,j), (i,j)(i+1,j+1)) +$$
$$\hat{\varphi}_1((i,j)(i+1,j+1), (i+1,j+1)(i+1,j+1+1)) +$$

-continued $$\sum_{q=2}^{r} \hat{\varphi}_1((i+1, j+1+q-2)(i+1, j+1+q-1),$$

$$(i+1, j+1+q-1)(i+1, j+1+q))$$

$$\overline{S}_{T_h T_h P^d|((i,j);r)} = h + h_h + \kappa(x_{i+1}, y_{j+1}) + \begin{cases} 0 & r = 0 \\ v_d + (r-1)v_v & r \geq 1 \end{cases}$$

$$T_v T_h P^d|((i,j);r) \triangleq ((i-1, j-1))((i-1, j))P^d|((i,j);r)$$

$$T_v T_h P^d|((i,j);r) = ((i-1, j-1))((i-1, j))P^d|((i,j);r)$$

$$= ((i-1, j-1))((i-1, j))((i, j), (i+1, j+1))P^|$$
$$((i+1, j+1);r)$$

$$= ((i-1, j-1))((i-1, j))((i, j), (i+1, j+1))$$
$$\begin{pmatrix} ((i+1, j+2), (i+1, j+3) \\ , \ldots (i+1, j+1+r) \end{pmatrix}$$

$$\overline{S}_{T_v T_h P^d|((i,j);r)} =$$

$$\hat{\varphi}_0((i-1, j-1)(i-1, j)) + \hat{\varphi}_1((i-1, j-1)(i-1, j), (i-1, j)(i, j)) +$$

$$\hat{\varphi}_1((i-1, j)(i, j), (i, j)(i+1, j+1)) +$$

$$\hat{\varphi}_1((i, j)(i+1, j+1), (i+1, j+1)(i+1, j+1+1)) +$$

$$\sum_{q=2}^{r} \hat{\varphi}_1((i+1, j+1+q-2)(i+1, j+1+q-1),$$

$$(i+1, j+1+q-1)(i+1, j+1+q))$$

$$\overline{S}_{T_v T_h P^d|((i,j);r)} = v + h_v + \kappa(x_{i+1}, y_{j+1}) + \begin{cases} 0 & r = 0 \\ v_d + (r-1)v_v & r \geq 1 \end{cases}$$

Not valid in all cases; right angle.

$$T_\phi T_h P^d|((i,j);r) = (\phi)((i-1, j))P^d|((i,j);r)$$

$$= ((i-1, j))((i, j), (i+1, j+1))P^|((i+1, j+1);r)$$

$$= ((i-1, j))((i, j), (i+1, j+1))$$
$$\begin{pmatrix} (i+1, j+1+1), (i+1, j+1+2), \\ \ldots (i+1, j+1+r) \end{pmatrix}$$

$$\overline{S}_{T_\phi T_h P^d|((i,j);r)} = \hat{\varphi}_0((i-1, j)(i, j)) + \hat{\varphi}_1((i-1, j)(i, j), (i, j)(i+1, j+1)) +$$

$$\hat{\varphi}_1((i, j)(i+1, j+1), (i+1, j+1)(i+1, j+1+1)) +$$

$$\sum_{q=2}^{r} \hat{\varphi}_1((i+1, j+1+q-2)(i+1, j+1+q-1),$$

$$(i+1, j+1+q-1)(i+1, j+1+q))$$

$$\overline{S}_{T_\phi T_h P^d|((i,j);r)} = h + \kappa(x_{i+1}, y_{j+1}) + \begin{cases} 0 & r = 0 \\ v_d + (r-1)v_v & r \geq 1 \end{cases}$$

Not valid in all locations for global alignment.
18. Case: i>1, j>1; A, B, C, and d; r≥0

$$T_d T_d P^v|((i, j+1);r) \triangleq T_d T_d((i, j+1))P^|((i, j+1);r) \quad (A)$$

$$T_h T_d P^v|((i, j+1);r) \triangleq T_h T_d((i, j+1))P^|((i, j+1);r) \quad (B)$$

$$T_v T_d P^v|((i, j+1);r) \triangleq T_v T_d((i, j+1))P^|((i, j+1);r) \quad (C)$$

$$T_\phi T_d P^v|((i, j+1);r) \triangleq T_\phi T_d((i, j+1))P^|((i, j+1);r) \quad (D)$$

$$T_d T_d P^v|((i, j+1);r) = ((i-2, j-1))((i-1, j))((i, j+1))P^|((i, j+1);r)$$

$$T_d T_d P^v|((i, j+1);r) = ((i-2, j-1))((i-1, j))P^{v|}((i, j+1);r)$$

$$= ((i-2, j-1))((i-1, j))((i, j+1))P^|((i, j+1);r)$$

$$= ((i-2, j-1))((i-1, j))((i, j+1))((i, j+1+1))$$
$$\begin{pmatrix} (i, j+1+2), \\ \ldots (i, j+1+r) \end{pmatrix}$$

$$\overline{S}_{T_d T_d P^v|((i,j+1);r)} =$$

$$\hat{\varphi}_0((i-2, j-1)(i-1, j)) + \hat{\varphi}_1((i-2, j-1)(i-1, j), (i-j)(i, j+1)) +$$

$$\hat{\varphi}_1((i-1, j)(i, j+1), (i, j+1)(i, j+1+1)) +$$

$$\sum_{q=2}^{r} \hat{\varphi}_1((i, j+1+q-(i, j+1+q-1), (i, j+1+q-1)(i, j+1+q))$$

$$\overline{S}_{T_d T_d P^v|((i,j+1);r)} = \kappa(x_{i-1}, y_j) + \kappa(x_i, y_{j+1}) + \begin{cases} 0 & \text{if } r = 0 \\ v_d + (r-1)v_v & \text{if } r \geq 1 \end{cases}$$

$$T_h T_d P^v|((i, j+1);r) = ((i-2, j))((i-1, j))((i, j+1))P^|((i, j+1);r)$$

$$T_h T_d P^v|((i, j+1);r) = ((i-2, j))((i-1, j))P^{v|}((i, j+1);r)$$

$$= ((i-2, j))((i-1, j))((i, j+1))P^|((i, j+1);r)$$

$$= ((i-2, j))((i-1, j))((i, j+1))((i, j+1+1))$$
$$((i, j+1+2), \ldots (i, j+1+r))$$

$$\overline{S}_{T_h T_d P^v|((i,j+1);r)} =$$

$$\hat{\varphi}_0((i-2, j)(i-1, j)) + \hat{\varphi}_1((i-2, j)(i-1, j), (i-1, j)(i, j+1)) +$$

$$\hat{\varphi}_1((i-1, j)(i, j+1), (i, j+1)(i, j+1+1)) +$$

$$\sum_{q=2}^{r} \hat{\varphi}_1((i, j+1+q-2)(i, j+1+q-1), (i, j+1+q-1)(i, j+1+q))$$

$$\overline{S}_{T_h T_d P^v|((i,j+1);r)} = h + \kappa(x_i, y_{j+1}) + \begin{cases} 0 & \text{if } r = 0 \\ v_d + (r-1)v_v & \text{if } r \geq 1 \end{cases}$$

$$T_v T_d P^v|((i, j+1);r) = T_v T_d((i, j+1))P^|((i, j+1);r)$$

Not valid in M; produces a right angle.

$$T_\phi T_d P^v|((i, j+1);r) \triangleq T_\phi T_d((i, j+1))P^|((i, j+1);r)$$

$$T_\phi T_d P^v|((i, j+1);r) = (\phi)((i-1, j))((i, j+1))P^|((i, j+1);r)$$

$$T_\phi T_d P^v|((i, j+1);r) = ((i-1, j))P^{v|}((i, j+1);r)$$

$$= ((i-1, j))((i, j+1))P^|((i, j+1);r)$$

$$= ((i-1, j))((i, j+1))((i, j+1+1))((i, j+1+2),$$
$$\ldots (i, j+1+r))$$

$$\overline{S}_{T_\phi T_d P^v|((i,j+1);r)} =$$

$$\hat{\varphi}_0((i-1, j)(i, j+1)) + \hat{\varphi}_1((i-1, j)(i, j+1), (i, j+1)(i, j+1+1)) +$$

$$\sum_{q=2}^{r} \hat{\varphi}_1((i, j+1+q-2)(i, j+1+q-1), (i, j+1+q-1)(i, j+1+q))$$

$$\overline{S}_{T_\phi T_d P^v|((i,j+1);r)} = \kappa(x_i, y_{j+1}) + \begin{cases} 0 & \text{if } r = 0 \\ v_d + (r-1)v_v & \text{if } r \geq 1 \end{cases}$$

Step 4) [ρ(A)–Score of W(B)] of all possible walks for ρ(A), and their corresponding W(B).
Difference of score of pairs of pairs: (DP,DQ), (HP,HQ), (VP,VQ), and (FP,FQ)
equivalently pairs: (α)(n), (b)(o), (c)(p), and (d)(q)
for i>1, j>1; r≥0.

$$\overline{S}_{T_d P^d|((i,j);r)} = \kappa(x_i, y_j) + \kappa(x_{i+1}, y_{j+1}) + \begin{cases} 0 & r = 0 \\ v_d + (r-1)v_v & r \geq 1 \end{cases}$$

$$\overline{S}_{T_d P^v|((i,j);s)} = \kappa(x_i, y_j) + v_d + (s-1)v_v, \text{ for } s \geq 1.$$

$$s = r + 1.$$

$$\overline{S}_{T_d P^v|((i,j);r+1)} = \kappa(x_i, y_j) + v_d + (r+1-1)v_v, \text{ for } r+1 \geq 1.$$

$$\overline{S}_{T_d P^v|((i,j);r+1)} = \kappa(x_i, y_j) + v_d + rv_v, \text{ for } r \geq 0.$$

-continued $\overline{S}_{T_d P^d|((i,j);r)} - \overline{S}_{T_d P^v|((i,j);r+1)} = \kappa(x_{i+1}, y_{j+1}) - v_d$, if $r = 0$ $\overline{S}_{T_d P^d|((i,j);r)} - \overline{S}_{T_d P^v|((i,j);r+1)} = \kappa(x_{i+1}, y_{j+1}) - v_v$, if $r \geq 1$ $\overline{S}_{T_h P^d|((i,j);r)} = h + \kappa(x_{i+1}, y_{j+1}) + \begin{cases} 0 & r = 0 \\ v_d + (r-1)v_v & r \geq 1 \end{cases}$ $\overline{S}_{T_h P^v|((i,j);s)} = h + v_h + (s-1)v_v$, for $s \geq 1$.

$s = r + 1$ $\overline{S}_{T_h P^v|((i,j);r+1)} = h + v_h + (r+1-1)v_v$, for $r + 1 \geq 1$.

$\overline{S}_{T_h P^v|((i,j);r+1)} = h + v_h + rv_v$, for $r \geq 0$.

$\overline{S}_{T_h P^d|((i,j);r)} - \overline{S}_{T_h P^v|((i,j);r+1)} = \kappa(x_{i+1}, y_{j+1}) - v_h$, if $r = 0$ $\overline{S}_{T_h P^d|((i,j);r)} - \overline{S}_{T_h P^v|((i,j);r+1)} = \kappa(x_{i+1}, y_{j+1}) + v_d - v_h - v_v$, if $r \geq 1$ $\overline{S}_{T_v P^d|((i,j);r)} = v + \kappa(x_{i+1}, y_{j+1}) + \begin{cases} 0 & r = 0 \\ v_d + (r-1)v_v & r \geq 1 \end{cases}$ $\overline{S}_{T_v P^v|((i,j);s)} = v + v_v + (s-1)v_v$, for $s \geq 1$.

$s = r + 1$ $\overline{S}_{T_v P^v|((i,j);r+1)} = v + v_v + (r+1-1)v_v$, for $r + 1 \geq 1$.

$\overline{S}_{T_v P^v|((i,j);r+1)} = v + v_v + rv_v$, for $r \geq 0$.

$\overline{S}_{T_v P^d|((i,j);r)} - \overline{S}_{T_v P^v|((i,j);r+1)} = \kappa(x_{i+1}, y_{j+1}) - v_v$, if $r = 0$ $\overline{S}_{T_v P^d|((i,j);r)} - \overline{S}_{T_v P^v|((i,j);r+1)} = \kappa(x_{i+1}, y_{j+1}) + v_d - v_v - v_v$, if $r \geq 1$ $\overline{S}_{T_\phi P^d|((i,j);r)} = \kappa(x_{i+1}, y_{j+1}) + \begin{cases} 0 & \text{if } r = 0 \\ v_d + (r-1)v_v & \text{if } r \geq 1 \end{cases}$ $\overline{S}_{T_\phi P^v|((i,j);s)} = v + (s-1)v_v$, for $s \geq 1$.

$s = r + 1$ $\overline{S}_{T_\phi P^v|((i,j);r+1)} = v + (r+1-1)v_v$, for $r + 1 \geq 1$.

$\overline{S}_{T_\phi P^d|((i,j);r)} = v + rv_v$, for $r \geq 0$.

$\overline{S}_{T_\phi P^d|((i,j);r)} - \overline{S}_{T_\phi P^d|((i,j);r)} = \kappa(x_{i+1}, y_{j+1}) - v$, if $r = 0$ $\overline{S}_{T_\phi P^d|((i,j);r)} - \overline{S}_{T_\phi P^d|((i,j);r)} = \kappa(x_{i+1}, y_{j+1}) + v_d - v - v_v$, if $r \geq 1$ Difference of score of pairs of pairs: (DU,DW), (HU, HW), (VU,VW), and (FU,FW)
equivalently pairs: (e)(n), (f)(o), (g)(p), and (h)(q)

for $i > 1, j > 1; r \geq 0$.

$\overline{S}_{T_d P^h|((i,j);r)} = \kappa(x_i, y_j) + h_d + \begin{cases} 0 & \text{if } r = 0 \\ v_h + (r-1)v_v & \text{if } r \geq 1 \end{cases}$ r=0 is not valid since r assumed is to be greater than 0.

$\overline{S}_{T_d P^v|((i,j);r)} = \kappa(x_i, y_j) + v_d + (r-1)v_v$, if $r \geq 1$.

$\overline{S}_{T_d P^h|((i,j);r)} - \overline{S}_{T_d P^v|((i,j);r)} = h_d + v_h - v_d$, if $r \geq 1$.

$\overline{S}_{T_h P^h|((i,j);r)} = h + h_h + \begin{cases} 0 & \text{if } r = 0 \\ v_h + (r-1)v_v & \text{if } r \geq 1 \end{cases}$ r=0 is not valid since r assumed is to be greater than 0.

$\overline{S}_{T_h P^v|((i,j);r)} = h + v_h + (r-1)v_v$, if $r \geq 1$.

$\overline{S}_{T_h P^h|((i,j);r)} - \overline{S}_{T_h P^v|((i,j);r)} = h_h$, if $r \geq 1$.

$\overline{S}_{T_v P^h|((i,j);r)} = v + h_v + \begin{cases} 0 & \text{if } r = 0 \\ v_h + (r-1)v_v & \text{if } r \geq 1 \end{cases}$ r=0 is not valid since r assumed is to be greater than 0.

$\overline{S}_{T_v P^v|((i,j);r)} = v + v_v + (r-1)v_v$, if $r \geq 1$.

$\overline{S}_{T_v P^h|((i,j);r)} - \overline{S}_{T_v P^v|((i,j);r)} = h_v + v_h - v_v$ $\overline{S}_{T_\phi P^h|((i,j);r)} = h + \begin{cases} 0 & \text{if } r = 0 \\ v_h + (r-1)v_v & \text{if } r \geq 1 \end{cases}$ r=0 is not valid since r assumed is to be greater than 0
r≥1 not valid global alignment since walks start from (0,0).

$\overline{S}_{T_\phi P^v|((i,j);r)} = v + (r-1)v_v$, for $r \geq 1$.

$\overline{S}_{T_\phi P^h|((i,j);r)} - \overline{S}_{T_\phi P^v|((i,j);r)} = h + v_h - v$, if $r \geq 1$ Difference of score of pairs of pairs: (DX,D), (HX,H), (VX,V), and (FX,F)
equivalently pairs: (i)(r), (j)(s), (k)(t), and (l)(u)
for $i > 1, j > 1$ $\overline{S}_{T_d P^f(i,j)} = \kappa(x_i, y_j) + h_d$ $\rho(i,j) \geq \overline{S}_{T_d((i,j))} = \kappa(x_i, y_j)$ $\overline{S}_{T_d P^f(i,j)} - \rho(i,j) \leq \kappa(x_i, y_j) + h_d - \kappa(x_i, y_j) = h_d$ $\overline{S}_{T_d P^f(i,j)} - \rho(i,j) \leq h_d$ $\overline{S}_{T_h P^f(i,j)} = h + h_h$ $\rho(i,j) \geq \overline{S}_{T_h((i,j))} = h$ $\overline{S}_{T_h P^f(i,j)} - \rho(i,j)h + h_h - h = h_h$ $\overline{S}_{T_h P^f(i,j)} - \rho(i,j) \leq h_h$ $\overline{S}_{T_v P^f(i,j)} = v + h_v$ $\rho(i,j) \geq \overline{S}_{T_v((i,j))} = v$ $\overline{S}_{T_v P^f(i,j)} - \rho(i,j) \leq v + h_v - v = h_v$ $\overline{S}_{T_v P^f(i,j)} - \rho(i,j) \leq h_v$ $\overline{S}_{T_\phi P^f(i,j)} = h$ $\rho(i,j) \geq \overline{S}_{T_\phi P^f(i,j)} \triangleq$ $\overline{S}_{T_\phi P^f(i,j)} - \rho(i,j) \leq h - 0$ $\overline{S}_{T_\phi P^f(i,j)} - \rho(i,j) \leq h$ Difference of score of pairs of pairs: (DHP,DDQ'), (HHP, HDQ'), (VHP,VDQ'), and (FHP,FDQ')
equivalently pairs: (v)(A), (w)(B), (x)(C), and (y)(D)
for i>1, j>1; r≥0;

$$T_d T_h P^d|((i, j); r) \triangleq ((i-2, j-1))((i-1, j))P^d|((i, j); r) \quad (v)$$

$$T_h T_h P^d|((i, j); r) \triangleq ((i-2, j))((i-1, j))P^d|((i, j); r) \quad (w)$$

$$T_v T_h P^d|((i, j); r) \triangleq ((i-1, j-1))((i-1, j))P^d|((i, j); r) \quad (x)$$

$$T_\phi T_h P^d|((i, j); r) \triangleq (\phi)((i-1, j))P^d|((i, j); r) \quad (y)$$

$$\overline{S}_{T_d T_h P^d|((i,j);r)} = \kappa(x_{i-1}, y_j) + h_d + \kappa(x_{i+1}, y_{j+1}) + \begin{cases} 0 & \text{if } r = 0 \\ v_d + (r-1)v_v & \text{if } r \geq 1 \end{cases}$$

$$\overline{S}_{T_d T_d P^v|((i,j+1);r)} = \kappa(x_{i-1}, y_j) + \kappa(x_i, y_{j+1}) + \begin{cases} 0 & \text{if } r = 0 \\ v_d + (r-1)v_v & \text{if } r \geq 1 \end{cases}$$

$$\overline{S}_{T_d T_h P^d|((i,j);r)} - \overline{S}_{T_d T_d P^v|((i,j+1);r)} = h_d + \kappa(x_{i+1}, y_{j+1}) - \kappa(x_i, y_{j+1}), \text{ for } r \geq 0.$$

$$\overline{S}_{T_h T_h P^d|((i,j);r)} = h + h_h + \kappa(x_{i+1}, y_{j+1}) + \begin{cases} 0 & \text{if } r = 0 \\ v_d + (r-1)v_v & \text{if } r \geq 1 \end{cases}$$

$$\overline{S}_{T_h T_d P^v|((i,j+1);r)} = h + \kappa(x_i, y_{j+1}) + \begin{cases} 0 & \text{if } r = 0 \\ v_d + (r-1)v_v & \text{if } r \geq 1 \end{cases}$$

$$\overline{S}_{T_h T_h P^d|((i,j);r)} - \overline{S}_{T_h T_d P^v|((i,j+1);r)} = h_h + \kappa(x_{i+1}, y_{j+1}) - \kappa(x_i, y_{j+1}), \text{ for } r \geq 0$$

-continued $$\overline{S}_{T_v T_h P^d|((i,j);r)} = v + h_v + \kappa(x_{i+1}, y_{j+1}) + \begin{cases} 0 & \text{if } r = 0 \\ v_d + (r-1)v_v & \text{if } r \geq 1 \end{cases}$$

Not valid in M; v followed by h!

$$T_v T_d P^v|((i, j+1); r) \triangleq T_v T_d((i, j+1))P|((i, j+1); r)$$

$$\overline{S}_{T_\phi T_h P^d|((i,j);r)} = h + \kappa(x_{i+1}, y_{j+1}) + \begin{cases} 0 & r = 0 \\ v_d + (r-1)v_v & r \geq 1 \end{cases}$$

Not-valid overlapping alignment.

$$\overline{S}_{T_\phi T_d P^v|((i,j+1);r)} \triangleq \kappa(x_i, y_{j+1}) + \begin{cases} 0 & r = 0 \\ v_d + (r-1)v_v & r \geq 1 \end{cases}$$

$$\overline{S}_{T_\phi T_h P^v|((i,j+1);r)} - \overline{S}_{T_\phi T_d P^v|((i,j+1);r)} = h + \kappa(x_{i+1}, y_{j+1}) - \kappa(x_i, y_{j+1}),$$

for $r \geq 0$

Step 5) Tabulation of all possible ρ(A)–Score of W(B)
The above results are extended for all valid (i,j) and tabulate the results below.
For AS

| | i = R and j = C | | R > 1<br>C ≥ 2 | R = 1<br>C = 2 | R = 1<br>C > 2 | R > 1<br>C = 1 | R = 1<br>C = 1 | R > 0<br>C = 0 | R = 0<br>C > 1 | R = 0<br>C = 1 | R = 0<br>C = 0 |
|---|---|---|---|---|---|---|---|---|---|---|---|
| 1 | DP<br>DQ | $\overline{S}_{T_d P^d|((i,j),r)} - \overline{S}_{T_d P^v|((i,j),r+1)} =$<br>$\kappa(x_{i+1}, y_{j+1}) - v_d$, if r = 0<br>$\overline{S}_{T_d P^d|((i,j),r)} - \overline{S}_{T_d P^v|((i,j),r+1)} =$<br>$\kappa(x_{i+1}, y_{j+1}) - v_v$, if r ≥ 1 | | | | | | NO | NO | NO | NO |
| 2 | HP<br>HQ | $\overline{S}_{T_h P^d|((i,j),r)} - \overline{S}_{T_h P^v|((i,j),r+1)} =$<br>$\kappa(x_{i+1}, y_{j+1}) - v_h$, if r = 0<br>$\overline{S}_{T_h P^d|((i,j),r)} - \overline{S}_{T_h P^v|((i,j),r+1)} =$<br>$\kappa(x_{i+1}, y_{j+1}) - v_h + v_d - v_v$, if r ≥ 1 | | | | | | NO | | NO | |
| 3 | VP<br>VQ | $\overline{S}_{T_v P^d|((i,j),r)} - \overline{S}_{T_v P^v|((i,j),r+1)} =$<br>$\kappa(x_{i+1}, y_{j+1}) - v_v$, if r = 0<br>$\overline{S}_{T_v P^d|((i,j),r)} - \overline{S}_{T_v P^v|((i,j),r+1)} =$<br>$\kappa(x_{i+1}, y_{j+1}) - v_v + v_d - v_v$, if r ≥ 1 | | | | | | NO | NO | NO | |
| 4 | FP<br>FQ | $\overline{S}_{T_\phi P^d|((i,j),r)} - \overline{S}_{T_\phi P^d|((i,j),r)} =$<br>$\kappa(x_{i+1}, y_{j+1}) - v$, if r = 0<br>$\overline{S}_{T_\phi P^d|((i,j),r)} - \overline{S}_{T_\phi P^d|((i,j),r)} =$<br>$\kappa(x_{i+1}, y_{j+1}) + v_d - v - v_v$, if r ≥ 1 | NO | NO | NO | NO | NO | NO | NO | NO | |
| 5 | DU<br>DW | $\overline{S}_{T_d P^h|((i,j),r)} - \overline{S}_{T_d P^v|((i,j),r)} =$<br>$h_d + v_h - v_d$, if r ≥ 1. | | | | | | NO | NO | NO | NO |
| 6 | HU<br>HW | $\overline{S}_{T_h P^h|((i,j),r)} - \overline{S}_{T_h P^v|((i,j),r)} =$<br>$h_h$, if r ≥ 1. | | | | | | NO | | NO | |
| 7 | VU<br>VW | $\overline{S}_{T_v P^h|((i,j),r)} - \overline{S}_{T_v P^v|((i,j),r)} =$<br>$h_v + v_h - v_v$ if r ≥ 1. | | | | | | NO | NO | NO | |
| 8 | FU<br>FW | $\overline{S}_{T_\phi P^h|((i,j),r)} - \overline{S}_{T_\phi P^v|((i,j),r)} =$<br>$h + v_h - v$, if r ≥ 1 | NO | NO | NO | NO | NO | NO | NO | NO | |
| 9 | DX<br>D | $\overline{S}_{T_d P^f(i,j)} - \overline{S}_{T_d(i,j)} \leq h_d$ | | | | | | | NO | NO | NO | NO |
| 10 | HX<br>H | $\overline{S}_{T_h P^f(i,j)} - \overline{S}_{T_h(i,j)} \leq h_h$ | | | | | | | NO | | NO | |
| 11 | VX<br>V | $\overline{S}_{T_v P^f(i,j)} - \overline{S}_{T_v(i,j)} \leq h_v$ | | | | | | | NO | NO | NO | |
| 12 | FX<br>F | $\overline{S}_{T_\phi P^f(0,0)} - \overline{S}_{T_\phi(0,0)} \leq h$ | NO | NO | NO | NO | NO | NO | NO | NO | |

We note $\overline{S}_{T_\phi(0,0)} = \rho(0,1) = 0$.

For M

M follows AS except in row index 2. The (R,C) values that have NO in row index 2 do not have a valid walk for $\rho(A)$, so they are ignored. But the (R,C) values that have X in row index 2 need a new walk for B since the one used for AS is not valid for M. For these (R,C)'s, we give a valid walk in the next table.

|   | i = R and j = C | | R > 1<br>C ≥ 2 | R = 1<br>C = 2 | R = 1<br>C > 2 | R > 1<br>C = 1 | R = 1<br>C = 1 | R > 0<br>C = 0 | R = 0<br>C > 1 | R = 0<br>C = 1 | R = 0<br>C = 0 |
|---|---|---|---|---|---|---|---|---|---|---|---|
| 1 | DP<br>DQ | $\overline{S}_{T_dP^d}((i,j);r) - \overline{S}_{T_dP^{v'}}((i,j);r+1) =$<br>$\kappa(x_{i+1}, y_{j+1}) - v_d$, if r = 0<br>$\overline{S}_{T_dP^d}((i,j);r) - \overline{S}_{T_dP^{v'}}((i,j);r+1) =$<br>$\kappa(x_{i+1}, y_{j+1}) - v_v$, if r ≥ 1 | | | | | | NO | NO | NO | NO |
| 2 | HP<br>HQ | see table below | X | X | X | X | X | NO | X | X | NO |
| 3 | VP<br>VQ | $\overline{S}_{T_vP^d}((i,j);r) - \overline{S}_{T_vP^{v'}}((i,j);r+1) =$<br>$\kappa(x_{i+1}, y_{j+1}) - v_v$, if r = 0<br>$\overline{S}_{T_vP^d}((i,j);r) - \overline{S}_{T_vP^{v'}}((i,j);r+1) =$<br>$\kappa(x_{i+1}, y_{j+1}) - v_v + v_d - v_v$, if r ≥ 1 | | ~~NO~~ | ~~NO~~ | | | NO | NO | NO | NO |
| 4 | FP<br>FQ | $\overline{S}_{T_\phi P^d}((i,j);r) - \overline{S}_{T_\phi P^{v'}}((i,j);r) =$<br>$\kappa(x_{i+1}, y_{j+1}) - v$, if r = 0<br>$\overline{S}_{T_\phi P^d}((i,j);r) - \overline{S}_{T_\phi P^{v'}}((i,j);r) =$<br>$\kappa(x_{i+1}, y_{j+1}) + v_d - v - v_v$, if r ≥ 1 | NO | NO | NO | NO | NO | NO | NO | NO | NO |
| 5 | DU<br>DW | $\overline{S}_{T_dP^h}((i,j);r) - \overline{S}_{T_dP^{v'}}((i,j);r) =$<br>$h_d + v_h - v_d$, if r ≥ 1. | NO | NO | NO | NO | NO | NO | NO | NO | NO |
| 6 | HU<br>HW | $\overline{S}_{T_hP^h}((i,j);r) - \overline{S}_{T_hP^{v'}}((i,j);r) =$<br>$h_h$, if r ≥ 1. | NO | NO | NO | NO | NO | NO | NO | NO | NO |
| 7 | VU<br>VW | $\overline{S}_{T_vP^h}((i,j);r) - \overline{S}_{T_vP^{v'}}((i,j);r) =$<br>$h_v + v_h - v_v$, if r ≥ 1. | NO | NO | NO | NO | NO | NO | NO | NO | NO |
| 8 | FU<br>FW | $\overline{S}_{T_\phi P^h}((i,j);r) - \overline{S}_{T_\phi P^{v'}}((i,j);r) =$<br>$h + v_h - v$, if r ≥ 1 | NO | NO | NO | NO | NO | NO | NO | NO | NO |
| 9 | DX<br>D | $\overline{S}_{T_dP}(i,j) - \overline{S}_{T_d}(i,j) \le h_d$ | | | | | | NO | NO | NO | NO |
| 10 | HX<br>H | $\overline{S}_{T_hP}(i,j) - \overline{S}_{T_h}(i,j) \le h_h$ | | ~~NO~~ | ~~NO~~ | NO | NO | | | NO | |
| 11 | VX<br>V | $\overline{S}_{T_vP}(i,j) - \overline{S}_{T_v}(i,j) \le h_v$ | NO | NO | NO | NO | NO | NO | NO | NO | |
| 12 | FX<br>F | $\overline{S}_{T_\phi P}(0,0) - \overline{S}_{T_\phi}(0,0) \le h$ | NO | NO | NO | NO | NO | NO | NO | | |

Below, bold font pairs are not valid in M, but the regular font pairs are valid; their score differences are given in the last column. The regular font pairs use a new walks for B, which are valid in M.

| 01<br>R > 1<br>C = 2 | HP<br>HQ<br>DHP<br>DDQ'<br>HHP<br>HDQ'<br>VHP<br>XXX | $\overline{S}_{T_dT_hP^d}((i,j);r) - \overline{S}_{T_dT_dP^{v'}}((i,j);r) = h_d + \kappa(x_{i+1}, y_{j+1}) -$<br>$\kappa(x_i, y_{j+1})$, for r ≥ 0.<br>$\overline{S}_{T_hT_hP^d}((i,j);r) - \overline{S}_{T_hT_dP^{v'}}((i,j);r) = h_h + \kappa(x_{i+1}, y_{j+1}) -$<br>$\kappa(x_i, y_{j+1})$, for r ≥ 0. |
|---|---|---|
| 02<br>R > 1<br>C > 2 | HP<br>HQ<br>DHP<br>DDQ'<br>HHP<br>HDQ'<br>VHP<br>XXX | $\overline{S}_{T_dT_hP^d}((i,j);r) - \overline{S}_{T_dT_dP^{v'}}((i,j);r) = h_d + \kappa(x_{i+1}, y_{j+1}) -$<br>$\kappa(x_i, y_{j+1})$, for r ≥ 0.<br>$\overline{S}_{T_hT_hP^d}((i,j);r) - \overline{S}_{T_hT_dP^{v'}}((i,j);r) = h_h + \kappa(x_{i+1}, y_{j+1}) -$<br>$\kappa(x_i, y_{j+1})$, for r ≥ 0 |
| 03<br>R = 1<br>C = 2 | HP<br>HQ<br>DHP<br>DDQ'<br>HHP<br>HDQ'<br>VHP<br>XXX | $\overline{S}_{T_dT_hP^d}((i,j);r) - \overline{S}_{T_dT_dP^{v'}}((i,j);r) = h_d + \kappa(x_{i+1}, y_{j+1}) -$<br>$\kappa(x_i, y_{j+1})$, for r ≥ 0.<br>$\overline{S}_{T_hT_hP^d}((i,j);r) - \overline{S}_{T_hT_dP^{v'}}((i,j);r) = h_h + \kappa(x_{i+1}, y_{j+1}) -$<br>$\kappa(x_i, y_{j+1})$, for r ≥ 0. |
| 04<br>R = 1<br>C > 2 | HP<br>HQ<br>DHP<br>DDQ'<br>HHP<br>HDQ' | $\overline{S}_{T_dT_hP^d}((i,j);r) - \overline{S}_{T_dT_dP^{v'}}((i,j+1);r) = h_d + \kappa(x_{i+1}, y_{j+1}) -$<br>$\kappa(x_i, y_{j+1})$, for r ≥ 0.<br>$\overline{S}_{T_hT_hP^d}((i,j);r) - \overline{S}_{T_hT_dP^{v'}}((i,j+1);r) = h_h + \kappa(x_{i+1}, y_{j+1}) -$<br>$\kappa(x_i, y_{j+1})$, for r ≥ 0 |
| | VHP<br>XXX | |
| 05<br>R > 1<br>C = 1 | HP<br>HQ<br>HP<br>DQ' | $\overline{S}_{T_hP^d}((i,j);r) - \overline{S}_{T_dP^{v'}}((i,j+1);r) = h + \kappa(x_{i+1}, y_{j+1}) -$<br>$\kappa(x_i, y_{j+1})$, if r ≥ 0 |
| 06<br>R = 1<br>C = 1 | HP<br>HQ<br>HP<br>DQ' | $\overline{S}_{T_hP^d}((i,j);r) - \overline{S}_{T_dP^{v'}}((i,j+1);r) = h + \kappa(x_{i+1}, y_{j+1}) -$<br>$\kappa(x_i, y_{j+1})$, if r ≥ 0 |
| 07<br>R > 0<br>C = 0 | HP<br>HQ | HP<br>HQ |
| 08<br>R = 0<br>C > 1 | HP<br>HQ<br>DHP<br>DDQ'<br>HHP<br>HDQ'<br>VHP<br>XXX | $\overline{S}_{T_hT_hP^d}((i,j);r) - \overline{S}_{T_hT_dP^{v'}}((i,j+1);r) = h_h + \kappa(x_{i+1}, y_{j+1}) -$<br>$\kappa(x_i, y_{j+1})$, for r ≥ 0. |
| 09<br>R = 0<br>C = 1 | HP<br>HQ<br>DHP<br>DDQ'<br>HHP<br>HDQ'<br>VHP<br>XXX<br>FHP<br>FDQ' | $\overline{S}_{T_\phi T_hP^d}((i,j);r) - \overline{S}_{T_\phi T_dP^{v'}}((i,j+1);r) = h + \kappa(x_{i+1}, y_{j+1}) -$<br>$\kappa(x_i, y_{j+1})$, for r ≥ 0 |

-continued

| | | |
|---|---|---|
| 10 | HP | HP |
| R = 0 | HQ | HQ |
| C = 0 | | |

Step 6) An overall upper bound for ρ(A)–Score of W(B) for affine, simplified and modified gap scores.

Next, we maximize the upper bounds in the tables of step 5) using $\kappa_{max}$, and $\kappa_{min}$, where $\kappa_{max}$=max $(\kappa(x_i,y_j))$ and $\kappa_{min}$=min $(\kappa(x_i,y_j))$.

For AS:

| | i = R and j = C | | R > 1, C ≥ 2 | R = 1, C = 2 | R = 1, C > 2 | R > 1, C = 1 | R = 1, C = 1 | R > 0, C = 0 | R = 0, C > 1 | R = 0, C = 1 | R = 0, C = 0 |
|---|---|---|---|---|---|---|---|---|---|---|---|
| 1 | DP DQ | $\overline{S}_{T_dP^d}((i,j);r) - \overline{S}_{T_dP^{vl}}((i,j);r+1) \leq$ $\kappa_{max} - v_d$, if r = 0 $\overline{S}_{T_dP^d}((i,j);r) - \overline{S}_{T_dP^{vl}}((i,j);r+1) \leq$ $\kappa_{max} - v_v$, if r ≥ 1 | | | | | | NO | NO | NO | NO |
| 2 | HP HQ | $\overline{S}_{T_hP^d}((i,j);r) - \overline{S}_{T_hP^{vl}}((i,j);r+1) \leq$ $\kappa_{max} - v_h$, if r = 0 $\overline{S}_{T_hP^d}((i,j);r) - \overline{S}_{T_hP^{vl}}((i,j);r+1) \leq$ $\kappa_{max} - v_h + v_d - v_v$, if r ≥ 1 | | | | | | NO | | NO | |
| 3 | VP VQ | $\overline{S}_{T_vP^d}((i,j);r) - \overline{S}_{T_vP^{vl}}((i,j);r+1) \leq$ $\kappa_{max} - v_v$, if r = 0 $\overline{S}_{T_vP^d}((i,j);r) - \overline{S}_{T_vP^{vl}}((i,j);r+1) \leq$ $\kappa_{max} - v_v + v_d - v_v$, if r ≥ 1 | | | | | | | NO | NO | NO |
| 4 | FP FQ | $\overline{S}_{T_\phi P^d}((i,j);r) - \overline{S}_{T_\phi P^d}((i,j);r) \leq$ $\kappa_{max} - v$, if r = 0 $\overline{S}_{T_\phi P^d}((i,j);r) - \overline{S}_{T_\phi P^d}((i,j);r) \leq$ $\kappa_{max} + v_d - v - v_v$, if r ≥ 1 | NO | NO | NO | NO | NO | NO | NO | | |
| 5 | DU DW | $\overline{S}_{T_dP^h}((i,j);r) - \overline{S}_{T_dP^{vl}}((i,j);r) =$ $h_d + v_h - v_d$, if r ≥ 1. | | | | | | NO | NO | NO | NO |
| 6 | HU HW | $\overline{S}_{T_hP^h}((i,j);r) - \overline{S}_{T_hP^{vl}}((i,j);r) =$ $h_h$, if r ≥ 1. | | | | | | NO | | NO | |
| 7 | VU VW | $\overline{S}_{T_vP^h}((i,j);r) - \overline{S}_{T_vP^{vl}}((i,j);r) =$ $h_v + v_h - v_v$ if r ≥ 1. | | | | | | | NO | NO | NO |
| 8 | FU FW | $\overline{S}_{T_\phi P^h}((i,j);r) - \overline{S}_{T_\phi P^{vl}}((i,j);r) =$ $h + v_h - v$, if r ≥ 1 | NO | NO | NO | NO | NO | NO | NO | | |
| 9 | DX D | $\overline{S}_{T_dP^f}(i,j) - \overline{S}_{T_d}(i,j) \leq h_d$ | | | | | | | NO | NO | NO |
| 10 | HX H | $\overline{S}_{T_hP^f}(i,j) - \overline{S}_{T_h}(i,j) \leq h_h$ | | | | | | NO | | NO | |
| 11 | VX V | $\overline{S}_{T_vP^f}(i,j) - \overline{S}_{T_v}(i,j) \leq h_v$ | | | | | | | NO | NO | |
| 12 | FX F | $\overline{S}_{T_\phi P^f}(0,0) - \overline{S}_{T_\phi}(0,0) \leq h$ | NO | NO | NO | NO | NO | NO | NO | NO | |

For M:

| | i = R and j = C | | R > 1, C ≥ 2 | R = 1, C = 2 | R = 1, C > 2 | R > 1, C = 1 | R = 1, C = 1 | R > 0, C = 0 | R = 0, C > 1 | R = 0, C = 1 | R = 0, C = 0 |
|---|---|---|---|---|---|---|---|---|---|---|---|
| 1 | DP DQ | $\overline{S}_{T_dP^d}((i,j);r) - \overline{S}_{T_dP^{vl}}((i,j);r+1) \leq$ $\kappa_{max} - v_d$, if r = 0 $\overline{S}_{T_dP^d}((i,j);r) - \overline{S}_{T_dP^{vl}}((i,j);r+1) \leq$ $\kappa_{max} - v_v$, if r ≥ 1 | | | | | | NO | NO | NO | NO |
| 2 | HP HQ | see table below | X | X | X | X | X | NO | X | X | NO |
| 3 | VP VQ | $\overline{S}_{T_vP^d}((i,j);r) - \overline{S}_{T_vP^{vl}}((i,j);r+1) \leq$ $\kappa_{max} - v_v$, if r = 0 $\overline{S}_{T_vP^d}((i,j);r) - \overline{S}_{T_vP^{vl}}((i,j);r+1) \leq$ $\kappa_{max} - v_v + v_d - v_v$, if r ≥ 1 | | ~~NO~~ | ~~NO~~ | | | | NO | NO | NO |
| 4 | FP FQ | $\overline{S}_{T_\phi P^d}((i,j);r) - \overline{S}_{T_\phi P^d}((i,j);r) \leq$ $\kappa_{max} - v$, if r = 0 $\overline{S}_{T_\phi P^d}((i,j);r) - \overline{S}_{T_\phi P^d}((i,j);r) \leq$ $\kappa_{max} + v_d - v - v_v$, if r ≥ 1 | NO | NO | NO | NO | NO | NO | NO | | |
| 5 | DU DW | $\overline{S}_{T_dP^h}((i,j);r) - \overline{S}_{T_dP^{vl}}((i,j);r) =$ $h_d + v_h - v_d$, if r ≥ 1. | NO | NO | NO | NO | NO | NO | NO | | |
| 6 | HU HW | $\overline{S}_{T_hP^h}((i,j);r) - \overline{S}_{T_hP^{vl}}((i,j);r) =$ $h_h$, if r ≥ 1. | NO | NO | NO | NO | NO | NO | NO | | |
| 7 | VU VW | $\overline{S}_{T_vP^h}((i,j);r) - \overline{S}_{T_vP^{vl}}((i,j);r) =$ $h_v + v_h - v_v$ if r ≥ 1. | NO | NO | NO | NO | NO | NO | NO | | |
| 8 | FU FW | $\overline{S}_{T_\phi P^h}((i,j);r) - \overline{S}_{T_\phi P^{vl}}((i,j);r) =$ $h + v_h - v$, if r ≥ 1 | NO | NO | NO | NO | NO | NO | NO | | |
| 9 | DX D | $\overline{S}_{T_dP^f}(i,j) - \overline{S}_{T_d}(i,j) \leq h_d$ | | | | | | | NO | NO | NO |
| 10 | HX H | $\overline{S}_{T_hP^f}(i,j) - \overline{S}_{T_h}(i,j) \leq h_h$ | | | | ~~NO~~ | ~~NO~~ | NO | | NO | |
| 11 | VX V | $\overline{S}_{T_vP^f}(i,j) - \overline{S}_{T_v}(i,j) \leq h_v$ | NO | NO | NO | NO | NO | NO | NO | NO | |

| i = R and j = C | R > 1 C ≥ 2 | R = 1 C = 2 | R = 1 C > 2 | R > 1 C = 1 | R = 1 C = 1 | R > 0 C = 0 | R = 0 C > 1 | R = 0 C = 1 | R = 0 C = 0 |
|---|---|---|---|---|---|---|---|---|---|
| 12 FXF $\overline{S}_{T_\phi P^f(0,0)} - \overline{S}_{T_\phi(0,0)} \le h$ | NO | NO | NO | NO | NO | NO | NO | NO | |

M: continues

| 01 R > 1 C = 2 | HP HQ DHP DDQ' HHP HDQ' VHP XXX | $\overline{S}_{T_d T_h P^d((i,j);r)} - \overline{S}_{T_d T_d P^{vl}((i,j+1);r)} \le h_d + \kappa_{max} - \kappa_{min}$, for r ≥ 0. $\overline{S}_{T_h T_h P^d((i,j);r)} - \overline{S}_{T_h T_d P^{vl}((i,j+1);r)} \le h_h + \kappa_{max} - \kappa_{min}$, for r ≥ 0. |
| 02 R > 1 C > 2 | HP HQ DHP DDQ' HHP HDQ' VHP XXX | $\overline{S}_{T_d T_h P^d((i,j);r)} - \overline{S}_{T_d T_d P^{vl}((i,j+1);r)} \le h_d + \kappa_{max} - \kappa_{min}$, for r ≥ 0. $\overline{S}_{T_h T_h P^d((i,j);r)} - \overline{S}_{T_h T_d P^{vl}((i,j+1);r)} \le h_h + \kappa_{max} - \kappa_{min}$, for r ≥ 0 |
| 03 R = 1 C = 2 | HP HQ DHP DDQ' HHP HDQ' VHP XXX | $\overline{S}_{T_d T_h P^d((i,j);r)} - \overline{S}_{T_d T_d P^{vl}((i,j+1);r)} \le h_d + \kappa_{max} - \kappa_{min}$, for r ≥ 0. $\overline{S}_{T_h T_h P^d((i,j);r)} - \overline{S}_{T_h T_d P^{vl}((i,j+1);r)} \le h_h + +\kappa_{max} - \kappa_{min}$, for r ≥ 0. |
| 04 R = 1 C > 2 | HP HQ DHP DDQ' HHP HDQ' VHP XXX | $\overline{S}_{T_d T_h P^d((i,j);r)} - \overline{S}_{T_d T_d P^{vl}((i,j+1);r)} \le h_d + \kappa_{max} - \kappa_{min}$, for r ≥ 0. $\overline{S}_{T_h T_h P^d((i,j);r)} - \overline{S}_{T_h T_d P^{vl}((i,j+1);r)} \le h_h + \kappa_{max} - \kappa_{min}$, for r ≥ 0 |
| 05 R > 1 C = 1 | HP HQ HP DQ' | $\overline{S}_{T_h P^d((i,j);r)} - \overline{S}_{T_d P^{vl}((i,j+1);r)} \le h + \kappa_{max} - \kappa_{min}$, if r ≥ 0 |
| 06 R = 1 C = 1 | HP HQ HP DQ' | $\overline{S}_{T_h P^d((i,j);r)} - \overline{S}_{T_d P^{vl}((i,j+1);r)} \le h + \kappa_{max} - \kappa_{min}$, if r ≥ 0 |
| 07 R > 0 C = 0 | HP HQ | HP HQ |
| 08 R = 0 C > 1 | HP HQ DHP DDQ' HHP HDQ' VHP XXX | $\overline{S}_{T_h T_h P^d((i,j);r)} - \overline{S}_{T_h T_d P^{vl}((i,j+1);r)} \le h_h + \kappa_{max} - \kappa_{min}$, for r ≥ 0 |
| 09 R = 0 C = 1 | HP HQ DHP DDQ' HHP HDQ' VHP XXX FHP FDQ' | $\overline{S}_{T_\phi T_h P^d((i,j);r)} - \overline{S}_{T_\phi T_d P^{vl}((i,j+1);r)} \le h + \kappa_{max} - \kappa_{min}$, for r ≥ 0 |
| 10 R = 0 C = 0 | HP HQ | HP HQ |

Next, upper bound to $\rho(A)-\rho(B)$ is found using the above tables, and the inequality $\rho(A)-\rho(B) \le \overline{S}_{T_d P^d((i,j);r)} - \overline{S}_{T_d P^{vl}((i,j);r+1)}$.

For AS:

$\rho(A) - \rho(B) \le \kappa_{max} - v_d$, if r = 0
$\rho(A) - \rho(B) \le \kappa_{max} - v_v$, if r ≥ 1
$\rho(A) - \rho(B) \le \kappa_{max} - v_h$, if r = 0
$\rho(A) - \rho(B) \le \kappa_{max} - v_h + v_d - v_v$, if r ≥ 1
$\rho(A) - \rho(B) \le \kappa_{max} - v_v$, if r = 0
$\rho(A) - \rho(B) \le \kappa_{max} - v_v + v_d - v_v$, if r ≥ 1
$\rho(A) - \rho(B) \le \kappa_{max} - v$, if r = 0
$\rho(A) - \rho(B) \le \kappa_{max} + v_d - v - v_v$, if r ≥ 1
$\rho(A) - \rho(B) \le h_d + v_h - v_d$, if r ≥ 1.
$\rho(A) - \rho(B) \le h_h$, if r ≥ 1.
$\rho(A) - \rho(B) \le h_v + v_h - v_v$, if r ≥ 1.
$\rho(A) - \rho(B) \le h + v_h - v$, if r ≥ 1
$\rho(A) - \rho(B) \le h_d$
$\rho(A) - \rho(B) \le h_h$
$\rho(A) - \rho(B) \le h_v$
$\rho(A) - \rho(B) \le h$ Therefore, $\rho(A) - \rho(B) \le \max\{M_1, M_2\}$, where $M_1 = \kappa_{max} + \max\{-v_d, -v_h, -v_v, -v, -v_h+v_d-v_v, -v_v+v_d-v_v, -v+v_d-v_v\}$, and $M_2 = \max\{h_d+v_h-v_d, h_v+v_h-v_v, h+v_h-v, h_d, h_h, h_v, h\}$ $M_1 = \kappa_{max} + \max\{-v_d, -v_v, +v_d-v_v\} = \kappa_{max} + \alpha + \beta$ $M_2 = -\beta$ $\max\{M_1, M_2\} = \max\{\kappa_{max}+\alpha+\beta, -\beta\}$.

Thus, $\rho(A)-\rho(B) \le \max\{\kappa_{max}+\alpha+\beta, -\beta\}$, for affine and simplified gap scores.

For M:
Using the two tables above for M, an upper bound for M is derived as follows.
$\rho(A)-\rho(B) \le \max\{\kappa_{max}+\alpha+\beta, -\beta, -\beta+\kappa_{max}-\kappa_{min}\}$ The first two terms, $\{\kappa_{max}+\alpha+\beta, -\beta\}$, in the argument of max are based on walks to B that are the same as in AS, and the last term, $\{-\beta+\kappa_{max}-\kappa_{min}\}$ is based on walks to B in M that are different from ones in AS.

Step 7) Upper bounds when $\kappa_{min} \le 0$ and $\kappa_{max} \ge 0$
Overlapping Alignment

| | affine | modified | simplified |
|---|---|---|---|
| Lemma 1.2 lower bound | $-\alpha - \beta$ | $\min\{-\alpha-\beta, \kappa_{min}+\beta\}$ | $-\alpha-\beta$ |
| Lemma 1.2 upper bound | $\kappa_{max} + \alpha + \beta$ | $\max\{\kappa_{max}+\alpha+\beta, -\beta, -\beta+\kappa_{max}-\kappa_{min}\}$ | $\kappa_{max}+\alpha+\beta$ |

Overlapping Alignment: $\kappa_{min} \le 0$ and $\kappa_{max} \ge 0$

| | affine | modified | simplified |
|---|---|---|---|
| Lemma 1.2 lower bound | $-\alpha - \beta$ | $\min\{-\alpha-\beta, \kappa_{min}+\beta\}$ | $-\alpha-\beta$ |

-continued

| | affine | modified | simplified |
|---|---|---|---|
| Lemma 1.2 upper bound | $\kappa_{max} + \alpha + \beta$ | $\max\{\kappa_{max} + \alpha + \beta, -\beta + \kappa_{max} - \kappa_{min}\}$ | $\kappa_{max} + \alpha + \beta$ |

B. Lemma 2.2—Lower Bound

We are given vertices $C=(i,j)$ and $A=(i,j+1)$, where $\rho(C)$ denotes the best score from $(0,0)$ to C, and $\sigma(A)$ denotes the best score from $(0,0)$ to A, over walks ending with a vertical arc. This lemma shows, $0 \leq \rho(C) - \sigma(A)$, for AS and M gap scores.

Proof:
1. Case 1) $C \neq (0,0)$
We have $A = C + (0,1)$, thus $A \neq (0,0)$, thus it has a $W_{\sigma(A)}$.

$$W_{\sigma(A)} \triangleq ((0,0) = (i_0, j_0), (i_1, j_1), \ldots, (i_{s-1}, j_{s-1}), (i_s, j_s)), \text{ for } s \geq 1$$

$$W_{\sigma(A)} \triangleq ((0,0) = (i_0, j_0), (i_1, j_1), \ldots, (i_{s-1}, j_{s-1}), (i_{s-1}, j_{s-1} + 1)), \text{ for } s \geq 1$$

Subcase 1.a) $s=1$
Not feasible for Case 1).
Subcase 1.b) $s>1$ $$W_{\sigma(A)} \triangleq ((0,0) = (i_0, j_0), (i_1, j_1), \ldots, (i_{s-1}, j_{s-1}), (i_{s-1}, j_{s-1} + 1)), \text{ for } s > 1$$

$$W_{\sigma(A)} = \acute{W}_{\sigma(A)}((i_{s-1}, j_{s-1})) \star ((i_{s-1}, j_{s-1} + 1))$$

if $W_{\sigma(A)}$ belongs to M clearly so does $\acute{W}_{\sigma(A)}((i_{s-1}, j_{s-1}))$.

$$\sigma(A) = \bar{S}_{W_{\sigma(A)}}$$
$$= \bar{S}_{\acute{W}_{\sigma(A)}((i_{s-1}, j_{s-1}))} + \hat{\varphi}_1((i_{s-2}, j_{s-2})(i_{s-1}, j_{s-1}),$$
$$(i_{s-1}, j_{s-1})(i_{s-1}, j_{s-1} + 1))$$

$$\rho(C) \geq \bar{S}_{\acute{W}_{\sigma(A)}((i_{s-1}, j_{s-1}))}$$

$$\rho(C) - \sigma(A) \geq -\hat{\varphi}_1((i_{s-2}, j_{s-2})(i_{s-1}, j_{s-1}), (i_{s-1}, j_{s-1})(i_{s-1}, j_{s-1} + 1))$$
$$\rho(C) - \sigma(A) \geq 0.$$

This also holds for banded case.
Let $\hat{\sigma}(A)$ denote a best path in the band, reaching A with last arc vertical, and let $\hat{\rho}(C)$ denote a best path in the band, reaching C.

Now, if A and C are in the band, then the above argument works when $\sigma(A)$ and $\rho(C)$ are replaced with $\hat{\sigma}(A)$ and $\hat{\rho}(C)$, respectively.

$$W_{\hat{\sigma}(A)} \triangleq ((0,0) = (i_0, j_0), (i_1, j_1), \ldots, (i_{s-1}, j_{s-1}), (i_{s-1}, j_{s-1} + 1)), \text{ for } s > 1$$

$$W_{\hat{\sigma}(A)} = \acute{W}_{\hat{\sigma}(A)}((i_{s-1}, j_{s-1})) \star ((i_{s-1}, j_{s-1} + 1))$$

if $W_{\hat{\sigma}(A)}$ belongs to M clearly so does $\acute{W}_{\hat{\sigma}(A)}((i_{s-1}, j_{s-1}))$.
if $W_{\hat{\sigma}(A)}$ belongs to the band, and C belongs to the band, then so does $\acute{W}_{\hat{\sigma}(A)}((i_{s-1}, j_{s-1}))$.

$$\hat{\sigma}(A) = \bar{S}_{W_{\hat{\sigma}(A)}}$$
$$= \bar{S}_{\acute{W}_{\hat{\sigma}(A)}((i_{s-1}, j_{s-1}))} + \hat{\varphi}_1((i_{s-2}, j_{s-2})(i_{s-1}, j_{s-1}),$$
$$(i_{s-1}, j_{s-1})(i_{s-1}, j_{s-1} + 1))$$

$$\hat{\rho}(C) \geq \bar{S}_{\acute{W}_{\hat{\sigma}(A)}((i_{s-1}, j_{s-1}))}$$

$$\hat{\rho}(C) - \hat{\sigma}(A) \geq -\hat{\varphi}_1((i_{s-2}, j_{s-2})(i_{s-1}, j_{s-1}), (i_{s-1}, j_{s-1})(i_{s-1}, j_{s-1} + 1))$$
$$\hat{\rho}(C) - \hat{\sigma}(A) \geq 0.$$

Case 2) $C = (0,0)$
We have $\rho(C) = 0$ by definition.

$A = (0,1)$
$\sigma(A) = v$
$\rho(C) - \sigma(A) = 0 - v$
$\rho(C) - \sigma(A) > 0.$ Again, the above argument works when $\sigma(A)$ and $\rho(C)$ are replaced with $\hat{\sigma}(A)$ and $\hat{\rho}(C)$, respectively.

C. Lemma 2.2 Upper Bound

We are given vertices $C=(i,j)$ and $A=(i,j+1)$, where $\rho(C)$ denotes the best score from $(0,0)$ to C, and $\sigma(A)$ denotes the best score from $(0,0)$ to A, over walks ending with a vertical arc. This lemma shows, $\rho(C) - \sigma(A) \leq \alpha + \beta$, for AS and $\rho(C) - \sigma(A) \leq \max\{\kappa_{max} - \kappa_{min} + \alpha + \beta, \kappa_{max} - 2\kappa_{min} + \alpha + \beta\}$, for M gap scores.

Proof:
For AS:
1. Case 1) $C \neq (0,0)$
We have $A = C + (0,1)$, thus $A \neq (0,0)$.
Since $C \neq (0,0)$, we have $W_{\rho(C)} \triangleq ((i_0, j_0), (i_1, j_1), \ldots, (i_{s-1}, j_{s-1}), (i_s, j_s))$, for $s \geq 1$.

Define $W \triangleq W_{\rho(C)} * ((i_s, j_s + 1))$ $$\sigma(A) \geq \bar{S}_W = \bar{S}_{W_{\rho(C)} * ((i_s, j_s + 1))} =$$
$$\bar{S}_{W_{\rho(C)}} + \hat{\varphi}_1((i_{s-1}, j_{s-1})(i_s, j_s), (i_s, j_s)(i_s, j_s + 1)) = \rho(C) + v_u$$

If $(i_{s-1}, j_{s-1})(i_s, j_s) \in A^d$, then $u = d$.
If $(i_{s-1}, j_{s-1})(i_s, j_s) \in A^h$, then $u = h$.
If $(i_{s-1}, j_{s-1})(i_s, j_s) \in A^v$, then $u = v$.

$\rho(C) - \sigma(A) \leq -v_u.$

2. Case 2) $C = (0,0)$
We have $\rho(C) = 0$ by definition.

$A = (0,1)$
$\sigma(A) = v$
$\rho(C) - \sigma(A) = 0 - v$
$\rho(C) - \sigma(A) = -v.$ Therefore, $\rho(C) - \sigma(A) \leq \alpha + \beta$.
Now, if A and C are in a band, then the above argument works when $\sigma(A)$ and $\rho(C)$ are replaced with $\hat{\sigma}(A)$ and $\hat{\rho}(C)$, respectively. More specifically, if C and A belong to the band, so do:
1) arc from C to A, and
2) $\bar{S}_{W_{\rho(C)} * ((i_s, j_s + 1))}$
And the argument holds.
For M:
3. Case 1) $C \neq (0,0)$
We have $A = C + (0,1)$, thus $A \neq (0,0)$.
Since $C \neq (0,0)$, we have $W_{\rho(C)} \triangleq ((i_0, j_0), (i_1, j_1), \ldots (i_{s-1}, j_{s-1}), (i_s, j_s))$, for $s \geq 1$.

Subcase 1.a) $(i_{s-1},j_{s-1})(i_s,j_s) \notin A^h$

Define $W \triangleq W_{\rho(C)}*((i_s,j_s+1))$. Claim walk W does not have a horizontal (vertical) arc followed by a vertical (horizontal) arc. Follows from 1) $W_{\rho(C)}$ does not have a horizontal (vertical) arc followed by a vertical (horizontal) arc, and 2) from 1.a) the assumption.

$$\sigma(A) \geq \overline{S}_W = \overline{S}_{W_{\rho(C)}*((i_s,j_s+1))} =$$
$$\overline{S}_{W_{\rho(C)}} + \hat{\varphi}_1((i_{s-1}, j_{s-1})(i_s, j_s), (i_s, j_s)(i_s, j_s+1)) = \rho(C) + v_u$$

If $(i_{s-1},j_{s-1})(i_s,j_s) \in A^d$, then u=d.
If $(i_{s-1},j_{s-1})(i_s,j_s) \in A^v$, then u=v.
It should be noted that $(i_{s-1},j_{s-1})(i_s,j_s) \notin A^h$ because of the 1.a) assumption.

$\rho(C) - \sigma(A) \leq -v_u$.

Subcase 1.b) $(i_{s-1},j_{s-1})(i_s,j_s) \in A^h$
Sub-subcase 1.b.a) $W_{\rho(C)}$ has no diagonal
Case 1) $C \neq (0,0)$
Subcase 1.b) $(i_{s-1},j_{s-1})(i_s,j_s) \in A^h$
Sub-subcase 1.b.a) $W_{\rho(C)}$ has no diagonal $==> W_{\rho(C)} = ((0,0),(0,1),\ldots(0,j_s),(1,j_s),(2,j_s),\ldots,(i_{s-1},j_{s-1}),(i_s,j_s))$ it can't have a 90-degree angle anywhere except with axis.

$==> \rho(C)=0$, if $j_s=0$ $==> \sigma(A) \geq p(C)+v$ $p(C) - \sigma(A) \leq -v$ $==> \rho(C)=h$ if $j_s>0$, and $i_s=1$ $\sigma(A) \geq \kappa(i_s,j_s)+v_d$ $p(C) - \sigma(A) \leq h - \kappa(i_s,j_s) - v_d$ $==> \rho(C)=h+(i_s-1)h_h$ if $j_s>0$, and $i_s>1$ $\sigma(A) \geq h+(i_s-2)h_h+\kappa(i_s,j_s)+v_d$ $p(C) - \sigma(A) \leq h_h - \kappa(i_s,j_s) - v_d$ Sub-subcase 1.b.b) $W_{\rho(C)}$ has a diagonal
4. Case 1) $C \neq (0,0)$
Subcase 1.b) $(i_{s-1},j_{s-1})(i_s,j_s) \in A^h$
Sub-subcase 1.b.b) $W_{\rho(C)}$ has a diagonal $W_{\rho(C)} \triangleq ((0,0)=(i_0,j_0),(i_1,i_1),\ldots,(i_{s-1},j_{s-1}),(i_s,j_s))$, for $s>1$ $i_s=i_{s-1}+1$ $j_s=j_{s-1}$ Based on 1.bb, there is an integer p,
$0 \leq p \leq s-2$, such that for $W_{\rho(C)}=((0,0)=(i_0,j_0),\ldots,(i_p,j_p),(i_{p+1},j_{p+1}),\ldots,(i_{s-1},j_{s-1}),(i_s,j_s))$ we have $i_{q+1}=i_q+1$, for $p \leq q \leq s-1$ $j_{p+1}=j_p+1$ $j_{q+1}=j_q$, for $p+1 \leq q \leq s-1$ thus, $W_{\rho(C)}=((i_0,j_0),\ldots,(i_p,j_p),(i_p+1,j_p+1),(i_p+2,j_p+1),\ldots,(i_p+s-1,j_p+1),(i_p+s,j_p+1))$ We define $W=((i_0,j_0),\ldots,(i_p,j_p),(i_p+1,j_p+1-1),(i_p+2,j_p+1-1),\ldots,(i_p+s-1,j_p+1-1),(i_p+s,j_p+1))\star((i_p+s,j_p+2))$ $\rho(C)=\overline{S}_{W_{\rho(C)}}$ $\sigma(A) \geq \overline{S}_W$ $\rho(C)-\sigma(A) \leq \overline{S}_{W_{\rho(C)}} - \overline{S}_W$ Part 1) p=0

$W_{\rho(C)}=((0,0)=(i_0,j_0),(i_0+1,j_0+1),(i_0+2,j_0+1),\ldots,(i_0+s-1,j_0+1),(i_0+s,j_0+1))$ $\overline{S}_{W_{\rho(C)}}=\hat{\varphi}_0((0,0),(1,1))+\hat{\varphi}_1((0,0)(1,1),(1,1)(2,1))+\sum_{l=3}^{s}\hat{\varphi}_1((l-2,1)(l-1,1),(l-1,1)(l,1))$ $\overline{S}_{W_{\rho(C)}}=\kappa(x_1,y_1)+h_d+(s-2)h_h$ $W=((0,0),(1,1-1),(2,1-1),\ldots,(s-1,1-1),(s,1))\star((s,2))$ $\overline{S}_W=\hat{\varphi}_0((0,0),(1,1-1))+\sum_{l=2}^{s-1}(l-2,0)(l-2+1,1-1),(l-2+1,1-1)(l-2+2,1-1))+\hat{\varphi}_1((s-2,0)(s-2+1,1-1),(s-2+1,1-1)(s-2+2,1))+\hat{\varphi}_1((s-2+1,1-1)(s-2+2,1),(s-2+2,1)(s-2+2,2))$ $\overline{S}_W=h+(s-2)h_h+\kappa(x_s,y_1)+v_d$ $\rho(C)-\sigma(A) \leq \overline{S}_{W_{\rho(C)}} - \overline{S}_W \leq \kappa(x_1,y_1)+h_d+(s-2)h_h-(h+(s-2)h_h+\kappa(x_s,y_1)+v_d)$ $\rho(C)-\sigma(A) \leq \kappa(x_1,y_1)+h_d-h-\kappa(x_s,y_1)-v_d$ Part 2) p>0 AND $(i_{p-1},j_{p-1})(i_p,j_p) \in A^v$ $W_{\rho(C)}=((0,0)=(i_0,j_0),\ldots,(i_p,j_p),(i_p+1,j_p+1),(i_p+2,j_p+1),\ldots,(i_p+s-1,j_p+1),(i_p+s,j_p+1))=\hat{W}_{\hat{\rho}(C)}((i_p,j_p))\star((i_p+1,j_p+1),(i_p+2,j_p+1),\ldots,(i_p+s-1,j_p+1),(i_p+s,j_p+1))$ $\overline{S}_{W_{\rho(C)}}=\overline{S}_{\hat{W}_{\rho(C)}((i_p,j_p))}+\hat{\varphi}_1((i_{p-1},j_{p-1})(i_p,j_p),(i_p,j_p)(i_p+1,j_p+1))+\hat{\varphi}_1((i_p,j_p)(i_p+1,j_p+1),(i_p+1,j_p+1)(i_p+2,j_p+1))+\sum_{l=3}^{s}\hat{\varphi}_1((i_p+l-2,j_p+1)(i_p+l-1,j_p+1),(i_p+l-1,j_p+1)(i_p+l,j_p+1))$ $\overline{S}_{W_{\rho(C)}}=\overline{S}_{\hat{W}_{\rho(C)}((i_p,j_p))}+\kappa(x_{i_p+1},y_{j_p+1})+h_d+(s-2)h_h$ $W=((i_0,j_0),\ldots,(i_p,j_p),(i_p+1,j_p+1-1),(i_p+2,j_p+1-1),\ldots,(i_p+s-1,j_p+1-1),(i_p+s,j_p+1))\star((i_p+s,j_p+2))=\hat{W}_{\rho(C)}((i_p,j_p))\star((i_p+1,j_p+1-1),(i_p+2,j_p+1-1),\ldots,(i_p+s-1,j_p+1-1),(i_p+s,j_p+1))\star((i_p+s,j_p+2))$ $\overline{S}_W=S_{\hat{W}_{\rho(C)}((i_p,j_p))}+\hat{\varphi}_1((i_{p-1},j_{p-1})(i_p,j_p),(i_p,j_p)(i_p+1,j_p))+\sum_{l=2}^{s-1}\hat{\varphi}_1((i_p+l-2,j_p)(i_p-2+1,j_p+1-1),(i_p+l-2+1,j_p+1-1)(i_p+l-2+2,j_p+1-1))+\hat{\varphi}_1((i_p+s-2,j_p)(i_p+s-2+1,j_p+1-1),(i_p+s-2+1,j_p+1-1)(i_p+s-2+2,j_p+1))+\hat{\varphi}_1((i_p+s-2+1,j_p+1-1)(i_p+s-2+2,j_p+1),(i_p+s-2+2,j_p+1)(i_p+s-2+2,j_p+2))$ $\overline{S}_W=\overline{S}_{W_{\rho(C)((i_p,j_p))}}+h_u+(s-2)h_h+\kappa(x_{i_p+s},y_{j_p+1})+v_d$ If $(i_{p-1},j_{p-1})(i_p,j_p) \in A^d$, then u=d.
If $(i_{p-1},j_{p-1})(i_p,j_p) \in A^h$, then u=h.
(If $(i_{p-1},j_{p-1})(i_p,j_p) \in A^v$, then u=v) this does not occur because of the assumption of part 2

$\rho(C)-\sigma(A) \leq \overline{S}_{W_{\rho(C)}} - \overline{S}_W \leq \overline{S}_{\hat{W}_{\rho(C)}((i_p,j_p))}+\kappa(x_{i_p+1},y_{j_p+1})+h_d+(s-2)h_h-(\overline{S}_{\hat{W}_{\rho(C)}((i_p,j_p))}+h_u+(s-2)h_h+\kappa(x_{i_p+s},y_{j_p+1})+v_d)$ $\rho(C)-\sigma(A) \leq \kappa(x_{i_p+1},y_{j_p+1})+h_d-h_u-\kappa(x_{i_p+s},y_{j_p+1})-v_d$ Part 3) p>0 AND $(i_{p-1},j_{p-1})(i_p,j_p) \in A^v$ AND p=1
The arc $(i_{p-1},j_{p-1})(i_p,j_p)$ is the first arc of $W_{\rho(C)}$ since p=1.

$W_{\rho(C)}=((0,0)=(i_0,j_0),\ldots,(i_p,j_p),(i_p+1,j_p+1),(i_p+2,j_p+1),\ldots,(i_p+s-1,j_p+1),(i_p+s,j_p+1))$ $W_{\rho(C)}=((0,0)=(i_0,j_0),\ldots,(i_1,j_1),(i_1+1,j_1+1),(i_1+2,j_1+1),\ldots,(i_1+s-1,j_1+1),(i_1+s,j_1+1))$ $W_{\rho(C)}=((0,0)=(i_0,j_0),(i_1,j_1),(i_1+1,j_1+1),(i_1+2,j_1+1),\ldots,(i_1+s-1,j_1+1),(i_1+s,j_1+1))$ $W_{\rho(C)}=((0,0),(0,1),(1,1+1),(2,1+1),\ldots,(s-1,1+1),(s,1+1))$ $\overline{S}_{W_{\rho(C)}}=\hat{\varphi}_0((0,0),(0,1))+\hat{\varphi}_1((0,0)(0,1),(0,1)(1,2))+\hat{\varphi}_1((0,1)(1,2),(1,2)(2,1+1))+\Sigma_{l=3}^s\hat{\varphi}_1((l-2,2)(l-1,1+1),(l-1,1+1)(l,1+1))$ $\overline{S}_{W_{\rho(C)}}=\kappa(x_1,y_2)+h_d+(s-2)h_h$ The above $\overline{S}_{W_{\rho(C)}}$ differs from global case.
Recall s≥2.

$W=((0,0),(1,1),(1+1,1),(1+2,1),\ldots,(1+s-2,1),(s,2))\star((s,3))$ $W = \begin{cases} ((0,0),(1,1),(2,2))\star((2,3)) & \text{if } s=2 \\ ((0,0),(1,1),(2,1),(3,2))\star((3,3)) & \text{if } s=3 \\ ((0,0),(1,1),(1+1,1),(1+2,1),\ldots,(1+s-2,1),(s,2))*((s,3)) & \text{if } s>3 \end{cases}$ If s=2, then $\overline{S}_W=\hat{\varphi}_0((0,0),(1,1))+\hat{\varphi}_1((0,0)(1,1),(1,1)(2,2))+\hat{\varphi}_1((1,1)(2,2),(2,2)(2,3))$ $\overline{S}_W=\kappa(x_1,y_1)+\kappa(x_2,y_2)+v_d$ If s=3, then $\overline{S}_W=\hat{\varphi}_0((0,0),(1,1))+\hat{\varphi}_1((0,0)(1,1),(1,1)(2,1))+\hat{\varphi}_1((1,1)(2,1),(2,1)(3,2))+\hat{\varphi}_1((2,1)(3,2),(3,2)(3,3))$ $\overline{S}_W=\kappa(x_1,y_1)+h_d+\kappa(x_3,y_2)+v_d$ $((0,0),(1,1),(1+1,1),(1+2,1),\ldots,(1+s-2,1),(s,2))\star((s,3))$ If s>3, then $\overline{S}_W = \hat{\varphi}_0((0,0),(1,1))+\hat{\varphi}_1((0,0)(1,1),(1,1)(2,1))+\sum_{l=3}^{s-1}\hat{\varphi}_1((l-2,1)(l-1,1),(l-1,1)(l,1))+\hat{\varphi}_1((s-2,1)(s-1,1),(s-1,1)(s,2),(s,2)(s,3))$ $\overline{S}_W = \kappa(x_1,y_1)+h_d+(s-3)h_h+\kappa(x_s,y_2)+v_d$ $\overline{S}_{W_{\rho(C)}} = \kappa(x_1,y_2)+h_d+(s-2)h_h$ $\rho(C)-\sigma(A) \leq \overline{S}_{W_{\rho(C)}}-\overline{S}_W =$ $\begin{cases} \kappa(x_1,y_2)+h_d+(s-2)h_h-(\kappa(x_1,y_1)+\kappa(x_2,y_2)+v_d) & \text{if } s=2 \\ \kappa(x_1,y_2)+h_d+(s-2)h_h-(\kappa(x_1,y_1)+h_d+\kappa(x_3,y_2)+v_d) & \text{if } s=3 \\ \kappa(x_1,y_2)+h_d+(s-2)h_h-(\kappa(x_1,y_1)+h_d+(s-3)h_h+\kappa(x_s,y_2)+v_d) & \text{if } s>3 \end{cases}$ $\rho(C)-\sigma(A) \leq \overline{S}_{W_{\rho(C)}}-\overline{S}_W = \begin{cases} \kappa(x_1,y_2)+h_d-(\kappa(x_1,y_1)+\kappa(x_2,y_2)+v_d) & \text{if } s=2 \\ \kappa(x_1,y_2)+h_h-(\kappa(x_1,y_1)+\kappa(x_3,y_2)+v_d) & \text{if } s \geq 3 \end{cases}$ The above bound differs from global case.
Part 4) p>0 AND $(i_{p-1},j_{p-1})(i_p,j_p) \in A^v$ AND p>1
Since p>1, the arc $(i_{p-1},j_{p-1})(i_p,j_p)$ is not the first arc of $W_{\rho(C)}$.

$W_{\rho(C)}=((i_0,j_0),\ldots,(i_p,j_p),(i_p+1,j_p+1),(i_p+2,j_p+1),\ldots,(i_p+s-1,j_p+1),(i_p+s,j_p+1))=\hat{W}_{\rho(C)}$ $((i_{p-1},j_{p-1}))*((i_p,j_p)(i_p+1,j_p+1),(i_p+2,j_p+1),\ldots,(i_p+s-1,j_p+1),(i_p+s,j_p+1))$ Since p>1, we have $\overline{S}_{W_{\rho(C)}}=\overline{S}_{\hat{W}_{\rho(C)}((i_{p-1},j_{p-1}))}+\hat{\varphi}_1((i_{p-2},j_{p-2})(i_{p-1},j_{p-1}),(i_{p-1},j_{p-1})(i_p,j_p))+\varphi_1((i_{p-1},j_{p-1})(i_p,j_p),(i_p,j_p)(i_p+1,j_p+1))+\varphi_1((i_p,j_p)(i_p+1,j_p+1),(i_p+1,j_p+1)(i_p+2,j_p+1))+\Sigma_{l=3}^s\varphi_1((i_p+l-2,j_p+1)(i_p+l-1,j_p+1),(i_p+l,j_p+1))$ $\overline{S}_{W_{\rho(C)}}=\overline{S}_{\hat{W}_{\rho(C)}((i_{p-1},j_{p-1}))}v_u+\kappa(x_{i_p+1},y_{j_p+1})+h_d+(s-2)h_h$ If $(i_{p-2},j_{p-2})(i_{p-1},j_{p-1}) \in A^d$, then u=d.
If $(i_{p-2},j_{p-2})(i_{p-1},j_{p-1}) \in A^h$, then u=h.
If $(i_{p-2},j_{p-2})(i_{p-1},j_{p-1}) \in A^v$, then u=v.
u=h this does not occur because $W_{\rho(C)}$ does not have a horizontal arc followed by a vertical arc due to M.

$W=((i_0,j_0),\ldots,(i_{p-1},j_{p-1}),(i_p+1,j_p),(i_p+2,j_p),(i_p+3,j_p),\ldots,(i_p+s-1,j_p),(i_p+s,j_p+1))*((i_p+s,j_p+2))=$
$\hat{W}_{\rho(C)}((i_{p-1},j_{p-1}))*((i_p+1,j_p),(i_p+2,j_p),\ldots,(i_p+s-1,j_p),(i_p+s,j_p+1))*((i_p+s,j_p+2))$ $\overline{S}_W=\overline{S}_{\hat{W}_{\rho(C)}((i_{p-1},j_{p-1}))}+\hat{\varphi}_1((i_{p-2},j_{p-2})(i_{p-1},j_{p-1}),(i_{p-1},j_{p-1})(i_p+1,j_p))+\hat{\varphi}_1((i_{p-1},j_{p-1})(i_p+1,j_p),(i_p+1,j_p)(i_p+2,j_p))+\Sigma_{l=3}^{s-1}\varphi_1((i_p+l-2,j_p)(i_p+l-1,j_p),(i_p+l-1,j_p)(i_p+l,j_p))+\varphi_1((i_p+s-2,j_p)(i_p+s-1,j_p),(i_p+s-1,j_p)(i_p+s,j_p+1))+\varphi_1((i_p+s-1,j_p)(i_p+s,j_p+1),(i_p+s,j_p+1)(i_p+s,j_p+2))$ $\overline{S}_W=\overline{S}_{\hat{W}_{\rho(C)}((i_{p-1},j_{p-1}))}+\kappa(x_{i_p+1},y_{j_p})+h_d+(s-3)h_h+\kappa(x_{i_p+s},y_{+1})+v_d$ $\rho(C)-\sigma(A) \leq \overline{S}_{W_{\rho(C)}}-\overline{S}_W \leq$
$\overline{S}_{\hat{W}_{\rho(C)}((i_{p-1},j_{p-1}))}v_u+\kappa(x_{i_p+1},y_{j_p+1})+h_d+(s-2)h_h-($
$\overline{S}_{\hat{W}_{\rho(C)}((i_{p-1},j_{p-1}))}+\kappa(x_{i_p+1},y_{j_p})+h_d+(s-3)h_h+\kappa(x_{i_p+s},y_{j_p+1})+v_d)$ $\rho(C)-\sigma(A) \leq v_u+\kappa(x_{i_p+1},y_{j_p+1})+h_h-\kappa(x_{i_p+1},y_{j_p+1})-\kappa(x_{i_p+s},y_{j_p+1})-v_d$ 5. Case 2) C=(0,0)
We have $\rho(C)=0$ by definition.

$A=(0,1)$ $\sigma(A)=v$ $\rho(C)-\sigma(A)=0-v$ $\rho(C)-\sigma(A)=-v.$

An overall upper bound based on the upper bounds above is obtained.

Overlapping Alignment

|  | affine | modified | simplified |
|---|---|---|---|
| Lemma 2.2 lower bound | 0 | 0 | 0 |
| Lemma 2.2 upper bound | $\alpha + \beta$ | $\max\{\alpha + \beta, -\kappa_{min} + \alpha, \kappa_{max} - \kappa_{min} + (\alpha + \beta), \kappa_{max} - 2\kappa_{min} + \alpha\}$ | $\alpha + \beta$ |

Overlapping Alignment: $\kappa_{min} \leq 0$ and $\kappa_{max} \geq 0$

|  | affine | modified | simplified |
|---|---|---|---|
| Lemma 2.2 lower bound | 0 | 0 | 0 |
| Lemma 2.2 upper bound | $\alpha + \beta$ | $\max\{\kappa_{max} - \kappa_{min} + (\alpha + \beta), \kappa_{max} - 2\kappa_{min} + \alpha\}$ | $\alpha + \beta$ |

D. Lemmas 3.2-7.2

Given the upper and lower bounds in Lemmas 1 and 2 for overlapping alignment, four more set of lower and upper bounds are driven. There are six vertices X, Y, A, B, C, and D. A is immediately above C, and X is immediately above A. D is immediately to the right of C, B is immediately to the right of A, and Y is immediately to the right of X.

Proof:
Overlapping Alignment

|  | affine | modified | simplified |
|---|---|---|---|
| Lemma 1.2 lower bound $L_1$ | $-\alpha - \beta$ | $\min\{-\alpha - \beta, \kappa_{min} + \beta\}$ | $-\alpha - \beta$ |
| Lemma 1.2 upper bound $U_1$ | $\kappa_{max} + \alpha + \beta$ | $\max\{\kappa_{max} + \alpha + \beta, -\beta + \kappa_{max} - \kappa_{min}\}$ | $\kappa_{max} + \alpha + \beta$ |

|  | affine | modified | simplified |
|---|---|---|---|
| Lemma 2.2 lower bound $L_2$ | 0 | 0 | 0 |
| Lemma 2.2 upper bound $U_2$ | $\alpha + \beta$ | $\max\{\kappa_{max} - \kappa_{min} + (\alpha + \beta), \kappa_{max} - 2\kappa_{min} + \alpha\}$ | $\alpha + \beta$ |

The rest is exactly the same as the global case.

| Lemma 1.2 | $L_1 \leq \rho(B) - \rho(A) \leq U_1$ |
|  | $L_1 \leq \rho(C) - \rho(A) \leq U_1$ |
| Lemma 2.2 | $L_2 \leq \rho(B) - \sigma(D) \leq U_2$ |
|  | $L_2 \leq \rho(C) - \tau(D) \leq U_2$ |
| Lemma 3.2 | $L_3 = L_1 + L_2 \leq \rho(B) - \sigma(B) \leq U_1 + U_2 = U_3$ |
|  | $L_3 = L_1 + L_2 \leq \rho(C) - \sigma(C) \leq U_1 + U_2 = U_3$ |
| Lemma 4.2 | $-U_1 + L_3 \leq \rho(A) - \sigma(B) \leq -L_1 + U_3$ |
|  | $-U_1 + L_3 \leq \rho(A) - \sigma(C) \leq -L_1 + U_3$ |
| Lemma 5.2 | $-U_1 + L_1 \leq \rho(B) - \rho(C) \leq -L_1 + U_1$ |
|  | $-U_1 + L_1 \leq \rho(B) - \rho(C) \leq -L_1 + U_1$ |

| Lemma 6.2 | $L_1 - U_1 + L_3 \leq \rho(B) - \tau(C) \leq U_1 - L_1 + U_3$ |
|  | $L_1 - U_1 + L_3 \leq \rho(C) - \sigma(B) \leq U_1 - L_1 + U_3$ |

1. Lemma 3.2:

$\rho(B)-\sigma(B)=\rho(B)-\rho(Y)+\rho(Y)-\sigma(B)=L_1+L_2 \leq \rho(B)-\sigma(B) \leq U_1+U_2$ Lemma 4.2:

$(\rho(A)-\sigma(B)=\rho(A)-\rho(B)+\rho(B)-\sigma(B)=-U_1+L_3 \leq \rho(A)-\sigma(B) \leq -L_1+U_3$ Lemma 5.2:

$\rho(B)-\rho(C)=\rho(B)-\rho(A)+\rho(A)-\sigma(C)=-U_1+L_1 \leq \rho(B)-\rho(C) \leq -L_1+U_1$ Lemma 6.2:

$\rho(B)-\tau(C)=\rho(B)-\rho(A)+\rho(A)-\rho(C)+\rho(C)-\sigma(C)=L_1-U_1+L_3 \leq \rho(B)-\tau(C) \leq U_1-L_1+U_3$ For Affine (Gotoh) gap score, the table below is generated based on above results.

Gotoh $L_1=-(\alpha+\beta) \quad U_1=\kappa_{max}+\alpha+\beta, \kappa_{max} \geq 0$ $L_2=0 \quad U_2=(\alpha+\beta)$

| Lemma 1.2 | $-(\alpha + \beta) \leq \rho(B) - \rho(A) \leq \kappa_{max} + (\alpha + \beta)$ |
|  | $-(\alpha + \beta) \leq \rho(C) - \rho(A) \leq \kappa_{max} + (\alpha + \beta)$ |
| Lemma 2.2 | $0 \leq \rho(B) - \sigma(D) \leq (\alpha + \beta)$ |
|  | $0 \leq \rho(C) - \tau(D) \leq (\alpha + \beta)$ |
| Lemma 3.2 | $-(\alpha + \beta) \leq \rho(B) - \sigma(B) \leq \kappa_{max} + 2(\alpha + \beta)$ |
|  | $-(\alpha + \beta) \leq \rho(C) - \sigma(C) \leq \kappa_{max} + 2(\alpha + \beta)$ |
| Lemma 4.2 | $-\kappa_{max} - 2(\alpha + \beta) \leq \rho(A) - \sigma(B) \leq \kappa_{max} + 3(\alpha + \beta)$ |
|  | $-\kappa_{max} - 2(\alpha + \beta) \leq \rho(A) - \sigma(C) \leq \kappa_{max} + 3(\alpha + \beta)$ |
| Lemma 5.2 | $-\kappa_{max} - 2(\alpha + \beta) \leq \rho(B) - \rho(C) \leq \kappa_{max} + 2(\alpha + \beta)$ |
|  | $-\kappa_{max} - 2(\alpha + \beta) \leq \rho(B) - \rho(C) \leq \kappa_{max} + 2(\alpha + \beta)$ |
| Lemma 6.2 | $-\kappa_{max} - 3(\alpha + \beta) \leq \rho(B) - \tau(C) \leq 2\kappa_{max} + 4(\alpha + \beta)$ |
|  | $-\kappa_{max} - 3(\alpha + \beta) \leq \rho(C) - \sigma(B) \leq 2\kappa_{max} + 4(\alpha + \beta)$ |

The above is repeated to obtain Lemma 4.2-6.2 for the simplified and modified versions.

Lemma 7.2: The difference of any pair of values 1)-5) below is in the interval:

[LB UB], where, $LB=\min\{-2\kappa_{max}-5(\alpha+\beta), -\kappa_{max}-2(\alpha+\beta)+\kappa_{min}+\beta\}$ $UB=\max\{2\kappa_{max}+5(\alpha+\beta), \kappa_{max}-\kappa_{min}\}$, and $\kappa_{max} \geq 0$ 1) $\rho(A)+\kappa(B)$
2) $\rho(B)-(\alpha+\beta)$
3) $\sigma(B)-\beta$
4) $\rho(C)-(\alpha+\beta)$
5) $\tau(C)-\beta$ Proof:
Difference of 1) and 2): from Lemmas 1.2-6.2

$(\alpha+\beta) \leq \rho(B)-\rho(A) \leq \kappa_{max}+(\alpha+\beta)$ $-(\alpha+\beta)-(\alpha+\beta)-\kappa(\beta) \leq (\rho(B)-(\alpha+\beta))-(\rho(A)+\kappa(B))+\kappa_{max}+(\alpha+\beta)-(\alpha+\beta)-\kappa(B)$ $-2(\alpha+\beta)-\kappa(B) \leq (\rho(B)-(\alpha+\beta))-(\rho(A)+m) \leq \kappa_{max}-\kappa(B)$ $-2(\alpha+\beta)-\kappa_{max} \leq (\rho(B)-(\alpha+\beta))-(\rho(A)+\kappa(B)) \leq \kappa_{max}-\kappa_{min}$ Difference of 1) and 3): from Lemmas 1.2-6.2

$$-\kappa_{max}-2(\alpha+\beta) \leq \rho(A)-\sigma(B) \leq \kappa_{max}+3(\alpha+\beta)$$

$$-\kappa_{max}-2(\alpha+\beta)+\kappa(B)+\beta \leq (\rho(A)+\kappa(B))-(\sigma(B)-\beta) \leq \kappa_{max}+3(\alpha+\beta)+\kappa(B)+\beta$$

$$-\kappa_{max}-2(\alpha+\beta)+\kappa_{min}+\beta \leq (\rho(A)+\kappa(B))-(\sigma(B)-\beta) \leq 2\kappa_{max}+3(\alpha+\beta)+\beta$$

Difference of 1) and 4): Same as difference of 1) and 2)
Difference of 1) and 5): Same as difference of 1) and 3)
Difference of 2) and 3): from Lemmas 1.2-6.2

$$-(\alpha+\beta) \leq \rho(B)-\sigma(B) \leq \kappa_{max}+2(\alpha+\beta)$$

$$-(\alpha+\beta)-(\alpha+\beta)+\beta \leq (\rho(B)-(\alpha+\beta))-(\sigma(B)-\beta) \leq \kappa_{max}+2(\alpha+\beta)-(\alpha+\beta)+\beta$$

$$-2(\alpha+\beta)+\beta \leq (\rho(B)-(\alpha+\beta))-(\sigma(B)-\beta) \leq \kappa_{max}+(\alpha+\beta)+\beta$$

Difference of 2) and 4): from Lemmas 1.2-6.2

$$-\kappa_{max}-2(\alpha+\beta) \leq \rho(B)-\rho(C) \leq \kappa_{max}+2(\alpha+\beta)$$

$$-\kappa_{max}-2(\alpha+\beta) \leq (\rho(B)-(\alpha+\beta))-(\rho(C)-(\alpha+\beta)) \leq \kappa_{max}+2(\alpha+\beta)$$

$$-\kappa_{max}-2(\alpha+\beta) \leq (\rho(B)-(\alpha+\beta))-(\rho(C)-(\alpha+1)) \leq \kappa_{max}+2(\alpha+\beta)$$

Difference of 2) and 5): from Lemmas 1.2-6.2

$$-\kappa_{max}-3(\alpha+\beta) \leq \rho(B)-\tau(C) \leq 2\kappa_{max}+4(\alpha+\beta)$$

$$-\kappa_{max}-3(\alpha+\beta)-(\alpha+\beta)+\beta \leq (\rho(B)-(\alpha+\beta))-(\tau(C)-\beta) \leq 2\kappa_{max}+4(\alpha+\beta)-(\alpha+\beta)+\beta$$

$$-\kappa_{max}-4(\alpha+\beta)+\beta \leq (\rho(B)-(\alpha+\beta))-(\tau(C)-\beta) \leq 2\kappa_{max}+3(\alpha+\beta)+\beta$$

Difference of 3) and 4): Same as 2) and 5)
Difference of 3) and 5): from Lemmas 1.2-6.2

$$2\kappa_{max}+5(\alpha+\beta) \leq \sigma(B)-\beta-(\tau(C)-\beta)=\sigma(B)-\tau(C) \leq 2\kappa_{max}+5(\alpha+\beta)$$

Difference of 4) and 5): Same as 2) and 3)
An interval that contains all the bounds is [LB UB], where, $$LB=\min\{-2\kappa_{max}-5(\alpha+\beta),-\kappa_{max}-2(\alpha+\beta)+\kappa_{min}+\beta\}$$

$$UB=\max\{2\kappa_{max}+5(\alpha+\beta),\kappa_{max}-\kappa_{min}\}, \text{and } \kappa_{max} \geq 0$$

Lemma 7.2 is repeated for simplified and modified similarly.

The bound for values 1)-5) that include the score of the arcs is used.

A similar bound may be used for values 1')-5') that do not include the score of the arcs. The overall expressions in of the recursion must be reduced to a modulus based on the bound used.

1') $\rho(A)$
2') $\rho(B)$
3') $\sigma(B)$
4') $\rho(C)$
5') $\tau(C)$

V. Banded Overlapping Alignment Proof

The proof for the banded global alignment applies to the overlapping alignment case for affine and simplified gaps scores. It should be noted that in both global and overlapping alignment it is assumed that (0, 0) belongs to the BAND.

For modified gap score the following is provided for the banded overlapping alignment. The main difference between banded overlapping and banded global is that the banded overlapping has few more cases in the derivation of the Lemma 1.2 upper bound. Specifically, the walks HHP, VP and HP cover HDQ', VQ and DQ', respectively (except B which is assumed to be in the band). Recall that Walk W1 covers a walk W2, if diagonals that pass vertices of W2 also pass-through vertices of W1. Recall. By a diagonal it means vertices (i,j) such that i+j equal a constant.

VI. Abridged Proof of Local Alignments According to the Present Invention

Here Lemma i.3, i=1-7 are used that are given below. Note Lemmas 1.3-7.3 of the local alignment are different than Lemmas 1.1-7.1 of the global alignment. Lemmas 1.1-7.1 of the global alignment are in files with names starting with 'Global' and Lemmas 1.3-7.3 of the local alignment are in files with names starting with 'local'.

Two vertices A and B are given, A is to the immediate right of B. In Lemma 1.3-lower bound, as described above for local-Lemma 1.3 lower bound, a lower bound is found for $\rho(A)-\rho(B)$, for each of the affine, simplified and modified versions.

In Lemma 1.3-upper bound, as described above for Local-Lemma 1.3 upper bound, an upper bound is found for $\rho(A)-\rho(B)$, for each of the affine, simplified and modified versions.

There are given two vertices A and C, A is immediately below C.

In Lemma 2.3-Lower bound, as described above for local-Lemma 2.3 lower bound, a lower bound is found for $\rho(C)-\sigma(A)$, for each of the affine, simplified and modified versions.

In Lemma 2.3-Upper bound, as described above for local Lemma 2.3 upper bound, an upper bound is found for $\rho(C)-\sigma(A)$, for each of the affine, simplified and modified versions.

Using Lemmas 1.3 and 2.3 results Lemma 3.3-6.3 is obtained for affine, simplified and modified cases, as described above with reference to local-Lemmas 3.3-7.3.

Using Lemmas 1.3-6.3 a bound is generate for modulus operation for affine (Gotoh) algorithm in Lemma 7.3, as described below.

Difference of any pair of values from 1)-5) falls in the range:

[LB UB], where, $$LB=\min\{-2\kappa_{max}-5(\alpha+\beta),-\kappa_{max}-2(\alpha+\beta)+\kappa_{min}+\beta\}$$

$$UB=\max\{2\kappa_{max}+5(\alpha+\beta),\kappa_{max}-\kappa_{min}\}, \text{and } \kappa_{max} \geq 0$$

1) $\rho(A)+\kappa(B)$
2) $\rho(B)-(\alpha+\beta)$
3) $\sigma(B)-\beta$
4) $\rho(C)-(\alpha+\beta)$
5) $\tau(C)-\beta$ Proof of Lemma 7.3 is provided below.

Next, it is shown that the Lemmas 1.3-7.3 apply for the banded local alignment. Therefore, the results extend to the banded local alignment case, as described above with reference to Banded Local Condition Section.

It should be noted that: (1) The local algorithm may be shown to run modular scores if we can null negative scores. (2) The method of the present embodiments for local alignment may be modified to perform the following. During application of the recursion equations for each vertex, it additionally performs finding the location of a vertex with maximal score along a path travelled to reach the current vertex, then it stores both the location and the score. These values are used at the to find the location and score of a vertex with an overall maximal score. There is no need to keep these values for all vertices. Once they are processed for the adjacent vertices they can be erased, except we need to keep them for relevant boundary vertices-those without a follower vertex. (3) To shorten the disclosure, we have not focused on specific terminating conditions for the alignments. These may be accomplished by someone skilled in the art, mostly based on existing methods.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented, and may be performed in any order(s). Further, steps that have been presented as being performed separately may in alternative embodiments be performed concurrently. Likewise, steps that have been presented as being performed concurrently may in alternative embodiments be performed separately.

A. Lemma 1.3—Lower Bound

Given vertices $B=(i,j)$ and $A=(i+1,j)$, we have $-\alpha-\beta \leq \rho(A)-\rho(B)$, for affine and affine simplified gap score, and $\min\{-\alpha-\beta, \kappa_{min}+\beta\} \leq \rho(A)-\rho(B)$, for modified gap score. Proof: Let $row(B)=i$ and $col(B)=j$. Also, M denotes modified gap score and AS denotes Affine and simplified gap scores.

1. Case: $Row(B)=0$ and $Col(B) \geq 0$

Vertex set of $D(\underline{x},\underline{y})$ is $\mathbb{V} = \{(i,j), \text{ for } 0 \leq i \leq n \text{ and } 0 \leq j \leq m\}$.

$B=(t,0)$, for an integer t, $0 \leq t \leq n-1$, hence $A=(t+1,0)$.

If $t=0$ then $B=(0,0)$ $A=(1,0)$ $\rho(B)=0$

Let walk W be $((0,0), (1,0))$.

$\rho(A) \geq \overline{S}_W = \hat{\varphi}_0((0,0), (1,0))$
$= h$

Therefore, $h \leq \rho(A)-\rho(B)$.
But if $0 < t \leq n-1$ then $B=(t,0)$ $A=(t+1,0)$ Now, $W_{\rho(B)}$ has length 1 by Lemma WT. Thus $W_{\rho(B)}=((t-1,0), (t,0))$, so $\rho(B) = \overline{S}_{W_{\rho(B)}}$
$= \hat{\varphi}_0((t-1,0), (t,0))$
$= h$ Similarly, $W_{\rho(A)}$ has length 1 by Lemma WT. Thus $W_{\rho(A)}=((t,0), (t+1,0))$, so $\rho(A) = \overline{S}_{W_{\rho(A)}}$
$= \hat{\varphi}_0((t,0), (t+1,0))$
$= h$ Therefore, $0 = \rho(A)-\rho(B)$.
Holds for AMS good for all cases.
Case: $row(B) > 0$ and $col(B)=0$
Vertex set of $D(\underline{x},\underline{y})$ is $\mathbb{V} = \{(i,j), \text{ f or } 0 \leq i \leq n \text{ and } 0 \leq j \leq m\}$.
We have $B=(0,t)$, for $1 < t \leq m$, hence $A=(1, t)$.
Now, $W_{\rho(B)}$ has length 1 by Lemma WT. Thus $W_{\rho(B)}=((0,t-1), (0,t))$, so $\rho(B) = \overline{S}_{W_{\rho(B)}}$
$= \hat{\varphi}_0((0, t-1), (0, t))$
$= v$ Also, since A NOT (0,0), we have $\rho(A) \geq \max(\{\kappa(x_1,y_t), h, v\})$ Therefor, $\rho(A)-\rho(B) \geq v-v=0$.

$0 \leq \rho(A)-\rho(B)$

Holds for AMS, good for all cases.
Case: $row(B) > 1$ and $col(B) > 1$
Vertex set of $D(\underline{x},\underline{y})$ is $\mathbb{V} = \{(i,j), \text{ for } 0 \leq i \leq n \text{ and } 0 \leq j \leq m\}$.

$B = (i_B, j_B)$ $W_{\rho(B)} = ((i_0, j_0), (i_1, j_1), \ldots, (i_s, j_s) = B), s > 0$.

$W = W_{\rho(B)}((i_A, j_A))$ $\rho(A) \geq \overline{S}_W = \overline{S}_{W_{\rho(B)}} + \hat{\varphi}_1((i_{s-1}, j_{s-1})(i_B, j_B), (i_B, j_B)(i_A, j_A))$
$= \overline{S}_{W_{\rho(B)}} + h_u$
$= \rho(B) + h_u$ $h_u \leq \rho(A) - \rho(B)$ If $(i_{s-1},j_{s-1})(i_B,j_B) \in A^d$, then $u=d$.
If $(i_{s-1},j_{s-1})(i_B,j_B) \in A^h$, then $u=h$.
If $(i_{s-1},j_{s-1})(i_B,j_B) \notin A^v$, then $u=v$.
OK for AS
OK for M except $u=v \Rightarrow h_v \Rightarrow W$ not a valid walk for $\rho(A)$ in M Below is in M space:
two cases:
1) s=1

$$W_{\rho(B)}((i_0,j_0),(i_s,j_s))=B$$

$$\rho(B)=v$$

$$\rho(A) \geq \max(\{\kappa(x_{i_A}, y_{j_A}), h, v\}) \text{ [SINCE } A \text{ IS NOT } (0,0)\text{]}$$

$$\rho(A) \geq v$$

$$0 \leq \rho(A) - \rho(B)$$

2) s>1

$$\hat{W}_{\rho(B)}((i_l, j_l)) \triangleq ((i_0,j_0),(i_1,j_1),\ldots,(i_l,j_l)), \text{ for } 0 \leq l \leq s.$$

$$W_{\rho(B)} = \hat{W}_{\rho(B)}((i_{s-1},j_{s-1}))(i_s,j_s)$$

$$W = \hat{W}_{\rho(B)}((i_{s-1},j_{s-1}))((i_A,j_A))$$

$$\rho(A) \geq \bar{S}_W = \bar{S}_{\hat{W}_{\rho(B)}((i_{s-1},j_{s-1}))} +$$
$$\hat{\varphi}_1((i_{s-2}, j_{s-2})(i_{s-1}, j_{s-1}), (i_{s-1}, j_{s-1})(i_A, j_A))$$
$$= \bar{S}_{\hat{W}_{\rho(B)}((i_{s-1},j_{s-1}))} + \kappa(x_{i_A}, y_{j_A})$$

$$\rho(B) = \bar{S}_{W_{\rho(B)}}$$
$$= \bar{S}_{\hat{W}_{\rho(B)}((i_{s-1},j_{s-1}))} +$$
$$\hat{\varphi}_1((i_{s-2}, j_{s-2})(i_{s-1}, j_{s-1}), (i_{s-1}, j_{s-1})(i_s, j_s))$$

$$\rho(A) - \rho(B) \geq \kappa(x_{i_A}, y_{j_A}) - \hat{\varphi}_1((i_{s-2}, j_{s-2})(i_{s-1}, j_{s-1}), (i_{s-1}, j_{s-1})(i_s, j_s)) = \kappa(x_{i_A}, y_{j_A}) - v_z$$

$$\kappa(x_{i_A}, y_{j_A}) - v_z \leq \rho(A) - \rho(B)$$

If $(i_{s-2},j_{s-2})(i_{s-1},j_{s-1}) \in A^d$, then z=d.
If $(i_{s-2},j_{s-2})(i_{s-1},j_{s-1}) \in A^h$, then z=h. $W_{\rho(B)}$ is not a valid walk in M. (unless $j_B$=1, which is not.)
If $(i_{s-2},j_{s-2})(i_{s-1},j_{s-1}) \in A^v$, then z=v.
Case: row(B)=1 and col(B)>1
Vertex set of D(x,y) is $\mathbb{V}$ ={(i,j), for 0≤i≤n and 0≤j≤m}.

$$B=(i_B, j_B)$$

$$W_{\rho(B)}=((i_0,j_0),(i_1,j_1),\ldots,(i_s,j_s))=B, s>0.$$

$$W=W_{\rho(B)}(i_A,j_A)$$

$$\rho(A) \geq \bar{S}_W = \bar{S}_{W_{\rho(B)}} + \hat{\varphi}_1((i_{s-1}, j_{s-1})(i_B, j_B), (i_B, j_B)(i_A, j_A))$$
$$= \bar{S}_{W_{\rho(B)}} + h_u$$
$$= \rho(B) + h_u$$

$$h_u \leq \rho(A) - \rho(B)$$

If $(i_{s-1},j_{s-1})(i_B,j_B) \in A^d$, then u=d.
If $(i_{s-1},j_{s-1})(i_B,j_B) \in A^h$, then u=h.
If $(i_{s-1},j_{s-1})(i_B,j_B) \in A^v$, then u=v.
OK for AS
OK for M except u=v=>h$_v$=>W not a valid walk for ρ(A) in M
Below is in M space:
two cases:
1) s=1

$$W_{\rho(B)}=((i_0,j_0),(i_s,j_s))=B$$

$$\rho(B)=v$$

$$\rho(A) \geq \max(\{\kappa(x_{i_A}, y_{j_A}), h, v\}) \text{ [SINCE } A \text{ IS NOT } (0,0)\text{]}$$

$$\rho(A) \geq v$$

$$0 \leq \rho(A) - \rho(B)$$

2) s>1

$$\hat{W}_{\rho(B)}((i_l, j_l)) \triangleq ((i_0,j_0),(i_1,j_1),\ldots,(i_l,j_l)), \text{ for } 0 \leq l \leq s.$$

$$W_{\rho(B)} = \hat{W}_{\rho(B)}((i_{s-1},j_{s-1}))(i_s,j_s)$$

$$W = \hat{W}_{\rho(B)}((i_{s-1},j_{s-1}))((i_A,j_A))$$

$$\rho(A) \geq \bar{S}_W = \bar{S}_{\hat{W}_{\rho(B)}((i_{s-1},j_{s-1}))} +$$
$$\hat{\varphi}_1((i_{s-2}, j_{s-2})(i_{s-1}, j_{s-1}), (i_{s-1}, j_{s-1})(i_A, j_A))$$
$$= \bar{S}_{\hat{W}_{\rho(B)}((i_{s-1},j_{s-1}))} + \kappa(x_{i_A}, y_{j_A})$$

$$\rho(B) = \bar{S}_{W_{\rho(B)}}$$
$$= \bar{S}_{\hat{W}_{\rho(B)}((i_{s-1},j_{s-1}))} +$$
$$\hat{\varphi}_1((i_{s-2}, j_{s-2})(i_{s-1}, j_{s-1}), (i_{s-1}, j_{s-1})(i_s, j_s))$$

$$\rho(A) - \rho(B) \geq \kappa(x_{i_A}, y_{j_A}) - \hat{\varphi}_1((i_{s-2}, j_{s-2})(i_{s-1}, j_{s-1}), (i_{s-1}, j_{s-1})(i_s, j_s)) = \kappa(x_{i_A}, y_{j_A}) - v_z$$

$$\kappa(x_{i_A}, y_{j_A}) - v_z \leq \rho(A) - \rho(B)$$

If $(i_{s-2},j_{s-2})(i_{s-1},j_{s-1}) \in A^d$, then z=d. Not valid arc $\mathbb{V}$;
If $(i_{s-2},j_{s-2})(i_{s-1},j_{s-1}) \in A^h$, then z=h. this does not happen in M;
If $(i_{s-2},j_{s-2})(i_{s-1},j_{s-1}) \in A^v$, then z=v. Not valid arc $\mathbb{V}$;
Case: row(B)>1 and col(B)=1 $\mathbb{V}$
Vertex set of D(x,Y) is $\mathbb{V}$ ={(i,j), for 0≤i≤n and 0≤j≤m}.

$$B=(i_B, j_B)$$

$$W_{\beta(B)}=((i_0,j_0),(i_1,j_1),\ldots,(i_s,j_s))=B, s>0.$$

$$W=W_{\beta(B)}((i_A,j_A))$$

$$\rho(A) \geq \bar{S}_W = \bar{S}_{W_{\rho(B)}} + \hat{\varphi}_1((i_{s-1}, j_{s-1})(i_B, j_B), (i_B, j_B)(i_A, j_A))$$
$$= \bar{S}_{W_{\rho(B)}} + h_u$$
$$= \rho(B) + h_u$$

$$h_u \leq \rho(A) - \rho(B)$$

If $(i_{s-1},j_{s-1})(i_B,j_B) \in A^d$, then u=d.
If $(i_{s-1},j_{s-1})(i_B,j_B) \in A^h$, then u=h.
If $(i_{s-1},j_{s-1})(i_B,j_B) \in A^v$, then u=v.
OK for AS
OK for M except u=v=>h$_v$=>W not a valid walk for ρ(A) in M
Below is in M space:
two cases:
1) s=1

$$W_{\rho(B)}=((i_0,j_0),(i_s,j_s))=B$$

$$\rho(B)=v$$

$$\rho(A) \geq \max(\{\kappa(x_{i_A}, y_{j_A}), h, v\}) \text{ [SINCE } A \text{ IS NOT } (0,0)\text{]}$$

$$\rho(A) \geq v$$

$$0 \leq \rho(A) - \rho(B)$$

2) s>1

$\hat{W}_{\beta(B)}((i_l,j_l)) \triangleq ((i_0,j_0),(i_1,j_1), \ldots ,(i_l,j_l))$, for $0 \leq l \leq s$.

$W_{\rho(B)} = \hat{W}_{\rho(B)}(i_{s-1},j_{s-1}))(i_s,j_s)$ $W = \hat{W}_{\beta(B)}(i_{s-1},i_{s-1}))(i_A,j_A))$ $\rho(A) \geq \overline{S}_W = \overline{S}_{\hat{W}_{\rho(B)}((i_{s-1},j_{s-1}))} +$
$\hat{\varphi}_1((i_{s-2}, j_{s-2})(i_{s-1}, j_{s-1}), (i_{s-1}, j_{s-1})(i_A, j_A))$
$= \overline{S}_{\hat{W}_{\rho(B)}((i_{s-1},j_{s-1}))} + \kappa(x_{i_A}, y_{j_A})$ $\rho(B) = \overline{S}_{W_{\rho(B)}}$
$= \overline{S}_{\hat{W}_{\rho(B)}((i_{s-1},j_{s-1}))} +$
$\hat{\varphi}_1((i_{s-2}, j_{s-2})(i_{s-1}, j_{s-1}), (i_{s-1}, j_{s-1})(i_s, j_s))$ $\rho(A) - \rho(B) \geq \kappa(x_{i_A}, y_{j_A}) - \hat{\varphi}_1((i_{s-2}, j_{s-2})(i_{s-1}, j_{s-1}), (i_{s-1}, j_{s-1})(i_s, j_s)) =$
$\kappa(x_{i_A}, y_{i_A}) - v_z$ $\kappa(x_{i_A}, y_{j_A}) - v_z \leq \rho(A) - \rho(B)$ if u=v and s>1 and z=d, then $\kappa(x_{i_A},y_{j_A})-v_d \leq \rho(A)-\rho(B)$ in M if u=v and s>1 and z=h, then $\kappa(x_{i_A},y_{j_A})-v_h \leq \rho(A)-\rho(B)$ does not happen in M if u=v and s>1 and z=v and $j_B$=2, then $\kappa(x_{i_A},y_{j_A})-v_v \leq \rho(A)-\rho(B)$ $W_{\rho(B)}$ not valid based on Lemma WT.

if u=v and s>1 and z=v and $j_B$>2, then $\kappa(x_{i_A},y_{j_A})-v_v \leq \rho(A)-\rho(B)$ in M Case: row(B)=1 and col(B)=1
Vertex set of $D(\underline{x},\underline{y})$ is $\mathbb{V}$ {(i,j), for $0 \leq i \leq n$ and $0 \leq j \leq m$}.

$B=(i_B,j_B)$ $W_{\beta(B)}=((i_0,j_0),(i_1,j_1), \ldots ,(i_s,j_s)=B)$, s>0.

$W=W_{\beta(B)}((i_A,j_A))$ $\rho(A) \geq \overline{S}_W = \overline{S}_{W_{\rho(B)}} + \hat{\varphi}_1((i_{s-1}, j_{s-1})(i_B, j_B), (i_B, j_B)(i_A, j_A))$
$= \overline{S}_{W_{\rho(B)}} + h_u$
$= \rho(B) + h_u$ $h_u \leq \rho(A) - \rho(B)$ If $(i_{s-1},j_{s-1})(i_B,j_B) \in A^d$, then u=d.
If $(i_{s-1},j_{s-1})(i_B,j_B) \in A^h$, then u=h.
If $(i_{s-1},j_{s-1})(i_B,j_B) \in A^v$, then u=v.
OK for AS
OK for M except u=v=>$h_v$=>W not a valid walk for $\rho(A)$ in M
Below is in M space:
two cases:
1) s=1

$W_{\rho(B)}=((i_0,j_0),(i_s,j_s)=B)$ $\rho(B)=v$ $\rho(A) \geq \max(\{\kappa(x_{i_A},y_{j_A}),h,v\})$ [SINCE A IS NOT (0,0)]

$\rho(A) \geq v$ $0 \leq \rho(A)-\rho(B)$ 2) s>1

$\hat{W}_{\beta(B)}((i_l,j_l)) \triangleq ((i_0,j_0),(i_1,j_1), \ldots ,(i_l,j_l))$, for $0 \leq l \leq s$.

$W_{\rho(B)} = \hat{W}_{\rho(B)}(i_{s-1},j_{s-1}))(i_s,j_s)$ $W = \hat{W}_{\beta(B)}(i_{s-1},i_{s-1}))(i_A,j_A))$ $\rho(A) \geq \overline{S}_W$
$= \overline{S}_{\hat{W}_{\rho(B)}((i_{s-1},j_{s-1}))} + \hat{\varphi}_1((i_{s-2}, j_{s-2})(i_{s-1}, j_{s-1}), (i_{s-1}, j_{s-1})(i_A, j_A))$
$= \overline{S}_{\hat{W}_{\rho(B)}(i_{s-1},j_{s-1}))} + \kappa(x_{i_A}, y_{j_A})$ $\rho(B) = \overline{S}_{W_{\rho(B)}}$ $\overline{S}_{\hat{W}_{\rho(B)}((i_{s-1},j_{s-1}))} + \hat{\varphi}_1((i_{s-2}, j_{s-2})(i_{s-1}, j_{s-1}), (i_{s-1}, j_{s-1})(i_s, j_s))$ $\rho(A) - \rho(B) \geq \kappa(x_{i_A}, y_{j_A}) - \hat{\varphi}_1((i_{s-2}, j_{s-2})(i_{s-1}, j_{s-1}), (i_{s-1}, j_{s-1})(i_s, j_s))$
$= \kappa(x_{i_A}, y_{j_A}) - v_z$ $\kappa(x_{i_A}, y_{j_A}) - v_z \leq \rho(A) - \rho(B)$ if u=v and s>1 and z=d, then $\kappa(x_{i_A},y_{j_A})-v_d\rho(A)-\rho(B)$; not valid arc of $\mathbb{V}$ if u=v and s>1 and z=h, then $\kappa(x_{i_A},y_{j_A})-v_h \leq \rho(A)-\rho(B)$ does not happen in M if u=v and s>1 and z=v, then $\kappa(x_{i_A},y_{j_A})-v_v \leq \rho(A)-\rho(B)$; not valid arc of $\mathbb{V}$ For AS $h \leq \rho(A)-\rho(B)$ $0 = \rho(A)-\rho(B)$ $h_u \leq \rho(A)-\rho(B)$ u=d, h, or v
least lower bound AS=min{0, h, $h_d$, $h_h$, $h_v$}=$-(\alpha+\beta)$
least lower bound AS=$-(\alpha+\beta)$
For M $0 \leq \rho(A)-\rho(B)$ $\kappa(x_{i_A},y_{j_A})-v_z \leq \rho(A)-\rho(B)$ z=dv least lower bound M=min{0,$-(\alpha+\beta)$,$\kappa_{min}-v_d$,$\kappa_{min}-v_v$}=min{$-(\alpha+\beta)$,$\kappa_{min}+(\alpha+\beta)$,$\kappa_{min}+\beta$}=min{$-(\alpha+\beta)$,$\kappa_{min}+\beta$} least lower bound M=min{$-(\alpha+\beta)$,$\kappa_{min}+\beta$}

| | affine | modified | simplified |
|---|---|---|---|
| Lemma 1.3 L | $-\alpha-\beta$ | min{$-\alpha-\beta$, $\kappa_{min}+\beta$} | $-\alpha-\beta$ |
| Lemma 1.3 R | | | |
| Lemma 2.3 L | | | |
| Lemma 2.3 R | | | |

| | affine | modified | simplified |
|---|---|---|---|
| Lemma 1.3 L | $-\alpha-\beta$ | min{$-\alpha-\beta$, $\kappa_{min}+\beta$} | $-\alpha-\beta$ |
| Lemma 1.3 R | | | |
| Lemma 2.3 L | | | |
| Lemma 2.3 R | | | |

B. Lemma 1.3—Upper Bound

Given vertices B=(i,j) and A=(i+1,j), $\rho(A)-\rho(B) \leq \max\{\kappa_{max}+\alpha+\beta, 0\}$, for affine and affine simplified gap score, and $\rho(A)-\rho(B) \leq \max\{\kappa_{max}+\alpha+\beta, -\beta, -\beta+\kappa_{max}-\kappa_{min}\}$, for modified gap score. Proof: Briefly, for every possible walk for $\rho(A)$, we find a walk W(B) of B such that $\rho(A)$-Score of (W(B))≤upper bound.

Step 1) All possible walks for $\rho(A)$:

This section characterized all possible walks for $\rho(A)$, and their corresponding W(B)

In order to find an upper bound to $\rho(A)-\rho(B)$, following cases are considered.

Notations:

row=row of the dark circle in digraph D(x,y).

col=column of the dark circle on digraph D.

ticker lines are possible walks of $\rho(A)$.

thinner lines are possible arcs leading to B.

D, H and V mark a diagonal, horizontal and vertical arc, respectively.

dashed thick lines are invalid for $\rho(A)$ for modified gap score.

dashed thin lines are invalid for certain walks to B for modified gap score.

1. Case 1: Row>1 and Col=2

FIG. 28A shows a table 2801 that for each affine gap function, characterized all pairs of walks that diverge from a vertex in a row>1 and column=2, such that one ends in A and the other ends in B, according to various aspects of the present disclosure. Both walks being valid with respect to local alignment with the specific affine gap function.

Table 2801 has 4 rows and 6 columns. Note these are different from the row and columns on Digraph D. The second row and fifth column of Table 2801 shows portions of three possible walks for $\rho(A)$ for AS.

The first portion has the arc H ending on vertex O, followed by a diagonal edge, followed by r (r≥0) vertical arc(s) ending on A. Let's use, P, to denote the walk from the dark circle to A. Let's denote this walk by HP.

The second portion has the arc D ending on vertex O, followed by P. Let's denote this walk by DP. The third portion has the arc V ending on vertex O, followed by P. Let's denote this walk by VP. The second row and fifth column of Table 2801 also shows portions of three possible walks ending on B for AS.

The first portion has the arc H ending on vertex O, followed by one or more vertical arcs ending on B. Let's use, Q, to denote the vertical walk from the dark circle to B. Let's denote the first walk by HQ. The second portion has the arc D ending on vertex O, followed by Q. Let's denote this walk by HQ. The third portion has the arc V ending on vertex O, followed by Q. Let's denote this walk by VP. If $\rho(A)$ contains HP, then we will use HQ to obtain an upper bound for $\rho(A)-\rho(B)$. If $\rho(A)$ contains DP, then we will use DQ to obtain an upper bound for $\rho(A)-\rho(B)$. If $\rho(A)$ contains VP, then we will use VQ to obtain an upper bound for $\rho(A)-\rho(B)$.

It should be noted that the fourth and sixth columns of the table are for cases when the dark circle is on vertex (0,0). These cases are not valid for row>1 and col=2.

The third row and fifth column of Table 2801 shows additional portions of three possible walks for $\rho(A)$ for AS.

The first portion has the arc H ending on vertex O, followed by a horizontal edge, followed by r (r≥1) vertical arc(s) ending on A. Let's use, U, to denote the walk from the dark circle to A. Let's denote this walk by HU. The second portion has the arc D ending on vertex O, followed by U. Let's denote this walk by DU. The third portion has the arc V ending on vertex O, followed by U. Let's denote this walk by VU.

The third row and fifth column of Table 2801 also shows portions of three possible walks ending on B for AS. The first portion has the arc H ending on vertex O, followed by one or more vertical arcs ending on B.

Let's use, W, to denote the vertical walk from the dark circle to B. Let's denote the first walk by HW. The second portion has the arc D ending on vertex O, followed by W. Let's denote this walk by HW.

The third portion has the arc V ending on vertex O, followed by W. Let's denote this walk by VW.

If $\rho(A)$ contains HU, then we will use HW to obtain an upper bound for $\rho(A)-\rho(B)$. If $\rho(A)$ contains DU, then we will use DW to obtain an upper bound for $\rho(A)-\rho(B)$. If $\rho(A)$ contains VU, then we will use VW to obtain an upper bound for $\rho(A)-\rho(B)$.

The fourth row and fifth column of Table 2801 shows yet more portions of three possible walks for $\rho(A)$ for AS. The first portion has the arc H ending on vertex O, followed by a horizontal arc to A. Let's use, X, to denote the arc from the dark circle to A. Let's denote this walk by HX. The second portion has the arc D ending on vertex O, followed by X. Let's denote this walk by DX. The third portion has the arc V ending on vertex O, followed by X. Let's denote this walk by VX. The fourth row and fifth column of Table 2801 also shows portions of three possible walks for $\rho(A)$ for AS.

The first portion has the arc H ending on vertex O, but vertex O and vertex B are the same here. Let's call this walk H. The second portion has the arc D ending on vertex B (O). Let's denote this walk by D. The third portion has the arc V ending on vertex B. Let's denote this walk by V.

If $\rho(A)$ contains HX, then we will use H to obtain an upper bound for $\rho(A)-\rho(B)$. If $\rho(A)$ contains DX, then we will use D to obtain an upper bound for $\rho(A)-\rho(B)$. If $\rho(A)$ contains VX, then we will use V to obtain an upper bound for $\rho(A)-\rho(B)$.

The second row and third column of Table 2801 shows the walks HP, DP and VP of $\rho(A)$ for M.

Here, HQ is not a valid walk to reach B since no right angles are allowed. Therefore, for H, we need to find another walk for B, which is valid in M. To this end, the arc H is extended backwards by arcs H1, D1, and V1.

Now, H1 is not valid for $\rho(A)$ since col=2 and it would generate a 90 degree turn from the col=0.

Also, V1 is not valid for $\rho(A)$ since it is perpendicular to H.

But D1 is a valid extension. We demote a walk for $\rho(A)$ that uses H by D1HP, and a walk for B corresponding to D1HP by D1D0Q', where Q' is the walk from the empty circle square to B.

If $\rho(A)$ contains D1HP in M, then D1D0Q' is used to obtain an upper bound for $\rho(A)-\rho(B)$.

The third row and third column of Table 2801 shows the walks HU, DU and VU of $\rho(A)$ for M.

Here, U is not a valid walk for $\rho(A)$ for M since it has a right angle turn. Therefore, there are no walks of the type described in this the third row and third column of the table for $\rho(A)$ for M.

The fourth row and third column of the table also shows portions of three possible walks for $\rho(A)$ for M: HX, DX, and HX.

VX is not valid for M because of its right angle. Therefore,

If $\rho(A)$ contains HX, then H is used to obtain an upper bound for $\rho(A)-\rho(B)$.

If ρ(A) contains DX, then D is used to obtain an upper bound for ρ(A)−ρ(B).

FIG. 28B shows a table 2802 that for each affine gap function, characterized whether the walk from the top circle (row>1 and column=2) to A could be a valid walk for ρ(A) with respect to local alignment with the specific affine gap function, according to various aspects of the present disclosure. Table 2802 addresses additional cases when the walk for ρ(A) start not from vertex (0,0). The second row and the last column of the table shows a walk for ρ(A) for AS: FY. FY is the walk from the dark circle to A. The arc is called Y, and F denotes that the walk starts on the dark circle. If ρ(A) is FY, then ρ(B)≥v, is used to obtain an upper bound for ρ(A)−ρ(B).

The following cases 2-10, are derived as case 1.

2. Case 2: Row>1 and Col>2

FIG. 29A shows a table 2901 that for each affine gap function, characterized all pairs of walks that diverge from a vertex in a row>1 and column>2, such that one ends in A and the other ends in B, according to various aspects of the present disclosure. Both walks are valid with respect to local alignment with the specific affine gap function.

FIG. 29B shows a table 2902 that for each affine gap function, characterized whether the walk from the top circle (row>1 and column>2) to A could be a valid walk for ρ(A) with respect to local alignment with the specific affine gap function, according to various aspects of the present disclosure. Table 2903 addresses additional cases when the walk for ρ(A) start not from vertex (0,0).

3. Case 3: Row=1 and Col=2

FIG. 30A shows a table 3001 that for each affine gap function, characterized all pairs of walks that diverge from a vertex in a row=1 and column=2, such that one ends in A and the other ends in B according to various aspects of the present disclosure. Both walks being valid with respect to local alignment with the specific affine gap function.

FIG. 30B shows a table 3002 that for each affine gap function, characterized whether the walk from the top circle (row=1 and column=2) to A could be a valid walk for ρ(A) with respect to local alignment with the specific affine gap function according to various aspects of the present disclosure. Table 3002 below addresses additional cases when the walk for ρ(A) start not from vertex (0,0).

4. Case 4: Row=1 and Col>2

Figures 31A, 31B:
FIG. 31A shows a table that for each affine gap function, characterized all pairs of walks that diverge from a vertex in a row=1 and column>2, such that one ends in A and the other ends in B, according to various aspects of the present disclosure.
FIG. 31B shows a table that for each affine gap function, characterized all pairs of walks that diverge from a vertex in a row=1 and column>2, such that one ends in A and the other ends in A, according to various aspects of the present disclosure.

FIG. 31A shows a table 3101 that for each affine gap function, characterized all pairs of walks that diverge from a vertex in a row=1 and column>2, such that one ends in A and the other ends in B, according to various aspects of the present disclosure. Both walks are valid with respect to local alignment with the specific affine gap function.

FIG. 31B shows a table 3102 that for each affine gap function, characterized all pairs of walks that diverge from a vertex in a row=1 and column>2, such that one ends in A and the other ends in A, according to various aspects of the present disclosure. Both walks being valid with respect to local alignment with the specific affine gap function. Table 3102 addresses additional cases when the walk for ρ(A) start not from vertex (0,0).

5. Case 5: Row>1 and Col=1

Table below addresses additional cases when the walk for ρ(A) start not from vertex (0,0).

FIG. 32A shows a table 3201 that for each affine gap function, characterized all pairs of walks that diverge from a vertex in a row>1 and column=1, such that one ends in A and the other ends in B, according to various aspects of the present disclosure. Both walks are valid with respect to local alignment with the specific affine gap function.

FIG. 32B shows a table 3202 that for each affine gap function, characterized whether the walk from the top circle (row>1 and column=1) to A could be a valid walk for ρ(A) with respect to local alignment with the specific affine gap function, according to various aspects of the present disclosure.

6. Case 6: Row=1 and Col=1

FIG. 33A shows a table 3301 that for each affine gap function, characterized all pairs of walks that diverge from a vertex in a row=1 and column=1, such that one ends in A and the other ends in B, according to various aspects of the present disclosure. Both walks are valid with respect to local alignment with the specific affine gap function.

FIG. 33B shows a table 3302 that for each affine gap function, characterized whether the walk from the top circle (row=1 and column=1) to A could be a valid walk for ρ(A) with respect to local alignment with the specific affine gap function, according to various aspects of the present disclosure. Table 3302 addresses additional cases when the walk for ρ(A) start not from vertex (0,0).

7. Case 7: Row>0 and Col=0

FIG. 34A shows a table 3401 that for each affine gap function, characterized all pairs of walks that diverge from a vertex in a row=0 and column=0, such that one ends in A and the other ends in B, according to various aspects of the present disclosure. Both walks are valid with respect to local alignment with the specific affine gap function.

FIG. 34B shows a table 3402 that for each affine gap function, characterized whether the walk from the top circle (row=0 and column=0) to A could be a valid walk for ρ(A) with respect to local alignment with the specific affine gap function, according to various aspects of the present disclosure. Table 3402 addresses additional cases when the walk for ρ(A) start not from vertex (0,0).

8. Case 8: Row=1 and Col>1

FIG. 35A shows a table 3501 that for each affine gap function, characterized all pairs of walks that diverge from a vertex in a row=1 and column>1, such that one ends in A and the other ends in B, according to various aspects of the present disclosure. Both walks are valid with respect to local alignment with the specific affine gap function.

FIG. 35B shows a table 3502 that for each affine gap function, characterized whether the walk from the top circle (row=1 and column>1) to A could be a valid walk for ρ(A) with respect to local alignment with the specific affine gap function, according to various aspects of the present disclosure. Table 3502 addresses additional cases when the walk for ρ(A) start not from vertex (0,0).

9. Case 9: Row=0 and Col=1

FIG. 36A gives a table 3601 that for each affine gap function, characterized all pairs of walks that diverge from a vertex in a row=0 and column=1, such that one ends in A and the other ends in B, according to various aspects of the present disclosure. Both walks are valid with respect to local alignment with the specific affine gap function.

FIG. 36B gives a table 3602 that for each affine gap function, characterized whether the walk from the top circle (row=0 and column=1) to A could be a valid walk for ρ(A) with respect to local alignment with the specific affine gap function, according to various aspects of the present disclosure. Table 3602 addresses additional cases when the walk for ρ(A) start not from vertex (0,0).

10. Case 10: Row=0 and Col=0

FIG. 37A shows a table 3701 that for each affine gap function, characterized all pairs of walks that diverge from a vertex in a row=0 and column=0, such that one ends in A and the other ends in B, according to various aspects of the present disclosure. With reference to FIG. 37A, Q" is the last vertical arc ends in B. Both walks are valid with respect to local alignment with the specific affine gap function.

FIG. 37B shows a table 3702 that for each affine gap function, characterized whether the walk from the top circle (row=0 and column=0) to A could be a valid walk for ρ(A) with respect to local alignment with the specific affine gap function, according to various aspects of the present disclosure. Table 3702 addresses additional cases when the walk for ρ(A) start not from vertex (0,0).

Step 2) Tabulation of all possible walks for ρ(A), and their corresponding W(B).

Tables below describes all possible walks for ρ(A), and their corresponding W(B) for AS and M.

AS:
D=diagonal tail
H=horizontal tail
V=vertical tail
F=no tail

Based on the tables on pairs of walks on digraph D(x,y), table below gives pairs of walks that are valid for AS. The pairs in bold are not valid.

| | | | | | | | | | | | | | |
|---|---|---|---|---|---|---|---|---|---|---|---|---|---|
| 01 R > 1 C = 2 | DP DQ | HP HQ | VP VQ | FP FQ | DU DW | HU HW | VU VW | FU XX | DX D | HX H | VX V | FX F | FY |
| 02 R > 1 C > 2 | DP DQ | HP HQ | VP VQ | FP XX | DU DW | HU HW | VU VW | FU XX | DX D | HX H | VX V | FX F | FY |
| 03 R = 1 C = 2 | DP DQ | HP HQ | VP VQ | FP XX | DU DW | HU HW | VU VW | FU XX | DX D | HX H | VX V | FX F | FY |
| 04 R = 1 C > 2 | DP DQ | HP HQ | VP VQ | FP XX | DU DW | HU HW | VU VW | FU XX | DX D | HX H | VX V | FX F | FY |
| 05 R > 1 C = 1 | DP DQ | HP HQ | VP VQ | FP XX | DU DW | HU HW | VU VW | FU XX | DX D | HX H | VX V | FX F | FY |
| 06 R = 1 C = 1 | DP DQ | HP HQ | VP VQ | FP XX | DU DW | HU HW | VU VW | FU XX | DX D | HX H | VX V | FX F | FY |
| 07 R > 0 C = 0 | DP DQ | HP HQ | VP VQ | FP XX | DU DW | HU HW | VU VW | FU XX | DX D | HX H | VX V | FX F | FY F |
| 08 R = 0 C > 1 | DP DQ | HP HQ | VP VQ | FP DQ' | DU DW | HU HW | VU VW | FU XX | DX D | HX H | VX V | FX F | FY |
| 09 R = 0 C = 1 | DP DQ | HP HQ | VP VQ | FP DQ' | DU DW | HU HW | VU VW | FU XX | DX D | HX H | VX V | FX F | FY |
| 10 R = 0 C = 0 | DP DQ | HP HQ | VP VQ | FP Q' | DU DW | HU HW | VU VW | FU FW | DX D | HX H | VX V | FX F | FY F |

M:
Based on the tables on pairs of walks on digraph D(x,y), table below gives pairs of walks that are valid for M. The pairs in bold are not valid.
Underbar means not valid for AS, as well.

| | | | | | | | | | | | | | |
|---|---|---|---|---|---|---|---|---|---|---|---|---|---|
| 01 R > 1 C = 2 | DP DQ | HP HQ DHP DDQ' HHP HDQ' VHP VDQ' FHP FDQ' | VP VQ | FP XX | DU XX | HU XX | VU XX | FU XX | DX D | HX H | VX V | FX F | FY |
| 02 R > 1 C > 2 | DP DQ | HP HQ DHP DDQ' HHP HDQ' VHP VDQ' FHP FDQ' | VQ VQ | FP FQ | DU XX | HU XX | VU XX | FU XX | DX D | HX H | VX V | FX F | FY |

| | | | | | | | | | | | | | |
|---|---|---|---|---|---|---|---|---|---|---|---|---|---|
| 03 R=1 C=2 | DP DQ | HP HQ DHP DDQ' HHP HDQ' VHP VDQ' FHP FDQ' | VP VQ | FP XX | DU XX | HU XX | VU XX | FU XX | DX D | HX H | VX V | FX F | FY |
| 04 R=1 C>2 | DP DQ | HP HQ DHP DDQ' HHP HDQ' VHP VDQ' FHP FDQ' | VP VQ | FP XX | DU XX | HU XX | VU XX | FU XX | DX D | HX H | VX V | FX F | FY |
| 05 R>1 C=1 | DP DQ | HP HQ HP DQ' | VP VQ | FP XX | DU XX | HU XX | VU XX | FU XX | DX D | HX H | VX V VX not valid in M | FX F | FY |
| 06 R=1 C=1 | DP DQ | HP HQ | VP VQ | FP XX | DU XX | HU XX | VU XX | FU XX | DX D | HX H | VX V | FX F | FY |
| 07 R>0 C=0 | DP DQ | HP HQ | VP VQ | FP XX | DU XX | HU XX | VU XX | FU XX | DX D | HX H | VX V | FX F | FY |
| 08 R=0 C>1 | DP DQ | HP HQ | VP VQ | FP DQ' | DU XX | HU XX | VU XX | FU XX | DX D | HX H | VX V | FX F | FY |
| 09 R=0 C=1 | DP DQ | HP HQ | VP VQ | FP DQ' | DU XX | HU XX | VU XX | FU XX | DX D | HX H | VX V | FX F | FY |
| 10 R=0 C=0 | DP DQ | HP HQ | VP VQ | FP Q' | DU XX | HU XX | VU XX | FU XX | DX D | HX H | VX V | FX F | FY |

Step 3) The scores of all possible walks for ρ(A), and their corresponding W(B).

This step we calculate the score of all the walk in the tables of step 2).

We start with the following definitions.

Definitions:

$A = (i_A, j_A)$ $W_{\rho(A)} = ((i_0, j_0)), (i_1, j_1), \ldots, (i_t, j_t) = A), t > 0.$ $\dot{W}_{\rho(A)}((i_l, j_l)) \triangleq (i_0, j_0), (i_1, j_1), \ldots, (i_l, j_l))$, for $0 \le l \le t$.

$\ddot{W}_{\rho(A)}((i_l, j_l)) \triangleq (i_l, j_l), (i_{l+1}, j_{l+1}), \ldots, (i_t, j_t) = A)$, for $0 \le l \le t$.

$P^{|}((i,j); r) \triangleq ((i, j+1), (i, j+2), \ldots (i, j+r))$, for integers, $i \ge 0$, $j \ge 0$ and $r \ge 0$.

$P^{|}((i,j); 0) \triangleq (\phi)$ $P^{d|}((i,j); r) \triangleq ((i,j), (i+1, j+1)) P^{|}((i+1, j+1); r)$, for integers, $i \ge 0$, $j \ge 0$ and $r \ge 0$.

(We use $W_1 W_2$ and $W_1 \star W_2$ to represent the concatenation of the sequences (or walks) $W_1$ and $W_2$).

$P^{h|}((i, j); r) \triangleq ((i, j), (i+1, j)) P^{|}((i+1, j); r)$, for integers, $i \ge 0$, $j \ge 0$ and $r \ge 0$.

$P^{f}((i,j)) \triangleq ((i, j), (i+1, j))$, for integers $i \ge 0$ and $j \ge 0$.

$P^{v|}((i,j); r) \triangleq ((i,j)) P^{|}((i,j); r)$, for integers, $i \ge 0$, $j \ge 0$ and $r \ge 0$.

$\rho((0,0)) \triangleq 0$

Lemma T. Given two walks $W_1$ and $W_2$, $W_1 = (i_0, j_0), (i_1, j_1), \ldots, (i_{k-1}, j_{k-1}), (i_k, j_k)(i_{k+1}, j_{k+1}), (1_{k+2}, j_{k+2}), \ldots, (i_p, j_p))$ $W_2 = (i'_0, j'_0), (i'_1, j'_1), \ldots, (i'_{k-1}, j'_{k-1}), (i'_k, j'_k)(i'_{k+1}, j'_{k+1}), (i'_{k+2}, j'_{k+2}), \ldots, (i'_p, j'_p))$ that agree in vertices: $(i_m, j_m) = (i'_m, j'_m)$, $m \le k$, we have $\bar{S}_{W_1} - \bar{S}_{W_2} = \Sigma_{q=k}^{p}(\hat{\varphi}_1((i_{q-1}, j_{q-1})(i_q, j_q), (i_q, j_q)(i_{q+1}, j_{q+1})) - \hat{\varphi}_1((i'_{q-1}, j'_{q-1})(i'_q, j'_q), (i'_q, j'_q)(i'_{q+1}, j'_{q+1})))$ We use the following correspondence.

| | |
|---|---|
| (a) | DP |
| (b) | HD |
| (c) | VD |
| (d) | FD |
| (e) | DU |
| (f) | HU |
| (g) | VH |
| (h) | FU |
| (i) | DX |
| (j) | HX |
| (k) | VX |
| (l) | FX |
| (m) | FY |
| (n) | DP |
| (o) | HD |
| (p) | VD |
| (q) | FD |
| (n) | DU |
| (o) | HU |
| (p) | VH |

-continued

| | |
|---|---|
| (q) | FU |
| (r) | DX |
| (s) | HX |
| (t) | VX |
| (u) | FX |
| (i) | FY |
| (v) | DHP |
| (w) | HHD |
| (x) | VHD |
| (y) | FHD |
| AA | DDQ' |
| BB | HDQ' |
| CC | VDQ' |
| DD | FDQ' |

We define more notions to identify the walks of interest. For AS:

$r \geq 0$ $T_d P^{d|}((i,j);r) \triangleq ((i-1,j-1))P^{d|}((i,j);r)$ (a)

$T_h P^{d|}((i,j);r) \triangleq ((i-1,j))P^{d|}((i,j);r)$ (b)

$T_v^{d|}((i,j);r) \triangleq ((i,j-1))P^{d|}((i,j);r)$ (c)

$T_\phi P^{d|}((i,j);r) \triangleq (\phi)P^{d|}((i,j);r)$ (d)

$s > 0$ $T_d P^{h|}((i,j);s) \triangleq ((i-1,j-1))P^{h|}((i,j);s)$ (e)

$T_h P^{h|}((i,j);s) \triangleq ((i-1,j))P^{h|}((i,j);s)$ (f)

$T_v P^{h|}((i,j);s) \triangleq ((i,j-1))P^{h|}((i,j);s)$ (g)

$T_\phi P^{h|}((i,j);s) \triangleq (\phi)p^{h|}((i\ j);s)$ (h)

$T_d P^f(i,j) \triangleq T_d((i,j)(i+1,j))$ (i)

$T_h P^f(i,j) \triangleq T_h((i,j)(i+1,j))$ (j)

$T_v P^f(i,j) \triangleq T_v((i,j)(i+1,j))$ (k)

$T_\phi P^f(i,j) \triangleq T_v((i,j)(i+1,j))$ (l)

$s = 1$ $T_\phi P^{v|}((i,j);r) \triangleq (\phi)((i,j))P^{|}((i,j);s)$ (m)

$s > 0$ $T_d P^{v|}((i,j);s) \triangleq T_d((i,j))P^{|}((i,j);s)$ (n)

$T_h P^{v|}((i,j);s) \triangleq T_h((i,j))P^{|}((i,j);s)$ (o)

$T_v P^{v|}((i,j);s) \triangleq T_v((i,j))P^{|}((i,j);s)$ (p)

$T_\phi P^{v|}((i,j);s) \triangleq T_\phi((i,j))P^{|}((i,j);s)$ (q)

$T_d((i,j))$ (r)

$T_h((i,j))$ (s)

$T_v((i,j))$ (t)

$T_\phi((i,j))$ (u)

For M:

$r \geq 0$ $T_d T_h P^{d|}((i,j);r) \triangleq ((i-2,j-1))((i-1,j))P^{d|}((i,j);r)$ (v)

$T_h T_h P^{d|}((i,j);r) \triangleq ((i-2,j))((i-1,j))P^{d|}((i,j);r)$ (w)

$T_v T_h P^{d|}((i,j);r) \triangleq ((i-1,j-1))((i-1,j))P^{d|}((i,j);r)$ (x)

$T_\phi T_h P^{d|}((i,j);r) \triangleq (\phi)((i-1,j))P^{d|}((i,j);r)$ (y)

$r \geq 0$ $T_d T_d P^{v|}((i,j+1);r) \triangleq T_d T_d((i,j+1))P^{|}((i,j+1);r)$ (AA)

$T_h T_d P^{v|}((i,j+1);r) \triangleq T_h T_d((i,j+1))P^{|}((i,j+1);r)$ (BB)

$T_v T_d P^{v|}((i,j+1);r) \triangleq T_v T_d((i,j+1))P^{|}((i,j+1);r)$ (CC)

$T_\phi T_d P^{v|}((i,j+1);r) \triangleq T_\phi T_d((i,j+1))P^{|}((i,j+1);r)$ (DD)

Below we compute the score of the walks characterized above:

Case: $i > 1$, $j > 1$; (a)(b)(c)(d); $r \geq 0$ $T_d P^{d|}((i,j);r) = (i-1, j-1)P^{d|}((i,j);r)$ $= (i-1, j-1)((i,j), (i+1, j+1))P^{|}((i+1, j+1); r)$ $= (i-1, j-1)((i,j), (i+1, j+1))\begin{pmatrix}(i+1, j+1+1), (i+1, j+1+2), \\ \ldots (i+1, j+1+r)\end{pmatrix}$ $\overline{S}_{T_h P^{d|}((i,j);r)} =$
$\hat{\varphi}_0((i-1, j-1)(i, j)) + \hat{\varphi}_1((i-1, j-1)(i, j), (i, j)(i+1, j+1)) +$
$\hat{\varphi}_1((i, j)(i+1, j+1), (i+1, j+1)(i+1, j+1+1)) +$
$\sum_{q=2}^{r} \hat{\varphi}_1((i+1, j+1+q-2)(i+1, j+1+q-1),$
$(i+1, j+1+q-1)(i+1, j+1+q))$ $\overline{S}_{T_h P^{d|}((i,j);r)} = \kappa(x_i, y_j) + \kappa(x_{i+1}, y_{j+1}) + \begin{cases} 0 & r = 0 \\ v_d + (r-1)v_v & r \geq 1 \end{cases}$ $T_v P^{d|}((i, j); r) = (i-1, j)P^{d|}((i, j); r)$ $= (i-1, j)((i, j), (i+1, j+1))P^{|}((i+1, j+1); r)$ $= (i-1, j)((i, j), (i+1, j+1))\begin{pmatrix}(i+1, j+1+1), (i+1, j+1+2), \\ \ldots (i+1, j+1+r)\end{pmatrix}$ $\overline{S}_{T_v P^{d|}((i,j);r)} = \hat{\varphi}_0((i-1, j)(i, j)) + \hat{\varphi}_1((i-1, j)(i, j), (i, j)(i+1, j+1)) +$
$\hat{\varphi}_1((i, j)(i+1, j+1), (i+1, j+1)(i+1, j+1+1)) +$
$\sum_{q=2}^{r} \hat{\varphi}_1((i+1, j+1+q-2)(i+1, j+1+q-1),$
$(i+1, j+1+q-1)(i+1, j+1+q))$ $\overline{S}_{T_v P^{d|}((i,j);r)} = v + \kappa(x_{i+1}, y_{j+1}) + \begin{cases} 0 & r = 0 \\ v_d + (r-1)v_v & r \geq 1 \end{cases}$ $T_\phi P^{d|}((i, j); r) = (\phi)P^{d|}((i, j); r)$ $= ((i, j), (i+1, j+1))P^{|}((i+1, j+1); r)$ $= ((i, j), (i+1, j+1))((i+1, j+1+1), (i+1, j+1+2),$
$\ldots (i+1, j+1+r)$ $\overline{S}_{T_\phi P^{d|}((i,j);r)} = \hat{\varphi}_0((i, j)(i+1, j+1)) +$
$\hat{\varphi}_1((i, j)(i+1, j+1), (i+1, j+1)(i+1, j+1+1)) +$
$\sum_{q=2}^{r} \hat{\varphi}_1((i+1, j+1+q-2)(i+1, j+1+q-1),$
$(i+1, j+1+q-1)(i+1, j+1+q))$ $\overline{S}_{T_\phi P^{d|}((i,j);r)} = \kappa(x_{i+1}, y_{j+1}) + \begin{cases} 0 & \text{if } r = 0 \\ v_d + (r-1)v_v & \text{if } r \geq 1 \end{cases}$ Case: i>1, j>1; (e)(f)(g)(h); s>0

$$T_d P^{h|}((i,j);s) = ((i-1,j-1))P^{h|}((i,j);s)$$
$$= ((i-1,j-1))((i,j),(i+1,j))P^{|}((i+1,j);s)$$
$$= ((i-1,j-1))((i,j),(i+1,j))((i+1,j+1),$$
$$(i+1,j+2), \ldots (i+1,j+s))$$

$$\overline{S}_{T_d P^{h|}((i,j);s)} = \hat{\varphi}_0((i-1,j-1)(i,j)) + \hat{\varphi}_1((i-1,j-1)(i,j),(i,j)(i+1,j)) +$$
$$\hat{\varphi}_1((i,j)(i+1,j),(i+1,j)(i+1,j+1)) +$$
$$\sum_{q=2}^{s} \hat{\varphi}_1((i+1,j+q-2)(i+1,j+q-1),(i+1,j+q-1)(i+1,j+q))$$

$$\overline{S}_{T_d P^{h|}((i,j);s)} = \kappa(x_i, y_j) + h_d + \begin{cases} 0 & \text{if } s = 0 \\ v_h + (s-1)v_v & \text{if } s \geq 1 \end{cases}$$

s=0 not valid since we assumed it is greater than 0.

$$T_h P^{h|}((i,j);s) = ((i-1,j))P^{h|}((i,j);s)$$
$$= ((i-1,j))((i,j),(i+1,j))P^{|}((i+1,j);s)$$
$$= ((i-1,j))((i,j),(i+1,j))((i+1,j+1),(i+1,j+2), \ldots (i+1,j+s))$$

$$\overline{S}_{T_h P^{h|}((i,j);s)} = \hat{\varphi}_0((i-1,j)(i,j)) +$$
$$\hat{\varphi}_1((i-1,j)(i,j),(i,j)(i+1,j)) + \hat{\varphi}_1((i,j)(i+1,j),(i+1,j)(i+1,j+1)) +$$
$$\sum_{q=2}^{s} \hat{\varphi}_1((i+1,j+q-2)(i+1,j+q-1),(i+1,j+q-1)(i+1,j+q))$$

$$\overline{S}_{T_h P^{h|}((i,j);s)} = h + h_h + \begin{cases} 0 & \text{if } s = 0 \\ v_h + (s-1)v_v & \text{if } s \geq 1 \end{cases}$$

s=0 not valid since we assumed it is greater than 0.

$$T_v P^{h|}((i,j);s) = ((i,j-1))P^{h|}((i,j);s)$$
$$= ((i,j-1))((i,j),(i+1,j))P^{|}((i+1,j);s)$$
$$= ((i,j-1))((i,j),(i+1,j))((i+1,j+1),(i+1,j+2), \ldots (i+1,j+s))$$

$$\overline{S}_{T_v P^{h|}((i,j);s)} = \hat{\varphi}_0((i,j-1)(i,j)) +$$
$$\hat{\varphi}_1((i,j-1)(i,j),(i,j)(i+1,j)) + \hat{\varphi}_1((i,j)(i+1,j),(i+1,j)(i+1,j+1)) +$$
$$\sum_{q=2}^{s} \hat{\varphi}_1((i+1,j+q-2)(i+1,j+q-1),(i+1,j+q-1)(i+1,j+q))$$

$$\overline{S}_{T_v P^{h|}((i,j);s)} = v + h_v + \begin{cases} 0 & \text{if } s = 0 \\ v_h + (s-1)v_v & \text{if } s \geq 1 \end{cases}$$

s=0 not valid since we assumed it is greater than 0.

$$T_\phi P^{h|}((i,j);s) = (\phi)P^{h|}((i,j);s)$$
$$= ((i,j),(i+1,j))p^{|}((i+1,j);s)$$
$$= ((i,j),(i+1,j))((i+1,j+1),(i+1,j+2), \ldots (i+1,j+s))$$

$$\overline{S}_{T_\phi P^{h|}((i,j);s)} = \hat{\varphi}_0((i,j)(i+1,j)) + \hat{\varphi}_1((i,j)(i+1,j),(i+1,j)(i+1,j+1)) +$$
$$\sum_{q=2}^{s} \hat{\varphi}_1((i+1,j+q-2)(i+1,j+q-1),(i+1,j+q-1)(i+1,j+q))$$

$$\overline{S}_{T_\phi P^{h|}((i,j);s)} = h + \begin{cases} 0 & \text{if } s = 0 \\ v_h + (s-1)v_v & \text{if } s \geq 1 \end{cases}$$

s=0 not valid since we assumed it is greater than 0.

Case: i>1, j>1; (i)(j)(k)(l); no r in this case.

$$P^f((i,j)) \triangleq ((i,j),(i+1,j)), \text{ for integers, } i \geq 0 \text{ and } j \geq 0$$

$$T_d P^f((i,j)) \triangleq T_d((i,j)(i+1,j))$$
$$T_d P^f((i,j)) = T_d((i,j)(i+1,j))$$
$$= ((i-1,j-1))((i,j)(i+1,j))$$

$$\overline{S}_{T_d P^f((i,j))} = \hat{\varphi}_0((i-1,j-1)(i,j)) + \hat{\varphi}_1((i-1,j-1)(i,j),(i,j)(i+1,j))$$

$$\overline{S}_{T_d P^f((i,j))} = \kappa(x_i, y_j) + h_d$$

$$T_h P^f((i,j)) \triangleq T_h((i,j)(i+1,j))$$
$$T_h P^f((i,j)) = T_h((i,j)(i+1,j))$$
$$= ((i-1,j))((i,j)(i+1,j))$$

$$\overline{S}_{T_h P^f((i,j))} = \hat{\varphi}_0((i-1,j)(i,j)) + \hat{\varphi}_1((i-1,j)(i,j),(i,j)(i+1,j))$$

$$\overline{S}_{T_h P^f((i,j))} = h + h_h$$

$$T_v P^f((i,j)) \triangleq T_v((i,j)(i+1,j))$$
$$T_v P^f((i,j)) = T_v((i,j)(i+1,j))$$
$$= ((i,j-1))((i,j)(i+1,j))$$

$$\overline{S}_{T_v P^f((i,j))} = \hat{\varphi}_0((i,j-1)(i,j)) + \hat{\varphi}_1((i,j-1)(i,j),(i,j)(i+1,j))$$

$$\overline{S}_{T_v P^f((i,j))} = v + h_v$$

$$T_\phi P^f((i,j)) \triangleq T_\phi((i,j)(i+1,j))$$
$$T_\phi P^f((i,j)) = T_\phi((i,j)(i+1,j))$$
$$= (\phi)((i,j)(i+1,j))$$
$$= ((i,j)(i+1,j))$$

$$\overline{S}_{T_\phi,P^f((i,j))} = \hat{\varphi}_0((i,j)(i+1,j))$$

$$\overline{S}_{T_\phi,P^f((i,j))} = h$$

Case: i>1, j>1; (m); below; r≥1

$$s = 1$$
$$T_\phi P^{v|}((i,j);r) \triangleq (\phi)((i,j))P^{|}((i,j);s) \quad (m)$$
$$T_\phi P^{v|}((i,j);r=1) = \hat{\varphi}_0((i,j)(i,j+1)) = v$$

Case: i>1, j>1; (n)(o)(p)(q); s≥1

$$T_d P^{v|}((i,j);s) \triangleq T_d((i,j))P^{|}((i,j);s)$$
$$T_d P^{v|}((i,j);s) = T_d P^{v|}((i,j);s)P^{|}((i,j);s)$$
$$= ((i-1,j-1))((i,j))P^{|}((i,j);s)$$
$$= ((i-1,j-1))((i,j))((i,j+1),((i,j+2), \ldots (i,j+s))$$

$$\overline{S}_{T_d P^{v|}((i,j);s)} = \hat{\varphi}_0((i-1,j-1)(i,j)) + \hat{\varphi}_1((i-1,j-1)(i,j),(i,j)(i,j+1)) +$$
$$\sum_{q=2}^{s} \hat{\varphi}_1((i,j+q-2)(i,j+q-1),(i,j+q-1)(i,j+q))$$

$$\overline{S}_{T_d P^{v|}((i,j);s)} = \kappa(x_i, y_j) + v_d + (s-1)v_v, \text{ for } s \geq 1.$$

$$T_h P^{v|}((i,j);s) \triangleq T_h((i,j))P^{|}((i,j);s)$$

-continued $$T_h P^{v|}((i,j);s) = T_h((i,j))P^|((i,j);s)$$
$$= ((i-1,j))((i,j))P^|((i,j);s)$$
$$= ((i-1,j))((i,j))(i,j+1),(i,j+2),\ldots(i,j+s))$$

$$\overline{S}_{T_h P^{v|}((i,j);s)} = \hat{\varphi}_0((i-1,j)(i,j)) + \hat{\varphi}_1((i-1,j)(i,j),(i,j)(i,j+1)) +$$
$$\sum_{q=2}^{s} \hat{\varphi}_1((i,j+q-2)(i,j+q-1),(i,j+q-1)(i,j+q))$$

$$\overline{S}_{T_h P^{v|}((i,j);s)} = h + v_h + (s-1)v_v, \text{ for } 2 \geq 1.$$

$$T_v P^{v|}((i,j);s) \triangleq T_v((i,j))P^|((i,j);s)$$

$$T_v P^{v|}((i,j);s) = T_v((i,j))P^|((i,j);s)$$
$$= ((i,j-1))((i,j))P^|((i,j);s)$$
$$= ((i,j-1))((i,j))((i,j+1),(i,j+2),\ldots(i,j+s))$$

$$\overline{S}_{T_v P^{v|}((i,j);s)} = \hat{\varphi}_0((i,j-1)(i,j)) + \hat{\varphi}_1((i,j-1)(i,j),(i,j)(i,j+1)) +$$
$$\sum_{q=2}^{s} \hat{\varphi}_1((i,j+q-2)(i,j+q-1),(i,j+q-1)(i,j+q))$$

$$\overline{S}_{T_v P^{v|}((i,j);s)} = +v_v + (s-1)v_v, \text{ for } 2 \geq 1.$$

$$T_\phi P^{v|}((i,j);s) \triangleq (\phi)((i,j))P^|((i,j);s)$$

$$P^{v|}((i,j);s) \triangleq ((i,j))P^|((i,j);s)$$

$$T_\phi P^{v|}((i,j);s) = T_\phi((i,j))P^|((i,j);s)$$
$$= (\phi)((i,j))P^|((i,j);s)$$
$$= ((i,j))((i,j+1),(i,j+2),\ldots(i,j+s))$$

$$\overline{S}_{T_\phi P^{v|}((i,j);s)} =$$
$$\hat{\varphi}_0((i,j)(i,j+1)) + \sum_{q=2}^{s} \hat{\varphi}_1((i,j+q-2)(i,j+q-1),(i,j+q-1)(i,j+q))$$

$$\overline{S}_{T_\phi P^{v|}((i,j);s)} = v + (s-1)v_v, \text{ for } s \geq 1$$

Case: $i>1, j>1$; (r)(s)(t)(u)

$$T_d((i,j)) \quad (r)$$
$$T_h((i,j)) \quad (s)$$
$$T_v((i,j)) \quad (t)$$
$$T_\phi((i,j)) \quad (u)$$
$$\overline{S}_{T_d((i,j))} = \kappa(x_i, y_j)$$
$$\overline{S}_{T_h((i,j))} = h$$
$$\overline{S}_{T_v((i,j))} = v$$
$$\overline{S}_{T_\phi((i,j))} \triangleq 0$$

Case: $i>1, j>1$; (v)(w)(x)(y); $r \geq 0$ $$T_d T_h P^{d|}((i,j);r) \triangleq ((i-2,j-1))((i-1,j))P^{d|}((i,j);r) \quad (v)$$
$$T_h T_h P^{d|}((i,j);r) \triangleq ((i-2,j))((i-1,j))P^{d|}((i,j);r) \quad (w)$$
$$T_v T_h P^{d|}((i,j);r) \triangleq (\phi)((i-1,j-1))((i-1,j))P^{d|}((i,j);r) \quad (x)$$
$$T_\phi T_h P^{d|}((i,j);r) \triangleq (\phi)((i-1,j))P^{d|}((i,j);r) \quad (y)$$

$$T_d T_h P^{d|}((i,j);r) \triangleq ((i-2,j-1))((i-1,j))P^{d|}((i,j);r)$$
$$T_d T_h P^{d|}((i,j);r) = ((i-2,j-1))((i-1,j))P^{d|}((i,j);r)$$
$$= ((i-2,j-1))((i-1,j))((i,j),(i+1,j+1))P^|((i+1,j+1);r)$$

-continued $$= ((i-2,j-1))((i-1,j))((i,j),(i+1,j+1))$$
$$\begin{pmatrix}(i+1,j+1+1),\\ \ldots(i+1,j+1+r)\end{pmatrix}$$

$$\overline{S}_{T_d T_h P^{d|}((i,j);r)} =$$
$$\hat{\varphi}_0((i-2,j-1)(i-1,j)) + \hat{\varphi}_1((i-2,j-1)(i-1,j),(i-1,j)(i,j))$$
$$+ \hat{\varphi}_1((i-1,j)(i,j),(i,j)(i+j)(i+1,j+1))$$
$$+ \hat{\varphi}_1((i,j)(i+1,j+1),(i=1,j+1)(i+1,j+1))$$
$$+ \sum_{q=2}^{r} \hat{\varphi}_1((i+1,j+1+q-2)(i+1,j+1+q-1),$$
$$(i+1,j+1+q-1)(i+1,j+1+q))$$

$$\overline{S}_{T_d T_h P^{d|}((i,j);r)} = \kappa(x_{i-1}, y_j) + h_d + \kappa(x_{i+1}, y_{j+1}) + \begin{cases} 0 & r=0 \\ v_d + (r+1)v_v & r \geq 1\end{cases}$$

$$T_h T_h P^{d|}((i,j);r) \triangleq ((i-2,j))((i-1,j))P^{d|}((i,j);r)$$
$$T_h T_h P^{d|}((i,j);r) = ((i-2,j))((i-1,j))P^{d|}((i,j);r)$$
$$= ((i-2,j))((i-1,j))((i,j),(i+1,j+1))P^|$$
$$((i+1,j+1);r)$$
$$= ((i-2,j))((i-1,j))((i,j),(i+1,j+1))$$
$$\begin{pmatrix}(i+1,j+2),(i+1,j+3),\\ \ldots(i+1,j+1+r)\end{pmatrix}$$

$$\overline{S}_{T_h T_h P^{d|}((i,j);r)} = \hat{\varphi}_0((i-2,j)(i-1,j) + \hat{\varphi}_1((i-2,j)(i-1,j),(i-1,j)(i,j))$$
$$+ \hat{\varphi}_1((i-1,j)(i,j),(i,j)(i+1,j+1)) + \hat{\varphi}_1((i,j)(i+1,j+1),$$
$$(i+1,j+1)(i+1,j+1+1)) + \sum_{q=2}^{r} \hat{\varphi}_1((i+1,j+1+q-2)$$
$$(i+1,j+1+q-1),(i+1,j+1+q-1)(i+1,j+1+q))$$

$$\overline{S}_{T_h T_h P^{d|}((i,j);r)} = h + h_h + \kappa(x_{i+1}, y_{j+1}) + \begin{cases} 0 & r=0 \\ v_d + (r-1)v_v & r \geq 1\end{cases}$$

$$T_v T_h P^{d|}((i,j);r) \triangleq ((i-1,j-1))((i-1,j))P^{d|}((i,j);r)$$
$$T_v T_v P^{d|}((i,j);r) = ((i-1,j-1))((i-1,j))P^{d|}((i,j);r)$$
$$= ((i-1,j-1))((i-1,j))((i,j),(i+1,j+1))P^|$$
$$((i+1,j+1);r)$$
$$= ((i-1,j-1))((i-1,j))((i,j),(i+1,j+1))$$
$$\begin{pmatrix}(i+1,j+2),(i+1,j+3),\\ \ldots(i+1,j+1+r)\end{pmatrix}$$

$$\overline{S}_{T_v T_h P^{d|}((i,j);r)} =$$
$$\hat{\varphi}_0((i-1,j-1)(i-1,j) + \hat{\varphi}_1((i-1,j-1)(i-1,j),(i-1,j)(i,j))$$
$$+ \hat{\varphi}_1((i-1,j)(i,j),(i,j)(i+1,j+1)) + \hat{\varphi}_1((i,j)(i+1,j+1),(i+1,j+1),$$
$$(i+1,j+1+1)) + \sum_{q=2}^{r} \hat{\varphi}_1((i+1,j+1+q-2)(i+1,j+1+q-1),$$
$$(i+1,j+1+q-1)(i+1,j+1+q))$$

$$\overline{S}_{T_v T_h P^{d|}((i,j);r)} = v + h_v + \kappa(x_{i+1}, y_{j+1}) + \begin{cases} 0 & r=0 \\ v_d + (r-1)v_v & r \geq 1\end{cases}$$

Not valid in all cases; right angle.

$$T_\phi T_h P^{d|}((i,j);r) = (\phi)((i-1,j))P^{d|}((i,j);r)$$
$$= ((i-1,j))((i,j),(i+1,j+1))P^|((i+1,j+1);r)$$
$$= ((i-1,j))((i,j),(i+1,j+1))$$
$$\begin{pmatrix}(i+1,j+1+1),(i+1,j+1+2),\\ \ldots(i+1,j+1+r)\end{pmatrix}$$

$$\overline{S}_{T_\phi T_h P^{d|}((i,j);r)} = \hat{\varphi}_0$$
$$\Big((i-1,j)(i,j) + \hat{\varphi}_1((i-1,j)(i,j),(i,j)(i+1,j+1)) + \hat{\varphi}_1((i,j)(i+1,j+1),$$

-continued $$(i+1, j+1)(i+1, j+1+1)) + \sum_{q=2}^{r} \hat{\varphi}_1((i+1, j+1+q-2)$$

$$(i+1, j+1+q-1), (i+1, j+1+q-1)(i+1, j+1+q))$$

$$\overline{S}_{T_d T_h P^d|((i,j);r)} = h + \kappa(x_{i+1}, y_{j+1}) + \begin{cases} 0 & r=0 \\ v_d + (r-1)v_v & r \geq 1 \end{cases}$$

Case: i>1, j>1; AA, BB, CC, and DD; r≥0

$$T_d T_d P^v|((i, j+1); r) \stackrel{\Delta}{=} T_d T_d((i, j+1))P^|((i, j+1); r) \quad (A)$$

$$T_h T_d P^v|((i, j+1); r) \stackrel{\Delta}{=} T_h T_d((i, j+1))P^|((i, j+1); r) \quad (B)$$

$$T_v T_d P^v|((i, j+1); r) \stackrel{\Delta}{=} T_v T_d((i, j+1))P^|((i, j+1); r) \quad (C)$$

$$T_\phi T_d P^v|((i, j+1); r) \stackrel{\Delta}{=} T_\phi T_d((i, j+1))P^|((i, j+1); r) \quad (D)$$

$$T_d T_d P^v|(i, j+1); r) = ((i-2, j-1))((i-1, j))((i, j+1))P^|((i, j+1); r)$$

$$T_d T_d P^v|(i, j+1); r) = ((i-2, j-1))((i-1, j))P^v|((i, j+1); r)$$

$$= ((i-2, j-1))((i-1, j))((i, j+1))P^1((i, j+1); r)$$

$$= ((i-2, j-1))((i-1, j))((i, j+1))((i, j+1+1))$$

$$\begin{pmatrix} (i, j+1+2), \\ \ldots (i, j+1+r) \end{pmatrix}$$

$$\overline{S}_{T_d T_d P^v|((i,j+1);r)} =$$

$$\hat{\varphi}_0((i-2, j-1)(i-1, j)) + \hat{\varphi}_1((i-2, j-1)(i-1, j), (i-j)(i, j+1)) +$$

$$\hat{\varphi}_1((i-1, j)(i, j+1), (i, j+1)(i, j+1+1)) +$$

$$\sum_{q=2}^{r} \hat{\varphi}_1((i, j+1+q-2)(i, j+1+q-1), (i, j+1+q-1)(i, j+1+q))$$

$$\overline{S}_{T_d T_d P^v|((i,j+1);r)} = \kappa(x_{i-1}, y_j) + \kappa(x_i, y_{j+1}) + \begin{cases} 0 & \text{if } r=0 \\ v_d + (r-1)v_v & \text{if } r \geq 1 \end{cases}$$

$$T_h T_d P^v|((i, j+1); r) = ((i-2, j))((i-1, j))((i, j+1))P^|((i, j+1); r)$$

$$T_h T_d P^v|((i, j+1); r) = ((i-2, j))((i-1, j))P^v|((i, j+1); r)$$

$$= ((i-2, j))((i-1, j))((i, j+1))P^|((i, j+1); r)$$

$$= ((i-2, j))((i-1, j))((i, j+1))((i, j+1+1))$$
$$((i, j+1+2), \ldots (i, j+1+r))$$

$$\overline{S}_{T_h T_d P^v|((i,j+1);r)} =$$

$$\hat{\varphi}_0((i-2, j)(i-1, j)) + \hat{\varphi}_1((i-2, j)(i-1, j), (i-1, j)(i, j+1)) +$$

$$\hat{\varphi}_1((i-1, j)(i, j+1), (i, j+1)(i, j+1+1))$$

$$\sum_{q=2}^{r} \hat{\varphi}_1((i, j+1+q-2)(i, j+1+q-1), (i, j+1+q-1)(i, j+1+q))$$

$$\overline{S}_{T_h T_d P^v|((i,j+1);r)} = h + \kappa(x_i, y_{j+1}) + \begin{cases} 0 & \text{if } r=0 \\ v_d + (r-1)v_v & \text{if } r \geq 1 \end{cases}$$

$$T_v T_d P^v|((i, j+1); r) = T_v T_d((i, j+1))P^|((i, j+1); r)$$

Not valid in M; produces a right angle.

$$T_\phi T_d P^v|((i, j+1); r) \stackrel{\Delta}{=} T_\phi T_d((i, j+1))P^|((i, j+1); r)$$

$$T_\phi T_d P^v|((i, j+1); r) = (\phi)((i-1, j))((i, j+1))P^|((i, j+1); r)$$

$$T_\phi T_d P^v|((i, j+1); r) = ((i-1, j))P^v|((i, j+1); r)$$

$$= ((i-1, j))((i, j+1))P^|((i, j+1); r)$$

$$= ((i-1, j))((i, j+1))((i, j+1+1))((i, j+1+2),$$
$$\ldots (i, j+1+r))$$

-continued $$\overline{S}_{T_\phi T_d P^v|((i,j+1);r)} =$$

$$\hat{\varphi}_0((i-1, j)(i, j+1)) + \hat{\varphi}_1((i-1, j)(i, j+1), (i, j+1)(i, j+1+1)) +$$

$$\sum_{q=2}^{r} \hat{\varphi}_1((i, j+1+q-2)(i, j+1+q-1), (i, j+1+q-1)(i, j+1+q))$$

$$\overline{S}_{T_\phi T_d P^v|((i,j+1);r)} = \kappa(x_i, y_{j+1}) + \begin{cases} 0 & \text{if } r=0 \\ v_d + (r-1)v_v & \text{if } r \geq 1 \end{cases}$$

Step 4) [ρ(A)–Score of W(B)] of all possible walks for ρ(A), and their corresponding W(B).

Difference of score of pairs of pairs: (DP,DQ), (HP,HQ), (VP,VQ), and (FP,FQ)

equivalently pairs: (a)(n), (b)(o), (c)(p), and (d)(q)

for i>1, j>1; r≥0.

$$\overline{S}_{T_d P^d|((i,j);r)} = \kappa(x_i, y_j) + \kappa(x_{i+1}, y_{j+1}) + \begin{cases} 0 & r=0 \\ v_d + (r-1)v_v & r \geq 1 \end{cases}$$

$$\overline{S}_{T_d P^d|((i,j);s)} = \kappa(x_i, y_j) + v_d + (s-1)v_v, \text{ for } s \geq 1.$$

$$s = r+1.$$

$$\overline{S}_{T_d P^v|((i,j);r+1)} = \kappa(x_i, y_j) + v_d + (r+1-1)v_v, \text{ for } r+1 \geq 1.$$

$$\overline{S}_{T_d P^v|((i,j);r+1)} = \kappa(x_i, y_j) + v_d + rv_v, \text{ for } r \geq 0.$$

$$\overline{S}_{T_d P^d|((i,j);r)} - \overline{S}_{T_d P^v|((i,j);r+1)} = \kappa(x_{i+1}, y_{j+1}) - v_d, \text{ if } r=0$$

$$\overline{S}_{T_d P^d|((i,j);r)} - \overline{S}_{T_d P^v|((i,j);r+1)} = \kappa(x_{i+1}, y_{j+1}) - v_v, \text{ if } r \geq 1$$

$$\overline{S}_{T_h P^d|((i,j);r)} = h + \kappa(x_{i+1}, y_{j+1}) + \begin{cases} 0 & r=0 \\ v_d + (r-1)v_v & r \geq 1 \end{cases}$$

$$\overline{S}_{T_h P^v|((i,j);s)} = h + v_h + (s-1)v_v, \text{ for } s \geq 1.$$

$$s = r+1$$

$$\overline{S}_{T_h P^v|((i,j);r+1)} = h + v_h + (r+1-1)v_v, \text{ for } r+1 \geq 1.$$

$$\overline{S}_{T_h P^v|((i,j);r+1)} = h + v_h + rv_v, \text{ for } r \geq 0.$$

$$\overline{S}_{T_h P^d|((i,j);r)} - \overline{S}_{T_h P^v|((i,j);r+1)} = \kappa(x_{i+1}, y_{j+1}) - v_h, \text{ if } r=0$$

$$\overline{S}_{T_h P^d|((i,j);r)} - \overline{S}_{T_h P^v|((i,j);r+1)} = \kappa(x_{i+1}, y_{j+1}) + v_d - v_h - v_v, \text{ if } r \geq 1$$

$$\overline{S}_{T_v P^d|((i,j);r)} = v + \kappa(x_{i+1}, y_{j+1}) + \begin{cases} 0 & r=0 \\ v_d + (r-1)v_v & r \geq 1 \end{cases}$$

$$\overline{S}_{T_v P^v|((i,j);s)} = v + v_v + (s-1)v_v, \text{ for } s \geq 1.$$

$$s = r+1$$

$$\overline{S}_{T_v P^v|((i,j);r+1)} = v + v_v + (r+1-1)v_v, \text{ for } r+1 \geq 1.$$

$$\overline{S}_{T_v P^v|((i,j);r+1)} = v + v_v + rv_v, \text{ for } r \geq 0.$$

$$\overline{S}_{T_v P^d|((i,j);r)} - \overline{S}_{T_v P^v|((i,j);r+1)} = \kappa(x_{i+1}, y_{j+1}) - v_v, \text{ if } r=0$$

$$\overline{S}_{T_v P^d|((i,j);r)} - \overline{S}_{T_v P^v|((i,j);r+1)} = \kappa(x_{i+1}, y_{j+1}) + v_d - v_v - v_v, \text{ if } r \geq 1$$

$$\overline{S}_{T_\phi P^d|((i,j);r)} = \kappa(x_{i+1}, y_{j+1}) + \begin{cases} 0 & \text{if } r=0 \\ v_d + (r-1)v_v & \text{if } r \geq 1 \end{cases}$$

$$\overline{S}_{T_\phi P^v|((i,j);s)} = v + (s-1)v_v, \text{ for } s \geq 1.$$

$$s = r+1$$

$$\overline{S}_{T_\phi P^v|((i,j);r+1)} = v + (r+1-1)v_v, \text{ for } r+1 \geq 1.$$

$$\overline{S}_{T_\phi P^d|((i,j);r)} = v + rv_v, \text{ for } r \geq 0.$$

$$\overline{S}_{T_\phi P^d|((i,j);r)} - \overline{S}_{T_\phi P^d|((i,j);r)} = \kappa(x_{i+1}, y_{j+1}) - v, \text{ if } r=0$$

-continued $$\overline{S}_{T_\phi P^d|((i,j);r)} - \overline{S}_{T_\phi P^d|((i,j);r)} = \kappa(x_{i+1}, y_{j+1}) + v_d - v - v_v, \text{ if } r \geq 1$$

Difference of score of pairs of pairs: (DU,DW), (HU, HW), (VU,VW), and (FU,FW)
equivalently pairs: (e)(n), (f)(o), (g)(p), and (h)(q)
for i>1, j>1; r≥0.

$$\overline{S}_{T_d P^h|((i,j);r)} = \kappa(x_i, y_j) + h_d + \begin{cases} 0 & r = 0 \\ v_h + (r-1)v_v & r \geq 1 \end{cases}$$

r=0 not valid since we assumed it is greater than 0.

$$\overline{S}_{T_d P^v|((i,j);r)} = \kappa(x_i, y_j) + v_d + (r-1)v_v, \text{ if } r \geq 1.$$

$$\overline{S}_{T_d P^h|((i,j);r)} - \overline{S}_{T_d P^v|((i,j);r)} = h_d + v_h - v_d, \text{ if } r \geq 1.$$

$$\overline{S}_{T_h P^h|((i,j);r)} = h + h_h + \begin{cases} 0 & r = 0 \\ v_h + (r-1)v_v & r \geq 1 \end{cases}$$

r=0 not valid since we assumed it is greater than 0.

$$\overline{S}_{T_h P^v|((i,j);r)} = h + v_h + (r-1)v_v, \text{ if } r \geq 1.$$

$$\overline{S}_{T_h P^h|((i,j);r)} - \overline{S}_{T_h P^v|((i,j);r)} = h_h, \text{ if } r \geq 1.$$

$$\overline{S}_{T_v P^h|((i,j);r)} = v + h_v + \begin{cases} 0 & r = 0 \\ v_h + (r-1)v_v & r \geq 1 \end{cases}$$

r=0 not valid since we assumed it is greater than 0.

$$\overline{S}_{T_v P^v|((i,j);r)} = v + v_v + (r-1)v_v, \text{ if } r \geq 1.$$

$$\overline{S}_{T_v P^h|((i,j);r)} - \overline{S}_{T_v P^v|((i,j);r)} = h_v + v_h - v_v$$

$$\overline{S}_{T_\phi P^h|((i,j);r)} = h + \begin{cases} 0 & \text{if } r = 0 \\ v_h + (r-1)v_v & \text{if } r \geq 1 \end{cases}$$

r=0 not valid since we assumed it is greater than 0.

$$\overline{S}_{T_\phi P^v|((i,j);r)} = v + (r-1)v_v, \text{ for } r \geq 1.$$

$$\overline{S}_{T_\phi P^h|((i,j);r)} - \overline{S}_{T_\phi P^v|((i,j);r)} = h + v_h - v, \text{ if } r \geq 1$$

Difference of score of pairs of pairs: (DX,D), (HX,H), (VX,V), and (FX,F)
equivalently pairs: (i)(r), (j)(s), (k)(t), and (l)(u)
for i>1, j>1

$$\overline{S}_{T_d P^f(i,j)} = \kappa(x_i, y_j) + h_d$$

$$\rho(i,j) \geq \overline{S}_{T_d((i,j))} = \kappa(x_i, y_j)$$

$$\overline{S}_{T_d P^f(i,j)} - \rho(i,j) \leq \kappa(x_i, y_j) + h_d - \kappa(x_i, y_j) = h_d$$

$$\overline{S}_{T_d P^f(i,j)} - \rho(i,j) \leq h_d$$

$$\overline{S}_{T_h P^f(i,j)} = h + h_h$$

$$\rho(i,j) \geq \overline{S}_{T_h((i,j))} = h$$

$$\overline{S}_{T_h P^f(i,j)} - \rho(i,j) h + h_h - h = h_h$$

$$\overline{S}_{T_h P^f(i,j)} - \rho(i,j) \leq h_h$$

$$\overline{S}_{T_v P^f(i,j)} = v + h_v$$

$$\rho(i,j) \geq \overline{S}_{T_v((i,j))} = v$$

$$\overline{S}_{T_v P^f(i,j)} - \rho(i,j) \leq v + h_v - v = h_v$$

$$\overline{S}_{T_v P^f(i,j)} - \rho(i,j) \leq h_v$$

$$\overline{S}_{T_\phi P^f(i,j)} = h$$

$$\rho(i,j) \geq \overline{S}_{T_\phi P^f(i,j)} \triangleq$$

$$\overline{S}_{T_\phi P^f(i,j)} - \rho(i,j) \leq h - 0$$

$$\overline{S}_{T_\phi P^f(i,j)} - \rho(i,j) \leq h$$

Difference of score of pairs of pairs: (DHP,DDQ'), (HHP, HDQ'), (VHP,VDQ'), and (FHP,FDQ')
equivalently pairs: (v)(AA), (w)(BB), (x)(CC), and (y)(DD)

$$i > 1, j > 1; r \geq 0;$$

$$T_d T_h P^d|((i,j); r) \triangleq ((i-2, j-1)((i-1, j))P^d|((i,j); r) \quad \text{(v)}$$

$$T_h T_h P^d|((i,j); r) \triangleq ((i-2, j))((i-1, j))P^d|((i,j); r) \quad \text{(w)}$$

$$T_v T_h P^d|((i,j); r) \triangleq ((i-1, j-1)((i-1, j))P^d|((i,j); r) \quad \text{(x)}$$

$$T_\phi T_h P^d|((i,j); r) \triangleq (\phi)((i-1, j))P^d|((i,j); r) \quad \text{(y)}$$

$$\overline{S}_{T_d T_h P^d|((i,j);r)} = \kappa(x_{i-1}, y_j) + h_d + \kappa(x_{i+1}, y_{j+1}) + \begin{cases} 0 & r = 0 \\ v_d + (r-1)v_v & r \geq 1 \end{cases}$$

$$\overline{S}_{T_d T_d P^v|((i,j+1);r)} = \kappa(x_{i-1}, y_j) + \kappa(x_i, y_{j+1}) + \begin{cases} 0 & r = 0 \\ v_d + (r-1)v_v & r \geq 1 \end{cases}$$

$$\overline{S}_{T_d T_h P^d|((i,j);r)} - \overline{S}_{T_d T_d P^v|((i,j+1);r)} = h_d + \kappa(x_{i+1}, y_{j+1}) - \kappa(x_i, y_{j+1}), \text{ for } r \geq 0.$$

$$\overline{S}_{T_h T_h P^d|((i,j);r)} = h + h_h + \kappa(x_{i+1}, y_{j+1}) + \begin{cases} 0 & r = 0 \\ v_d + (r-1)v_v & r \geq 1 \end{cases}$$

$$\overline{S}_{T_h T_d P^v|((i,j+1);r)} = h + \kappa(x_i, y_{j+1}) + \begin{cases} 0 & \text{if } r = 0 \\ v_d + (r+1)v_v & \text{if } r \geq 1 \end{cases}$$

$$\overline{S}_{T_h T_h P^d|((i,j);r)} - \overline{S}_{T_h T_d P^v|((i,j+1);r)} = h_h + \kappa(x_{i+1}, y_{j+1}) - \kappa(x_i, y_{j+1}), \text{ for } r \geq 0$$

$$\overline{S}_{T_v T_h P^d|((i,j);r)} = v + h_v + \kappa(x_{i+1}, y_{j+1}) + \begin{cases} 0 & r = 0 \\ v_d + (r+1)v_v & r \geq 1 \end{cases}$$

Not valid in M; v followed by h!

$$T_v T_d P^v|((i,j+1); r) \triangleq T_v T_d((i,j+1))P^|((i,j+1); r)$$

$$\overline{S}_{T_\phi T_h P^d|((i,j);r)} = h + \kappa(x_{i+1}, y_{j+1}) + \begin{cases} 0 & r = 0 \\ v_d + (r-1)v_v & r \geq 1 \end{cases}$$

Not valid overlapping alignment.

$$\overline{S}_{T_\phi T_d P^v|((i,j+1);r)} = \kappa(x_i, y_{j+1}) + \begin{cases} 0 & r = 0 \\ v_d + (r+1)v_v & r \geq 1 \end{cases}$$

$$\overline{S}_{T_\phi T_h P^d|((i,j);r)} - \overline{S}_{T_\phi T_d P^v|((i,j+1);r)} = h + \kappa(x_{i+1}, y_{j+1}) - \kappa(x_i, y_{j+1}), \text{ for } r \geq 0$$

Step 5) Tabulation of all possible ρ(A)–Score of W(B)
We extend the above results for all valid (i,j) and tabulate the results below.

For AS

| | $i = R$ and $j = C$ | $R > 1$, $C \geq 2$ (1 & 2) | $R = 1$, $C = 2$ (3) | $R = 1$, $C > 2$ (4) | $R > 1$, $C = 1$ (5) | $R = 1$, $C = 1$ (6) | $R > 0$, $C = 0$ (7) | $R = 0$, $C > 1$ (8) | $R = 0$, $C = 1$ (9) | $R = 0$, $C = 0$ (10) |
|---|---|---|---|---|---|---|---|---|---|---|
| 1 DP DQ | $\overline{S}_{T_d P^d}((i,j);\, r) - \overline{S}_{T_d P^v}((i,j);\, r+1) = \kappa(x_{i+1}, y_{j+1}) - v_d$, if $r = 0$ <br> $\overline{S}_{T_d P^d}((i,j);\, r) - \overline{S}_{T_d P^v}((i,j);\, r+1) = \kappa(x_{i+1}, y_{j+1}) - v_v$, if $r \geq 1$ | | | | | | NO | NO | NO | NO |
| 2 HP HQ | $\overline{S}_{T_h P^d}((i,j);\, r) - \overline{S}_{T_h P^v}((i,j);\, r+1) = \kappa(x_{i+1}, y_{j+1}) - v_h$, if $r = 0$ <br> $\overline{S}_{T_h P^d}((i,j);\, r) - \overline{S}_{T_h P^v}((i,j);\, r+1) = \kappa(x_{i+1}, y_{j+1}) - v_h + v_d - v_v$, if $r \geq 1$ | | | NO | NO | NO | NO | NO | NO | |
| 3 VP VQ | $\overline{S}_{T_v P^d}((i,j);\, r) - \overline{S}_{T_v P^v}((i,j);\, r+1) = \kappa(x_{i+1}, y_{j+1}) - v_v$, if $r = 0$ <br> $\overline{S}_{T_v P^d}((i,j);\, r) - \overline{S}_{T_v P^v}((i,j);\, r+1) = \kappa(x_{i+1}, y_{j+1}) - v_v + v_d - v_v$, if $r \geq 1$ | | NO | NO | | NO | NO | NO | NO | NO |
| 4 FP FQ | $\overline{S}_{T_\phi P^d}((i,j);\, r) - \overline{S}_{T_\phi P^d}((i,j);\, r) = \kappa(x_{i+1}, y_{j+1}) - v$, if $r = 0$ <br> $\overline{S}_{T_\phi P^d}((i,j);\, r) - \overline{S}_{T_\phi P^d}((i,j);\, r) = \kappa(x_{i+1}, y_{j+1}) + v_d - v - v_v$, if $r \geq 1$ | | | | | | | X | X | X |
| 4 FP DQ' | $\overline{S}_{T_\phi P^d}((i,j);\, r) - \overline{S}_{T_\phi P^d}((i,j);\, r) = \kappa(x_{i+1}, y_{j+1}) - \kappa(x_i, y_{j+1})$ | X | X | X | X | X | X | | X | |
| 4 FP Q'' | $\overline{S}_{T_\phi P^d}((i,j);\, r) - \overline{S}_{T_\phi P^d}((i,j);\, r) = \kappa(x_{i+1}, y_{j+1}) - v$, if $r = 0$ <br> $\overline{S}_{T_\phi P^d}((i,j);\, r) - \overline{S}_{T_\phi P^d}((i,j);\, r) = \kappa(x_{i+1}, y_{j+1}) + v_d + (r-1)v_v - v$, if $r \geq 1$ | X | X | X | X | X | X | X | X | |
| 5 DU DW | $\overline{S}_{T_d P^h}((i,j);\, r) - \overline{S}_{T_d P^v}((i,j);\, r) = h_d + v_h - v_d$, if $r \geq 1$. | | | | | | NO | NO | NO | NO |
| 6 HU HW | $\overline{S}_{T_h P^h}((i,j);\, r) - \overline{S}_{T_h P^v}((i,j);\, r) = h_h$, if $r \geq 1$. | | | | NO | NO | NO | | NO | |
| 7 VU VW | $\overline{S}_{T_v P^h}((i,j);\, r) - \overline{S}_{T_v P^v}((i,j);\, r) = h_v + v_h - v_v$ if $r \geq 1$. | | NO | NO | | NO | NO | NO | NO | NO |
| 8 FU FW | $\overline{S}_{T_\phi P^h}((i,j);\, r) - \overline{S}_{T_\phi P^v}((i,j);\, r) = h + v_h - v$, if $r \geq 1$ | NO | NO | NO | NO | NO | NO | NO | NO | |
| 9 DX D | $\overline{S}_{T_d P}(i,j) - \overline{S}_{T_d}(i,j) \leq h_d$ | | | | | | NO | NO | NO | NO |
| 10 HX H | $\overline{S}_{T_h P}(i,j) - \overline{S}_{T_h}(i,j) \leq h_h$ | | | | NO | NO | NO | NO | NO | NO |
| 11 VX V | $\overline{S}_{T_v P}(i,j) - \overline{S}_{T_v}(i,j) \leq h_v$ | | NO | NO | | NO | NO | NO | NO | NO |
| 12 FX F | $\overline{S}_{T_\phi P}(0,0) - \overline{S}_{T_\phi}(0,0) \leq h$ | | | | | | | | | |
| 13 FY FQ'' | $\rho(A) - \rho(B) \leq 0$ | | | | | | NO | | NO | |
| | | 1 | 3 | 4 | 5 | 6 | 7 | 8 | 9 | 10 |

Here we note $\overline{S}_{T_\phi}(0,0) = \rho(0,0) = 0$.

For M

M follows AS except in row index 2. The (R,C) values that have NO in row index 2 do not have a valid walk for $\rho(A)$, so they are ignored. But the (R,C) values that have X in row index 2 need a new walk for B since the one used for AS is not valid for M. For these (R,C)'s, we give a valid walk in the next table.

| | $i = R$ and $j = C$ | $R > 1$, $C \geq 2$ (1 & 2) | $R = 1$, $C = 2$ (3) | $R = 1$, $C > 2$ (4) | $R > 1$, $C = 1$ (5) | $R = 1$, $C = 1$ (6) | $R > 0$, $C = 0$ (7) | $R = 0$, $C > 1$ (8) | $R = 0$, $C = 1$ (9) | $R = 0$, $C = 0$ (10) |
|---|---|---|---|---|---|---|---|---|---|---|
| 1 DP DQ | $\overline{S}_{T_d P^d}((i,j);\, r) - \overline{S}_{T_d P^v}((i,j);\, r+1) = \kappa(x_{i+1}, y_{j+1}) - v_d$, if $r = 0$ <br> $\overline{S}_{T_d P^d}((i,j);\, r) - \overline{S}_{T_d P^v}((i,j);\, r+1) = \kappa(x_{i+1}, y_{j+1}) - v_v$, if $r \geq 1$ | | | | | | NO | NO | NO | NO |
| 2 HP HQ | see table below | X | X | X | X | X | NO | X | X | NO |
| 3 VP VQ | $\overline{S}_{T_v P^d}((i,j);\, r) - \overline{S}_{T_v P^v}((i,j);\, r+1) = \kappa(x_{i+1}, y_{j+1}) - v_v$, if $r = 0$ <br> $\overline{S}_{T_v P^d}((i,j);\, r) - \overline{S}_{T_v P^v}((i,j);\, r+1) = \kappa(x_{i+1}, y_{j+1}) - v_v + v_d - v_v$, if $r \geq 1$ | | NO | NO | | NO | NO | NO | NO | NO |
| 4 FP FQ | $\overline{S}_{T_\phi P^d}((i,j);\, r) - \overline{S}_{T_\phi P^d}((i,j);\, r) = \kappa(x_{i+1}, y_{j+1}) - v$, if $r = 0$ <br> $\overline{S}_{T_\phi P^d}((i,j);\, r) - \overline{S}_{T_\phi P^d}((i,j);\, r) = \kappa(x_{i+1}, y_{j+1}) + v_d - v - v_v$, if $r \geq 1$ | | | | | | | | | |
| 5 DU DW | $\overline{S}_{T_d P^h}((i,j);\, r) - \overline{S}_{T_d P^v}((i,j);\, r) = h_d + v_h - v_d$, if $r \geq 1$. | NO | NO | NO | NO | NO | NO | NO | NO | NO |

-continued

| | i = R and j = C | R > 1 C ≥ 2 1 & 2 | R = 1 C = 2 3 | R = 1 C > 2 4 | R > 1 C = 1 5 | R = 1 C = 1 6 | R > 0 C = 0 7 | R = 0 C > 1 8 | R = 0 C = 1 9 | R = 0 C = 0 10 |
|---|---|---|---|---|---|---|---|---|---|---|
| 6 HU HW | $\overline{S}_{T_h P^{h}((i,j);\,r)} - \overline{S}_{T_h P^{v}((i,j);\,r)} = h_h$, if r ≥ 1. | NO | NO | NO | NO | NO | NO | NO | NO | NO |
| 7 VU VW | $\overline{S}_{T_v P^{h}((i,j);\,r)} - \overline{S}_{T_v P^{v}((i,j);\,r)} = h_v + v_h - v_v$, if r ≥ 1. | NO | NO | NO | NO | NO | NO | NO | NO | NO |
| 8 FU FW | $\overline{S}_{T_\phi P^{h}((i,j);\,r)} - \overline{S}_{T_\phi P^{v}((i,j);\,r)} = h + v_h - v$, if r ≥ 1 | NO | NO | NO | NO | NO | NO | NO | NO | NO |
| 9 DX D | $\overline{S}_{T_d P^{f}(i,j)} - \overline{S}_{T_d(i,j)} \le h_d$ | | | | | | NO | NO | NO | NO |
| 10 HX H | $\overline{S}_{T_h P^{f}(i,j)} - \overline{S}_{T_h(i,j)} \le h_h$ | | | | NO | NO | NO | NO | NO | NO |
| 11 VX V | $\overline{S}_{T_v P^{f}(i,j)} - \overline{S}_{T_v(i,j)} \le h_v$ | NO | NO | NO | NO | NO | NO | NO | NO | NO |
| 12 FX F | $\overline{S}_{T_\phi P^{f}(0,0)} - \overline{S}_{T_\phi(0,0)} \le h$ | | | | | | | | | |
| 13 FY FQ" | $\overline{S}_{T_\phi P^{f}(0,0)} - \overline{S}_{T_\phi(0,0)} \le h$ | NO | NO | NO | NO | NO | NO | NO | NO | NO |

Below, bold font pairs are not valid in M, but the regular font pairs are valid; their score differences are given in the last column. The regular font pairs use a new walks for B, which are valid in M.

Underbar means not valid for AS, as well.

| 01 R > 1 C = 2 | HP HQ DHP DDQ' HHP HDQ' VHP VDQ' FHP FDQ' | $\overline{S}_{T_d T_h P^{d}((i,j);\,r)} - \overline{S}_{T_d T_h P^{v}((i,j+1);\,r)} = h_d + \kappa(x_{i+1}, y_{j+1}) - \kappa(x_i, y_{j+1})$, for r ≥ 0. |
|---|---|---|
| 02 R > 1 C > 2 | HP HQ DHP DDQ' HHP HDQ' VHP VDQ' FHP FDQ' | $\overline{S}_{T_d T_h P^{d}((i,j);\,r)} - \overline{S}_{T_d T_h P^{v}((i,j+1);\,r)} = h_d + \kappa(x_{i+1}, y_{j+1}) - \kappa(x_i, y_{j+1})$, for r ≥ 0. <br> $\overline{S}_{T_h T_h P^{d}((i,j);\,r)} - \overline{S}_{T_h T_h P^{v}((i,j+1);\,r)} = h_h + \kappa(x_{i+1}, y_{j+1}) - \kappa(x_i, y_{j+1})$, for r ≥ 0 |
| 03 R = 1 C = 2 | HP HQ DHP DDQ' HHP HDQ' VHP VDQ' FHP FDQ' | $\overline{S}_{T_d T_h P^{d}((i,j);\,r)} - \overline{S}_{T_d T_h P^{v}((i,j+1);\,r)} = h_d + \kappa(x_{i+1}, y_{j+1}) - \kappa(x_i, y_{j+1})$, for r ≥ 0. |
| 04 R = 1 C > 2 | HP HQ DHP DDQ' HHP HDQ' VHP VDQ' FHP FDQ' | $\overline{S}_{T_d T_h P^{d}((i,j);\,r)} - \overline{S}_{T_d T_h P^{v}((i,j+1);\,r)} = h_d + \kappa(x_{i+1}, y_{j+1}) - \kappa(x_i, y_{j+1})$, for r ≥ 0. <br> $\overline{S}_{T_h T_h P^{d}((i,j);\,r)} - \overline{S}_{T_h T_h P^{v}((i,j+1);\,r)} = h_h + \kappa(x_{i+1}, y_{j+1}) - \kappa(x_i, y_{j+1})$, for r ≥ 0 |
| 05 R > 1 C = 1 | HP HQ HP DQ' | $\overline{S}_{T_h P^{d}((i,j);\,r)} - \overline{S}_{T_h P^{v}((i,j+1);\,r)} = h + \kappa(x_{i+1}, y_{j+1}) - \kappa(x_i, y_{j+1})$, if r ≥ 0 |
| 06 R = 1 C = 1 | HP HQ | |
| 07 R > 0 C = 0 | HP HQ | |
| 08 R = 0 C > 1 | HP HQ | |
| 09 R = 0 C = 1 | HP HQ | |
| 10 R = 0 C = 0 | HP HQ | |

Step 6) An overall upper bound for ρ(A)–Score of W(B) for affine, simplified and modified gap scores.

Next, we maximize the upper bounds in the tables of step 5) using $\kappa_{max}$ and $\kappa_{min}$, where $\kappa_{max}$=max ($\kappa(x_i,y_j)$) and $\kappa_{min}$=min ($\kappa(x_i,y_j)$).

For AS:

| | i = R and j = C | R > 1 C ≥ 2 | R = 1 C ≥ 2 | R > 1 C = 1 | R = 1 C = 1 | R > 0 C = 0 | R = 0 C > 1 | R = 0 C = 1 | R = 0 C = 0 |
|---|---|---|---|---|---|---|---|---|---|
| 1 DP DQ | $\overline{S}_{T_d P^{d}((i,j);\,r)} - \overline{S}_{T_d P^{v}((i,j);\,r+1)} \le$ <br> $\kappa_{max} - v_d$, if r = 0 <br> $\overline{S}_{T_d P^{d}((i,j);\,r)} - \overline{S}_{T_d P^{v}((i,j);\,r+1)} \le$ <br> $\kappa_{max} - v_v$, if r ≥ 1 | | | | | | NO | NO | NO | NO |
| 2 HP HQ | $\overline{S}_{T_h P^{d}((i,j);\,r)} - \overline{S}_{T_h P^{v}((i,j);\,r+1)} \le$ <br> $\kappa_{max} - v_h$, if r = 0 <br> $\overline{S}_{T_h P^{d}((i,j);\,r)} - \overline{S}_{T_h P^{v}((i,j);\,r+1)} \le$ <br> $\kappa_{max} - v_h + v_d - v_v$, if r ≥ 1 | | | | | | | NO | | NO |

-continued

| | | i = R and j = C | R > 1, C ≥ 2 | R = 1, C ≥ 2 | R > 1, C = 1 | R = 1, C = 1 | R > 0, C = 0 | R = 0, C > 1 | R = 0, C = 1 | R = 0, C = 0 |
|---|---|---|---|---|---|---|---|---|---|---|
| 3 | VP VQ | $\overline{S}_{T_v P^d}((i,j); r) - \overline{S}_{T_v P^v}((i,j); r+1) \leq$ $\kappa_{max} - v_v$, if r = 0 $\overline{S}_{T_v P^d}((i,j); r) - \overline{S}_{T_v P^v}((i,j); r+1) \leq$ $\kappa_{max} - v_v + v_d - v_v$, if r ≥ 1 | | | | | | NO | NO | NO |
| 4 | FP FQ | $\overline{S}_{T_\phi P^d}((i,j); r) - \overline{S}_{T_\phi P^d}((i,j); r) \leq$ $\kappa_{max} - v$, if r = 0 $\overline{S}_{T_\phi P^d}((i,j); r) - \overline{S}_{T_\phi P^d}((i,j); r) \leq$ $\kappa_{max} + v_d - v - v_v$, if r ≥ 1 | NO | NO | NO | NO | NO | NO | NO | |
| 5 | DU DW | $\overline{S}_{T_d P^h}((i,j); r) - \overline{S}_{T_d P^v}((i,j); r) =$ $h_d + v_h - v_d$, if r ≥ 1. | | | | | NO | NO | NO | NO |
| 6 | HU HW | $\overline{S}_{T_h P^h}((i,j); r) - \overline{S}_{T_h P^v}((i,j); r) =$ $h_h$, if r ≥ 1. | | | | | NO | | | NO |
| 7 | VU VW | $\overline{S}_{T_v P^h}((i,j); r) - \overline{S}_{T_v P^v}((i,j); r) =$ $h_v + v_h - v_v$, if r ≥ 1. | | | | | NO | NO | NO | |
| 8 | FU FW | $\overline{S}_{T_\phi P^h}((i,j); r) - \overline{S}_{T_\phi P^v}((i,j); r) =$ $h + v_h - v$, if r ≥ 1 | NO | NO | NO | NO | NO | NO | NO | |
| 9 | DX D | $\overline{S}_{T_d P^f}(i,j) - \overline{S}_{T_d}(i,j) \leq h_d$ | | | | | NO | NO | NO | NO |
| 10 | HX H | $\overline{S}_{T_h P^f}(i,j) - \overline{S}_{T_h}(i,j) \leq h_h$ | | | | | NO | | | NO |
| 11 | VX V | $\overline{S}_{T_v P^f}(i,j) - \overline{S}_{T_v}(i,j) \leq h_v$ | | | | | | NO | NO | NO |
| 12 | FX F | $\overline{S}_{T_\phi P^f}(0,0) - \overline{S}_{T_\phi}(0,0) \leq h$ | NO | NO | NO | NO | NO | NO | NO | |

For M:

| | | i = R and j = C | R > 1, C ≥ 2 | R = 1, C ≥ 2 | R > 1, C = 1 | R = 1, C = 1 | R > 0, C = 0 | R = 0, C > 1 | R = 0, C = 1 | R = 0, C = 0 |
|---|---|---|---|---|---|---|---|---|---|---|
| 1 | DP DQ | $\overline{S}_{T_d P^d}((i,j); r) - \overline{S}_{T_d P^v}((i,j); r+1) \leq$ $\kappa_{max} - v_d$, if r = 0 $\overline{S}_{T_d P^d}((i,j); r) - \overline{S}_{T_d P^v}((i,j); r+1) \leq$ $\kappa_{max} - v_v$, if r ≥ 1 | | | | | NO | NO | NO | NO |
| 2 | HP HQ | see table below | X | X | X | X | NO | X | X | NO |
| 3 | VP VQ | $\overline{S}_{T_v P^d}((i,j); r) - \overline{S}_{T_v P^v}((i,j); r+1) \leq$ $\kappa_{max} - v_v$, if r = 0 $\overline{S}_{T_v P^d}((i,j); r) - \overline{S}_{T_v P^v}((i,j); r+1) \leq$ $\kappa_{max} - v_v + v_d - v_v$, if r ≥ 1 | | ~~NO~~ | | | NO | NO | NO | |
| 4 | FP FQ | $\overline{S}_{T_\phi P^d}((i,j); r) - \overline{S}_{T_\phi P^d}((i,j); r) \leq$ $\kappa_{max} - v$, if r = 0 $\overline{S}_{T_\phi P^d}((i,j); r) - \overline{S}_{T_\phi P^d}((i,j); r) \leq$ $\kappa_{max} + v_d - v - v_v$, if r ≥ 1 | NO | NO | NO | NO | NO | NO | NO | |
| 5 | DU DW | $\overline{S}_{T_d P^h}((i,j); r) - \overline{S}_{T_d P^v}((i,j); r) =$ $h_d + v_h - v_d$, if r ≥ 1. | NO | NO | NO | NO | NO | NO | NO | |
| 6 | HU HW | $\overline{S}_{T_h P^h}((i,j); r) - \overline{S}_{T_h P^v}((i,j); r) =$ $h_h$, if r ≥ 1. | NO | NO | NO | NO | NO | NO | NO | |
| 7 | VU VW | $\overline{S}_{T_v P^h}((i,j); r) - \overline{S}_{T_v P^v}((i,j); r) =$ $h_v + v_h - v_v$, if r ≥ 1. | NO | NO | NO | NO | NO | NO | NO | |
| 8 | FU FW | $\overline{S}_{T_\phi P^h}((i,j); r) - \overline{S}_{T_\phi P^v}((i,j); r) =$ $h + v_h - v$, if r ≥ 1 | NO | NO | NO | NO | NO | NO | NO | |
| 9 | DX D | $\overline{S}_{T_d P^f}(i,j) - \overline{S}_{T_d}(i,j) \leq h_d$ | | | | | NO | NO | NO | |
| 10 | HX H | $\overline{S}_{T_h P^f}(i,j) - \overline{S}_{T_h}(i,j) \leq h_h$ | | | ~~NO~~ | ~~NO~~ | NO | NO | | NO |
| 11 | VX V | $\overline{S}_{T_v P^f}(i,j) - \overline{S}_{T_v}(i,j) \leq h_v$ | NO | NO | NO | NO | NO | NO | NO | |
| 12 | FX F | $\overline{S}_{T_\phi P^f}(0,0) - \overline{S}_{T_\phi}(0,0) \leq h$ | NO | NO | NO | NO | NO | NO | NO | |

M: continues

| | | | |
|---|---|---|---|
| 01 R>1 C=2 | HP HQ DHP DDQ' HHP HDQ' VHP XXX | $\overline{S}_{T_dT_hP^d}((i,j);r) - \overline{S}_{T_dT_dP^{vl}}((i,j+1);r) \le h_d + \kappa_{max} - \kappa_{min}$, for $r \ge 0$. $\overline{S}_{T_hT_hP^d}((i,j);r) - \overline{S}_{T_hT_hP^{vl}}((i,j+1);r) \le h_h + \kappa_{max} - \kappa_{min}$, for $r \ge 0$. | |
| 02 R>1 C>2 | HP HQ DHP DDQ' HHP HDQ' VHP XXX | $\overline{S}_{T_dT_hP^d}((i,j);r) - \overline{S}_{T_dT_dP^{vl}}((i,j+1);r) \le h_d + \kappa_{max} - \kappa_{min}$, for $r \ge 0$. $\overline{S}_{T_hT_hP^d}((i,j);r) - \overline{S}_{T_hT_hP^{vl}}((i,j+1);r) \le h_h + \kappa_{max} - \kappa_{min}$, for $r \ge 0$ | |
| 03 R=1 C=2 | HP HQ DHP DDQ' HHP HDQ' VHP XXX | $\overline{S}_{T_dT_hP^d}((i,j);r) - \overline{S}_{T_dT_dP^{vl}}((i,j+1);r) \le h_d + \kappa_{max} - \kappa_{min}$, for $r \ge 0$. $\overline{S}_{T_hT_hP^d}((i,j);r) - \overline{S}_{T_hT_hP^{vl}}((i,j+1);r) \le h_h + \kappa_{max} - \kappa_{min}$, for $r \ge 0$. | |
| 04 R=1 C>2 | HP HQ DHP DDQ' HHP HDQ' VHP XXX | $\overline{S}_{T_dT_hP^d}((i,j);r) - \overline{S}_{T_dT_dP^{vl}}((i,j+1);r) \le h_d + \kappa_{max} - \kappa_{min}$, for $r \ge 0$. $\overline{S}_{T_hT_hP^d}((i,j);r) - \overline{S}_{T_hT_hP^{vl}}((i,j+1);r) \le h_h + \kappa_{max} - \kappa_{min}$, for $r \ge 0$ | |
| 05 R>1 C=1 | HP HQ HP DQ' | $\overline{S}_{T_hP^d}((i,j);r) - \overline{S}_{T_dP^{vl}}((i,j+1);r) \le h + \kappa_{max} - \kappa_{min}$, if $r \ge 0$ | |
| 06 R=1 C=1 | HP HQ HP DQ' | $\overline{S}_{T_hP^d}((i,j);r) - \overline{S}_{T_dP^{vl}}((i,j+1);r) \le h + \kappa_{max} - \kappa_{min}$, if $r \ge 0$ | |
| 07 R>0 C=0 | HP HQ | HP HQ | |
| 08 R=0 C>1 | HP HQ DHP DDQ' HHP HDQ' VHP XXX | $\overline{S}_{T_hT_hP^d}((i,j);r) - \overline{S}_{T_hT_hP^{vl}}((i,j+1);r) \le h_h + \kappa_{max} - \kappa_{min}$, for $r \ge 0$ | |
| 09 R=0 C=1 | HP HQ DHP DDQ' HHP HDQ' VHP XXX FHP FDQ' | $\overline{S}_{T_\phi T_hP^d}((i,j);r) - \overline{S}_{T_\phi T_dP^{vl}}((i,j+1);r) \le h + \kappa_{max} - \kappa_{min}$, for $r \ge 0$ | |
| 10 R=0 C=0 | HP HQ | HP HQ | |

Next, we find an upper bound to $\rho(A)-\rho(B)$ using the above tables, and the inequality $\rho(A)-\rho(B) \le \overline{S}_{T_dP^d}((i,j);r) - \overline{S}_{T_dP^{vl}}((i,j);r+1)$.

For AS

| | | R>1 |
|---|---|---|
| i = R and j = C | | C = 2 |
| DP | $\overline{S}_{T_dP^d}((i,j);r) - \overline{S}_{T_dP^{vl}}((i,j);r+1) = \kappa_{max} - v_d$, if $r = 0$ | |
| DQ | $\overline{S}_{T_dP^d}((i,j);r) - \overline{S}_{T_dP^{vl}}((i,j);r+1) = \kappa_{max} - v_v$, if $r \ge 1$ | |

-continued

| | | R>1 |
|---|---|---|
| i = R and j = C | | C = 2 |
| HP HQ | $\overline{S}_{T_hP^d}((i,j);r) - \overline{S}_{T_hP^{vl}}((i,j);r+1) = \kappa_{max} - v_h$, if $r = 0$ $\overline{S}_{T_hP^d}((i,j);r) - \overline{S}_{T_hP^{vl}}((i,j);r+1) = \kappa_{max} - v_h + v_d - v_v$, if $r \ge 1$ | |
| VP VQ | $\overline{S}_{T_vP^d}((i,j);r) - \overline{S}_{T_vP^{vl}}((i,j);r+1) = \kappa_{max} - v_v$, if $r = 0$ $\overline{S}_{T_vP^d}((i,j);r) - \overline{S}_{T_vP^{vl}}((i,j);r+1) = \kappa_{max} - v_v + v_d - v_v$, if $r \ge 1$ | |
| FP FQ FP DQ' | $\overline{S}_{T_\phi P^d}((i,j);r) - \overline{S}_{T_\phi P^{vl}}((i,j);r) = \kappa_{max} - v$, if $r = 0$ $\overline{S}_{T_\phi P^d}((i,j);r) - \overline{S}_{T_\phi P^{vl}}((i,j);r) = \kappa_{max} + v_d - v - v_v$, if $r \ge 1$ $\overline{S}_{T_\phi P^d}((i,j);r) - \overline{S}_{T_\phi P^{vl}}((i,j);r) = \kappa_{max} - \kappa_{min}$ | |
| FP Q'' | $\overline{S}_{T_\phi P^d}((i,j);r) - \overline{S}_{T_\phi P^{vl}}((i,j);r) = \kappa_{max} - v$, if $r = 0$ $\overline{S}_{T_\phi P^d}((i,j);r) - \overline{S}_{T_\phi P^{vl}}((i,j);r) = \kappa_{max} + v_d + (r-1)v_v - v$, if $r \ge 1$ | |
| DU DW | $\overline{S}_{T_dP^{hl}}((i,j);r) - \overline{S}_{T_dP^{vl}}((i,j);r) = h_d + v_h - v_d$, if $r \ge 1$. | |
| HU HW | $\overline{S}_{T_hP^{hl}}((i,j);r) - \overline{S}_{T_hP^{vl}}((i,j);r) = h_h$, if $r \ge 1$. | |
| VU VW | $\overline{S}_{T_vP^{hl}}((i,j);r) - \overline{S}_{T_vP^{vl}}((i,j);r) = h_v + v_h - v_v$, if $r \ge 1$. | |
| FU FW | $\overline{S}_{T_\phi P^{hl}}((i,j);r) - \overline{S}_{T_\phi P^{vl}}((i,j);r) = h + v_h - v$, if $r \ge 1$. | NO |
| DX D | $\overline{S}_{T_dP}(i,j) - \overline{S}_{T_d}(i,j) \le h_d$ | |
| HX H | $\overline{S}_{T_hP}(i,j) - \overline{S}_{T_h}(i,j) \le h_h$ | |
| VX V | $\overline{S}_{T_vP}(i,j) - \overline{S}_{T_v}(i,j) \le h_v$ | |
| FX F | $\overline{S}_{T_\phi P}(0,0) - \overline{S}_{T_\phi}(0,0) \le h$ | |
| FY FQ'' | $\rho(A) - \rho(B) \le 0$ | |

Therefore, $\rho(A)-\rho(B) \le \max\{\kappa_{max}+\alpha+\beta, 0\}$
For M:

$\rho(A)-\rho(B) \le \max\{\kappa_{max}+\alpha+\beta, -\beta, -\beta+\kappa_{max}-\kappa_{min}\}$ Step 7) Upper bounds when $\kappa_{min} \le 0$ and $\kappa_{max} \ge 0$
Local Alignment

| | affine | modified | simplified |
|---|---|---|---|
| Lemma 1.3 lower bound | $-\alpha - \beta$ | $\min\{-\alpha - \beta, \kappa_{min} + \beta\}$ | $-\alpha - \beta$ |
| Lemma 1.3 upper bound | $\max\{\kappa_{max} + \alpha + \beta, 0\}$ | $\max\{\kappa_{max} + \alpha + \beta, -\beta, -\beta + \kappa_{max} - \kappa_{min}\}$ | $\{\kappa_{max} + \alpha + \beta, 0\}$ |

C. Lemma 2.3 Lower Bound

We are given vertices $C=(i,j)$ and $A=(i,j+1)$, where $\rho(C)$ denotes the best score from $(0,0)$ to C, and $\sigma(A)$ denotes the best score from $(i_0,j_0)$ to A, over walks ending with a vertical arc. This lemma shows, $0 \le \rho(C)-\sigma(A)$, for AS and M gap scores.

Proof:
1. Case 1) $C \ne (0,0)$
We have $A = C+(0,1)$, thus $A \ne (0,0)$, thus it has a $W_{\sigma(A)}$.

$W_{\sigma(A)} \triangleq ((i_0,j_0),(i_1,j_1),\ldots,(i_{s-1},j_{s-1}),(i_s,j_s))$, for $s \ge 1$ $W_{\sigma(A)} \triangleq ((i_0,j_0),(i_1,j_1),\ldots,(i_{s-1},j_{s-1}),(i_{s-1},j_{s-1}+1))$, for $s \ge 1$ Subcase 1.a) s=1
Not feasible for Case 1).
Subcase 1.b) s>1

$W_{\sigma(A)} \triangleq (i_0,j_0),(i_1,j_1),\ldots,(i_{s-1},j_{s-1}),(i_{s-1},j_{s-1}+1))$, for $s>1$ $W_{\sigma(A)} = \dot{W}_{\sigma(A)}((i_{s-1},j_{s-1}))*((i_{s-1},j_{s-1}+1))$ if $W_{\sigma(A)}$ belongs to M clearly so does $\hat{W}_{\sigma(A)}(i_{s-1},j_{s-1}))$.

$\sigma(A) = \overline{S}_{W_{\sigma(A)}}$ $= \overline{S}_{\hat{W}_{\sigma(A)}((i_{s-1},j_{s-1}))} + \hat{\varphi}_1((i_{s-2}, j_{s-2})(i_{s-1}, j_{s-1}), (i_{s-1}, j_{s-1})$ $(i_{s-1}, j_{s-1} + 1))$ $\rho(C) \geq \overline{S}_{\hat{W}_{\sigma(A)}((i_{s-1},j_{s-1}))}$ $\rho(C) - \sigma(A) \geq -\hat{\varphi}_1((i_{s-2}, j_{s-2})(i_{s-1}, j_{s-1}), (i_{s-1}, j_{s-1})(i_{s-1}, j_{s-1} + 1))$ $\rho(C) - \sigma(A) \geq 0.$ This also holds for banded case.

Let $\hat{\sigma}(A)$ denote a best path in the band, reaching A with last arc vertical, and let $\hat{\rho}(C)$ denote a best path in the band, reaching C.

Now, if A and C are in the band, then the above argument works when we replace $\sigma(A)$ and $\rho(C)$ with $\hat{\sigma}(A)$ and $\hat{\rho}(C)$, respectively.

$W_{\hat{\sigma}(A)} \triangleq (i_0,j_0),(i_1,j_1), \ldots ,(i_{s-1},j_{s-1}),(i_{s-1},j_{s-1}+1))$, for $s>1$ $W_{\hat{\sigma}(A)} = \hat{W}_{\sigma(A)}((i_{s-1},j_{s-1}))*((i_{s-1},j_{s-1}+1))$ if $W_{\hat{\sigma}(A)}$ belongs to M clearly so does $\hat{W}_{\hat{\sigma}(A)}((i_{s-1},j_{s-1}))$.
if $W_{\hat{\sigma}(A)}$ belongs to the band, and C belongs to the band, then so does $\hat{W}_{\hat{\sigma}(A)}((i_{s-1},j_{s-1}))$.

$\hat{\sigma}(A) = \overline{S}_{W_{\hat{\sigma}(A)}}$ $= \overline{S}_{\hat{W}_{\hat{\sigma}(A)}((i_{s-1},j_{s-1}))} + \hat{\varphi}_1((i_{s-2}, j_{s-2})(i_{s-1}, j_{s-1}), (i_{s-1}, j_{s-1})$ $(i_{s-1}, j_{s-1} + 1))$ $\hat{\rho}(C) \geq \overline{S}_{\hat{W}_{\hat{\sigma}(A)}((i_{s-1},j_{s-1}))}$ $\hat{\rho}(C) - \hat{\sigma}(A) \geq -\hat{\varphi}_1((i_{s-2}, j_{s-2})(i_{s-1}, j_{s-1}), (i_{s-1}, j_{s-1})(i_{s-1}, j_{s-1} + 1))$ $\hat{\rho}(C) - \hat{\sigma}(A) \geq 0.$ Case 2) C=(0,0)
We have $\rho(C)=0$ by definition.

$A=(0,1)$ $\sigma(A)=v$ $\rho(C)-\sigma(A)=0-v$ $\rho(C)-\sigma(A)>0.$

Again, the above argument works when we replace $\sigma(A)$ and $\rho(C)$ with $\hat{\sigma}(A)$ and $\hat{\rho}(C)$, respectively.

|  | affine | modified | simplified |
|---|---|---|---|
| Lemma 1.3 lower bound | $-\alpha - \beta$ | $\min\{-\alpha - \beta, \kappa_{min} + \beta\}$ | $-\alpha - \beta$ |
| Lemma 1.3 upper bound | $\max\{\kappa_{max} + \alpha + \beta, 0\}$ | $\max\{\kappa_{max} + \alpha + \beta, -\beta, -\beta + \kappa_{max} - \kappa_{min}\}$ | $\{\kappa_{max} + \alpha + \beta, 0\}$ |

Local Alignment
Local Alignment: $\kappa_{min} \leq 0$ and $\kappa_{max} \geq 0$

|  | affine | modified | simplified |
|---|---|---|---|
| Lemma 1.3 lower bound | $-\alpha - \beta$ | $\min\{-\alpha - \beta, \kappa_{min} + \beta\}$ | $-\alpha - \beta$ |
| Lemma 1.3 upper bound | $\kappa_{max} + \alpha + \beta$ | $\max\{\kappa_{max} + \alpha + \beta, -\beta + \kappa_{max} - \kappa_{min}\}$ | $\kappa_{max} + \alpha + \beta$ |

Local Alignment:

|  | affine | modified | simplified |
|---|---|---|---|
| Lemma 2.3 lower bound Lemma 2.3 upper bound | 0 | 0 | 0 |

Local Alignment: $\kappa_{min} \leq 0$ and $\kappa_{max} \geq 0$

|  | affine | modified | simplified |
|---|---|---|---|
| Lemma 2.3 lower bound Lemma 2.3 upper bound | 0 | 0 | 0 |

D. Lemma 2.3 Upper Bound

We are given vertices C=(i,j) and A=(i,j+1), where $\rho(C)$ denotes the best score from $(i_0,j_0)$ to C, and $\sigma(A)$ denotes the best score from $(i_0,j_0)$ to A, over walks ending with a vertical arc. This lemma shows, $\rho(C)-\sigma(A) \leq \alpha+\beta$, for AS and $\rho(C)-\sigma(A) \leq \max\{0,\alpha+\beta, \kappa_{max}-\kappa_{min}+(\alpha+\beta), \kappa_{max}-2\kappa_{min}+\alpha-\beta\}$, for M gap scores.

Proof:
For AS:
1. Case 1) C≠(0,0)
We have A=C+(0,1), thus A≠(0,0).
Since C≠(0,0), we have $W_{\rho(C)} \triangleq ((i_0,j_0), (i_1,j_1), \ldots, (i_{s-1},j_{s-1}) (i_s,j_s))$ for $s \geq 1$.
Define $W \triangleq W_{\rho(C)}*((i_s,j_s+1))$ $\sigma(A) \geq \overline{S}_W$ $= \overline{S}_{W_{\rho(C)}*((i_s,j_s+1))}$ $= \overline{S}_{W_{\rho(C)}} + \hat{\varphi}_1((i_{s-1}, j_{s-1})(i_s, j_s), (i_s, j_s)(i_s, j_s + 1))$ $= \rho(C) + v_u$ If $(i_{s-1},j_{s-1})(i_s,j_s) \in A^d$, then u=d.
If $(i_{s-1},j_{s-1})(i_s,j_s) \in A^h$, then u=h.
If $(i_{s-1},j_{s-1})(i_s,j_s) \in A^v$, then u=v.

$\rho(C)-\sigma(A) \leq -v_u.$

2. Case 2) C=(0,0)
We have $\rho(C)=0$ by definition.

$A=(0,1)$ $\sigma(A)=v$ $\rho(C)-\sigma(A)=0-v$ $\rho(C)-\sigma(A)=-v.$

Therefore, $\rho(C)-\sigma(A) \leq \alpha+\beta$.

Now, if A and C are in a band, then the above argument works when we replace $\sigma(A)$ and $\rho(C)$ with $\hat\sigma(A)$ and $\hat\rho(C)$, respectively. More specifically, if C and A belong to the band, so do:
1) arc from C to A, and
2) $\overline{S}_{W_{\rho(C)}*((i_s,j_s+1))}$
And the argument holds.
For M:
Case 1) $C \neq (0,0)$
We have $A = C+(0,1)$, thus $A \neq (0,0)$. Since $C \neq (0,0)$, we have $W_{\rho(C)} \triangleq ((i_0,j_0), (i_1,j_1), \ldots, (i_{s-1},j_{s-1}), (i_s,j_s))$, for $s \geq 1$.
Subcase 1.a) $(i_{s-1},j_{s-1})(i_s,j_s) \notin A^h$
Define $W \triangleq W_{\rho(C)}*(i_s,j_s+1))$. Claim walk W does not have a horizontal arc followed by a vertical. Follows from 1) $W_{\rho(C)}$ does not have a horizontal arc followed by a vertical, and 2) from 1.a) the assumption.

$$\sigma(A) \geq \overline{S}_W$$
$$= \overline{S}_{W_{\rho(C)}*((i_s,j_s+1))}$$
$$= \overline{S}_{W_{\rho(C)}} + \hat\varphi_1((i_{s-1},j_{s-1})(i_s,j_s),(i_s,j_s)(i_s,j_s+1))$$
$$= \rho(C) + v_u$$

If $(i_{s-1},j_{s-1})(i_s,j_s) \in A^d$, then u=d.
If $(i_{s-1},j_{s-1})(i_s,j_s) \in A^v$, then u=v.
We note $(i_{s-1},j_{s-1})(i_s,j_s) \notin A^h$ because of the 1.a) assumption.

$$\rho(C) - \sigma(A) \leq -v_u$$

Subcase 1.b) $(i_{s-1},j_{s-1})(i_s,j_s) \in A^h$
Sub-subcase 1.b.a) $s=1$ $$W_{\rho(C)} = ((i_0,j_0),(i_0+1,j_0))$$
$$\rho(C) = \overline{S}_{W_{\rho(C)}} = \hat\varphi_0((i_0,j_0),(i_0+1,j_0)) = h$$
$$W_1 \triangleq (i_s,j_s)(i_s,j_s+1)$$
$$\sigma(A) \geq \overline{S}_{W_1} = \hat\varphi_0((i_s,j_s),(i_s,j_s+1)) = v$$
$$\rho(C) - \sigma(A) \leq h - v$$

Sub-subcase 1.b.a) $s>1$
$$W_{\rho(C)} \triangleq ((i_0,j_0),(i_1,j_1),\ldots,(i_{s-1},j_{s-1}),(i_s,j_s)), \text{ for } s>1$$
$$i_s = i_{s-1}+1$$
$$j_s = j_{s-1}$$

Based on Lemma WT, there is an integer p, $0 \leq p \leq s-2$, such that for
$$W_{\rho(C)} = ((i_0,j_0),\ldots,(i_p,j_p),(i_{p+1},j_{p+1}),\ldots,(i_{s-1},j_s),(i_s,j_s))$$
we have $i_{q+1}=i_q+1$, for $p \leq q \leq s-1$, $j_{p+1}=j_p+1$, and $j_{q+1}=j_q$, for $p+1 \leq q \leq s-1$. Thus, $W_{\rho(C)} = ((i_0,j_0),\ldots,(i_p,j_p),(i_p+1,j_p+1),(i_p+2,j_p+1),\ldots,(i_p+s-1,j_p+1),(i_p+s,j_p+1))$
We define $W = ((i_0,j_0),\ldots,(i_p,j_p),(i_p+1,j_p+1-1),(i_p+2,j_p+1-1),\ldots,(i_p+s-1,j_p+1-1),(i_p+s,j_p+1))*((i_p+s,j_p+2))$ $$\rho(C) = \overline{S}_{W_{\rho(C)}}, \sigma(A) \geq \overline{S}_W, \rho(C)-\sigma(A) \leq \overline{S}_{W_{\rho(C)}} - \overline{S}_W$$

Part 1) $p=0$
$$W_{\rho(C)} = ((i_0,j_0),(i_0+1,j_0),(i_0+2,j_0+1),\ldots,(i_0+s-1,j_0+1),(i_0+s,j_0+1))$$

$$\overline{S}_{W_{\rho(C)}} = \hat\varphi_0((i_0,j_0),(i_0+1,j_0+1)) + \hat\varphi_1((i_0,j_0)(i_0+1,j_0+1),(i_0+1,j_0+1)(i_0+2,j_0+1)) + \Sigma_{l=3}^s \varphi_1(i_0+l-2,j_0+1)(i_0+l-1,j_0+1)(i_0+l-1,j_0+1)(i_0+l,j_0+1))$$

$$\overline{S}_{W_{\rho(C)}} = \kappa(x_{i_0+1},y_{j_0+1}) + h_d + (s-2)h_h$$

$$W = ((i_0,j_0),(i_0+1,j_0+1-1),(i_0+2,j_0+1-1),\ldots,(i_0+s-1,j_0+1-1),(i_0+s,j_0+1))*((i_p+s,j_p+2))$$

$$\overline{S}_W = \hat\varphi_0((i_0,j_0),(i_0+1,j_0+1-1)) + \Sigma_{l=2}^{s-1} \hat\varphi_1((i_0+l-2,j_0)(i_0+l-1,j_0+1-1),(i_0+l-1,j_0+1-1)(i_0+l,j_0+1-1)) + \varphi_1((i_0+s-2,j_0)(i_0+s-1,j_0+1-1),(i_0+s-1,j_0+1-1)(i_0+s-2+2,j_0+1)) + \varphi_1((i_0+s-2+1,j_0+1-1)(i_0+s-2+2,j_0+1),(i_0+s-2+1,j_0+1)(i_0+s-2+2,j_0+2))$$

$$\overline{S}_W = h + (s-2)h_h + \kappa(x_{i_0+s},y_{j_0+1}) + v_d$$

$$\rho(C)-\sigma(A) \leq \overline{S}_{W_{\rho(C)}} - \overline{S}_W \leq \kappa(x_{i_0+1},y_{j_0+1}) + h_d + (s-2)h_h - (h+(s-2)h_h + \kappa(x_{i_0+s},y_{j_0+1}) + v_d)$$

$$\rho(C)-\sigma(A) \leq \kappa(x_{i_0+1},y_{j_0+1}) + h_d - h - \kappa(x_{i_0+s},y_{j_0+1}) - v_d$$

Part 2) $p>0$ AND $(i_{p-1},j_{p-1})(i_p,j_p) \notin A^v$ $$W_{\rho(A)}((i_l,j_l)) \triangleq ((i_0,j_0),(i_1,j_1),\ldots,(i_l,j_l)), \text{ for } 0 \leq l \leq t.$$

$$W_{\rho(C)} = ((i_0,j_0),\ldots,(i_p,j_p),(i_p+1,j_p+1),(i_p+2,j_p+1),\ldots,(i_p+s-1,j_p+1),(i_p+s,j_p+1)) = \hat W_{\rho(C)}((i_p,j_p))*((i_p+1,j_p+1),(i_p+2,j_p+1),\ldots,(i_p+s-1,j_p+1),(i_p+s,j_p+1))$$

$$\overline{S}_{W_{\rho(C)}} = \overline{S}_{\hat W_{\rho(C)}((i_p,j_p))} + \hat\varphi_1(i_{p-1},j_{p-1})(i_p,j_p),(i_p,j_p)(i_p+1,j_p+1)) + \varphi_1((i_p,j_p)(i_p+1,j_p+1),(i_p+1,j_p+1)(i_p+2,j_p+1)) + \Sigma_{l=3}^s \varphi_1((i_p+l-2,j_p+1)(i_p+l-1,j_p+1),(i_p+l-1,j_p+1)(i_p+l,j_p+1))$$

$$\overline{S}_{W_{\rho(C)}} = \overline{S}_{\hat W_{\rho(C)}((i_p,j_p))} + \kappa(x_{i_p+1},y_{j_p+1}) + h_d + (s-2)h_h$$

$$W = ((i_0,j_0),\ldots,(i_p,j_p),(i_p+1,j_p+1-1),(i_p+2,j_p+1-1),\ldots,(i_p+s-1,j_p+1-1),(i_p+s,j_p+1))*((i_p+s,j_p+2)) = \hat W_{\rho(C)}((i_p,j_p))*((i_p+1,j_p+1-1),(i+2,j_p+1-1),\ldots,(i_p+s-1,j_p+1-1),(i_p+s,j_p+1))*((i_p+s,j_p+2))$$

$$\overline{S}_W = \overline{S}_{\hat W_{\rho(C)}((i_p,j_p))} + \hat\varphi_1((i_{p-1},j_{p-1})(i_p,j_p),(i_p,j_p)(i_p+1,j_p)) + \Sigma_{l=2}^{s-1} \hat\varphi_1((i_p+l-2,j_p)(i_p+l-2+1,j_p+1-1),(i_p+l-2+1,j_p+1-1)(i_p+l-2+2,j_p+1-1)) + \varphi_1((i_p+s-2,j_p)(i_p+s-2+1,j_p+1-1),(i_p+s-2+1,j_p+1-1)(i_p+s-2+1,j_p+1)) + \hat\varphi_1((i_p+s-2+1,j_p+1-1)(i_p+s-2+1,j_p+1),(i_p+s-2+2,j_p+1)(i_p+s-2+2,j_p+2))$$

$$\overline{S}_W = \overline{S}_{\hat W_{\rho(C)}((i_p,j_p))} + h_u + (s-2)h_h + \kappa(x_{i_p+s},y_{j_p+1}) + v_d$$

If $(i_{p-1},j_{p-1})(i_p,j_p) \in A^d$, then u=d.
If $(i_{p-1},j_{p-1})(i_p,j_p) \in A^h$, then u=h.
(If $(i_{p-1},j_{p-1})(i_p,j_p) \in A^v$, then u=v) this does not occur because of the assumption of part 2.

$$\rho(C)-\sigma(A) \leq \overline{S}_{W_{\rho(C)}} - \overline{S}_W \leq \overline{S}_{\hat W_{\rho(C)}((i_p,j_p))} + \kappa(x_{i_p+1},y_{j_p+1}) + h_d + (s-2)h_h - (\overline{S}_{\hat W_{\rho(C)}((i_p,j_p))} + h_u + (s-2)h_h + \kappa(x_{i_p+s},y_{j_p+1}) + v_d)$$

$$\rho(C)-\sigma(A) \leq \kappa(x_{i_p+1},y_{j_p+1}) + h_d - h_u - \kappa(x_{i_p+s},y_{j_p+1}) - v_d$$

Part 3) $p>0$ AND $(i_{p-1},j_{p-1})(i_p,j_p) \in A^v$ $$\hat W_{\rho(C)}((i_l,j_l)) \triangleq ((i_0,j_0),(i_1,j_1),\ldots,(i_l,j_l)), \text{ for } 0 \leq l \leq t.$$

The arc $(i_{p-1},j_{p-1})(i_p,j_p)$ is not the first arc of $W_{\rho(C)}$ because of Lemma WT. Hence, $p>1$.

$$W_{\rho(C)} = ((i_0,j_0),\ldots,(i_p,j_p),(i_p+1,j_p+1),(i_p+2,j_p+1),\ldots,(i_p+s-1,j_p+1),(i_p+s,j_p+1)) = \hat W_{\rho(C)}((i_{p-1},j_{p-1}))*((i_p,j_p)(i_p+1,j_p+1),(i_p+2,j_p+1),\ldots,(i_p+s-1,j_p+1),(i_p+s,j_p+1))$$

Since $p>1$, we have $$\overline{S}_{W_{\rho(C)}} = \overline{S}_{\hat W_{\rho(C)}((i_{p-1},j_{p-1}))} + \hat\varphi_1((i_{p-2},j_{p-2})(i_{p-1},j_{p-1}),(i_{p-1},j_{p-1})(i_p,j_p)) + \varphi_1((i_{p-1},j_{p-1})(i_p,j_p),(i_p,j_p)(i_p+1,j_p+1)) + \varphi_1((i_p,j_p)(i_p+1,j_p+1),(i_p+1,j_p+1)(i_p+2,j_p+1)) + \Sigma_{l=3}^s \varphi_1((i_p+l-2,j_p+1)(i_p+l-1,j_p+1),(i+l-1,j_p+1)(i_p+l,j_p+1))$$

$$\overline{S}_{W_{\rho(C)}} = \overline{S}_{\hat W_{\rho(C)}((i_{p-1},j_{p-1}))} + v_u + \kappa(x_{i_p+1},y_{j_p+1}) + h_d + (s-2)h_h$$

If $(i_{p-2},j_{p-2})(i_{p-1},j_{p-1}) \in A^d$, then $u=d$. If $(i_{p-2},j_{p-2})(i_{p-1},j_{p-1}) \in A^h$, then $u=h$. If $(i_{p-2},j_{p-2})(i_{p-1},j_{p-1}) \in A^v$, then $u=v$.

$u=h$ this does not occur because $W_{\rho(C)}$ does not have a horizontal arc followed by a vertical arc due to M.

$$W=((i_0,j_0), \ldots, (i_{p-1},j_{p-1}),(i_p+1,j_p),(i_p+2,j_p),(i_p+3,j_p), \ldots, (i_p+s-1,j_p),(i_p+s,j_p+1))^*((i_p+s,j_p+2)) = \hat{W}_{\rho(C)}((i_{p-1},j_{p-1}))^*((i_p+1,j_p),(i_p+2,j_p), \ldots, (i_p+s-1,j_p),(i_p+s,j_p+1))^*((i_p+s,j_p+2))$$

$$\overline{S}_W = \overline{S}_{W\rho(C)((i_{p-1},j_{p-1}))} + \hat{\varphi}_1(i_{p-2},j_{p-2})(i_{p-1},j_{p-1}),(i_{p-1},j_{p-1})(i_p+1,j_p)) + \varphi_1((i_{p-1},j_{p-1})(i_p+1,j_p),(i_p+1,j_p)(i_p+2,j_p)) + \Sigma_{l=3}^{s-1}\varphi_1((i_p+l-2,j_p)(i_p+l-1,j_p),(i_p+l-1,j_p)(i_p+l,j_p)) + \varphi_1((i_p+s-2,j_p)(i_p+s-1,j_p),(i_p+s-1,j_p)(i_p+s,j_p+1)) + \varphi_1((i_p+s-1,j_p)(i_p+s,j_p+1),(i_p+s,j_p+1)(i_p+s,j_p+2))$$

$$\overline{S}_W = \overline{S}_{W\rho(C)((i_{p-1},j_{p-1}))} + \kappa(x_{i_p+1},y_{j_p}) + h_d + (s-3)h_h + \kappa(x_{i_p+s},y_{p+1}) + v_d$$

$$\rho(C)-\sigma(A) \le \overline{S}_{W\rho(C)} - \overline{S}_W \le \overline{S}_{W\rho(C)((i_{p-1},j_{p-1}))} + v_u + \kappa(x_{i_p+1},y_{j_p+1}) + h_d + (s-2)h_h - (\overline{S}_{W\rho(C)((i_{p-1},j_{p-1}))} + \kappa((x_{i_p+1},y_{j_p}) + h_d + (s-3)h_h + \kappa(x_{i_p+s},y_{p+1}) + v_d)$$

$$\rho(C)-\sigma(A) \le v_u + \kappa(x_{i_p+1},y_{j_p+1}) + h_h - \kappa(x_{i_p+1},y_{j_p}) - \kappa(x_{i_p+s},y_{p+1}) - v_d$$

Case 2) $C=(0,0)$

We have $\rho(C)=0$ by definition. $A=(0,1)$, $\sigma(A)=v$, and $\rho(C)-\sigma(A)=0-v$, $\rho(C)-\sigma(A)=-v$. We obtain an overall upper bound based on the upper bounds above.

Local Alignment

|  | affine | modified | simplified |
|---|---|---|---|
| Lemma 2.3 lower bound | 0 | 0 | 0 |
| Lemma 2.3 upper bound | $\alpha + \beta$ | max$\{0, \alpha + \beta, \kappa_{max} - \kappa_{min} + (\alpha + \beta), \kappa_{max} - 2\kappa_{min} + \alpha - \beta\}$ | $\alpha + \beta$ |

Local Alignment: $\kappa_{min} \le 0$ and $\kappa_{max} \ge 0$

|  | affine | modified | simplified |
|---|---|---|---|
| Lemma 2.3 lower bound | 0 | 0 | 0 |
| Lemma 2.3 upper bound | $\alpha + \beta$ | max$\{\kappa_{max} - \kappa_{min} + (\alpha + \beta), \kappa_{max} - 2\kappa_{min} + \alpha - \beta\}$ | $\alpha + \beta$ |

E. Lemma WT

We are given a vertex, $A$, $A \in \mathbb{V}$ and $A \ne (0,0)$ and a walk $W_{\rho(A)} = ((i_0,j_0), (i_1,j_1), \ldots, (i_k,j_k))$. Now if $k>1$, then $(i_0,j_0)(i_1,j_1) \in A^d$.

We are also given that (i) score gap constants are negative and (ii) symmetric:

Just $h=v$ is enough no need for $h^d=v^d$, $h=v^h$, and $h^v=v^v$.

Proof:

Given $\rho(A) = \overline{S}_{W_{\rho(A)}} = \hat{\varphi}_0((i_0,j_0)(i_1,j_1)) + \Sigma_{t=2}^k \hat{\varphi}_1((i_{t-2},j_{t-2})(i_{t-1},j_{t-1}),(i_{t-1},j_{t-1})(i_t,j_t))$ and we have $\hat{\varphi}_0((i_0,j_0)(i_1,j_1)) = h<0 \text{ for}(i_0,j_0)(i_1,j_1) \in A^h$ and $\hat{\varphi}_0((i_0,j_0)(i_1,j_1)) = v<0 \text{ for}(i_0,j_0)(i_1,j_1) \in A^v$.

if $(i_0,j_0)(i_1,j_1) \notin A^d$, then we will show below that $\overline{S}_W > \overline{S}_{W_{\rho(A)}}$, where walk $W$ is $((i_1,j_1), \ldots, (i_k,j_k))$.

$\overline{S}_W - \overline{S}_{W_{\rho(A)}} = \hat{\varphi}_0((i_1,j_1)(i_2,j_2)) + \Sigma_{t=3}^k \hat{\varphi}_1((i_{t-2},j_{t-2})(i_{t-1},j_{t-1}),(i_{t-1},j_{t-1})(i_t,j_t)) - \hat{\varphi}_0((i_0,j_0)(i_1,j_1)) - \Sigma_{t=2}^k \hat{\varphi}_1((i_{t-2},j_{t-2})(i_{t-1},j_{t-1}),(i_{t-1},j_{t-1})(i_t,j_t))$ $(i_t,j_t)) = \hat{\varphi}_0((i_1,j_1)(i_2,j_2)) + \Sigma_{t=3}^k \hat{\varphi}_1((i_{t-2},j_{t-2})(i_{t-1},j_{t-1}),(i_{t-1},j_{t-1})(i_t,j_t)) - \hat{\varphi}_0((i_0,j_0)(i_1,j_1)) - \hat{\varphi}_1((i_0,j_0)(i_1,j_1),(i_1,j_1)(i_2,j_2)) - \Sigma_{t=3}^k \hat{\varphi}_1((i_{t-2},j_{t-2})(i_{t-1},j_{t-1}),(i_{t-1},j_{t-1})))$ $\overline{S}_W - \overline{S}_{W_{\rho(A)}} = \hat{\varphi}_0((i_1,j_1)(i_2,j_2)) - \hat{\varphi}_0((i_0,j_0)(i_1,j_1)) - \varphi_1((i_0,j_0)(i_1,j_1),(i_1,j_1)(i_2,j_2))$ if $(i_1,j_1)(i_2,j_2) \in A^d$, then $\hat{\varphi}_0((i_1,j_1)(i_2,j_2)) - \hat{\varphi}_0((i_0,j_0)(i_1,j_1)) - \hat{\varphi}_1((i_0,j_0)(i_1,j_1),(i_1,j_1)(i_2,j_2)) = -\hat{\varphi}_0((i_0,j_0)(i_1,j_1))$ and $\overline{S}_W - \overline{S}_{W_{\rho(A)}} = -\hat{\varphi}_0((i_0,j_0)(i_1,j_1)) > 0$ if $(i_1,j_1)(i_2,j_2) \in A^h$, then $\hat{\varphi}_0((i_1,j_1)(i_2,j_2)) - \hat{\varphi}_0((i_0,j_0)(i_1,j_1)) - \hat{\varphi}_1((i_0,j_0)(i_1,j_1),(i_1,j_1)(i_2,j_2)) = h - \hat{\varphi}_0((i_0,j_0)(i_1,j_1)) - \{h^d, h^h, \text{ or } h^v\} = h - \hat{\varphi}_0((i_0,j_0)(i_1,j_1)) - \{h^d, h^h, \text{ or } h^v\}$ and $\overline{S}_W - \overline{S}_{W_{\rho(A)}} = -\{h^d, h^h, \text{ or } h^v\} > 0$ if $(i_1,j_1)(i_2,j_2) \in A^v$, then $\hat{\varphi}_0((i_1,j_1)(i_2,j_2)) - \hat{\varphi}_0((i_0,j_0)(i_1,j_1)) - \hat{\varphi}_1((i_0,j_0)(i_1,j_1),(i_1,j_1)(i_2,j_2)) = v - \hat{\varphi}_0((i_0,j_0)(i_1,j_1)) - \{v^d, v^h, \text{ or } v^v\}$ and $\overline{S}_W - \overline{S}_{W_{\rho(A)}} = -\{v^d, v^h, \text{ or } v^v\} > 0$ F. Lemmas 3.3-7.3

Given the upper and lower bounds in Lemmas 1 and 2 for local alignment, we drive four more set of lower and upper bounds. We have six vertices X, Y, A, B, C, and D. A is immediately above C, and X is immediately above A. D is immediately to the right of C, B is immediately to the right of A, and Y is immediately to the right of X.

Proof:

Local Alignment: $\kappa_{min} \le 0$ and $\kappa_{max} \ge 0$

|  | affine | modified | simplified |
|---|---|---|---|
| Lemma 1.3 upper bound $L_1$ | $-\alpha - \beta$ | min$\{-\alpha - \beta, \kappa_{min} + \beta\}$ | $-\alpha - \beta$ |
| Lemma 1.3 upper bound $U_1$ | $\kappa_{max} + \alpha + \beta$ | max$\{\kappa_{max} + \alpha + \beta, -\beta + \kappa_{max} - \kappa_{min}\}$ | $\kappa_{max} + \alpha + \beta$ |

Local Alignment: $\kappa_{min} \le 0$ and $\kappa_{max} \ge 0$

|  | affine | modified | simplified |
|---|---|---|---|
| Lemma 2.3 upper bound $L_2$ | 0 | 0 | 0 |
| Lemma 2.3 upper bound $U_2$ | $\alpha + \beta$ | max$\{\kappa_{max} - \kappa_{min} + (\alpha + \beta), \kappa_{max} - 2\kappa_{min} + \alpha - \beta\}$ | $\alpha + \beta$ |

The rest is exactly the same as the global case.

| Lemma 1.3 | $L_1 \le \rho(B) - \rho(A) \le U_1$ |
|---|---|
|  | $L_1 \le \rho(C) - \rho(A) \le U_1$ |
| Lemma 2.3 | $L_2 \le \rho(B) - \sigma(D) \le U_2$ |
|  | $L_2 \le \rho(C) - \tau(D) \le U_2$ |
| Lemma 3.3 | $L_3 = L_1 + L_2 \le \rho(B) - \sigma(C) \le U_1 + U_2 = U_3$ |
|  | $L_3 = L_1 + L_2 \le \rho(C) - \sigma(C) \le U_1 + U_2 = U_3$ |
| Lemma 4.3 | $-U_1 + L_3 \le \rho(A) - \sigma(B) \le -L_1 + U_3$ |
|  | $-U_1 + L_3 \le \rho(A) - \sigma(C) \le -L_1 + U_3$ |

| | |
|---|---|
| Lemma 5.3 | $-U_1 + L_1 \le \rho(B) - \rho(C) \le -L_1 + U_1$ |
| | $-U_1 + L_1 \le \rho(B) - \rho(C) \le -L_1 + U_1$ |
| Lemma 6.3 | $L_1 - U_1 + L_3 \le \rho(B) - \tau(C) \le U_1 - L_1 + U_3$ |
| | $L_1 - U_1 + L_3 \le \rho(C) - \sigma(B) \le U_1 - L_1 + U_3$ |

1. Lemma 3.3:

$$\rho(B) - \sigma(B) =$$
$$\rho(B) - \rho(Y) + \rho(Y) - \sigma(B) =$$
$$T1 + T2$$
$$L_1 + L_2 \le \rho(B) - \sigma(B) \le U_1 + U_2$$

Lemma 4.3:

$$\rho(A) - \sigma(B) =$$
$$\rho(A) - \rho(B) + \rho(B) - \sigma(B) =$$
$$-T1 + T3$$
$$-U_1 + L_3 \le \rho(A) - \sigma(B) \le -L_1 + U_3$$

Lemma 5.3:

$$\rho(B) - \rho(C) =$$
$$\rho(B) - \rho(A) + \rho(A) - \sigma(C) =$$
$$T1 - T3$$
$$-U_1 + L_1 \le \rho(B) - \rho(C) \le -L_1 + U_1$$

Lemma 6.3:

$$\rho(B) - \tau(C) =$$
$$\rho(B) - \rho(A) + \rho(A) - \rho(C) + \rho(C) - \sigma(C) =$$
$$T1 - T1 + T3$$
$$L_1 - U_1 + L_3 \le \rho(B) - \tau(C) \le U_1 - L_1 + U_3$$

For Affine (Gotoh) gap score, we generate the table below based on above results.

Gotoh $$L_1 = -(\alpha+\beta) \quad U_1 = \kappa_{max} + \alpha + \beta, \kappa_{max} \ge 0$$

$$L_2 = 0 \quad U_2 = (\alpha+\beta)$$

| | |
|---|---|
| Lemma 1.3 | $-(\alpha + \beta) \le \rho(B) - \rho(A) \le \kappa_{max} + (\alpha + \beta)$ |
| | $-(\alpha + \beta) \le \rho(C) - \rho(A) \le \kappa_{max} + (\alpha + \beta)$ |
| Lemma 2.3 | $0 \le \rho(B) - \sigma(D) \le (\alpha + \beta)$ |
| | $0 \le \rho(C) - \tau(D) \le (\alpha + \beta)$ |
| Lemma 3.3 | $-(\alpha + \beta) \le \rho(B) - \sigma(B) \le \kappa_{max} + 2(\alpha + \beta)$ |
| | $-(\alpha + \beta) \le \rho(C) - \sigma(C) \le \kappa_{max} + 2(\alpha + \beta)$ |
| Lemma 4.3 | $-\kappa_{max} - 2(\alpha + \beta) \le \rho(A) - \sigma(B) \le \kappa_{max} + 3(\alpha + \beta)$ |
| | $-\kappa_{max} - 2(\alpha + \beta) \le \rho(A) - \sigma(C) \le \kappa_{max} + 3(\alpha + \beta)$ |
| Lemma 5.3 | $-\kappa_{max} - 2(\alpha + \beta) \le \rho(B) - \rho(C) \le \kappa_{max} + 2(\alpha + \beta)$ |
| | $-\kappa_{max} - 2(\alpha + \beta) \le \rho(B) - \rho(C) \le \kappa_{max} + 2(\alpha + \beta)$ |
| Lemma 6.3 | $-\kappa_{max} - 3(\alpha + \beta) \le \rho(B) - \tau(C) \le 2\kappa_{max} + 4(\alpha + \beta)$ |
| | $-\kappa_{max} - 3(\alpha + \beta) \le \rho(C) - \sigma(B) \le 2\kappa_{max} + 4(\alpha + \beta)$ |

We repeat the above to obtain Lemma 4.3-6.3 for the simplified and modified versions.

Lemma 7.3: The difference of any pair of values 1)-5) below is in the interval:
[LB UB], where, $$LB = \min\{-2\kappa_{max} - 5(\alpha+\beta), -\kappa_{max} - 2(\alpha+\beta) + \kappa_{min} + \beta\}$$

$$UB = \max\{2\kappa_{max} + 5(\alpha+\beta), \kappa_{max} - \kappa_{min}\}, \text{and } \kappa_{max} \ge 0$$

1) $\rho(A) + \kappa(B)$
2) $\rho(B) - (\alpha+\beta)$
3) $\sigma(B) - \beta$
4) $\rho(C) - (\alpha+\beta)$
5) $\tau(C) - \beta$ Proof:
Difference of 1) and 2): from Lemmas 1.3-6.3

$$(\alpha+\beta) \le \rho(B) - \rho(A) \le \kappa_{max} + (\alpha+\beta)$$

$$-(\alpha+\beta) - (\alpha+\beta) - \kappa(B) \le (\rho(B) - (\alpha+\beta)) - (\rho(A) + \kappa(B)) \le \kappa_{max} + (\alpha+\beta) - (\alpha+\beta) - \kappa(B)$$

$$-2(\alpha+\beta) - \kappa(B) \le (\rho(B) - (\alpha+\beta)) - (\rho(A) + m) \le \kappa_{max} - \kappa(B)$$

$$-2(\alpha+\beta) - \kappa_{max}(\rho(B) - (\alpha+\beta)) - (\rho(A) + \kappa(B)) \le \kappa_{max} - \kappa_{min}$$

Difference of 1) and 3): from Lemmas 1.3-6.3

$$-\kappa_{max} - 2(\alpha+\beta) \le \rho(A) - \sigma(B) \le \kappa_{max} + 3(\alpha+\beta)$$

$$-\kappa_{max} - 2(\alpha+\beta) + \kappa(B) + \beta \le (\rho(A) + \kappa(B)) - (\sigma(B) - \beta) \le \kappa_{max} + 3(\alpha+\beta) + \kappa(B) + \beta$$

$$-\kappa_{max} - 2(\alpha+\beta) + \kappa_{min} + \beta \le (\rho(A) + \kappa(B)) - (\sigma(B) - \beta) \le 2\kappa_{max} + 3(\alpha+\beta) + \beta$$

Difference of 1) and 4): Same as difference of 1) and 2)
Difference of 1) and 5): Same as difference of 1) and 3)
Difference of 2) and 3): from Lemmas 1.3-6.3

$$-(\alpha+\beta) \le \rho(B) - \sigma(B) \le \kappa_{max} + 2(\alpha+\beta)$$

$$-(\alpha+\beta) - (\alpha+\beta) + \beta \le (\rho(B) - (\alpha+\beta)) - (\sigma(B) - \beta) \le \kappa_{max} + 2(\alpha+\beta) - (\alpha+\beta) + \beta$$

$$-2(\alpha+\beta) + \beta \le (\rho(B) - (\alpha+\beta)) - (\sigma(B) - \beta) \le \kappa_{max} + (\alpha+\beta) + \beta$$

Difference of 2) and 4): from Lemmas 1.3-6.3

$$-\kappa_{max} - 2(\alpha+\beta) \le \rho(B) - \rho(C) \le \kappa_{max} + 2(\alpha+\beta)$$

$$-\kappa_{max} - 2(\alpha+\beta) \le (\rho(B) - (\alpha+\beta)) - (\rho(C) - (\alpha+\beta)) \le \kappa_{max} + 2(\alpha+\beta)$$

$$-\kappa_{max} - 2(\alpha+\beta) \le (\rho(B) - (\alpha+\beta)) - (\rho(C) - (\alpha+\beta)) \le \kappa_{max} + 2(\alpha+\beta)$$

Difference of 2) and 5): from Lemmas 1.3-6.3

$$-\kappa_{max} - 3(\alpha+\beta) \le \rho(B) - \tau(C) \le 2\kappa_{max} + 4(\alpha+\beta)$$

$$-\kappa_{max} - 3(\alpha+\beta) - (\alpha+\beta) + \beta \le (\rho(B) - (\alpha+\beta)) - (\tau(C) - \beta) \le 2\kappa_{max} + 4(\alpha+\beta) - (\alpha+\beta) + \beta$$

$-\kappa_{max}-4(\alpha+\beta)+\beta \le (\rho(B)-(\alpha+\beta))-(\tau(C)-\beta) \le 2\kappa_{max}+3$
$(\alpha+4(\alpha+\beta)-(\alpha+\beta)+\beta$ Difference of 3) and 4): Same as 2) and 5)
Difference of 3) and 5): from Lemmas 1.3-63

$2\kappa_{max}+5(\alpha+\beta) \le \sigma(B)-\beta-(\tau(C)-\beta)=\sigma(B)-\tau(C) \le 2\kappa_{max}+ 5(\alpha+\beta)$ Difference of 4) and 5): Same as 2) and 3)
An interval that contains all the bounds is [LB UB], where, $LB=\min\{-2\kappa_{max}-5(\alpha+\beta),-\kappa_{max}-2(\alpha+\beta)+\kappa_{min}+\beta\}$ $UB=\max\{2\kappa_{max}+5(\alpha+\beta),\kappa_{max}-\kappa_{min}\}$, and $\kappa_{max} \ge 0$ We repeat Lemma 7.3 for simplified and modified similarly.

We use the bound for values 1)-5) that include the score of the arcs.

1') $\rho(A)+\kappa(B)$. 2') $\rho(B)-(\alpha+\beta)$. 3') $\sigma(B)-\beta$. 4') $\rho(C)-(\alpha+\beta)$. 5') $\tau(C)-\beta$ Alternatively, it is possible to use a similar bound for values 1')-5') that do not include the score of the arcs. The overall expressions in of the recursion must be reduced to a modulus based on the bound we use.

VII. Banded Local Alignment Proof

To prove that the local alignment results apply to the banded local alignment it suffices to show that in the following lemmas we have the proper covering, as mentioned in for global and overlapping cases.

Lemma 1.3—Lower-Bound:
Briefly, in all cases resulting a lower bound to $\rho(A)-\rho(B)$, we have a walk, W, to A and $W_{\rho(B)}=((i_0,j_0), (i_1,j_1), \ldots, (i_s,j_s)=B)$. Further we have $W=(i_0,j_0),(i_1,j_1),\ldots,(i_s,j_s)((i_A,j_A))$ or $W=(i_0,j_0),(i_1,j_1),\ldots,(i_{s-1},j_{s-1})((i_A,j_A))$.

Therefore, since A and B are in the BAND, if $W_{\rho(B)}$ is in the BAND so is W.

Lemma 1.3—Upper-Bound:
1) We assume A, B and $\hat{\rho}(A)$ belong to the BAND.
2) Now, given that the sequence denoted by (a) is in the BAND, then the sequence (n) is in the BAND because all its vertices belong to the diagonals that pass through {the vertices of $(\alpha)$}$\cup\{B\}$.

With the same argument, given sequences denoted by (b), (c), (d), (e), (f), (g), (h), (i), (j), (k), and (l) are in the BAND, then the sequences (o), (p), (q), (n), (o), (p), (q), (r), (s), (t), and (u) are in the BAND, respectively.

For the same reason, if (m)$\cup\{B\}$ is in the BAND, then (i) is the BAND, where (i) is the vertical arc ending in B.

Again for the same reason, if (v), (w), (x) and (y) are in the BAND and B is in the BAND, then AA, BB, CC, and DD are in the band.

Lemma 2.3—Lower-Bound:
if $W_{\sigma(A)} \triangleq ((i_0,j_0), (i_1,j_1), \ldots, (i_{s-1},j_{s-1}), (i_{s-1},j_{s-1}+1))$ is in the BAND, then $((i_0,j_0), (i_1,j_1), \ldots, (i_{s-1},j_{s-1}))$ is in the BAND.

Lemma 2.3—Upper-Bound:
We have $W_{\rho(C)} \triangleq ((i_0,j_0), (i_1,j_1), \ldots, (i_{s-1},j_{s-1}), (i_s,j_s))$, for $s \ge 1$.

Define $W1 \triangleq W_{\rho(C)}*((i_s,j_s+1))$
If W1 is the walk to A and if $W_{\rho(C)}$ is in the BAND and A is in the BAND=>W1 is in the BAND done.

Briefly,
In Sub-subcase 1.b.a) part 1: if $W_{\rho(C)}$ and A are in the BAND so is W.
In Sub-subcase 1.b.a) part 2: if $W_{\rho(C)}$ and A are in the BAND so is W.
In Sub-subcase 1.b.a) part 3: if $W_{\rho(C)}$ and A are in the BAND so is W.

VIII. Simplified and Modified Gap Scores

In several embodiments described above, the affine gap score is used as an example. Other embodiments may use a simplified or a modified gap score. The same parameters: $\kappa_{max}=15$, $\kappa_{min}=-5$, $\alpha=10$, and $\beta=1$ are used in the following examples.

The followings describe the use of the simplified gap score:
step 1) the lower and upper bounds of Lemma 1.1 are the same for affine and simplified gap scores.
step 2) the lower and upper bounds of Lemma 2.1 are the same for affine and simplified gap scores.
step 3) therefore the lower and upper bounds of Lemmas 3.1-7.1 are the same for affine and simplified gap scores.
step 4) thus the Q of Lemma 7.1 is the same for affine and simplified gap scores. Thus, Q=85, see the first example.
step 5) the same modulus $\mathcal{M}=2Q+1=171$, may be selected for simplified gap score.
step 6) in the first embodiment, when we use simplified gap score instead of affine gap score, the same 8 bits representation is selected for each $r_1$-$r_5$.

The followings describe the use of the modified gap score:
step 1) the lower and upper bounds of Lemma 1.1 are not the same for affine and modified gap scores.
step 2) the lower and upper bounds of Lemma 2.1 are not the same for affine and modified gap scores.
step 3) generate upper and lower bounds for each difference of a pair of distinct terms of $\rho(A)+\kappa(B)$, $\rho(B)-(\alpha+\beta)$, $\sigma(B)-\beta$, $\rho(C)-(\alpha+\beta)$, and $\tau(C)-\beta$ based on the bounds below.

| | |
|---|---|
| Lemma 1.1 | $L_1 \le \rho(B) - \rho(A) \le U_1$ |
| | $L_1 \le \rho(C) - \rho(A) \le U_1$ |
| Lemma 2.1 | $L_2 \le \rho(B) - \sigma(D) \le U_2$ |
| | $L_2 \le \rho(C) - \tau(D) \le U_2$ |
| Lemma 3.1 | $L_3 = L_1 + L_2 \le \rho(B) - \sigma(B) \le U_1 + U_2 = U_3$ |
| | $L_3 = L_1 + L_2 \le \rho(C) - \sigma(C) \le U_1 + U_2 = U_3$ |
| Lemma 4.1 | $-U_1 + L_3 \le \rho(A) - \sigma(B) \le -L_1 + U_3$ |
| | $-U_1 + L_3 \le \rho(A) - \sigma(C) \le -L_1 + U_3$ |
| Lemma 5.1 | $-U_1 + L_1 \le \rho(B) - \rho(C) \le -L_1 + U_1$ |
| | $-U_1 + L_1 \le \rho(B) - \rho(C) \le -L_1 + U_1$ |
| Lemma 6.1 | $L_1 - U_1 + L_3 \le \rho(B) - \tau(C) \le U_1 - L_1 + U_3$ |
| | $L_1 - U_1 + L_3 \le \rho(C) - \sigma(B) \le U_1 - L_1 + U_3$ |

Difference of 1) and 2):

$-U_1+L_3-(\alpha+\beta)-\kappa_{max} \le -U_1+L_3-(\alpha+\beta)-\kappa(B) \le \rho(A)- (\alpha+\beta)-\sigma(B)-\kappa(B) \le -L_1+U_3-(\alpha+\beta)-\kappa(B) \le -L_1+ U_3-(\alpha+\beta)-\kappa_{min}$ $-U_1+L_3-(\alpha+\beta)-\kappa_{max} \le \rho(A)-(\alpha+\beta)-\sigma(B)-\kappa(B) \le -L_1+ U_3-(\alpha+\beta)-\kappa_{min}$ Difference of 1) and 3):

$-U_1+L_3+\kappa_{min}+\beta \le -U_1+L_3+\kappa(B)+\beta \le \rho(A)+\kappa(B)-(\sigma(B)+ \beta) \le -L_1+U_3+\kappa(B)+\beta \le -L_1+U_3+\kappa_{max}+\beta$ $-U_1+L_3+\kappa_{min}+\beta \le \rho(A)+\kappa(B)-\sigma(B)+\beta \le -L_1+U_3+ \kappa_{max}+\beta$ Difference of 1) and 4): same as Difference of 1) and 2).
Difference of 1) and 5): same as Difference of 1) and 3).

Difference of 2) and 3):

$$L_1+L_2-(\alpha+\beta)+\beta \leq \rho(B)-(\alpha+\beta)-\sigma(B)+\beta \leq U_1+U_2-(\alpha+\beta)+\beta$$

Difference of 2) and 4):

$$-U_1+L_1 \leq \rho(B)-\rho(C) \leq -L_1+U_1$$

$$-U_1+L_1-(\alpha+\beta)+(\alpha+\beta) \leq \rho(B)-(\alpha+\beta)-\rho(C)+(\alpha+\beta) \leq -L_1+U_1-(\alpha+\beta)+(\alpha+\beta)$$

$$-U_1+L_1 \leq \rho(B)-(\alpha+\beta)-\rho(C)+(\alpha+\beta) \leq -L_1+U_1$$

Difference of 2) and 5):

$$L_1-U_1+L_3 \leq \rho(B)-\tau(C) \leq U_1-L_1+U_3$$

$$L_1-U_1+L_3-(\alpha+\beta)+\beta \leq \rho(B)-(\alpha+\beta)-\tau(C)+\beta \leq U_1-L_1+U_3-(\alpha+\beta)+\beta$$

$$L_1-U_1+L_3-\alpha \leq \rho(B)-(\alpha+\beta)-\tau(C)+\beta \leq U_1-L_1+U_3-\alpha$$

Difference of 3) and 4): same as Difference of 2) and 5).
Difference of 3) and 5):

$$X=(\tau(C)-\beta)-(\sigma(B)-\beta)=((\rho(A)+\kappa(B))-(\sigma(B)-\beta))-((\rho(A)+\kappa(B))-(\tau(C)-\beta))=\text{diff}(1,3)-\text{diff}(1,5)$$

$$-U_1+L_3+\kappa_{min}+\beta \leq \rho(A)+\kappa(B)-\sigma(B)+\beta \leq -L_1+U_3+\kappa_{max}+\beta$$

$$-U_1+L_3+\kappa_{min}+\beta-(-L_1+U_3+\kappa_{max}+\beta) \leq X \leq -L_1+U_3+\kappa_{max}+\beta-(-U_1+L_3+\kappa_{min}+\beta)$$

$$-U_1-U_3+L_3+L_1+\kappa_{min}-\kappa_{max} \leq X \leq -L_1-L_3+U_3+U_1+\kappa_{max}-\kappa_{min}$$

Difference of 4) and 5): same as Difference of 2) and 3).
step 4) Use the same parameters: $\kappa_{max}=15$, $\kappa_{min}=-5$, $\alpha=10$, and $\beta=1$, we evaluate the bounds of the differences:
Difference of 1) and 2): [−42 67]

$$-43 \leq \rho(A)-(\alpha+\beta)-\sigma(B)-\kappa(B) \leq 67$$

Difference of 1) and 3): [−41 89]

$$-41 \leq \rho(A)+\kappa(B)-\sigma(B)+\beta \leq 89$$

Difference of 1) and 4): same as Difference of 1) and 2).
Difference of 1) and 5): same as Difference of 1) and 3).
Difference of 2) and 3): [−21 52]

$$-21 \leq \rho(B)-(\alpha+\beta)-\sigma(B)+\beta \leq 52$$

Difference of 2) and 4): [−37 37]

$$-37 \leq \rho(B)-(\alpha+\beta)-\rho(C)+(\alpha+\beta) \leq 37$$

Difference of 2) and 5): [−58 89]

$$-58 \leq \rho(B)-(\alpha+\beta)-\tau(C)+\beta \leq 89$$

Difference of 3) and 4): same as Difference of 2) and 5).
Difference of 3) and 5): [−130 130]

$$-130 \leq (\tau(C)-\beta)-(\sigma(B)-\beta) \leq 130$$

Difference of 4) and 5): same as Difference of 2) and 3).
step 5) we pick, u-max, the largest upper bound, and l-min, the smallest lower bound.
u-max=130. l-min=−130. And we pick Q=maximum ({magnitude(u-max)=130, magnitude(l-min)=130})=130.
step 6) we use modulus $\mathcal{M}=2Q+1=2*130+1=261$, for modified gap score.

step 7) in the first embodiment, when we use modified gap score instead of affine gap score, the need 9 bits representations for each $r_1$-$r_5$, instead of 8 bits because 9>log 2(261)>8.

A. Minimal Formulation

In some cases, the goal of an alignment is to minimize a distance between two sequences instead of maximizing a score. There is usually an equivalence between distance and score (or similarity) measures or values on sequence, in the sense that a distance values equivalent to a score values produces the same optimal alignments. See "On order equivalences between distance and similarity measures on sequences and trees" by Martin Emms and Hector-Hugo Franco-Penya, School of Computer Science and Statistics, Trinity College, Dublin, Ireland.

When such an equivalence exists, the minimization problem of a distance may be translated to the maximization problem of its equivalent score. And apply the solutions given in this disclosure.

Further, the following changes in the formulations of this disclosure will apply to problems of minimization of a distance.

All the parameters of key recursive equations are redefined to point to paths with least score instead of maximum score. For example, $\rho(A)$ denotes the least (instead of the maximum) score over all allowable paths ending on vertex A.

All the Lemmas 1-7, will have upper and lower bounds reversed, and $\kappa_{max}$ and $\kappa_{min}$ interchanged.

In a first aspect, a computing device for aligning genetic material sequences is provided. The computing device comprises a processor comprising a plurality of processor registers. The processor is configured to receive first and second genetic material sequences, each genetic material sequence comprising a plurality of bases of a genetic base alphabetic. The processor is configured to augment a beginning of each of the first and second genetic material sequence with an auxiliary base not in the genetic base alphabet. The processor is configured to define a two-dimensional matrix comprising a plurality of rows and columns, each row having a length equal to a number of bases in the augmented first genetic material sequence, each column having a length equal to a number of bases in the augmented second genetic material sequence, the matrix comprising a plurality of nodes arranged in a two-dimensional positional order comprising a first node located at an intersection of a first row and a first column of the matrix, and a last node located at an intersection of a last row and a last column of the matrix, each node of the matrix corresponding to a base from the augmented first genetic material sequence and a base from the augmented second genetic material sequence. The processor is configured to compute a first integer value as a function of a substitution value matrix and a plurality of gap score constants. The processor is configured to initialize first, second, and third scores of the first node of the matrix to a set of known values. The processor is configured to, for each node of the matrix other than the first node: compute a first residue of a first score of the node based on a plurality of residue of scores of a node in a previous positional order in a same column of the matrix as the node modulo the first integer value; store the first residue of the first score of the node in a processor register of the plurality of processor registers; compute a second residue of a second score of the node based on a plurality of residue of scores of a node in a previous positional order in a same row of the matrix as the node modulo the first integer value; store the second residue of the second score of the node in a processor register of the plurality of processor registers; compute a third residue of a third score of the node based on a residue of a score of a node in a previous positional order in a same diagonal of the matrix as the node modulo the first integer value and a plurality of residue of the scores of the node modulo the first integer value; and store the third residue of the third score of the node in a processor register of the plurality of processor registers.

In an embodiment of the first aspect, the first integer value is calculated as function of a maximum of the substitution score map, a minimum of the substitution score map, and one or more gap score constants in the plurality of gap score constants.

In another embodiment of the first aspect, the plurality of residue of scores of the node in the previous positional order in the same column of the matrix comprises the first residue and the third residue of the previous node in the same column of the matrix.

In another embodiment of the first aspect, the plurality of residue of scores of the node in the previous positional order in the same row of the matrix comprises the second residue and the third residue of the previous node in the same row of the matrix.

In another embodiment of the first aspect, the residue of the score of the node in the previous positional order in the same diagonal of the matrix as the node comprises the third residue of the previous node diagonally located in the matrix, and wherein the plurality of residue of the scores of the node comprise the first and second residues of the node.

In another embodiment of the first aspect, the substitution score map comprises a set of score values for matches and mismatches of the bases in the genetic base alphabet, and wherein and the plurality of gap score constants comprises a set of score values for gaps between aligned bases of the augmented first and second genetic material sequences.

In a second aspect, a method of optimizing computer storage requirements for aligning two genetic material sequences is provided. The method is performed by a processor of a computing device, where the processor comprises a plurality of processor registers. The method comprises receiving first and second genetic material sequences, each genetic material sequence comprising a plurality of bases of a genetic base alphabetic. The method comprises augmenting a beginning of each of the first and second genetic material sequence with an auxiliary base not in the genetic base alphabet. The method comprises defining a two-dimensional matrix comprising a plurality of rows and columns, each row having a length equal to a number of bases in the augmented first genetic material sequence, each column having a length equal to a number of bases in the augmented second genetic material sequence, the matrix comprising a plurality of nodes arranged in a two-dimensional positional order comprising a first node located at an intersection of a first row and a first column of the matrix, and a last node located at an intersection of a last row and a last column of the matrix, each node of the matrix corresponding to a base from the augmented first genetic material sequence and a base from the augmented second genetic material sequence. The method comprises computing a first integer value as a function of a substitution value matrix and a plurality of gap score constants. The method comprises initializing first, second, and third scores of the first node of the matrix to a set of known values. The method comprises, for each node of the matrix other than the first node, computing a first residue of a first score of the node based on a plurality of residue of scores of a node in a previous positional order in a same column of the matrix as the node modulo the first integer value; storing the first residue of the first score of the node in a processor register of the plurality of processor registers; computing a second residue of a second score of the node based on a plurality of residue of scores of a node in a previous positional order in a same row of the matrix as the node modulo the first integer value; storing the second residue of the second score of the node in a processor register of the plurality of processor registers; computing a third residue of a third score of the node based on a residue of a score of a node in a previous positional order in a same diagonal of the matrix as the node modulo the first integer value and a plurality of residue of the scores of the node modulo the first integer value; and storing the third residue of the third score of the node in a processor register of the plurality of processor registers.

In an embodiment of the second aspect, the first integer value is calculated as function of a maximum of the substitution score map, a minimum of the substitution score map, and one or more gap score constants in the plurality of gap score constants.

In another embodiment of the second aspect, the plurality of residue of scores of the node in the previous positional order in the same column of the matrix comprises the first residue and the third residue of the previous node in the same column of the matrix.

In another embodiment of the second aspect, the plurality of residue of scores of the node in the previous positional order in the same row of the matrix comprises the second residue and the third residue of the previous node in the same row of the matrix.

In another embodiment of the second aspect, the residue of the score of the node in the previous positional order in the same diagonal of the matrix as the node comprises the third residue of the previous node diagonally located in the matrix, and wherein the plurality of residue of the scores of the node comprise the first and second residues of the node.

In another embodiment of the second aspect, the substitution score map comprises a set of score values for matches and mismatches of the bases in the genetic base alphabet, and wherein and the plurality of gap score constants comprises a set of score values for gaps between aligned bases of the augmented first and second genetic material sequences.

In a third aspect, a computer readable media storing a program for optimizing computer storage requirements for aligning two genetic material sequences is provided. The program is executable by a processor of a computing device, where the processor comprises a plurality of processor registers. The program comprises a set of instructions for receiving first and second genetic material sequences, each genetic material sequence comprising a plurality of bases of a genetic base alphabetic. The program comprises a set of instructions for augmenting a beginning of each of the first and second genetic material sequence with an auxiliary base not in the genetic base alphabet. The program comprises a set of instructions for defining a two-dimensional matrix comprising a plurality of rows and columns, each row having a length equal to a number of bases in the augmented first genetic material sequence, each column having a length equal to a number of bases in the augmented second genetic material sequence, the matrix comprising a plurality of nodes arranged in a two-dimensional positional order comprising a first node located at an intersection of a first row and a first column of the matrix, and a last node located at an intersection of a last row and a last column of the matrix, each node of the matrix corresponding to a base from the augmented first genetic material sequence and a base from the augmented second genetic material sequence. The program comprises a set of instructions for computing a first integer value as a function of a substitution value matrix and a plurality of gap score constants. The program comprises a set of instructions for initializing first, second, and third scores of the first node of the matrix to a set of known values. The program comprises a set of instructions for each node of the matrix other than the first node for, computing a first residue of a first score of the node based on a plurality of residue of scores of a node in a previous positional order in a same column of the matrix as the node modulo the first integer value; storing the first residue of the first score of the node in a processor register of the plurality of processor registers; computing a second residue of a second score of the node based on a plurality of residue of scores of a node in a previous positional order in a same row of the matrix as the node modulo the first integer value; storing the second residue of the second score of the node in a processor register of the plurality of processor registers; computing a third residue of a third score of the node based on a residue of a score of a node in a previous positional order in a same diagonal of the matrix as the node modulo the first integer value and a plurality of residue of the scores of the node modulo the first integer value; and storing the third residue of the third score of the node in a processor register of the plurality of processor registers.

As used in this specification, the terms "computer," "server," "processor," "processing unit," "controller," and "memory" all refer to electronic or other technological devices. These terms exclude people or groups of people. For the purposes of the specification, the terms display or displaying means displaying on an electronic device. As used in this specification, the terms "computer readable medium," "computer readable media," and "machine readable medium" are entirely restricted to non-transitory, tangible, physical objects that store information in a form that is readable by a computer. These terms exclude any wireless signals, wired download signals, and any other ephemeral or transitory signals.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. A computing device for aligning genetic material sequences, the computing device comprising:
   a first function generator comprising first, second, and third adders, a first inverter, and a first multiplexer;
   a second function generator comprising fourth, fifth, and sixth adders, a second inverter, and a second multiplexer;
   a third function generator comprising a seventh adder, a comparator, and a third multiplexer; and
   a processor configured to:
      receive first and second genetic material sequences, each genetic material sequence comprising a plurality of bases of a genetic base alphabet;
      augment a beginning of each of the first and second genetic material sequence with an auxiliary base not in the genetic base alphabet;
      define a two-dimensional matrix comprising a plurality of rows and columns, each row having a length equal to a number of bases in the augmented first genetic material sequence, each column having a length equal to a number of bases in the augmented second genetic material sequence, the matrix comprising a plurality of nodes arranged in a two-dimensional positional order comprising a corner node located at an intersection of a first row and a first column of the matrix, and a last node located at an intersection of a last row and a last column of the matrix, each node of the matrix corresponding to a base from the augmented first genetic material sequence and a base from the augmented second genetic material sequence;
      initialize first, second, and third scores of the corner node of the matrix to a set of known values;
      for each node of the matrix other than the corner node:
         the first function generator configured to:
            add, at the first adder, a residue of a first score of a first node in a previous positional order in a same column of the matrix as the node, to a residue of a first gap score constant;
            add, at the second adder, a residue of a second score of the first node to a residue of a second gap score constant; and
            select, by the third adder, the first inverter, and the first multiplexer, a residue of a smaller of the first score of the first node plus the first gap score constant, and the second score of the first node plus the second gap score constant as a residue of a first score of the node;
         the second function generator configured to:
            add, at the fourth adder, a residue of a first score of a second node in a previous positional order in a same row of the matrix as the node to a third gap score constant;
            add, at the fifth adder, a residue of a second score of the second node to a fourth gap score constant; and
            select, by the sixth adder, the second inverter, and the second multiplexer, a residue of a smaller of the first score of the second node plus the third gap score constant, and the second score of the second node plus the fourth gap score constant as a residue of a second score of the node;
         the third function generator configured to:
            add, at the seventh adder, a residue of a score of a third node in a previous positional order in a same diagonal of the matrix as the node to a residue of a substitution value associated with the third node and the node; and
            select, by the comparator and the third multiplexer, a residue of a smallest of (i) the first score of the node, (ii) the second score of the node, and (iii) the score of the third node plus the substitution value as a residue of a third score of the node;
the processor further configured to:
perform a recursive traceback on the two-dimensional matrix starting with the last node and ending to the corner node to compute a maximal score walk on the two-dimensional matrix based on the residue of the first score of the plurality of nodes of the two-dimensional matrix, the residue of the second score of the plurality of nodes of the two-dimensional matrix, and the residue of the third score of the plurality of nodes of the two-dimensional matrix; and
align the first and second genetic material sequences using the maximal score walk.

2. The computing device of claim 1,
wherein the processor of the computing device is configured to compute a first integer value as function of a substitution value matrix and a plurality of gap score constants; and
wherein the first, second, and third function generators of the computing device are configured to:
receive the first integer value; and
perform residue computations as modulo operations over the first integer value.

3. The computing device of claim 1,
wherein the residue of the first score of the first node in the previous positional order in the same column of the matrix comprises a residue of a cost of traversing the two-dimensional matrix from the corner node to a fourth node in a previous positional order in a same column of the matrix as the first node plus a cost of travelling in a vertical direction from the fourth node to the first node, and
wherein the residue of the second score of the first node comprises a residue of a maximal score of traversing the two-dimensional matrix from the corner node to the first node.

4. The computing device of claim 1,
wherein the residue of the first score of the second node in the previous positional order in the same row of the matrix comprises a residue of a cost of traversing the two-dimensional matrix from the corner node to a fourth node in a previous positional order in a same row of the matrix as the second node plus a cost of travelling in a horizontal direction from the fourth node to the second node, and
wherein the residue of the second score of the second node comprises a residue of a maximal score of traversing the two-dimensional matrix from the corner node to the second node.

5. The computing device of claim 1, wherein the residue of the score of the third node in the previous positional order in the same diagonal of the matrix as the node comprises a residue of a maximal score of traversing the two-dimensional matrix from the corner node to the third node.

6. The computing device of claim 1, wherein the substitution value comprises one of a set of score values for matches and mismatches of the bases in the genetic base alphabet.

7. A method of optimizing computer storage requirements for aligning two genetic material sequences, the method comprising:
by a processor of a computing device:
receiving first and second genetic material sequences, each genetic material sequence comprising a plurality of bases of a genetic base alphabet;
augmenting a beginning of each of the first and second genetic material sequence with an auxiliary base not in the genetic base alphabet;
defining a two-dimensional matrix comprising a plurality of rows and columns, each row having a length equal to a number of bases in the augmented first genetic material sequence, each column having a length equal to a number of bases in the augmented second genetic material sequence, the matrix comprising a plurality of nodes arranged in a two-dimensional positional order comprising a corner node located at an intersection of a first row and a first column of the matrix, and a last node located at an intersection of a last row and a last column of the matrix, each node of the matrix corresponding to a base from the augmented first genetic material sequence and a base from the augmented second genetic material sequence;
initializing first, second, and third scores of the corner node of the matrix to a set of known values;
for each node of the matrix other than the corner node:
by a first adder of a first function generator of the computing device, adding a residue of a first score of a first node in a previous positional order in a same column of the matrix as the node, to a residue of a first gap score constant;
by a second adder of the first function generator of the computing device, adding a residue of a second score of the first node to a residue of a second gap score constant;
by a third adder, a first inverter, and a first comparator of the computing device, selecting a residue of a smaller of the first score of the first node plus the first gap score, and the second score of the first node plus the second gap score as a residue of a first score of the node;
by a fourth adder of a second function generator of the computing device, adding a residue of a first score of a second node in a previous order in a same row of the matrix as the node to a third gap score constant;
by a fifth adder of the second function generator of the computing device, adding a residue of a second score of the second node to a fourth gap score constant;
by a sixth adder of the second function generator, second inverter, and a second multiplexer of the computing device, selecting a residue of a smaller of the first score of the second node plus the third gap score, and the second score of the second node plus the fourth gap score as a residue of a second score of the node
by a seventh adder of a third function generator of the computing device, adding a residue of a score of a third node in a previous positional order in a same diagonal of the matrix as the node to a residue of a substitution value associated with the third node and the node; and
by a comparator and a third multiplexer of the third generator of the computing device, selecting a residue of a smallest of (i) the first score of the node, (ii) the second score of the node, and (iii) the score of the third node plus the substitution value as a residue of a third score of the node;
by the processor of the computing device:
performing a recursive traceback on the two-dimensional matrix starting with the last node and ending to the corner node to compute a maximal score walk on the two-dimensional matrix based on the residue of the first score of the plurality of nodes of the two-dimensional matrix, the residue of the second score of the plurality of nodes of the two-dimensional matrix, and the residue of the third score of the plurality of nodes of the two-dimensional matrix; and aligning the first and second genetic material sequences using the maximal score walk.

8. The method of claim 7, further comprising:

by the processor of the computing device, computing a first integer value as function of a substitution value matrix and a plurality of gap score constants; and by the first, second, and third function generators of the computing device:

receiving the first integer value; and performing residue computations as modulo operations over the first integer value.

9. The method of claim 7, wherein the residue of the first score of the first node in the previous positional order in the same column of the matrix comprises a residue of a cost of traversing the two-dimensional matrix from the corner node to a fourth node in a previous positional order in a same column of the matrix as the first node plus a cost of travelling in a vertical direction from the fourth node to the first node, and wherein the residue of the second score of the first node comprises a residue of a maximal score of traversing the two-dimensional matrix from the corner node to the first node.

10. The method of claim 7, wherein the residue of the first score of the second node in the previous positional order in the same row of the matrix comprises a residue of a cost of traversing the two-dimensional matrix from the corner node to a fourth node in a previous positional order in a same row of matrix as the second node plus a cost of travelling in a horizontal direction from the fourth node to the second node, and wherein the residue of the second score of the second node comprises a residue of a maximal score of traversing the two-dimensional matrix from the corner node to the second node.

11. The method of claim 7, wherein the residue of the score of the third node in the previous positional order in the same diagonal of the matrix as the node comprises a residue of a maximal score of traversing the two-dimensional matrix from the corner node to the third node.

12. The method of claim 7, wherein the substitution value comprises one of a set of score values for matches and mismatches of the bases in the genetic base alphabet.

13. The computing device of claim 1, wherein the first, second, third, and fourth gap score constants comprise score values for gaps between aligned bases of the augmented first and second genetic material sequences.

14. The method of claim 7, wherein the first, second, third, and fourth gap score constants comprise score values for gaps between aligned bases of the augmented first and second genetic material sequences.

* * * * *